United States Patent
Fujiwara et al.

(10) Patent No.: US 12,240,804 B2
(45) Date of Patent: Mar. 4, 2025

(54) ONIUM SALT, CHEMICALLY AMPLIFIED RESIST COMPOSITION AND PATTERNING PROCESS

(71) Applicant: Shin-Etsu Chemical Co., Ltd., Tokyo (JP)

(72) Inventors: Takayuki Fujiwara, Joetsu (JP); Satoshi Watanabe, Joetsu (JP); Kousuke Ohyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 35 days.

(21) Appl. No.: 17/495,166

(22) Filed: Oct. 6, 2021

(65) Prior Publication Data

US 2022/0127225 A1 Apr. 28, 2022

(30) Foreign Application Priority Data

Oct. 22, 2020 (JP) .................. 2020-177024

(51) Int. Cl.
*C07C 381/12* (2006.01)
*G03F 7/004* (2006.01)
(Continued)

(52) U.S. Cl.
CPC .......... *C07C 381/12* (2013.01); *G03F 7/0045* (2013.01); *G03F 7/0382* (2013.01);
(Continued)

(58) Field of Classification Search
CPC . C07C 381/12; C07C 323/62; C07C 2603/74; C07C 2601/14; C07C 317/12;
(Continued)

(56) References Cited

U.S. PATENT DOCUMENTS

| 6,991,888 B2* | 1/2006 | Padmanaban ......... G03F 7/0045 430/326 |
| 8,110,333 B2* | 2/2012 | Kamimura ............ G03F 7/0045 430/326 |

(Continued)

FOREIGN PATENT DOCUMENTS

| JP | 2006195283 A | * | 7/2006 |
| JP | 2007-045144 A | | 2/2007 |

(Continued)

OTHER PUBLICATIONS

Translated Description of Watanabe (Year: 2006).*
(Continued)

*Primary Examiner* — Sean M DeGuire
*Assistant Examiner* — Andrew Preston Traywick
(74) *Attorney, Agent, or Firm* — WHDA, LLP

(57) ABSTRACT

An onium salt having formula (1) serving as an acid diffusion inhibitor and a chemically amplified resist composition comprising the acid diffusion inhibitor are provided. When processed by lithography, the resist composition forms a pattern having minimal defects and excellent lithography performance factors such as CDU, LWR and DOF.

$$\underset{(R^3)_n}{R^2\diagdown X^+ - Ar - \overset{O}{\underset{\|}{C}} - O - R^1} \quad Z^- \qquad (1)$$

15 Claims, 20 Drawing Sheets

(51) Int. Cl.
  *G03F 7/038* (2006.01)
  *G03F 7/20* (2006.01)
  *G03F 7/32* (2006.01)
  *G03F 7/40* (2006.01)

(52) U.S. Cl.
  CPC ............ *G03F 7/2006* (2013.01); *G03F 7/327* (2013.01); *G03F 7/40* (2013.01)

(58) Field of Classification Search
  CPC ....... C07C 69/753; C07C 69/63; C07C 65/10; C07C 65/05; C07C 61/125; C07C 59/205; C07C 59/135; C07C 59/13; C07C 59/115; C07C 53/18; G03F 7/32; G03F 7/2004; G03F 7/0392; G03F 7/325; G03F 7/322; G03F 7/0397; G03F 7/40; G03F 7/327; G03F 7/2006; G03F 7/0382; G03F 7/0045; C07F 13/00; C07D 411/12; C07D 327/06; C07D 275/06; C07D 327/08; C07D 321/10; C07D 307/79; C07D 307/77
  See application file for complete search history.

(56) References Cited

U.S. PATENT DOCUMENTS

| | | | | |
|---|---|---|---|---|
| 8,574,817 | B2* | 11/2013 | Hatakeyama | G03F 7/0392 430/326 |
| 2006/0216642 | A1* | 9/2006 | Oohashi | B41C 1/1016 430/270.1 |
| 2007/0148592 | A1 | 6/2007 | Wada et al. | |
| 2009/0042124 | A1 | 2/2009 | Kamimura et al. | |
| 2010/0239978 | A1* | 9/2010 | Wada | C07D 493/14 430/322 |
| 2013/0157197 | A1* | 6/2013 | Komuro | G03F 7/0397 549/287 |
| 2014/0349221 | A1* | 11/2014 | Takizawa | G03F 7/027 430/311 |
| 2015/0086925 | A1* | 3/2015 | Ayothi | G03F 7/325 430/285.1 |
| 2017/0121437 | A1 | 5/2017 | Tsuchimura | |
| 2017/0329227 | A1* | 11/2017 | Ohashi | G03F 7/0397 |
| 2018/0039175 | A1* | 2/2018 | Masunaga | G03F 7/0045 |
| 2018/0267403 | A1* | 9/2018 | Hatakeyama | G03F 7/0046 |
| 2020/0008134 | A1 | 1/2020 | Wallentin et al. | |
| 2020/0223796 | A1 | 7/2020 | Fukushima et al. | |
| 2020/0301275 | A1 | 9/2020 | Taniguchi et al. | |

FOREIGN PATENT DOCUMENTS

| | | |
|---|---|---|
| JP | 2007-178848 A | 7/2007 |
| JP | 2009-058949 A | 3/2009 |
| JP | 4866605 B2 | 2/2012 |
| JP | 5542402 B2 | 7/2014 |
| JP | 2015-191216 A | 11/2015 |
| JP | 6169848 B2 | 7/2017 |
| JP | 2020-064305 A | 4/2020 |
| JP | 2020-154210 A | 9/2020 |
| JP | 2020-176117 A | 10/2020 |
| JP | 2020-176119 A | 10/2020 |
| KR | 2020-0030012 A | 3/2020 |
| KR | 2020-0089226 A | 7/2020 |
| TW | 201606445 A | 2/2016 |
| TW | 201808894 A | 3/2018 |

OTHER PUBLICATIONS

Office Action dated May 16, 2022, issued in counterpart TW Application No. 110138802. (10 pages).

Office Action dated Dec. 8, 2022, issued in counterpart TW application No. 110138802. (9 pages).

Office Action dated Jul. 31, 2023, issued in counterpart TW application No. 110138802. (8 pages).

Wyatt, Mark et al., "Analysis of Various Organic and Organometallic Compound Using Nanostructure-Assisted Laser Desorption/Ionization Time-of-Flight Mass Spectrometry (NALDI-TOFMS)", Journal of the American Society for Mass Spectrometry, 2010, vol. 21, pp. 1256-1259; Cited in JP Office Action dated Sep. 5, 2023. (9 pages).

Office Action dated Sep. 5, 2023, issued in counterpart JP Application No. 2020-177024, with English Translation. (9 pages).

Office Action dated Oct. 20, 2023, issued in counterpart KR application No. 10-2021-0139663, with English translation. (13 pages).

* cited by examiner

ONIUM SALT, CHEMICALLY AMPLIFIED RESIST COMPOSITION AND PATTERNING PROCESS

CROSS-REFERENCE TO RELATED APPLICATION

This non-provisional application claims priority under 35 U.S.C. § 119(a) on Patent Application No. 2020-177024 filed in Japan on Oct. 22, 2020, the entire contents of which are hereby incorporated by reference.

TECHNICAL FIELD

This invention relates to an onium salt, a chemically amplified resist composition, and a pattern forming process.

BACKGROUND ART

To meet the demand for higher integration and operating speeds in LSIs, further miniaturization of the pattern rule is desired. The requirement to form resist patterns of high resolution necessitates not only to improve lithography properties as typified by pattern profile, contrast, mask error factor (MEF), depth of focus (DOF), line width roughness (LWR), and critical dimension uniformity (CDU), but also to minimize defects on the resist pattern after development.

One of the causes for defectiveness and DOF degradation is cations in photoacid generators and acid diffusion inhibitors. Sulfonium and iodonium cations leave nonionic sulfide or iodized arene as the decomposed product after exposure. These photo-decomposition products are highly lipophilic and hence, less dissolvable in alkaline developer. Since the photo-decomposition reaction of cations is a polarity switch toward a contrast lowering, lithography performance is degraded.

For suppressing the influence of the photo-decomposition products of cations on lithography performance, for example, Patent Document 1 proposes to introduce an acid labile group into a cation, and Patent Document 2 discloses a photoacid generator in the form of a compound which is decomposed with alkali to generate a phenol group, as shown below. On use of these compounds as the photoacid generator or acid diffusion inhibitor, however, the results of various performance factors are far from satisfactory in the current generation of lithography where ultrafine processing by the ArF or EUV lithography process is required.

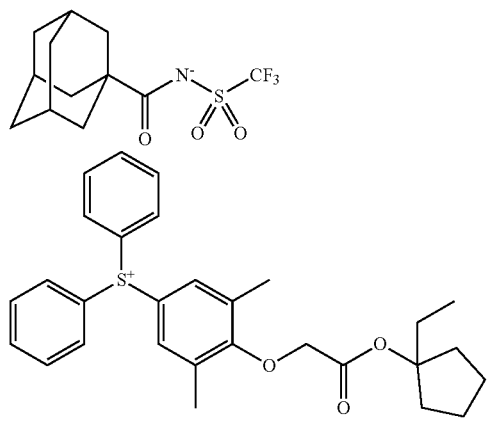

-continued

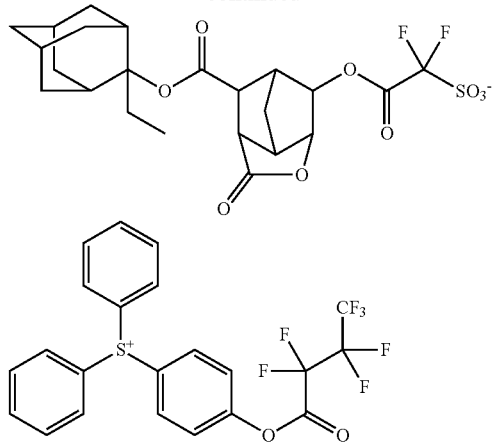

CITATION LIST

Patent Document 1: JP 5542402
Patent Document 2: JP 6169848

DISCLOSURE OF INVENTION

While resist patterns of high resolution are recently required, resist compositions comprising conventional acid diffusion inhibitors do not always meet lithography performance factors such as CDU, LWR and DOF.

An object of the invention is to provide a chemically amplified resist composition which when processed by lithography using high-energy radiation such as KrF or ArF excimer laser, EB or EUV, is improved in lithography performance factors such as CDU, LWR and DOF and minimized in defectiveness. Another object is to provide an acid diffusion inhibitor used in the resist composition and a pattern forming process using the resist composition.

The inventors have found that a chemically amplified resist composition comprising an onium salt of a specific structure as an acid diffusion inhibitor exhibits improved lithography performance factors such as CDU, LWR and DOF as well as minimal defectiveness, and is quite suited for precision micropatterning.

In one aspect, the invention provides an onium salt having the formula (1).

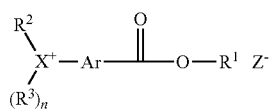

Herein X is sulfur or iodine; n is 1 when X is sulfur and n is 0 when X is iodine. $R^1$ is a $C_1$-$C_5$ hydrocarbyl group which may contain fluorine or oxygen. $R^2$ and $R^3$ are each independently a $C_1$-$C_{30}$ hydrocarbyl group which may contain a heteroatom, $R^2$ and $R^3$ may bond together to form a ring with X to which they are attached. Ar is a $C_6$-$C_{14}$ arylene group which may be substituted with a substituent selected from a halogen atom, hydroxy group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, and $C_2$-$C_{10}$ hydrocarbylcarbonyloxy group which may contain a heteroatom, $R^2$ and Ar may bond together to form a ring with X to which they are attached. $Z^-$ is a carboxylate, sulfonamide, sulfonimide or methide anion.

The preferred onium salt has the formula (2):

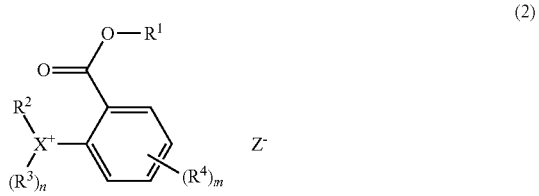

(2)

Herein $R^1$, $R^2$, $R^3$, n, X, and $Z^-$ are as defined above. $R^4$ is a halogen atom, hydroxy group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, or $C_2$-$C_{10}$ hydrocarbylcarbonyloxy group which may contain a heteroatom, and m is an integer of 0 to 4.

Preferably, $R^1$ is methyl, ethyl, propyl, isopropyl, n-butyl, 2,2,2-trifluoroethyl, 3,3,3-trifluoropropyl, 2,2,3,3,3-pentafluoropropyl, 1-trifluoromethyl-2,2,2-trifluoroethyl or 2-methoxyethyl.

Preferably, $Z^-$ is a carboxylate anion having at least one fluorine atom or trifluoromethyl group at α- or β-position relative to the carboxy group.

More preferably, $Z^-$ is an anion having any one of the formulae (Z-1) to (Z-5).

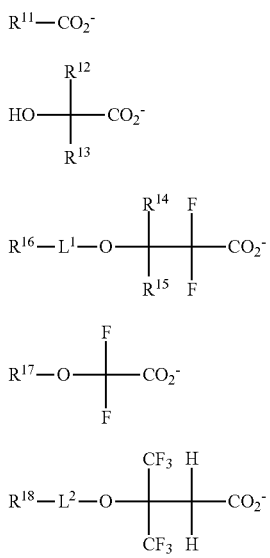

(Z-1)

(Z-2)

(Z-3)

(Z-4)

(Z-5)

Herein $R^{11}$ is a $C_1$-$C_4$ perfluoroalkyl group; $R^{12}$ and $R^{13}$ are each independently hydrogen, fluorine, methyl or trifluoromethyl, at least one of $R^{12}$ and $R^{13}$ is fluorine or trifluoromethyl; $R^{14}$ and $R^{15}$ are each independently hydrogen or a $C_1$-$C_{15}$ hydrocarbyl group which may contain a heteroatom; $R^{16}$, $R^{17}$ and $R^{18}$ are each independently hydrogen or a $C_1$-$C_{30}$ hydrocarbyl group which may contain a heteroatom; $L^1$ and $L^2$ are each independently a single bond, carbonyl group or sulfonyl group.

In another aspect, the invention provides an acid diffusion inhibitor comprising the onium salt defined above.

In a further aspect, the invention provides a chemically amplified resist composition comprising (A) a base polymer, (B) a photoacid generator, (C-1) the acid diffusion inhibitor defined above, and (D) an organic solvent; or a chemically amplified resist composition comprising (A') a base polymer adapted to generate an acid upon light exposure, (C-1) the acid diffusion inhibitor defined above, and (D) an organic solvent.

In a preferred embodiment, the base polymer comprises repeat units having the formula (a) or repeat units having the formula (b).

(a)

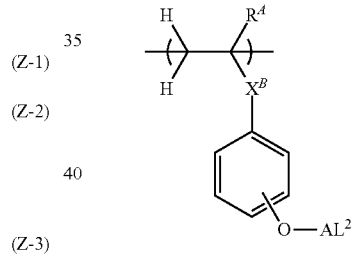

(b)

Herein $R^A$ is each independently hydrogen or methyl; $X^A$ is a single bond, phenylene group, naphthylene group or (backbone)-C(=O)-O-$X^{41}$-, $X^{41}$ is a $C_1$-$C_{15}$ hydrocarbylene group which may contain a hydroxy moiety, ether bond, ester bond, or lactone ring; $X^B$ is a single bond or ester bond; $AL^1$ and $AL^2$ are each independently an acid labile group.

Preferably, the acid labile group has the formula (L1):

(L1)

wherein $R^{21}$ is a $C_1$-$C_7$ hydrocarbyl group in which any constituent —$CH_2$— may be replaced by —O—, a is 1 or 2, and the broken line designates a valence bond.

In a preferred embodiment, the base polymer comprises repeat units having the formula (c):

(c)

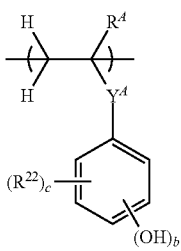

wherein $R^A$ is hydrogen or methyl; $Y^A$ is a single bond or ester bond; $R^{22}$ is fluorine, iodine, a carboxy group, formyl group, formyloxy group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, $C_2$-$C_{10}$ hydrocarbylcarbonyloxy group which may contain a heteroatom, or $C_2$-$C_{10}$ hydrocarbyloxycarbonyloxy group which may contain a heteroatom; b is an integer of 1 to 5, c is an integer of 0 to 4, and b+c is 1 to 5.

Preferably, the base polymer comprises repeat units adapted to generate an acid upon light exposure, having any one of the formulae (d1) to (d4).

(d1)

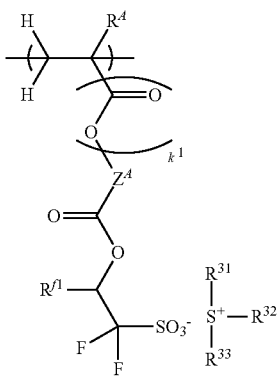

(d2)

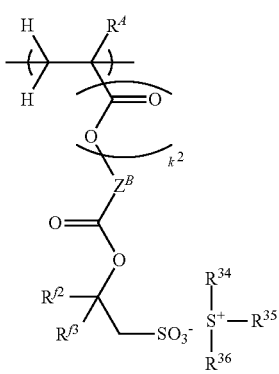

(d3)

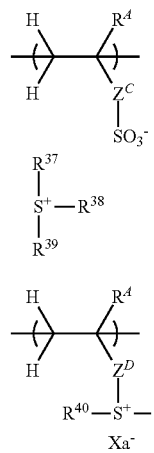

(d4)

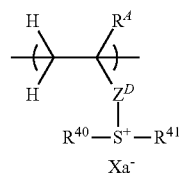

Herein $R^A$ is each independently hydrogen or methyl. $R^{f1}$, $R^{f2}$ and $R^{f3}$ are each independently hydrogen or trifluoromethyl. $Z^A$ and $Z^B$ are each independently a single bond or a $C_1$-$C_{20}$ hydrocarbylene group which may contain a heteroatom. $Z^C$ is a single bond, $-Z^{C1}-$, $-O-Z^{C1}-$, or $-C(=O)-O-Z^{C1}-$, wherein $Z^{C1}$ is a phenylene group which may be substituted with a substituent selected from a hydroxy group, fluorine, iodine, trifluoromethyl group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, and $C_2$-$C_{10}$ hydrocarbylcarbonyloxy group which may contain a heteroatom. $Z^D$ is a single bond, phenylene group, $-O-Z^{D1}-$, $-C(=O)-O-Z^{D1}-$ or $-C(=O)-NH-Z^{D1}-$, wherein $Z^{D1}$ is a hydrocarbylene group which may contain a heteroatom. $R^{31}$ to $R^{41}$ are each independently a $C_1$-$C_{30}$ hydrocarbyl group which may contain a heteroatom, a pair of $R^{31}$ and $R^{32}$, $R^{34}$ and $R^{35}$, $R^{37}$ and $R^{38}$, or $R^{40}$ and $R^{41}$ may bond together to form a ring with the sulfur atom to which they are attached; $k^1$ is 0 or 1, $k^1$ is 0 when $Z^A$ is a single bond, $k^2$ is 0 or 1, $k^2$ is 0 when $Z^B$ is a single bond. $Xa^-$ is a non-nucleophilic counter ion.

In a still further aspect, the invention provides a pattern forming process comprising the steps of applying the chemically amplified resist composition defined above to form a resist film on a substrate, exposing the resist film to KrF excimer laser, ArF excimer laser, EB, or EUV, and developing the exposed resist film in a developer.

In one preferred embodiment, the developing step uses an alkaline aqueous solution as the developer to form a positive pattern in which an exposed region of the resist film is dissolved away and an unexposed region of the resist film is not dissolved.

In another preferred embodiment, the developing step uses an organic solvent as the developer to form a negative pattern in which an unexposed region of the resist film is dissolved away and an exposed region of the resist film is not dissolved.

Advantageous Effects of Invention

When the chemically amplified resist composition comprising the onium salt according to the invention as an acid diffusion inhibitor is processed by lithography, a resist pattern having improved lithography performance factors such as CDU, LWR and DOF as well as minimal defectiveness can be formed.

DESCRIPTION OF THE PREFERRED EMBODIMENTS

Figure 1:
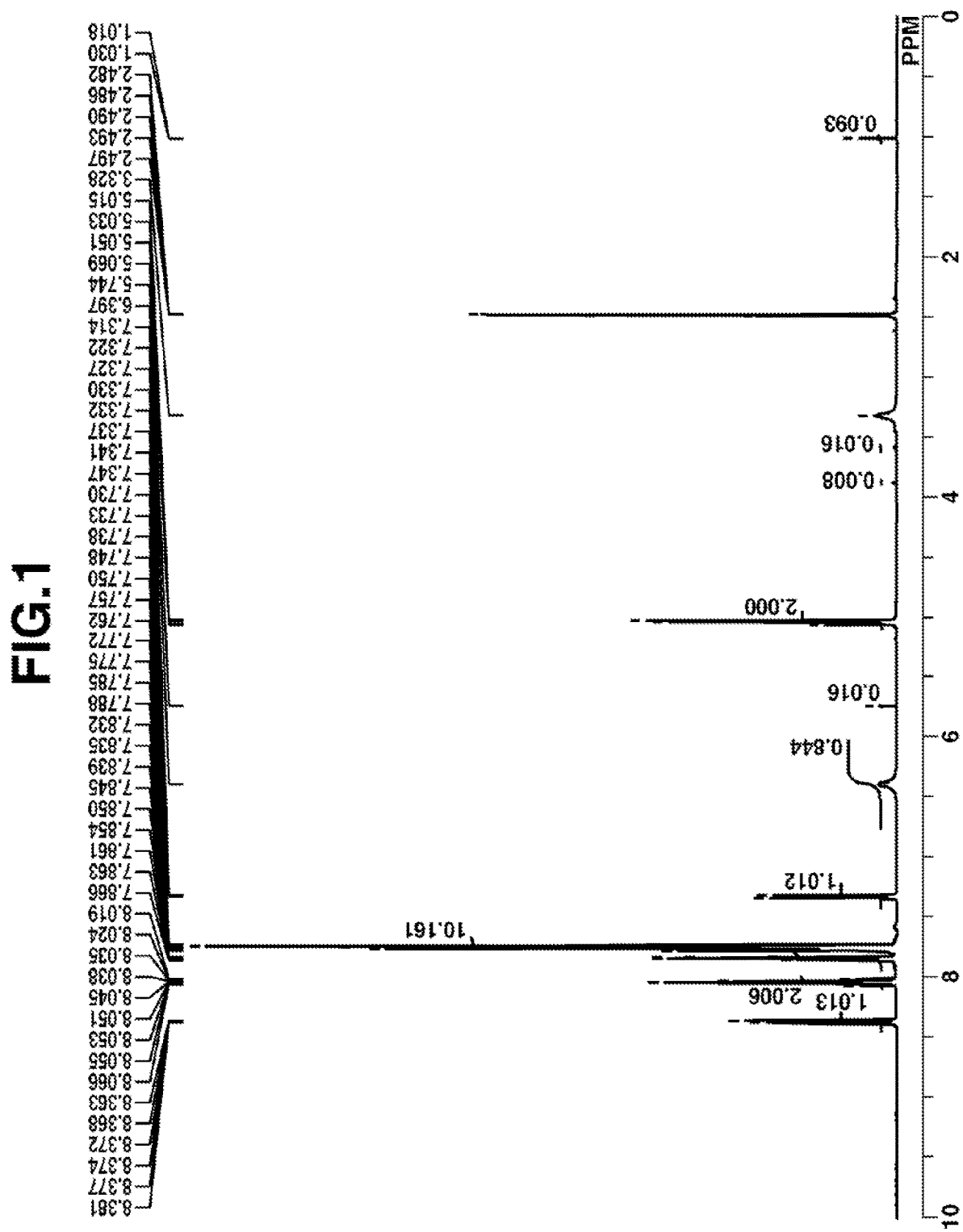
FIG. 1 is a diagram showing $^1$H-NMR spectrum of acid diffusion inhibitor Q-1 in Example 1-1.

The singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation (Cn-Cm) means a group containing from n to m carbon atoms per group. The terms "group" and "moiety" are interchangeable. In chemical formulae, the broken line denotes a valence bond; Me stands for methyl, tBu for tert-butyl, Ac for acetyl, and Ph for phenyl. It is understood that for some structures represented by chemical formulae, there can exist enantiomers and diastereomers because of the presence of asymmetric carbon atoms. In such a case, a single formula collectively represents all such isomers. The isomers may be used alone or in admixture.

The abbreviations have the following meaning.
EB: electron beam
EUV: extreme ultraviolet
GPC: gel permeation chromatography
Mw: weight average molecular weight
Mw/Mn: molecular weight dispersity
PAG: photoacid generator
PEB: post-exposure bake
LWR: line width roughness
CDU: critical dimension uniformity
DOF: depth of focus
Onium Salt The invention provides an onium salt having the formula (1).

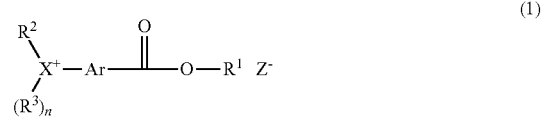

In formula (1), X is sulfur or iodine; n is 1 when X is sulfur and n is 0 when X is iodine.

In formula (1), $R^1$ is a $C_1$-$C_5$ hydrocarbyl group which may contain fluorine or oxygen. The $C_1$-$C_5$ hydrocarbyl group may be saturated or unsaturated and straight, branched or cyclic. Examples thereof include alkyl groups such as methyl, ethyl, propyl, isopropyl, n-butyl, sec-butyl, and n-pentyl. $R^1$ is preferably a $C_1$-$C_5$ straight or branched hydrocarbyl group, more preferably a $C_1$-$C_5$ straight hydrocarbyl group. Also preferably, $R^1$ is exclusive of a tertiary hydrocarbyl group. As used herein, the term "tertiary hydrocarbyl group" refers to a group obtained by removing hydrogen from tertiary carbon in a hydrocarbon. In the hydrocarbyl group, some or all of the hydrogen atoms may be substituted by fluorine atoms, and any constituent —$CH_2$— may be replaced by an ether bond (—O—). Preferably, $R^1$ is methyl, ethyl, propyl, isopropyl, n-butyl, 2,2,2-trifluoroethyl, 3,3,3-trifluoropropyl, 2,2,3,3,3-pentafluoropropyl, 1-trifluoromethyl-2,2,2-trifluoroethyl or 2-methoxyethyl.

In formula (1), $R^2$ and $R^3$ are each independently a $C_1$-$C_{30}$ hydrocarbyl group which may contain a heteroatom. The hydrocarbyl group may be saturated or unsaturated and straight, branched or cyclic. In the hydrocarbyl group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain fluorine, chlorine, bromine, iodine, hydroxy moiety, cyano moiety, carbonyl moiety, ether bond, ester bond, sulfonate bond, carbonate bond, lactone ring, sultone ring, carboxylic anhydride or haloalkyl moiety.

Examples of the optionally heteroatom-containing hydrocarbyl group represented by $R^2$ and $R^3$ include $C_1$-$C_{30}$ alkyl groups such as methyl, ethyl, propyl, isopropyl, n-butyl, sec-butyl, tert-butyl, n-pentyl, n-hexyl, n-octyl, 2-ethylhexyl, n-nonyl, n-decyl; $C_3$-$C_{30}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, adamantylmethyl; $C_2$-$C_{30}$ alkenyl groups such as vinyl, allyl, propenyl, butenyl, hexenyl; $C_3$-$C_{30}$ unsaturated alicyclic hydrocarbyl groups such as cyclohexenyl; $C_6$-$C_{30}$ aryl groups such as phenyl, 2-hydroxyphenyl, 4-hydroxyphenyl, 2-methoxyphenyl, 3-methoxyphenyl, 4-methoxyphenyl, 4-fluorophenyl, 4-iodophenyl, 4-n-butylphenyl, 4-tert-butylphenyl, 4-tert-butoxyphenyl, 4-trifluoromethylphenyl, 2,4-dimethylphenyl, 2,4,6-trimethylphenyl, 2,4,6-triisopropylphenyl, naphthyl, methylnaphthyl, methoxynaphthyl, ethoxynaphthyl, isopropoxynaphthyl, tert-butoxynaphthyl, dimethylnaphthyl, dihydroxynaphthyl, dimethoxynaphthyl; $C_7$-$C_{30}$ aralkyl groups such as benzyl, 1-phenylethyl, 2-phenylethyl; $C_3$-$C_{30}$ heteroaryl groups such as thienyl; and combinations thereof.

Preferably, $R^2$ and $R^3$ are optionally substituted phenyl groups. Suitable substituents include fluorine, iodine, trifluoromethyl, trifluoromethoxy, methyl, tert-butyl, hydroxy, methoxy, butoxy, methoxyethoxy, tert-butoxy, cyclohexylsulfonyl, and acetyl.

$R^2$ and $R^3$ may bond together to form a ring with X to which they are attached. Examples of the ring are shown below, but not limited thereto.

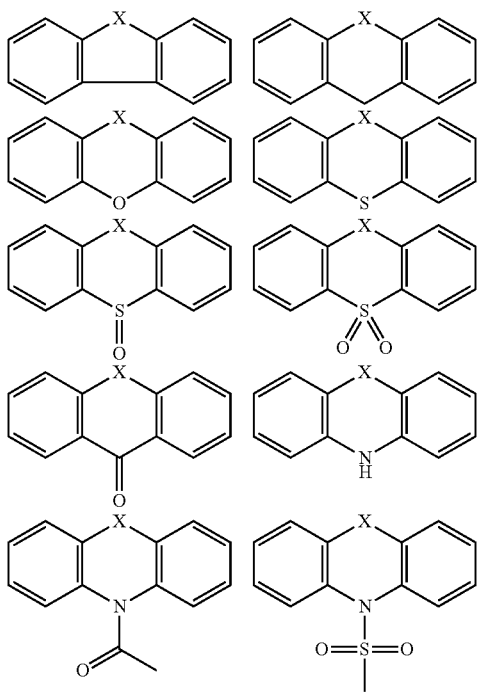

In formula (1), Ar is a $C_6$-$C_{14}$ arylene group which may be substituted with a substituent selected from a halogen atom, hydroxy group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, and $C_2$-$C_{10}$ hydrocarbylcarbonyloxy group which may contain a heteroatom.

Examples of the $C_6$-$C_{14}$ arylene group include phenylene, naphthylene, phenanthrenediyl, anthracenediyl, and furandiyl. Suitable substituents include fluorine, chlorine, bromine, iodine, trifluoromethyl, trifluoromethoxy, methyl, ethyl, propyl, isopropyl, n-butyl, tert-butyl, hydroxy, methoxy, ethoxy, propoxy, butoxy, methoxyethoxy, tert-butoxy, 2,2,2-trifluoroethoxy, 2-hydroxyethoxy, acetyl, phenylcarbonyl, acetoxy, cyclohexylcarbonyloxy, and 3,3,3-trifluoro-2-trifluoromethyl-2-hydroxypropoxy.

$R^2$ and Ar may bond together to form a ring with X to which they are attached. Examples of the ring formed by $R^2$ and Ar are as exemplified above for the ring formed by $R^2$ and $R^3$.

Of the onium salts having formula (1), salts having the formula (2) are preferred.

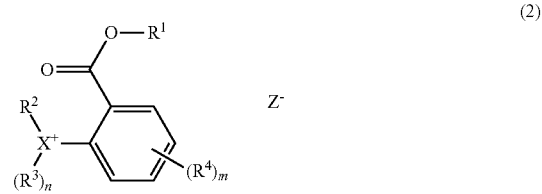

Herein $R^1$, $R^2$, $R^3$, n, X, and $Z^-$ are as defined above.

In formula (2), $R^4$ is a halogen atom, hydroxy group, $C_1$-$C_{10}$ hydrocarbyl group which may contain a heteroatom, hydrocarbyloxy group which may contain a heteroatom, $C_2$-$C_{10}$ hydrocarbylcarbonyl group which may contain a heteroatom, or $C_2$-$C_{10}$ hydrocarbylcarbonyloxy group which may contain a heteroatom. Examples of $R^4$ are as exemplified above for the substituent on Ar. Preferred are fluorine, iodine, trifluoromethyl, trifluoromethoxy, methyl, n-butyl, tert-butyl, hydroxy, methoxy, butoxy, methoxyethoxy, tert-butoxy, 2,2,2-trifluoroethoxy, acetyl, acetoxy, cyclohexylcarbonyloxy, and 3,3,3-trifluoro-2-trifluoromethyl-2-hydroxypropoxy.

In formula (2), m is an integer of 0 to 4, preferably 0, 1 or 2.

Examples of the cation in the onium salt having formula (1) are given below, but not limited thereto.

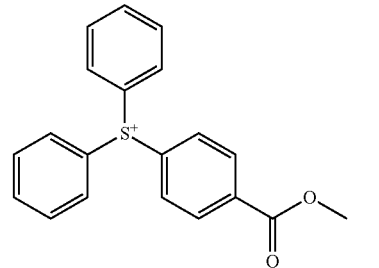

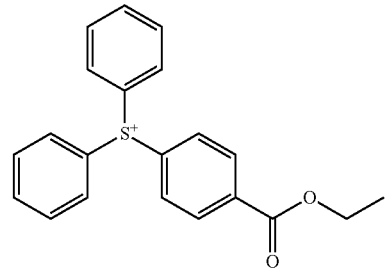

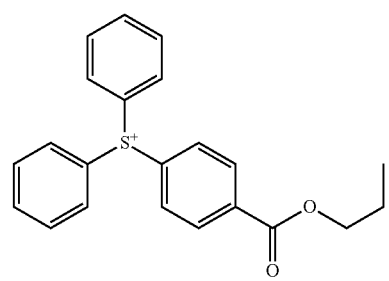

-continued
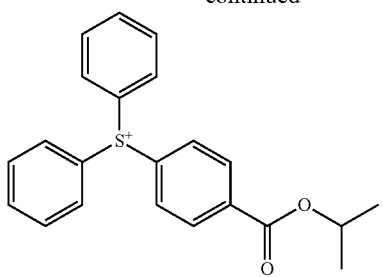
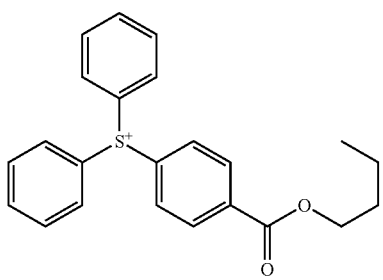
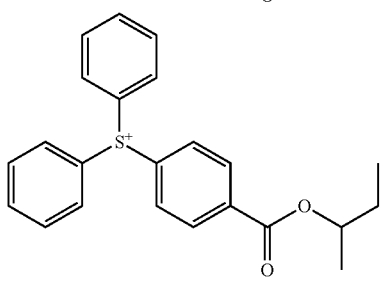
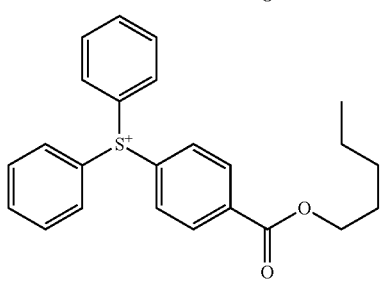
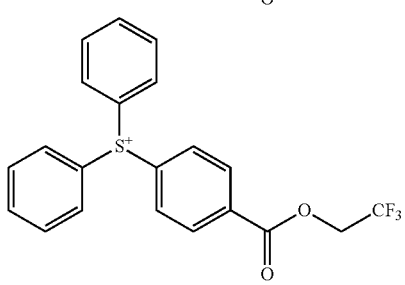
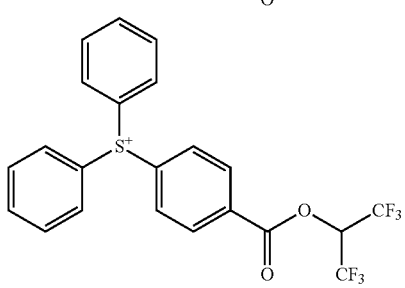
-continued
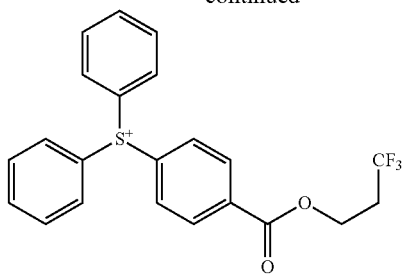
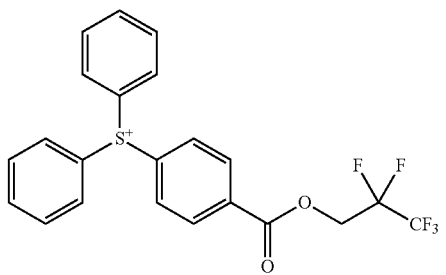
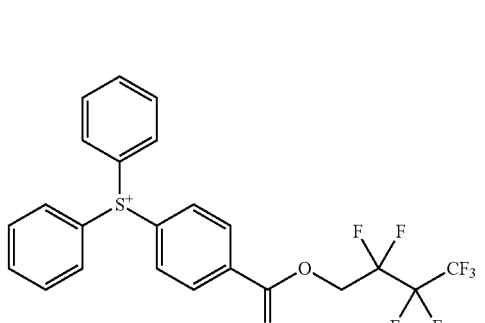
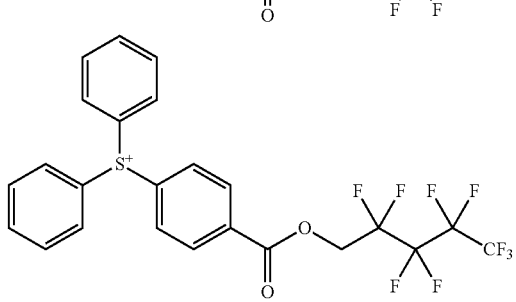
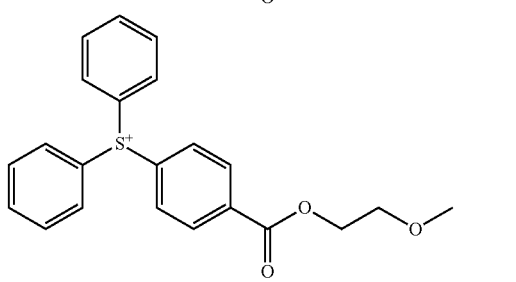
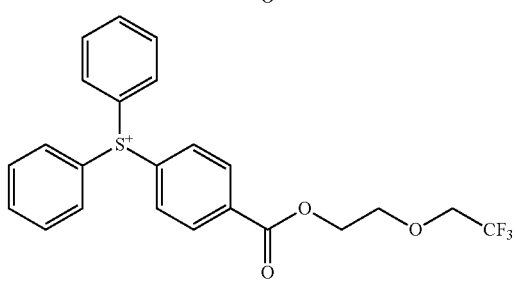

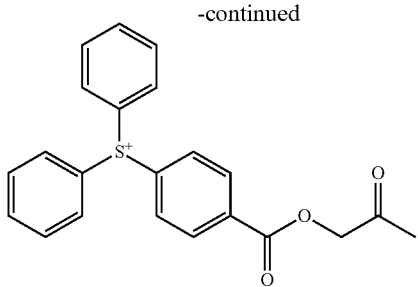
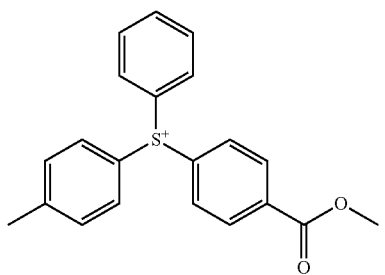
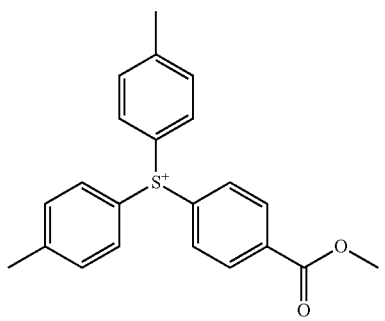
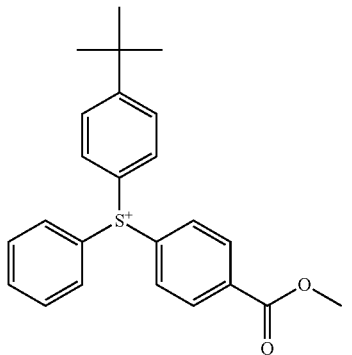
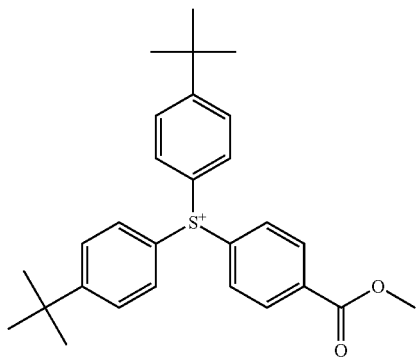
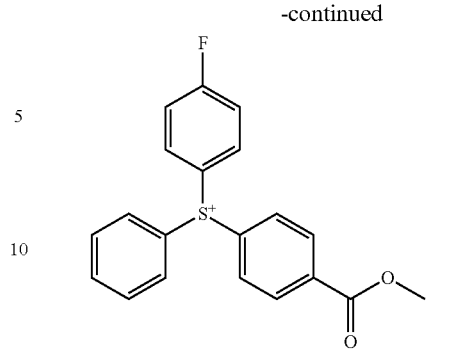
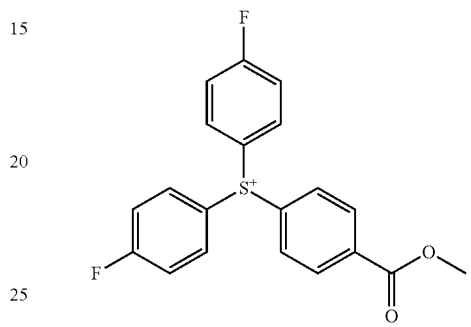
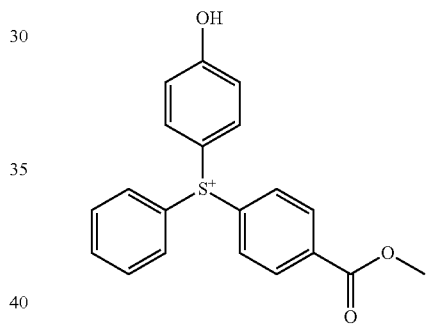
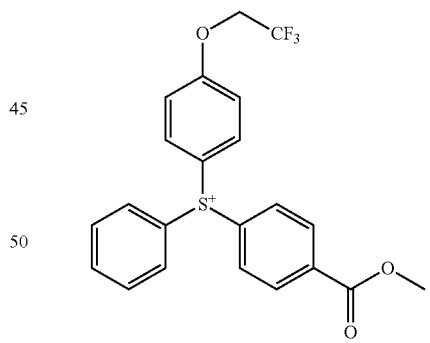
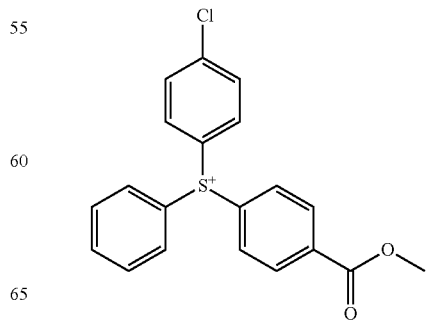

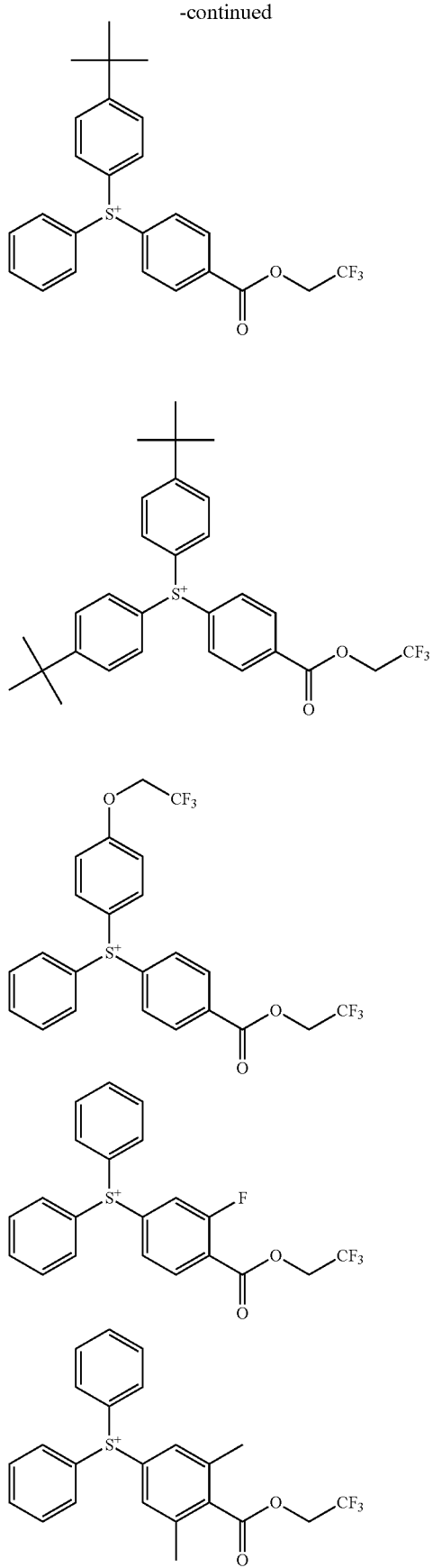
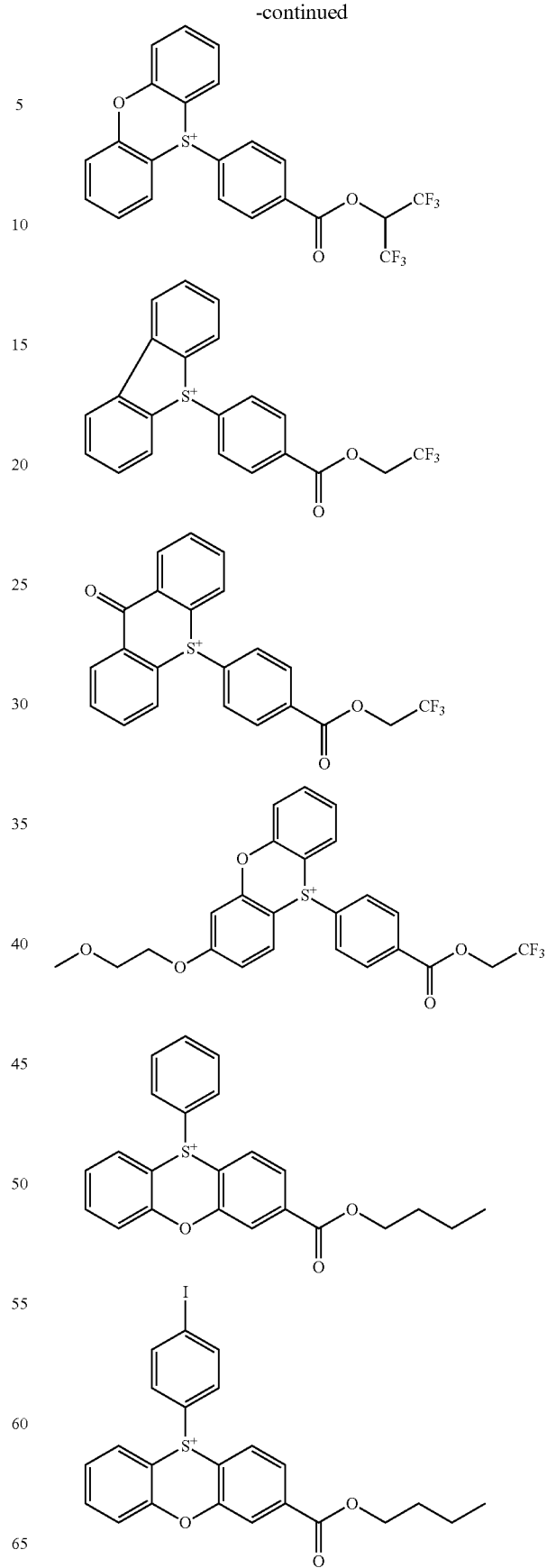

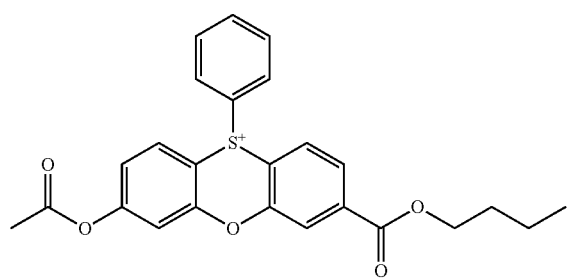
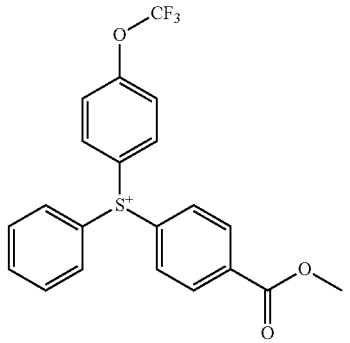

-continued
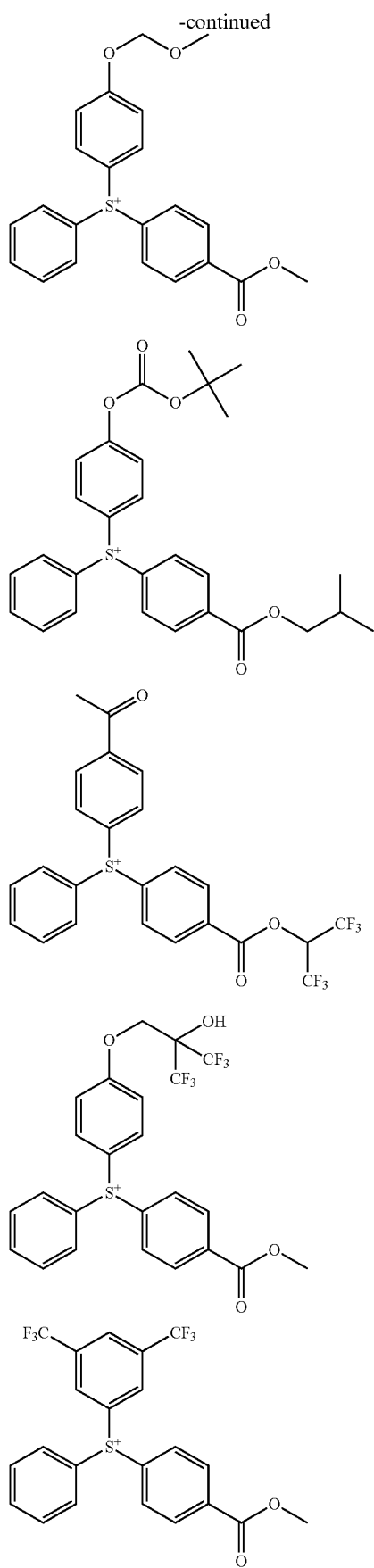
-continued
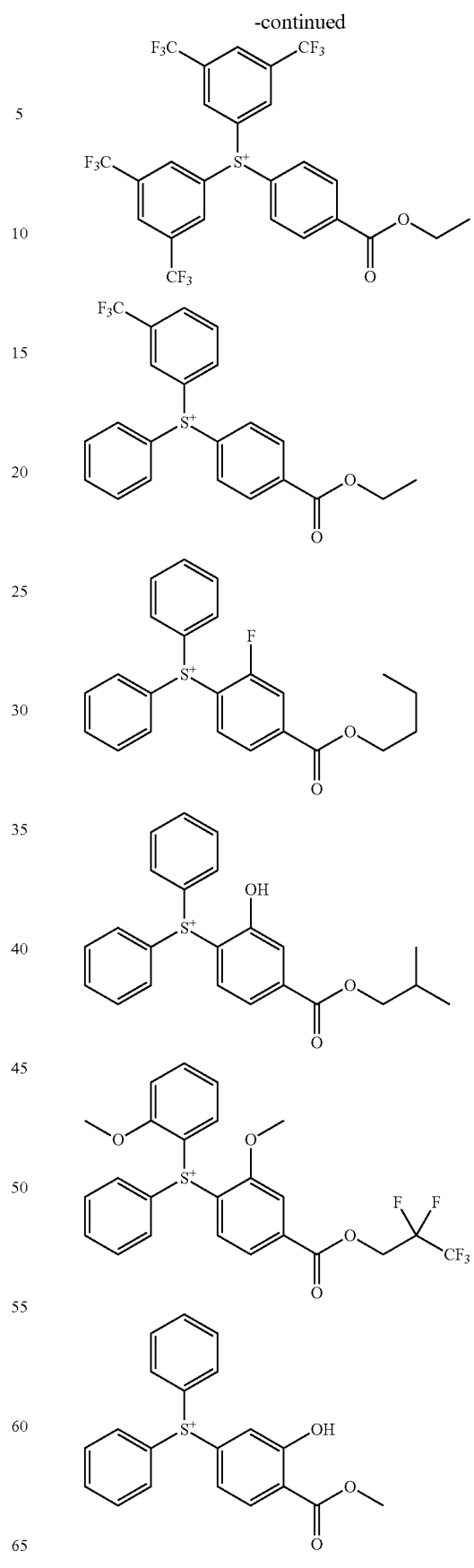

21
-continued
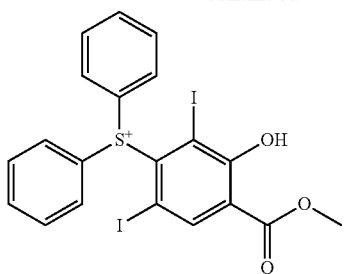
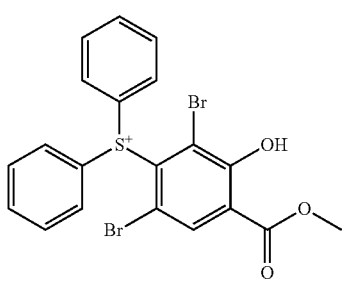
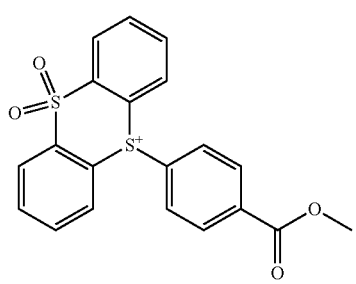
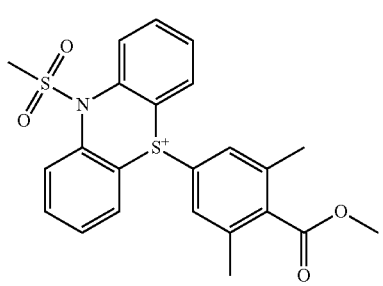
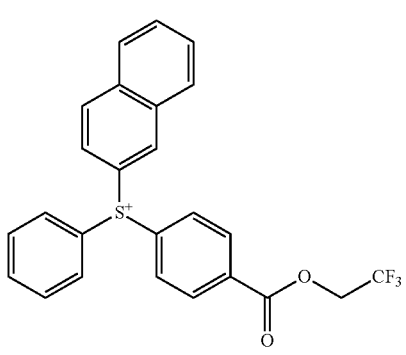
22
-continued
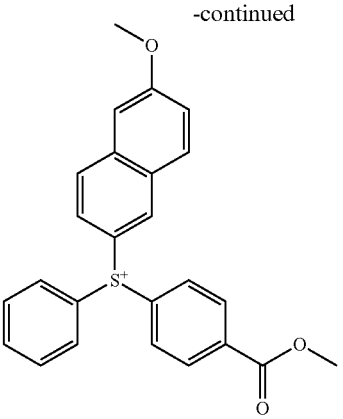
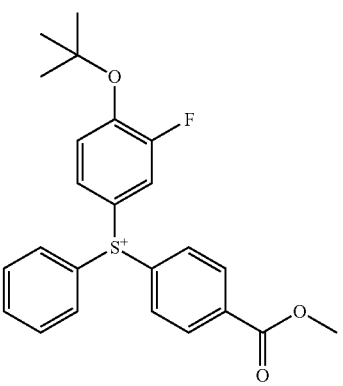
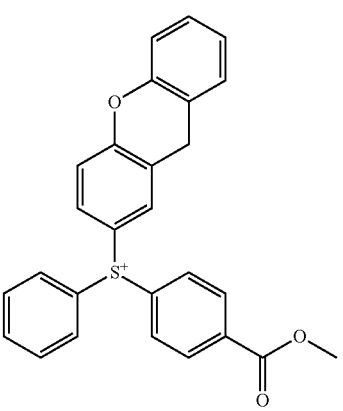
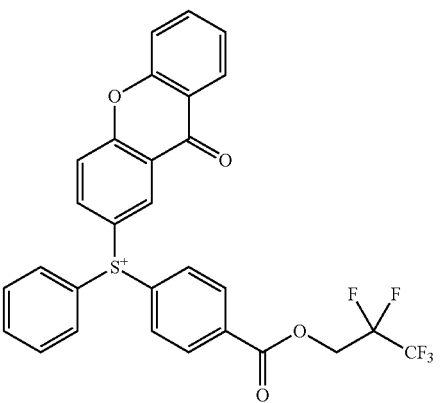

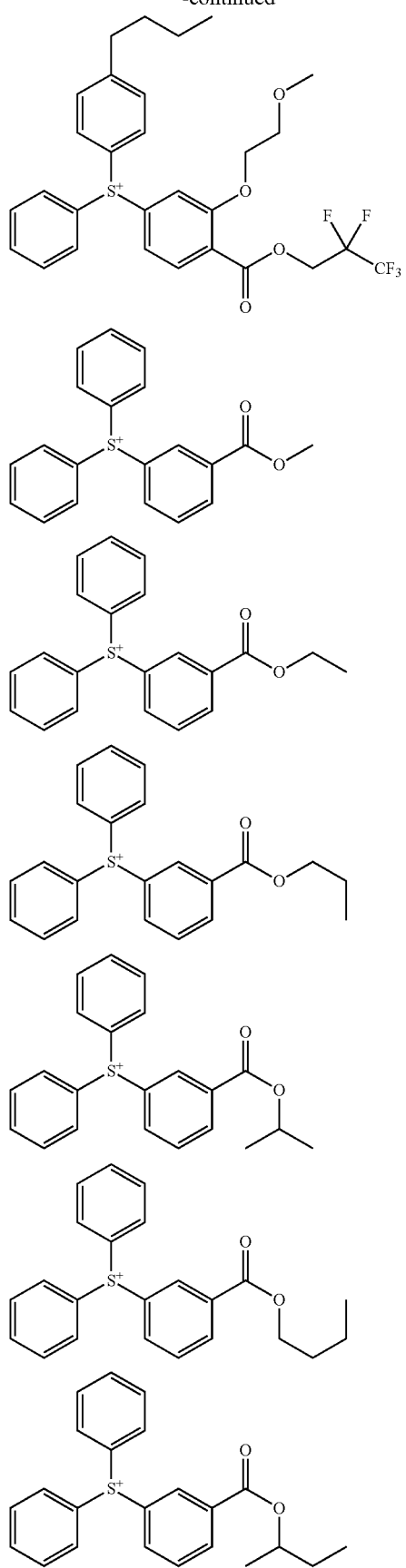
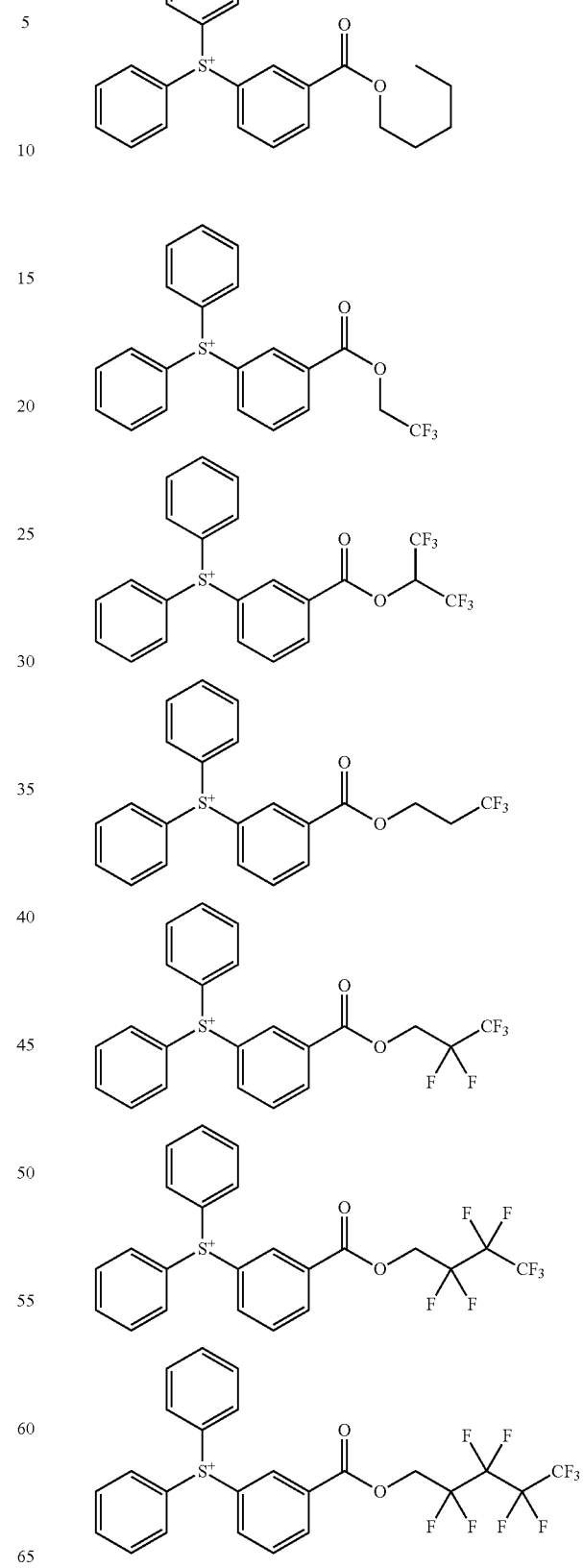

-continued
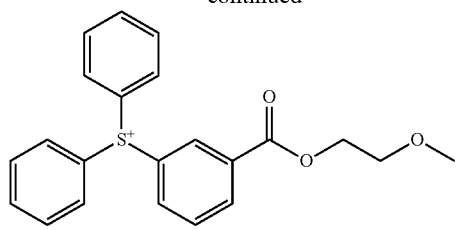
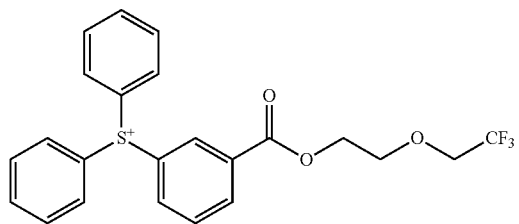
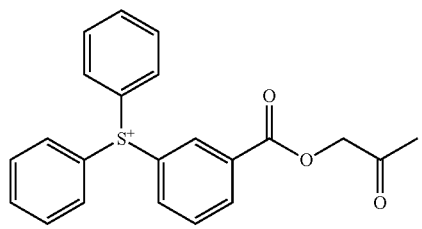
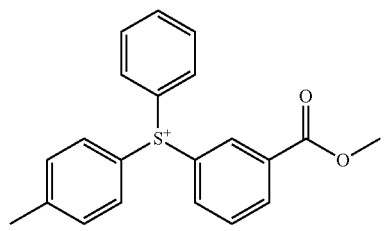
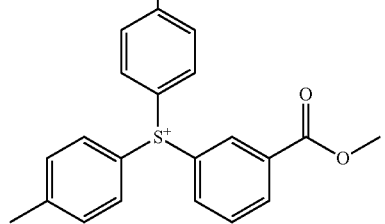
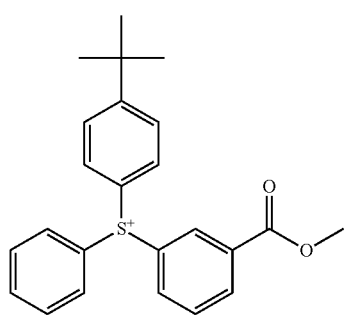
-continued
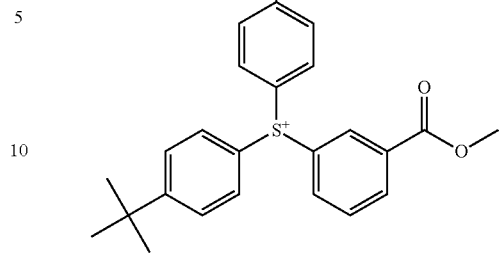
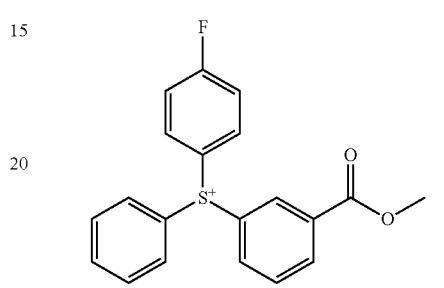
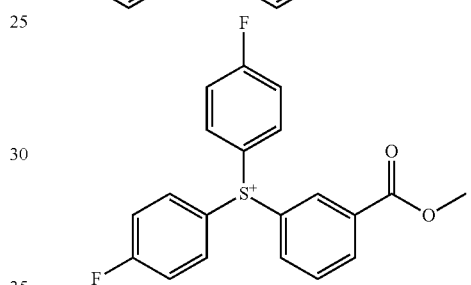
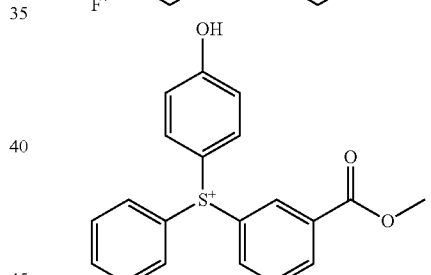
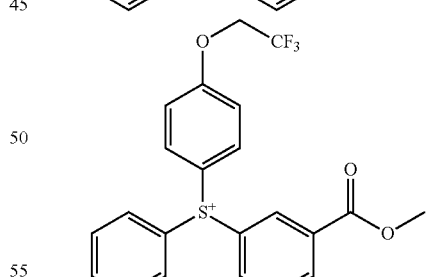
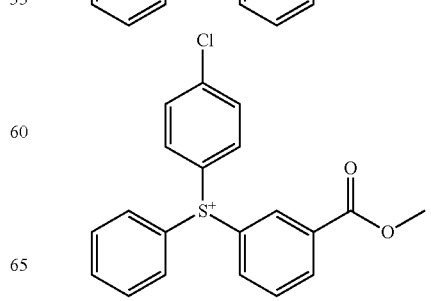

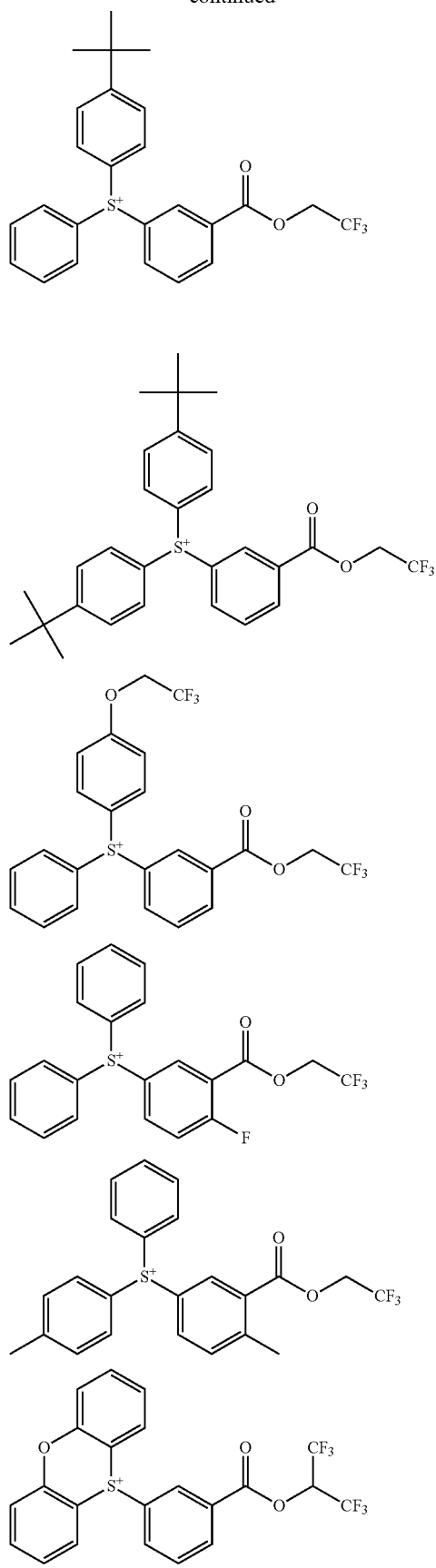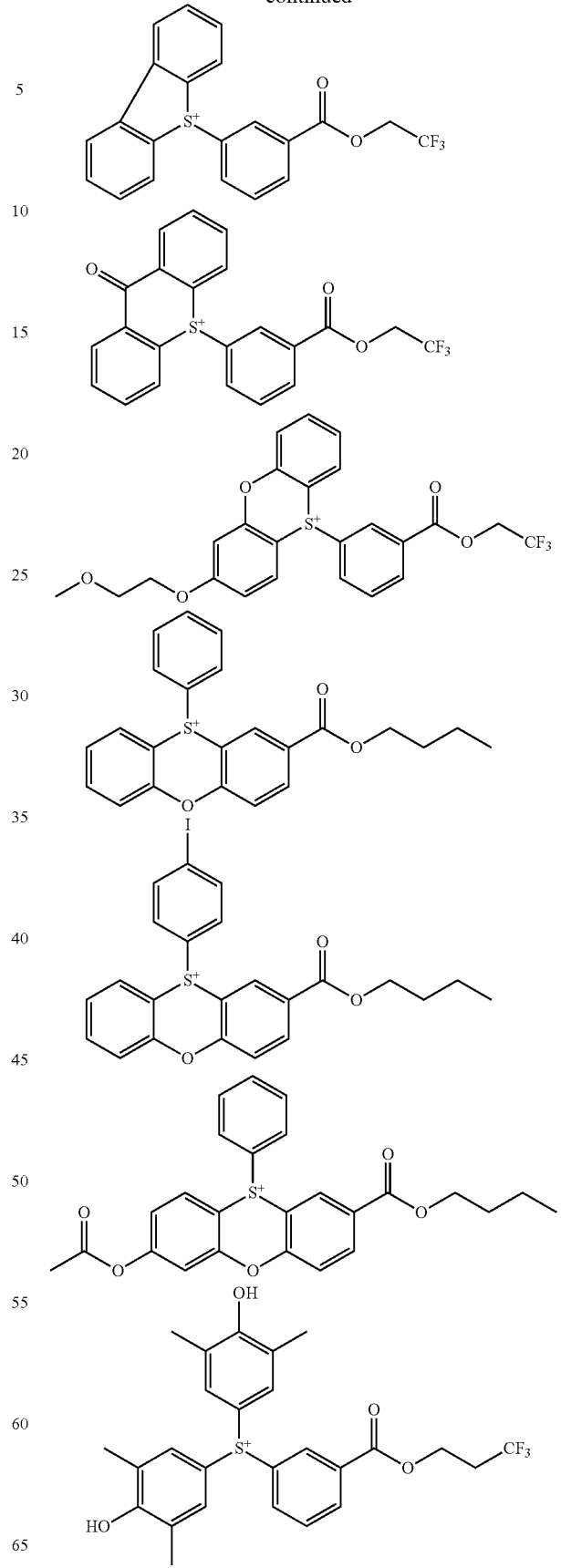

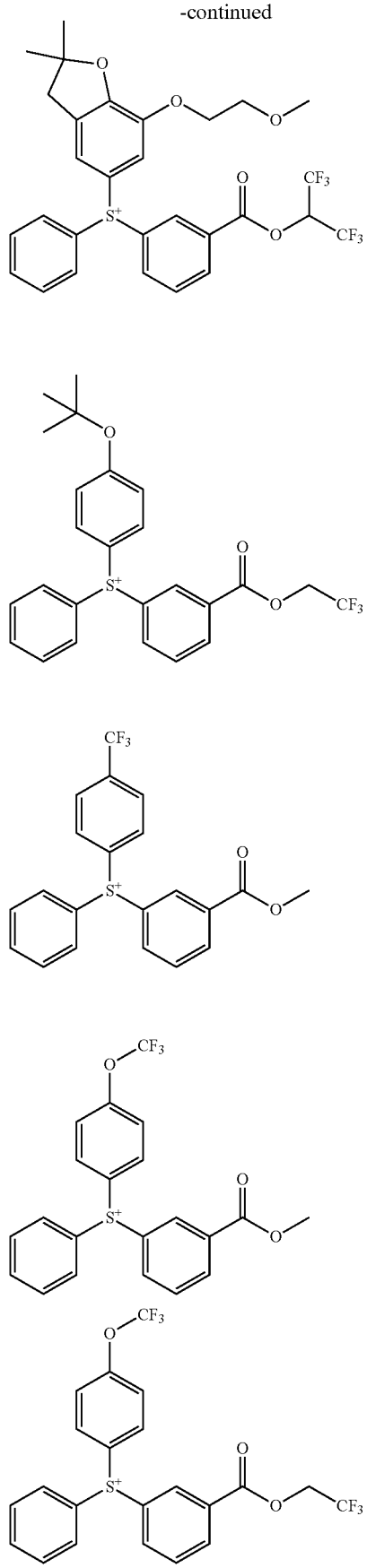
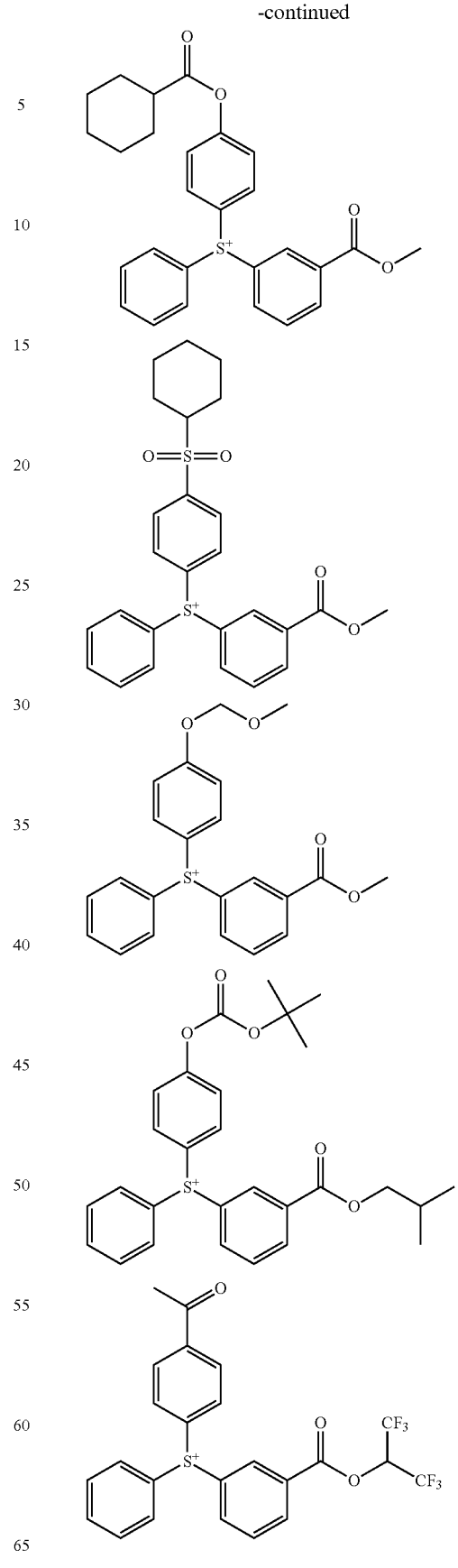

-continued
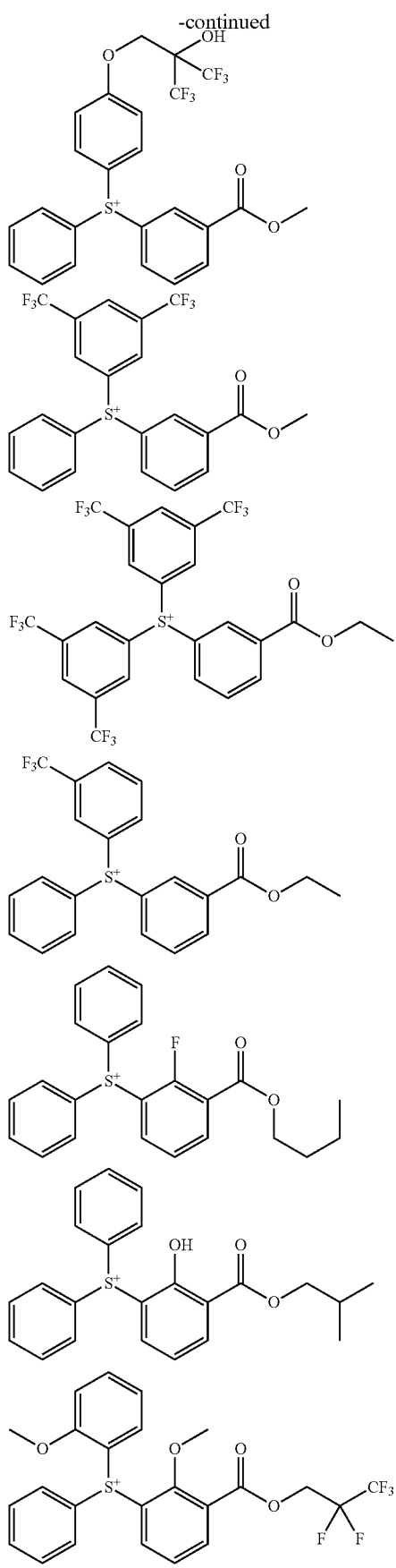
-continued
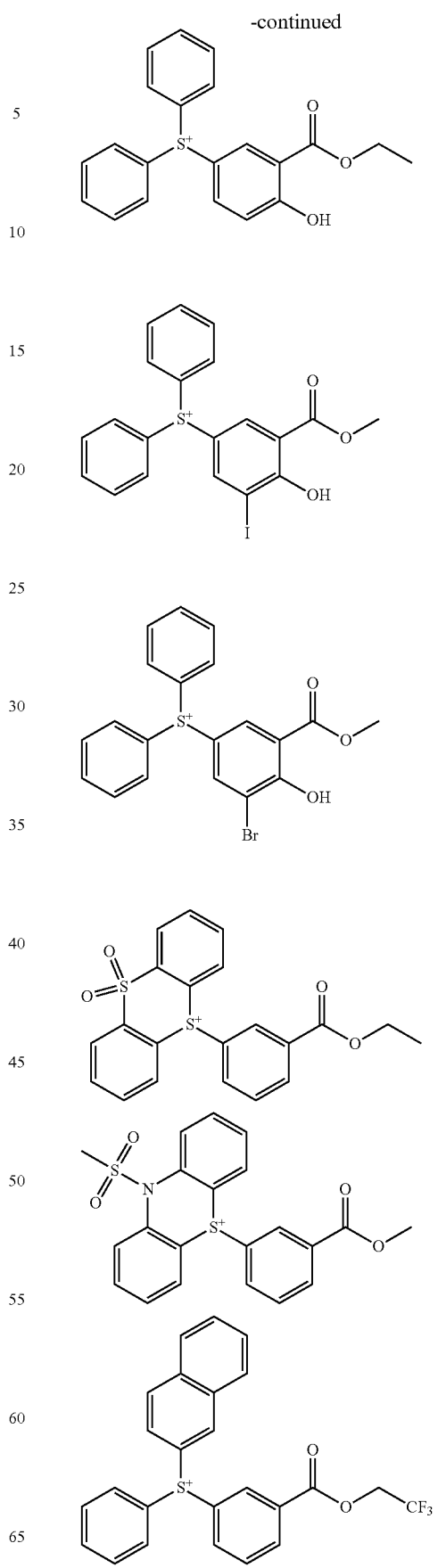

33
-continued
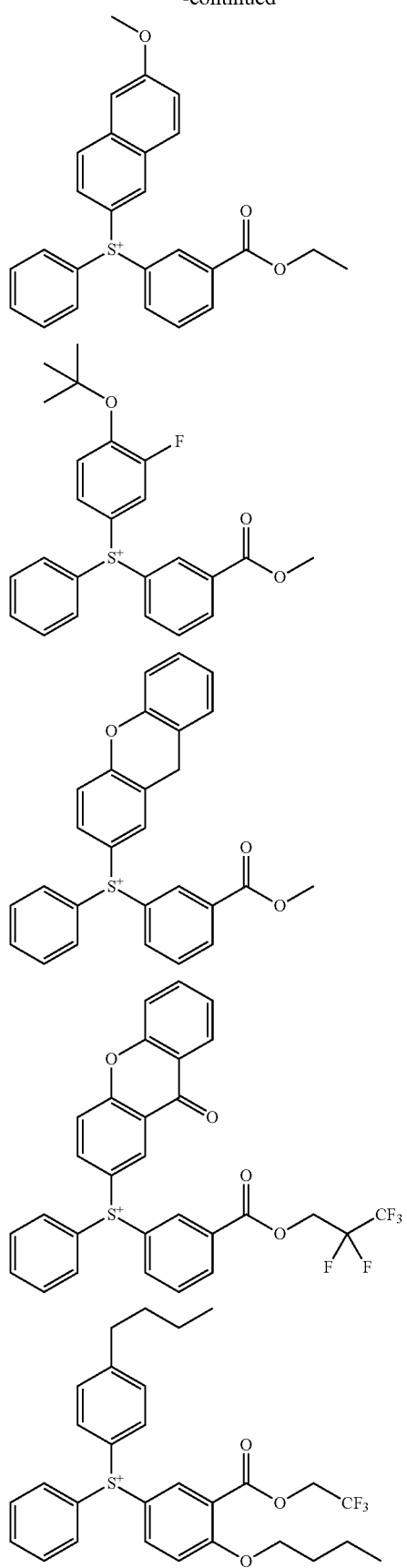
34
-continued
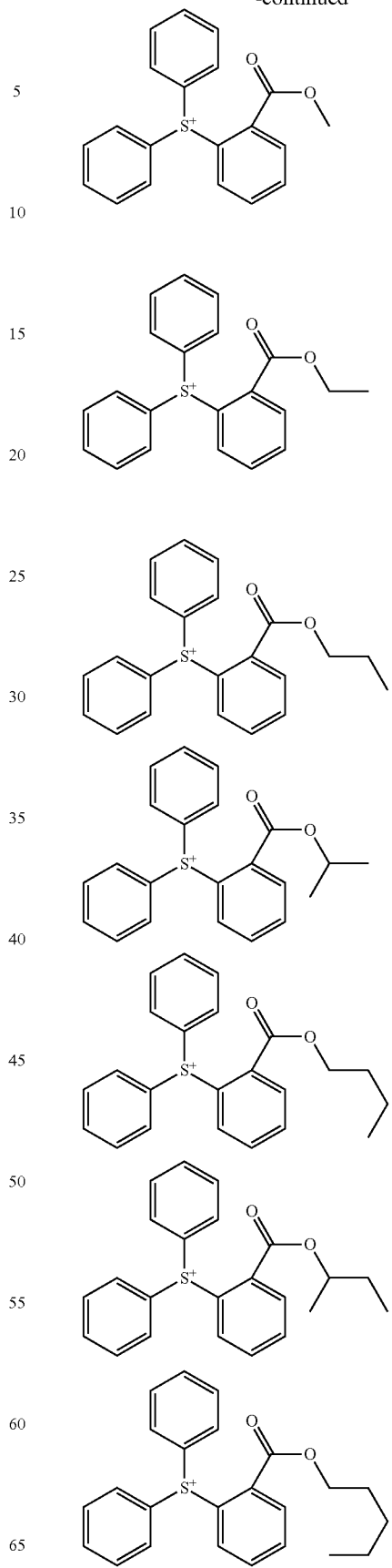

35
-continued
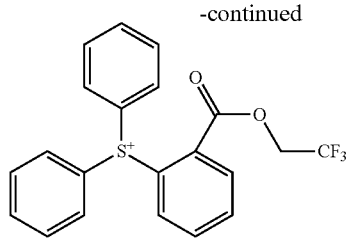
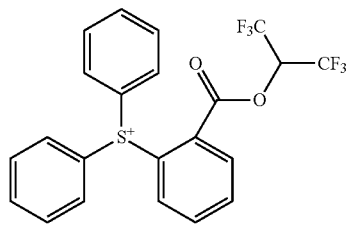
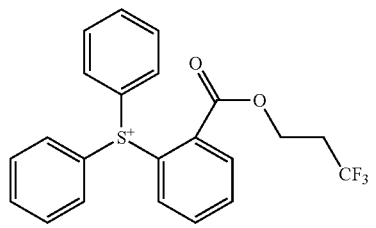
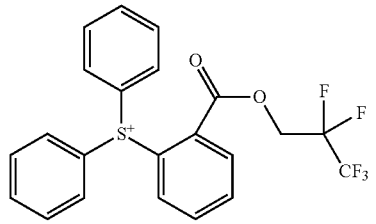
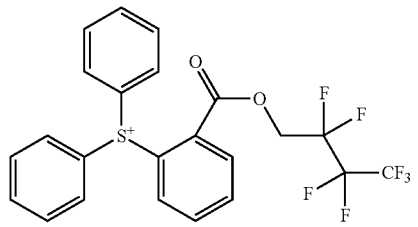
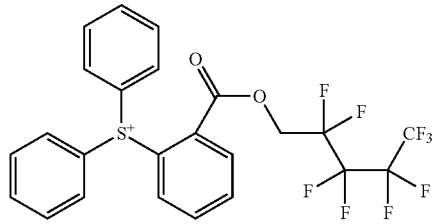
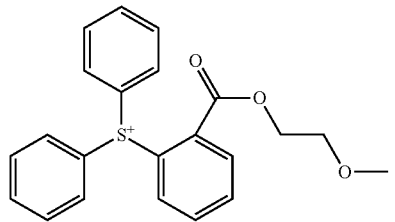
36
-continued
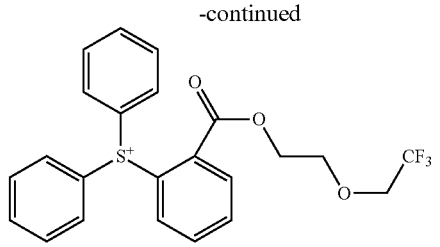
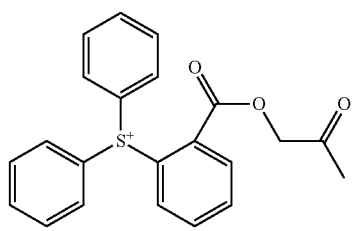
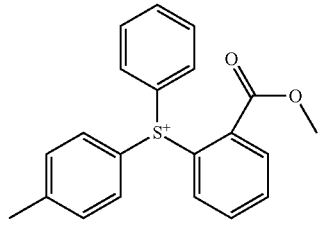
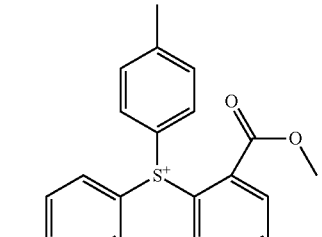
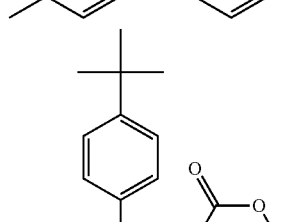
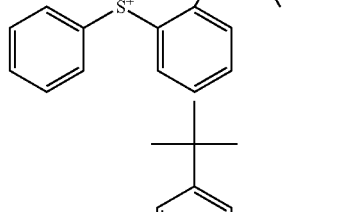
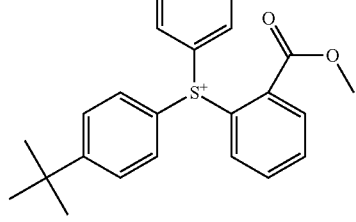

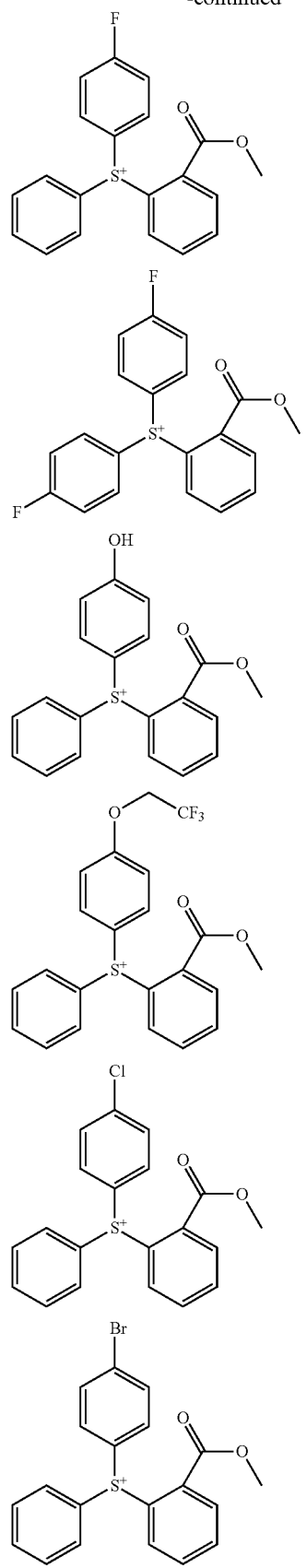
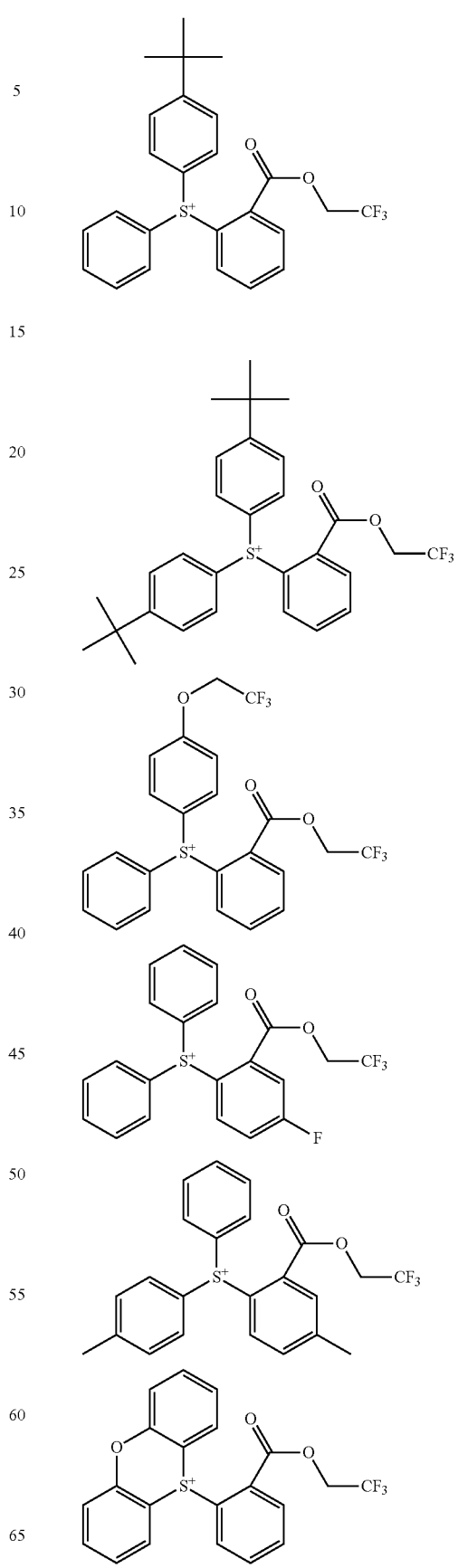

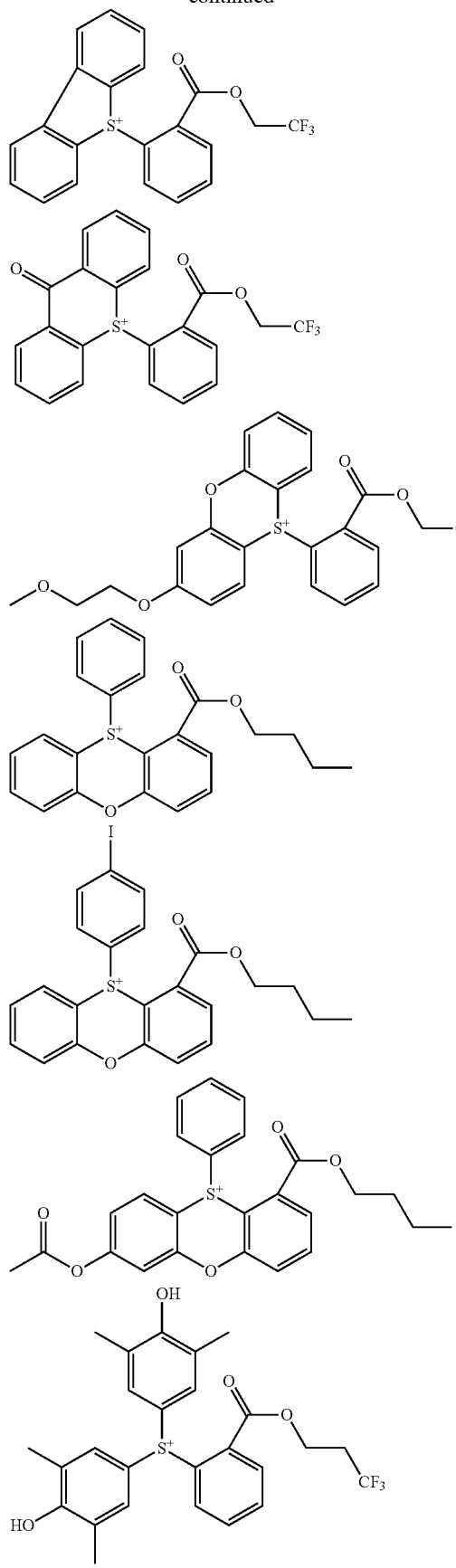
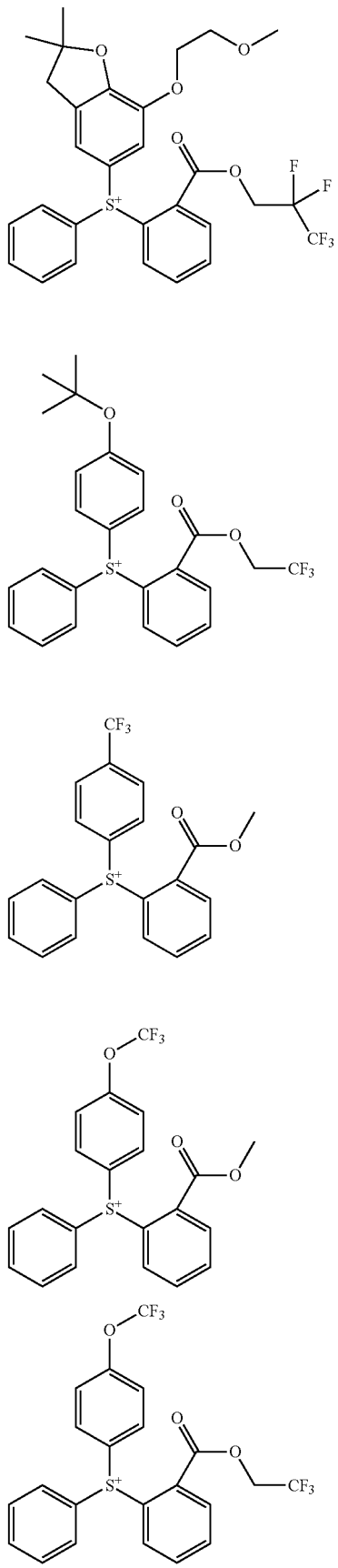

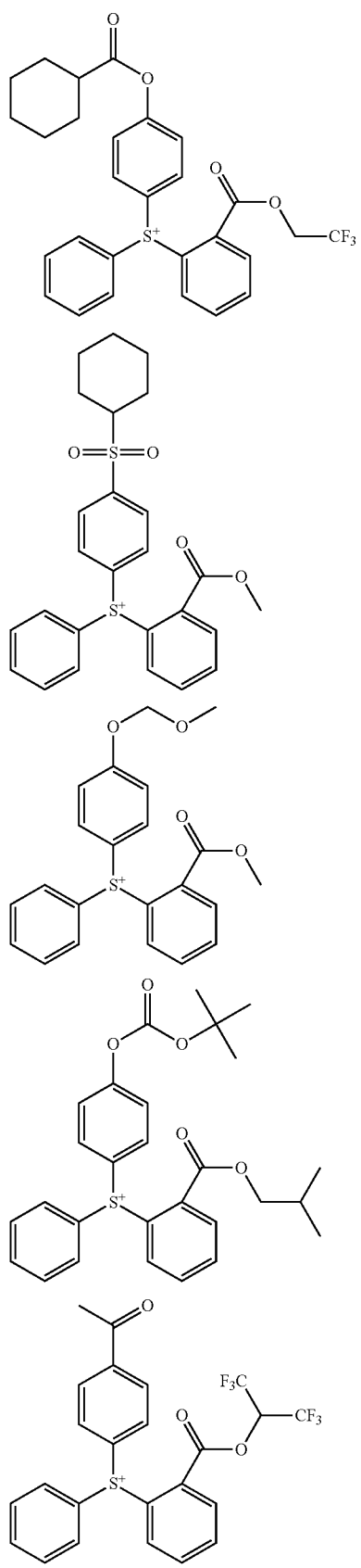
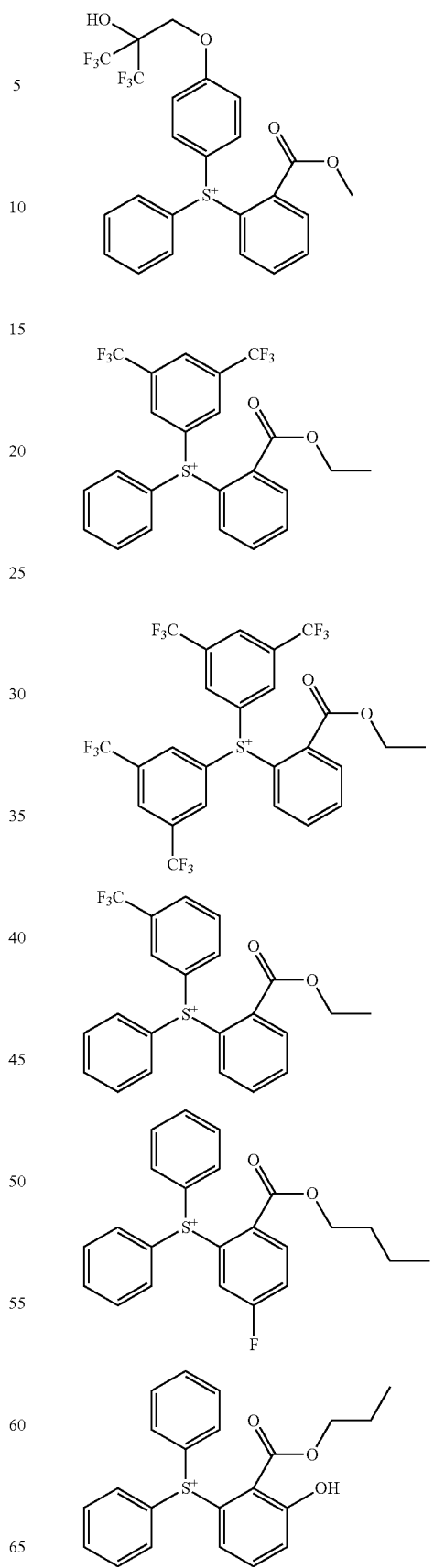

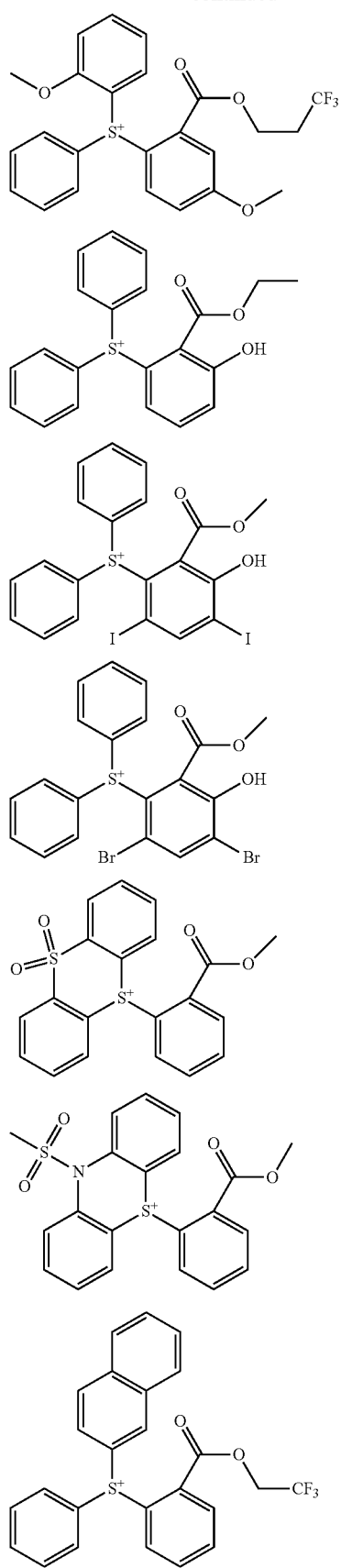
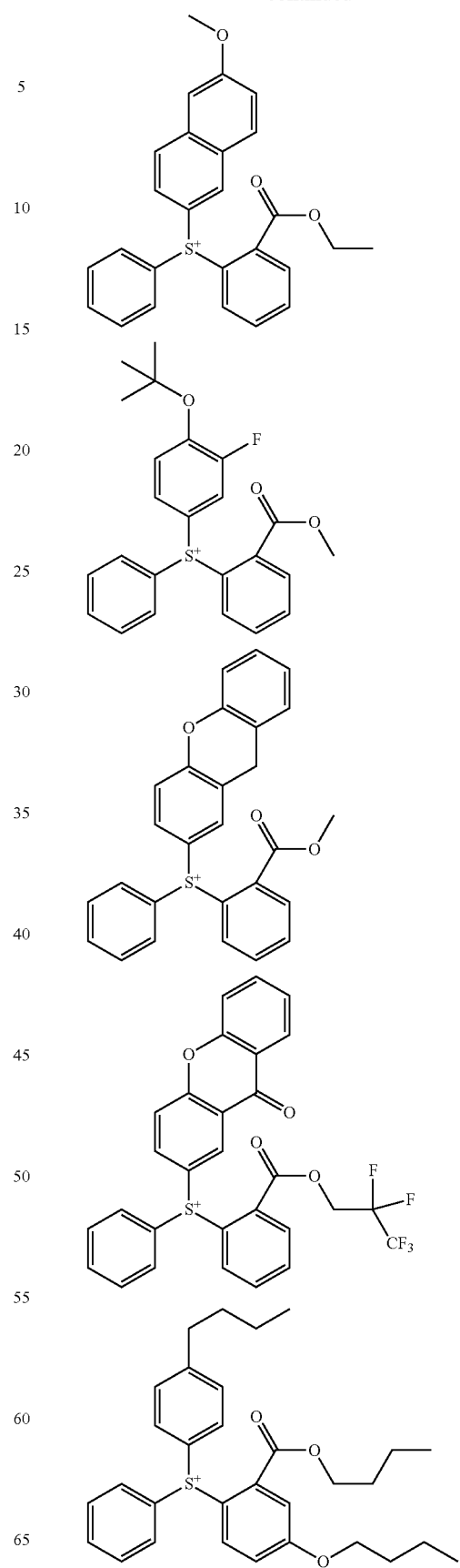

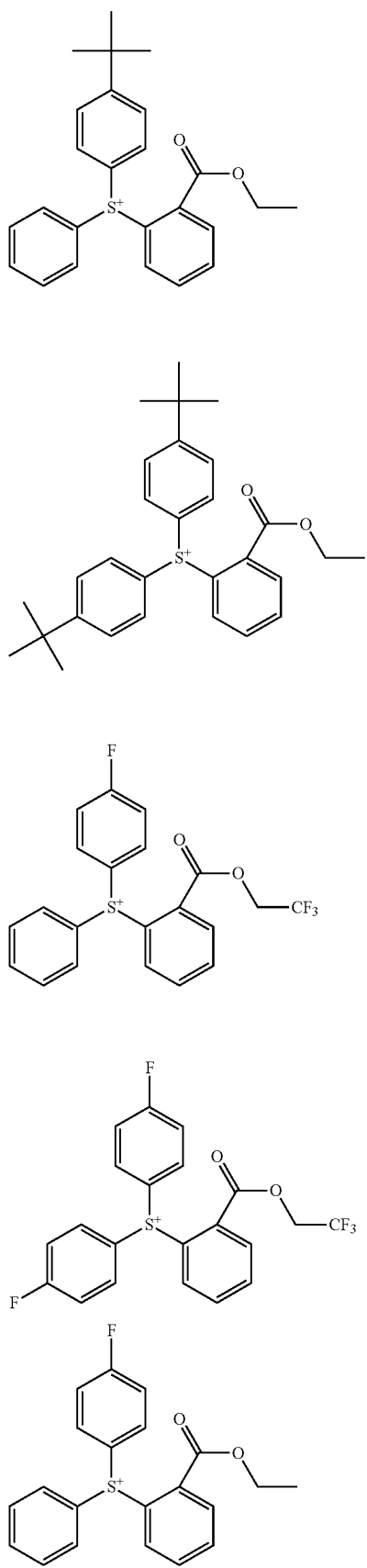
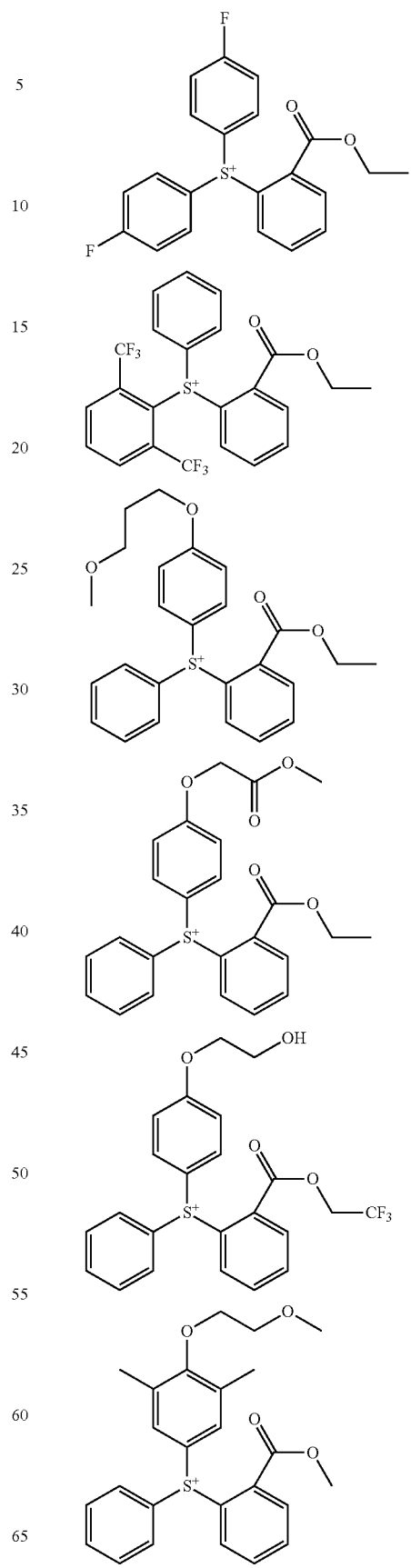

-continued
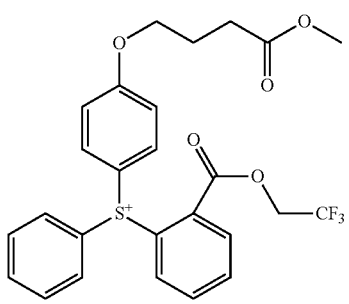
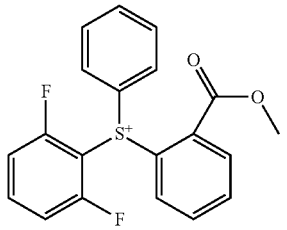
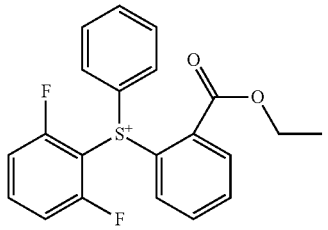
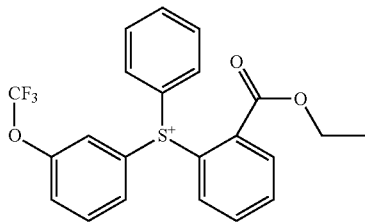
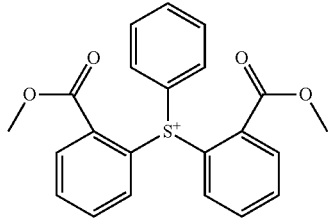
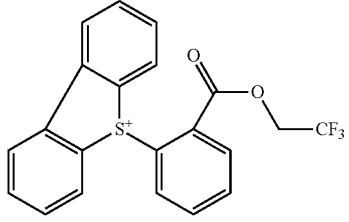
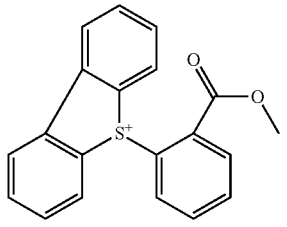
-continued
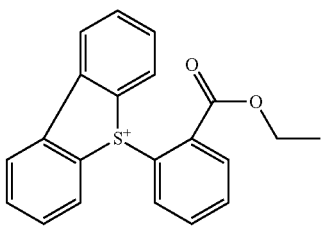
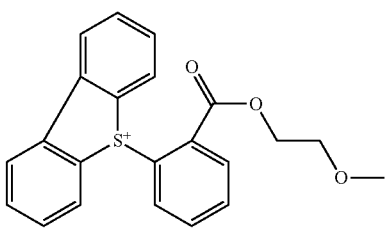
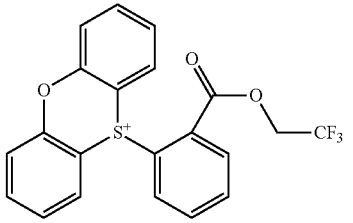
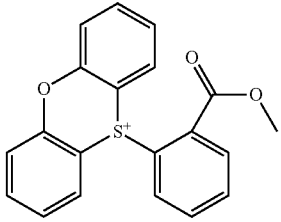
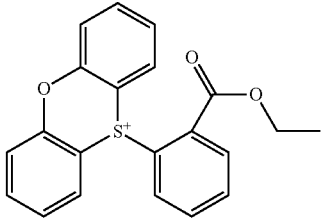
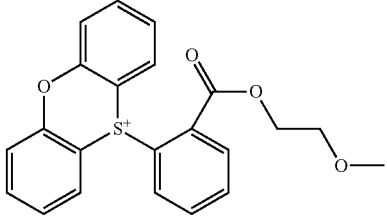
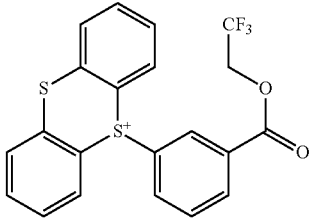

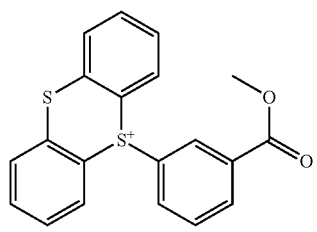
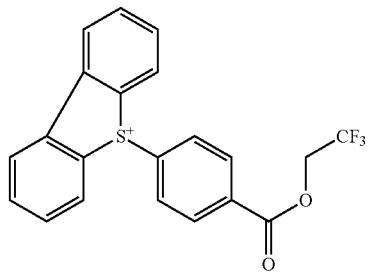
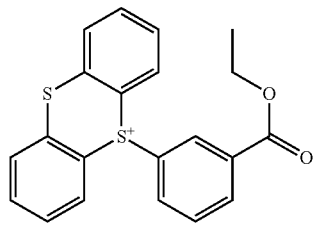
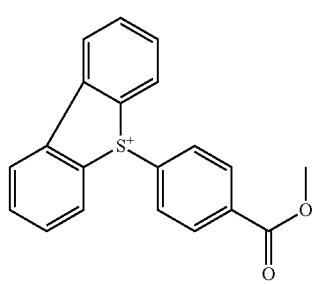
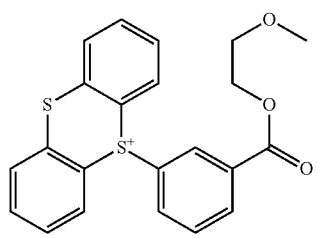
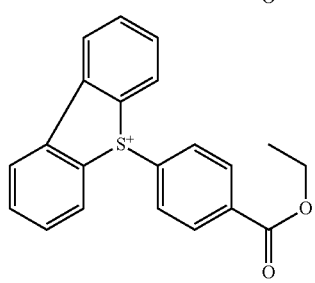
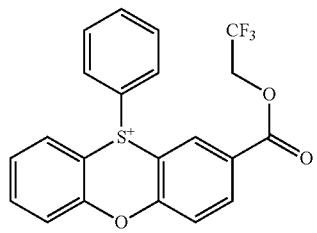
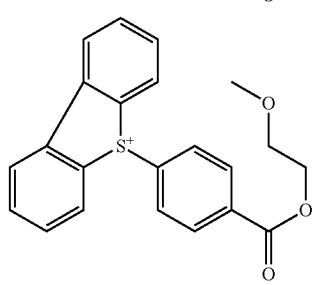
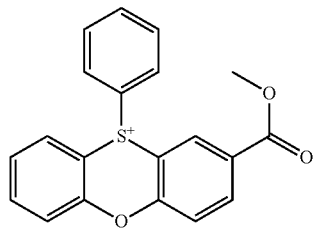
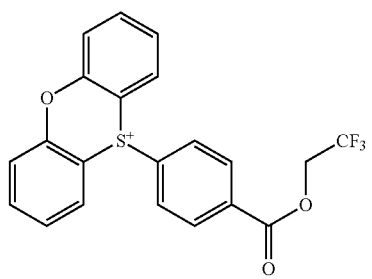
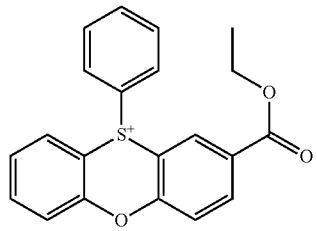
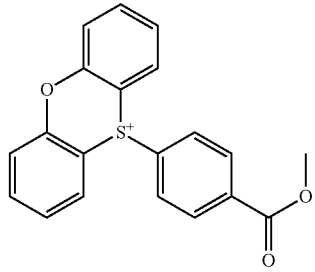
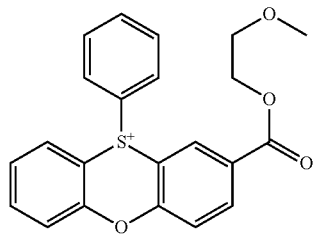

51
-continued
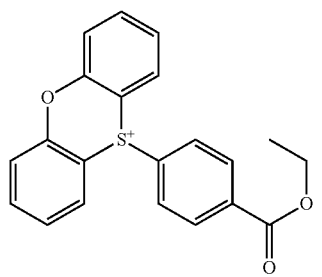
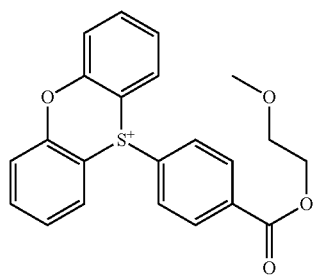
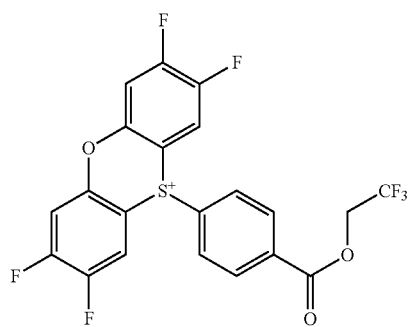
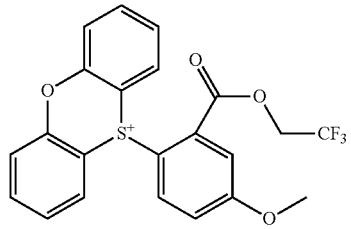
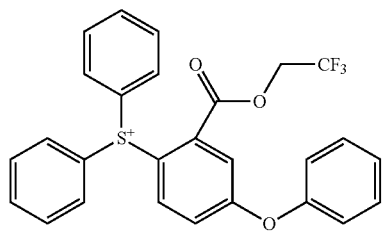
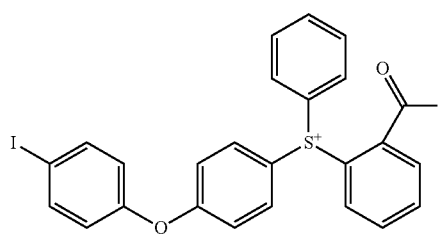
52
-continued
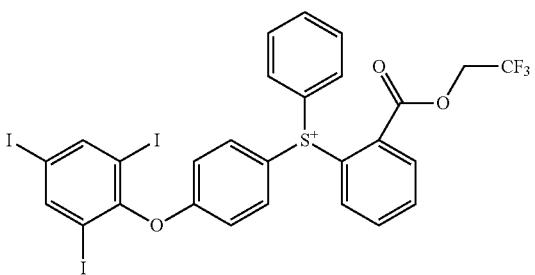
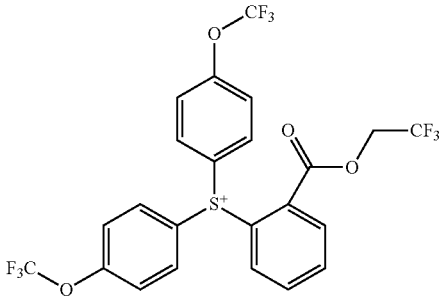
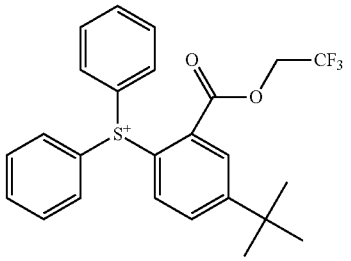
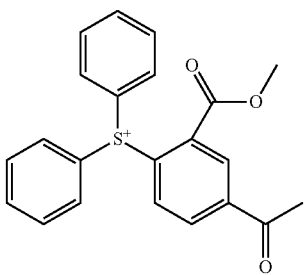
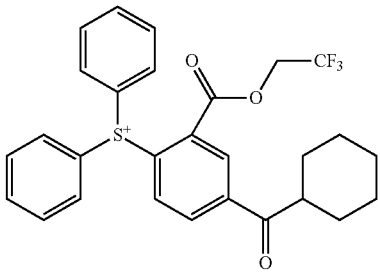
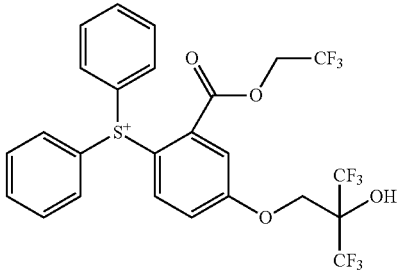

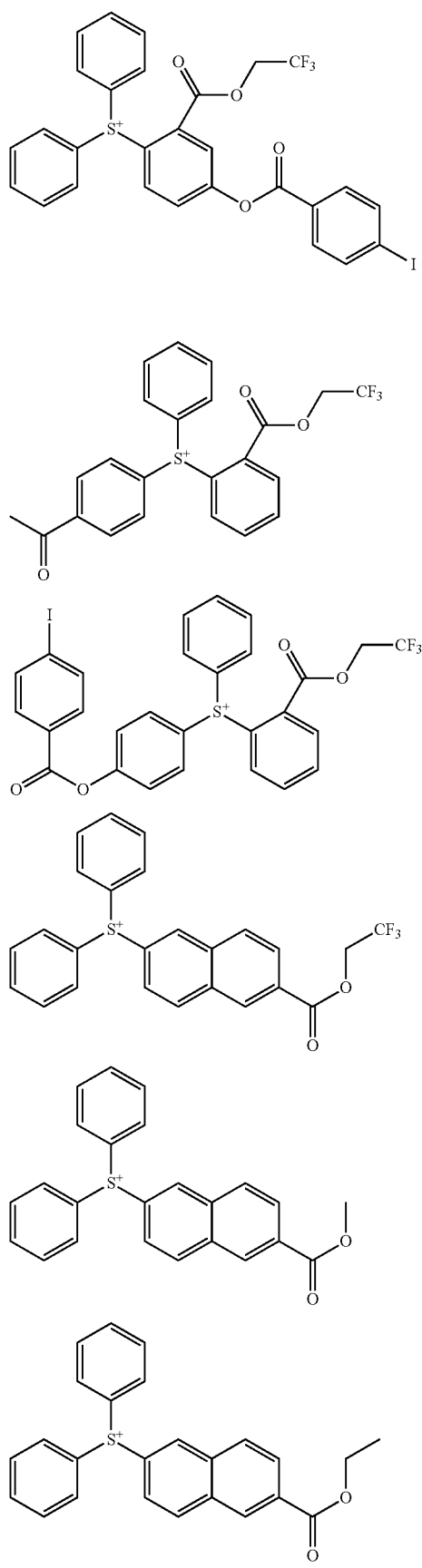
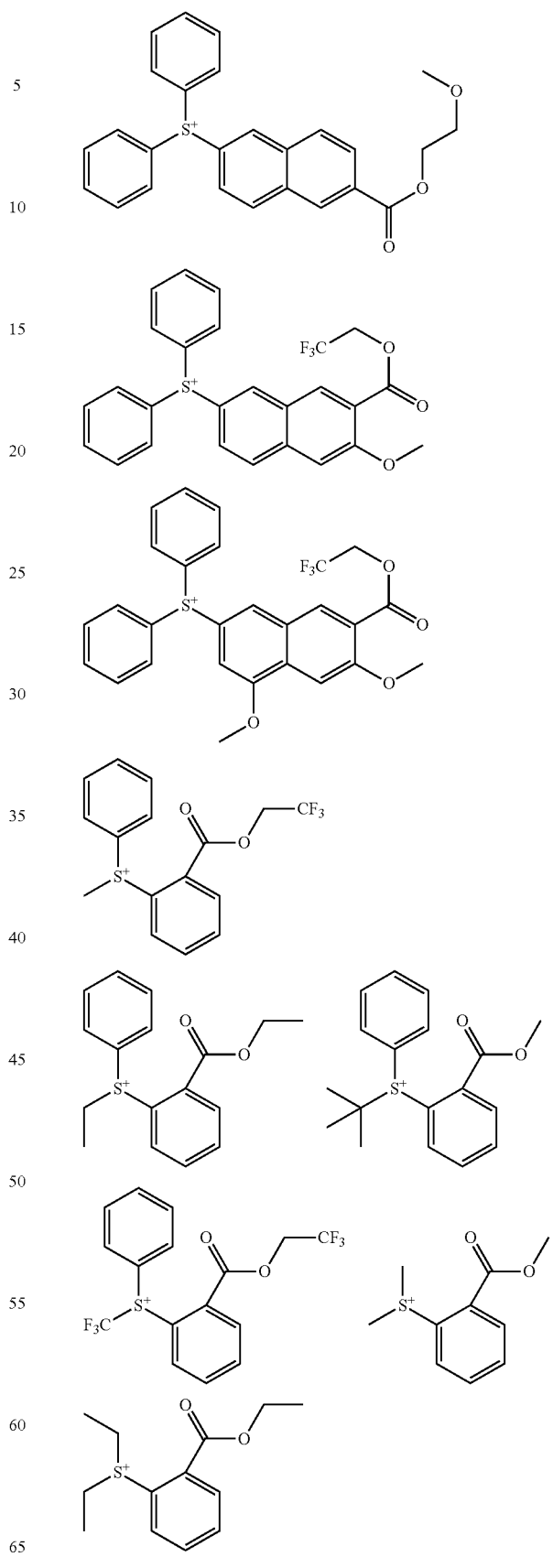

55
-continued
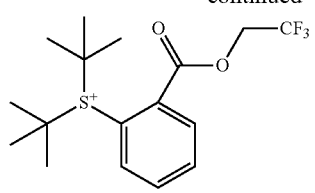
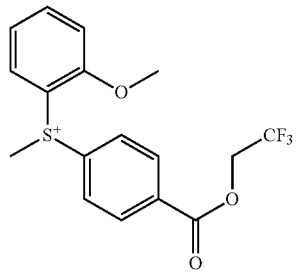
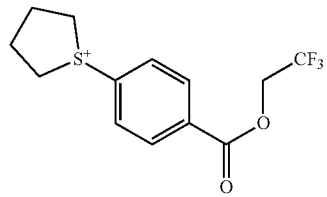
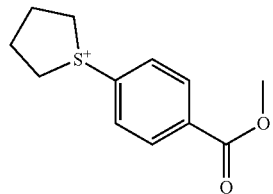
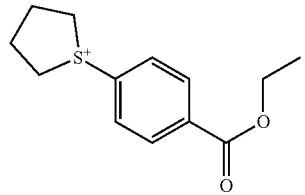
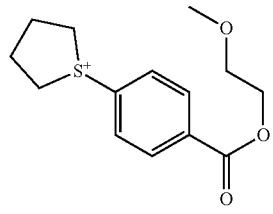
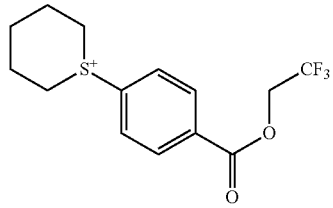
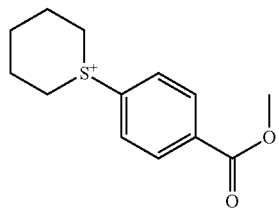
56
-continued
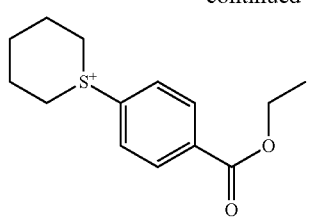
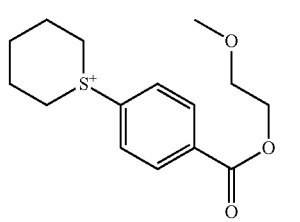
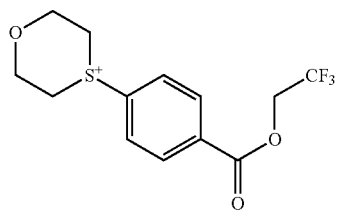
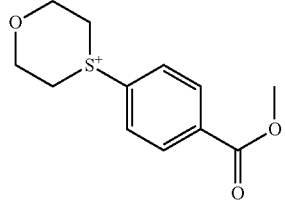
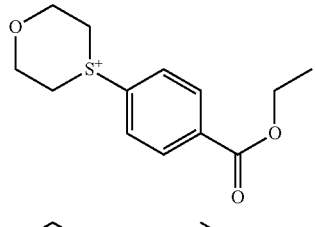
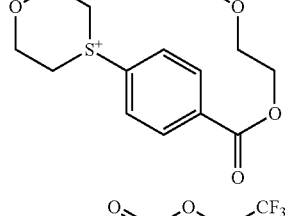
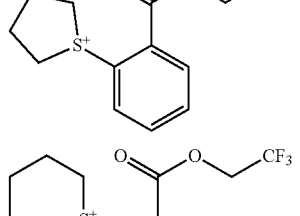

-continued
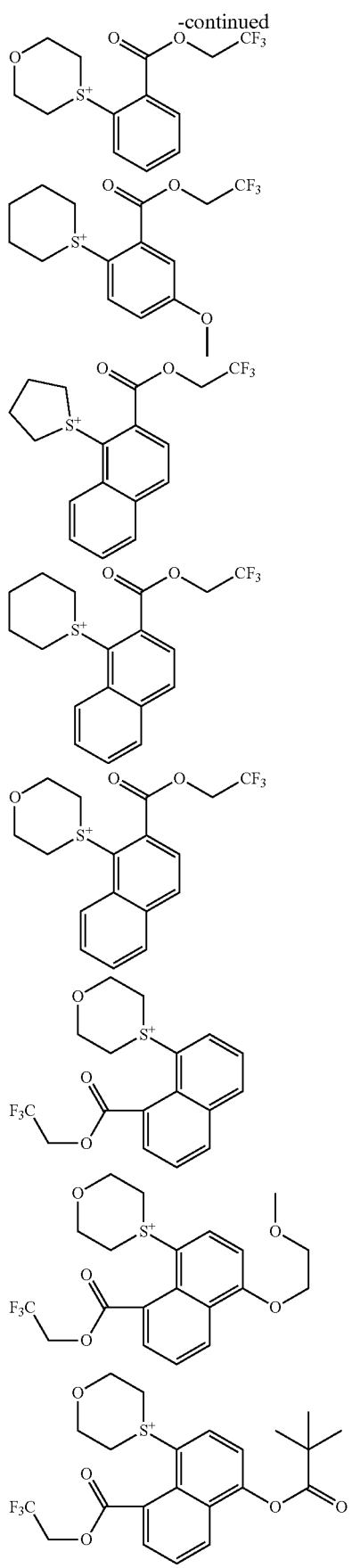
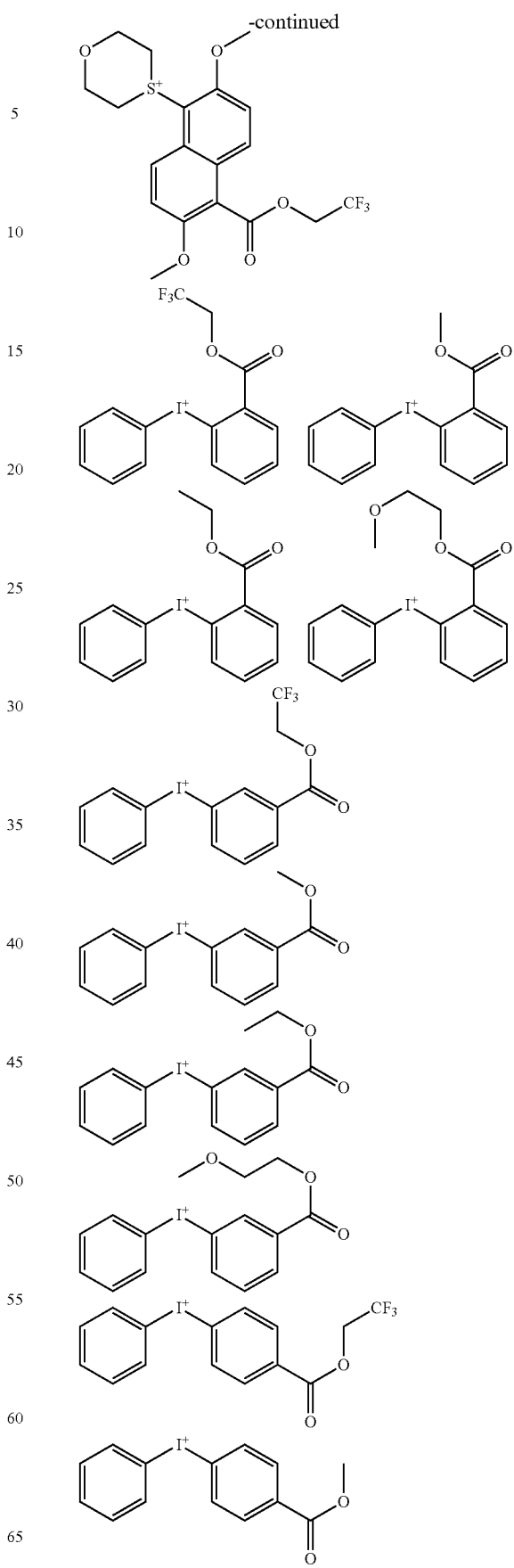

-continued

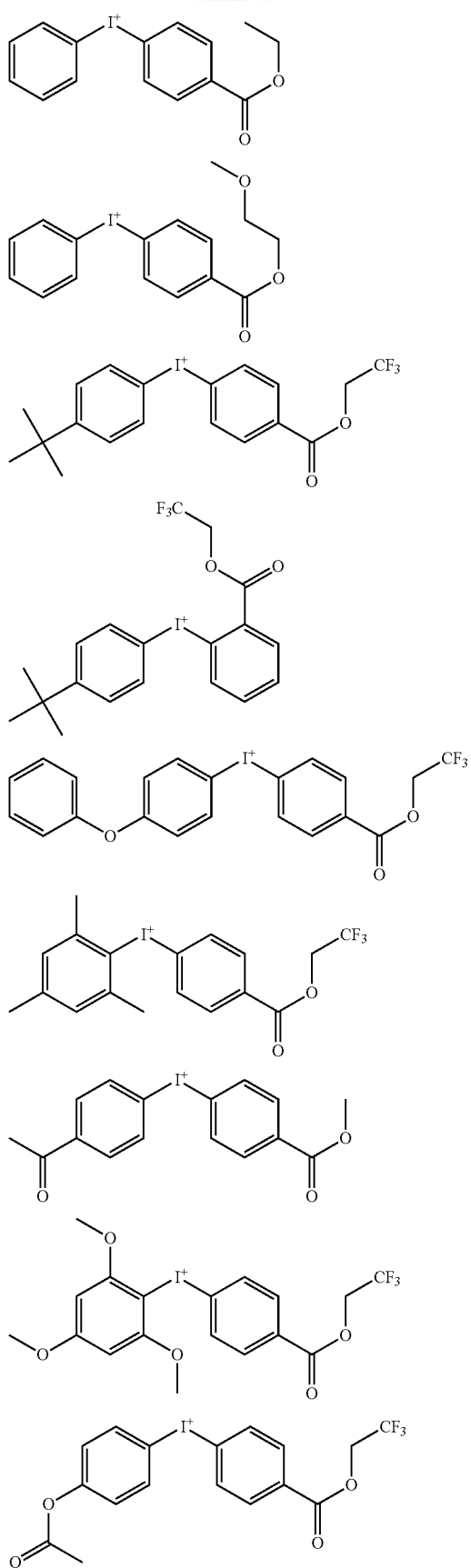

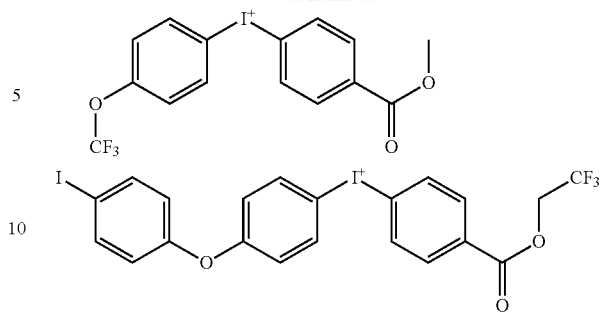

In formula (1), Z⁻ is a carboxylate, sulfonamide, sulfonimide or methide anion. Z⁻ is not particularly limited as long as it is selected from these anions. Preferably Z⁻ is such that a conjugated acid ZH may have a pKa value in the range of −1.5 to 3.5. Of the acids having a pKa value in the range, suitable carboxylic acids include benzoic acids substituted with an electron-withdrawing group and carboxylic acids having an electron-withdrawing group (e.g., halogen or carbonyl group) at α- or β-position. Suitable sulfonimides include bis(alkylsulfonyl)imides, bis(arylsulfonyl)imides, alkylsulfonyl(arylsulfonyl)imides, trifluoromethylsulfonyl(alkylcarbonyl)imides, and bis(trifluoromethylcarbonyl)imide. Suitable methide acids include tris(alkylsulfonyl)methides. It is noted that the pKa value is computed using ACD/ChemSketch of Advanced Chemistry Development Inc. (ACD/Labs). When Z⁻ is an anion which forms a conjugated acid having a pKa in the range, acid diffusion can be controlled without substantial sacrifice of the sensitivity of a resist composition, leading to improvements in lithography performance factors.

Examples of the anion Z⁻ are shown below.

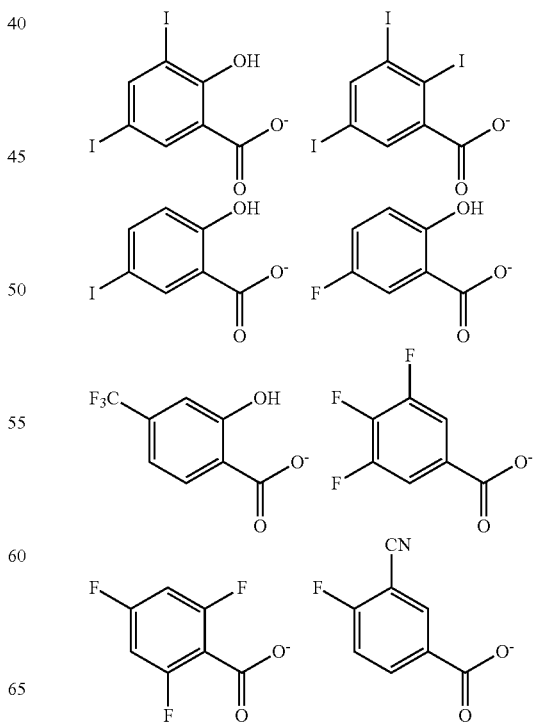

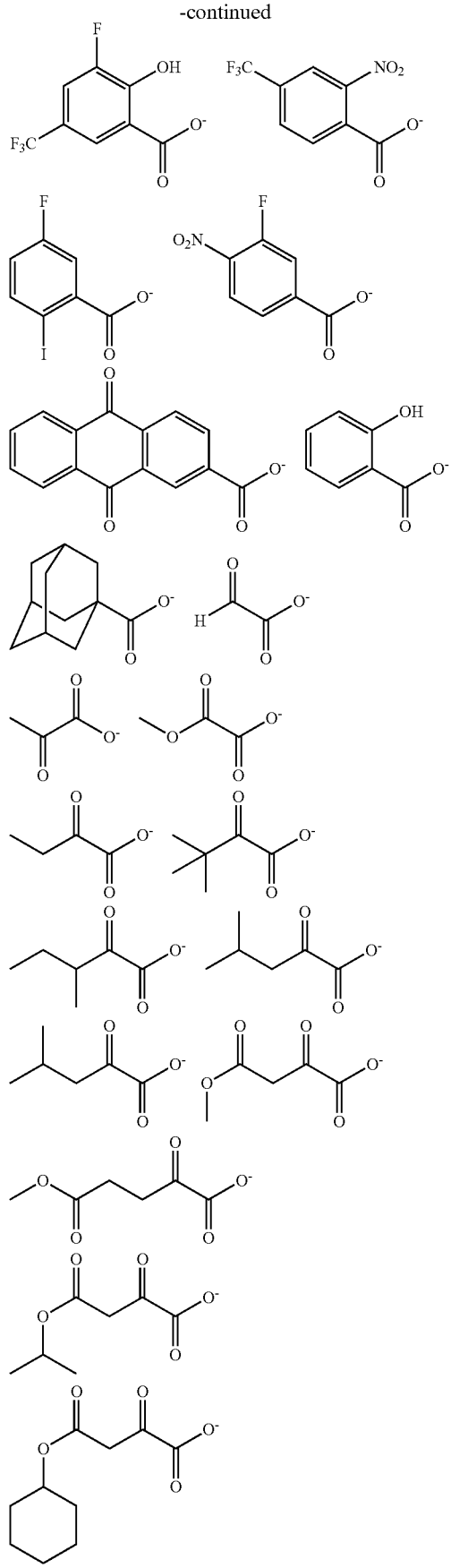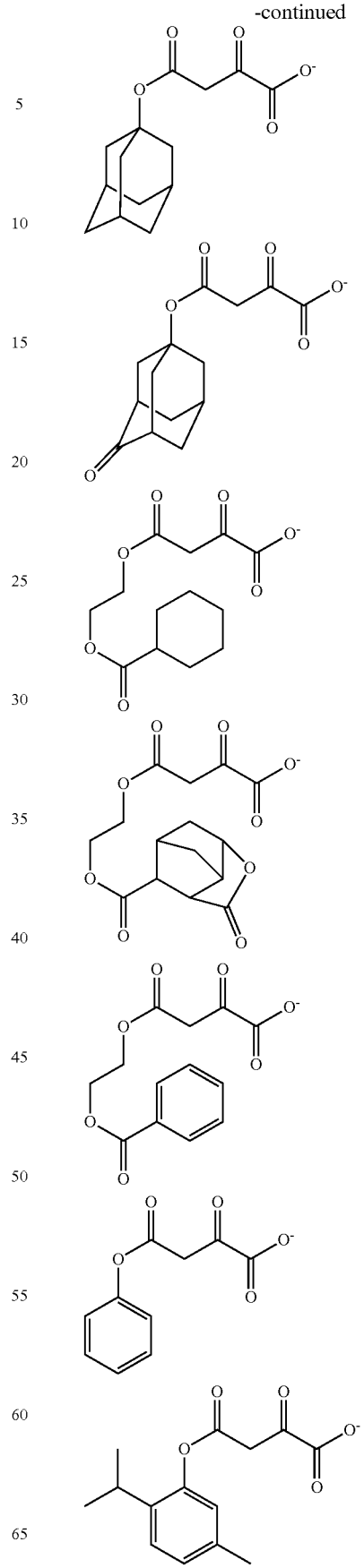

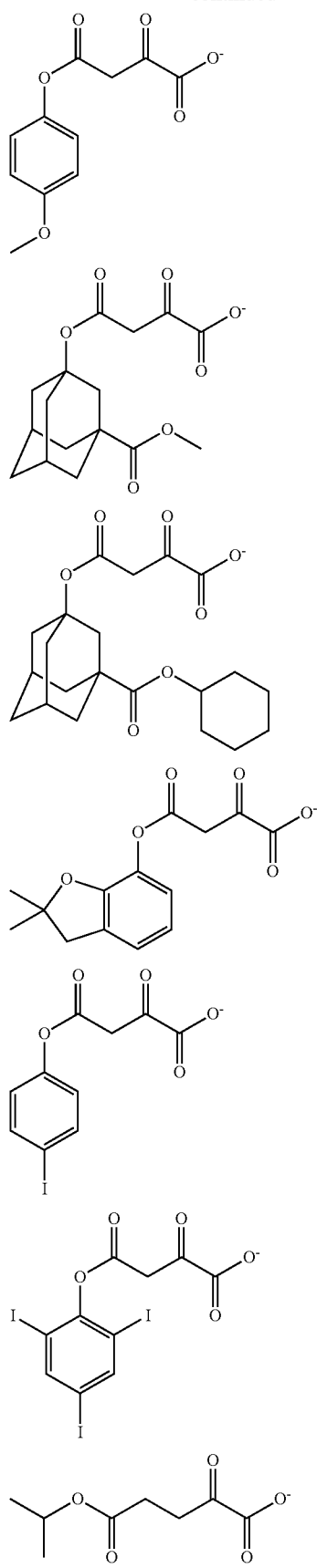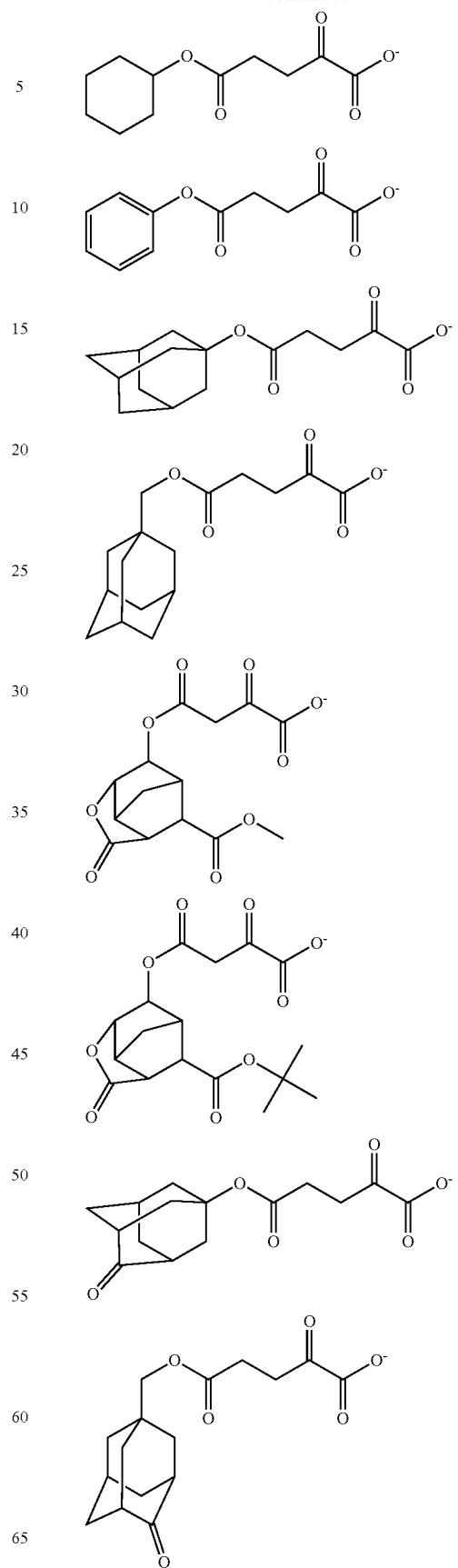

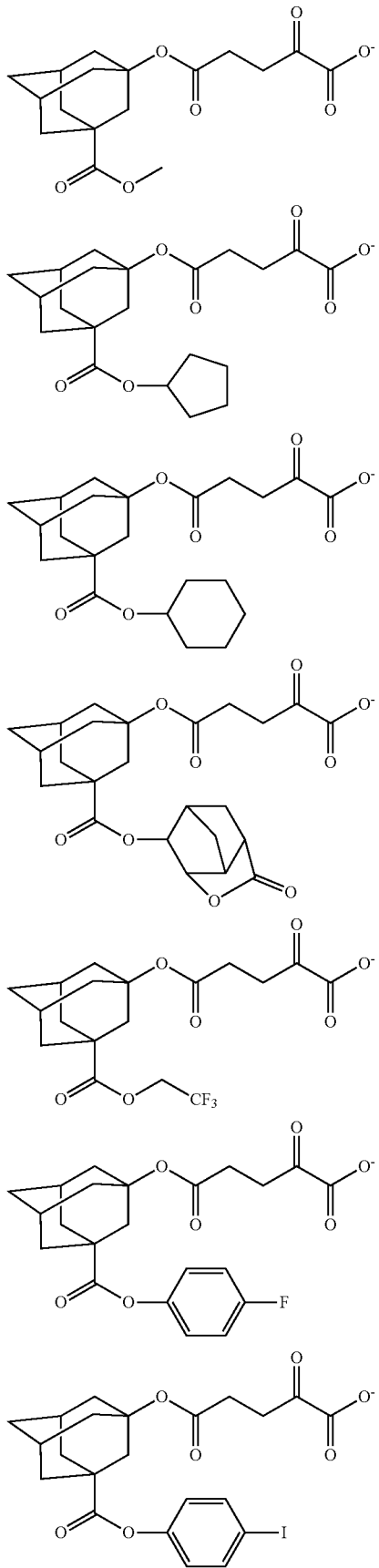
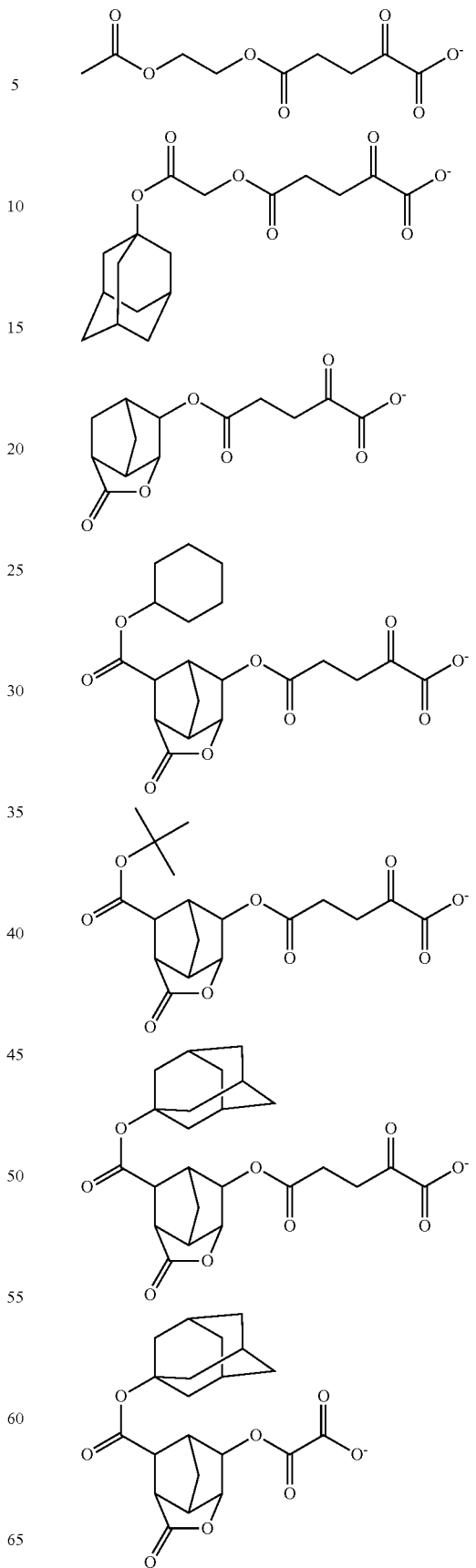

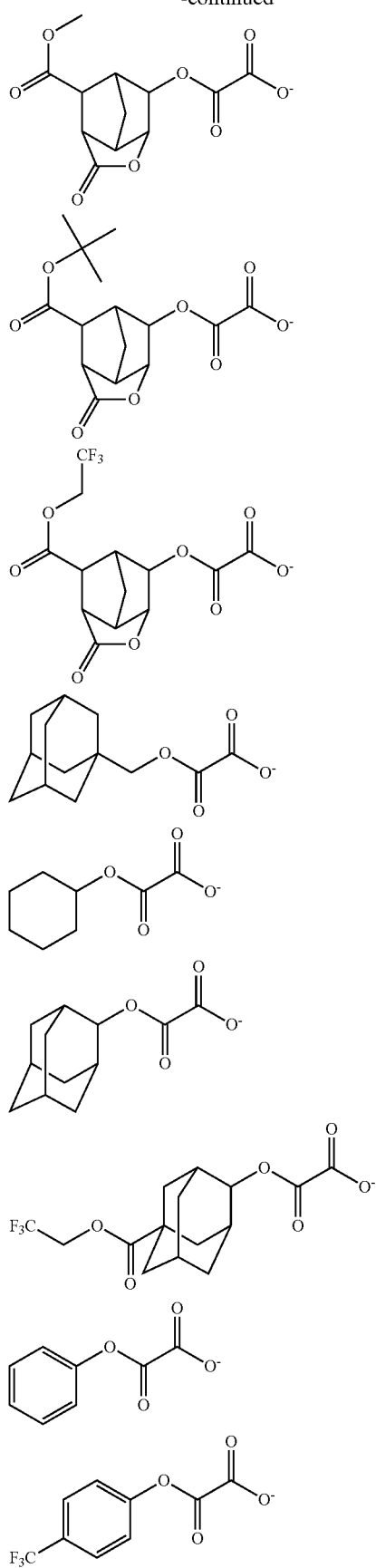
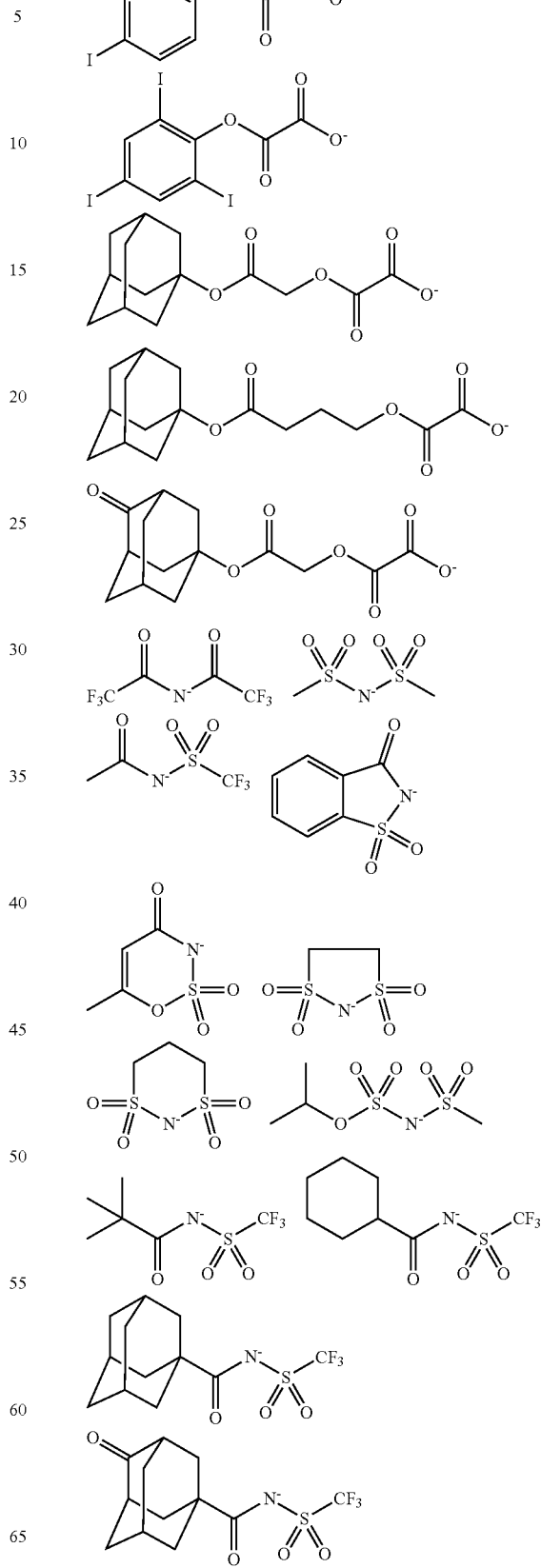

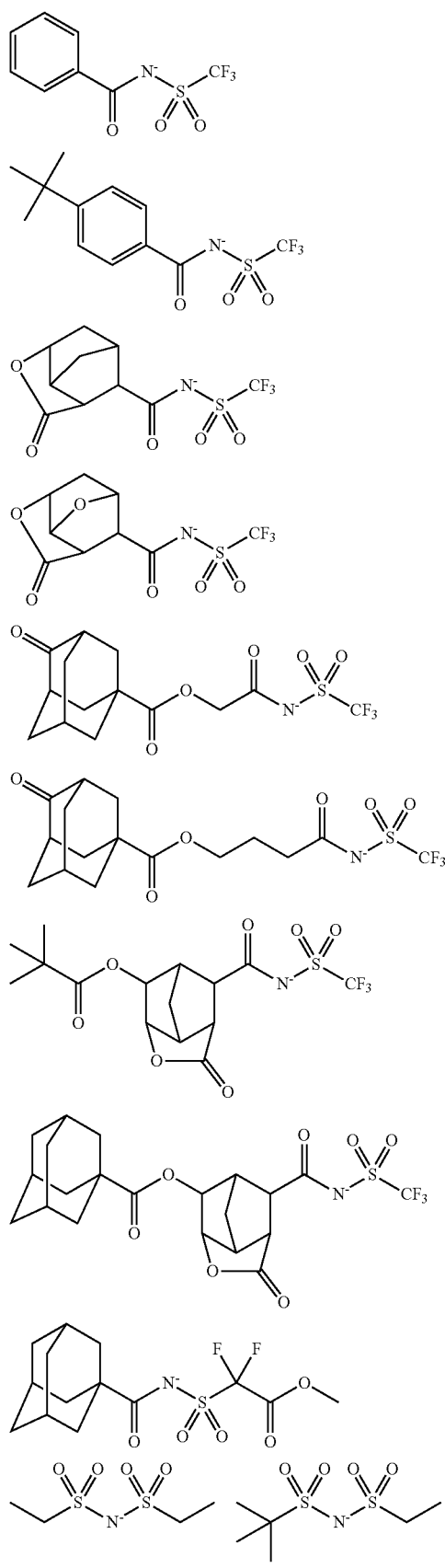
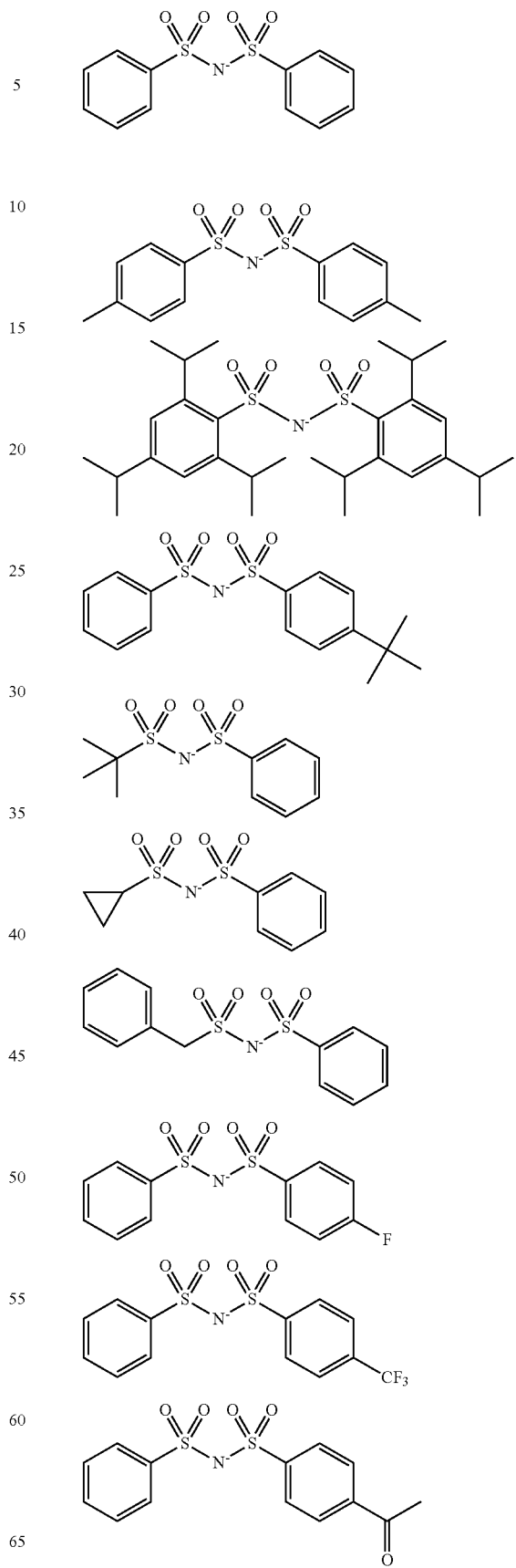

71
-continued
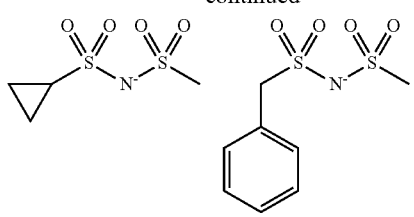
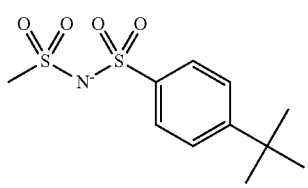
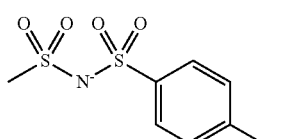
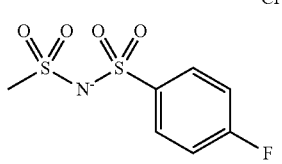
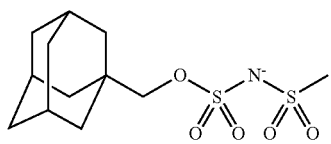
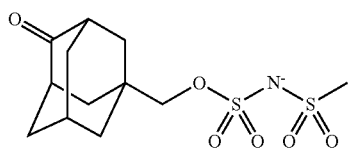
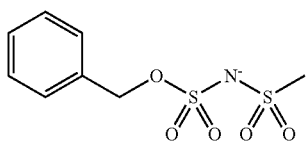
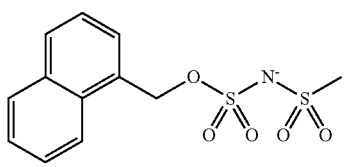
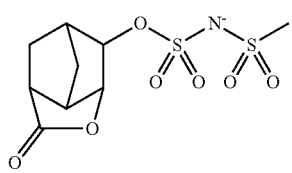
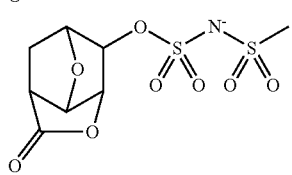
72
-continued
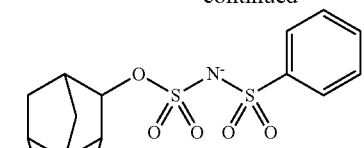
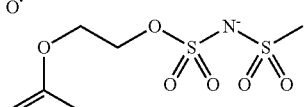
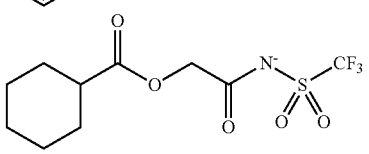
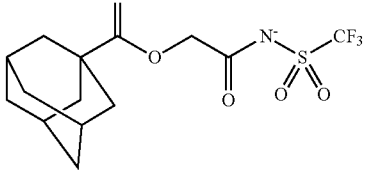
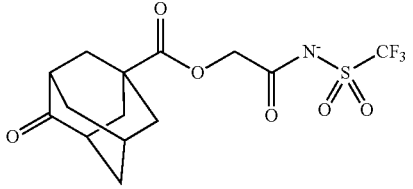
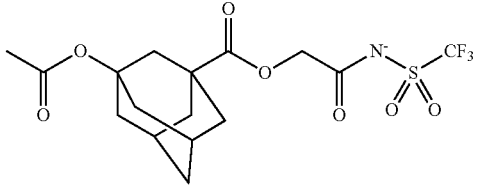
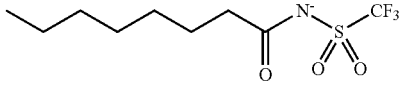
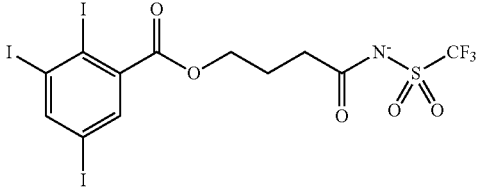
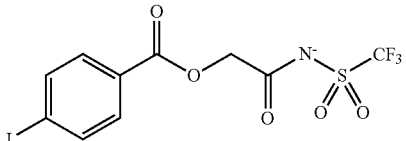
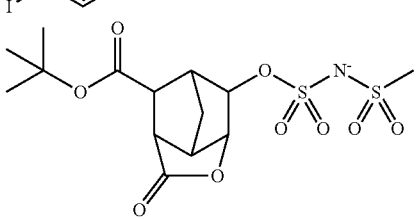

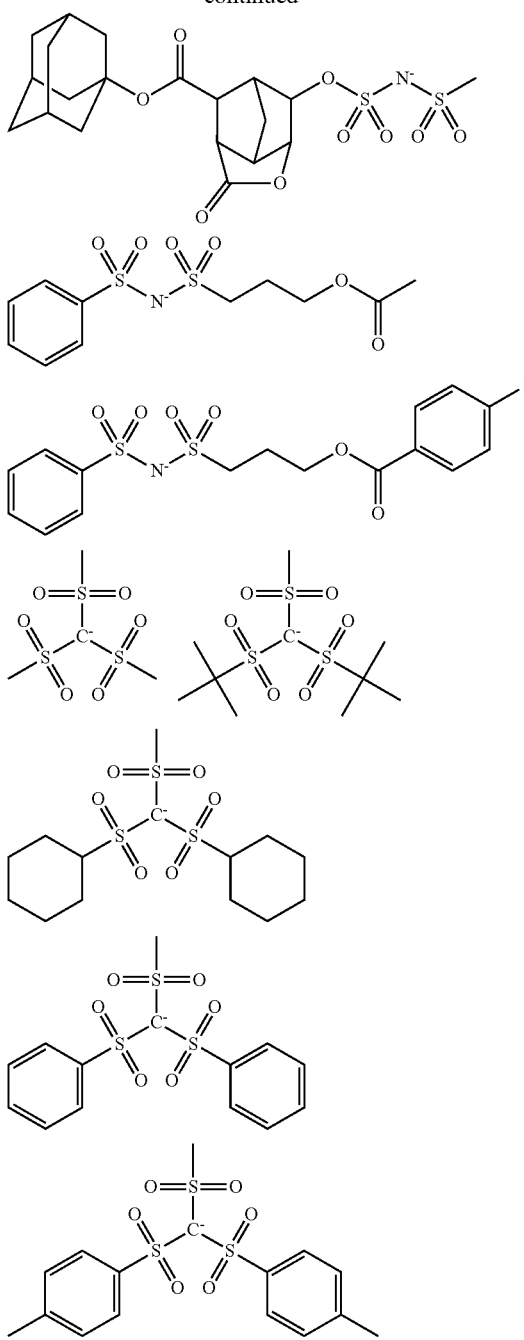

Besides the foregoing, Z⁻ is also preferably a carboxylate anion having at least one fluorine atom or trifluoromethyl group at α- or β-position relative to the carboxy group. Typical carboxylate anions have the formulae (Z-1) to (Z-5).

  (Z-1)

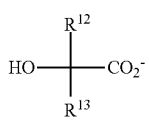  (Z-2)

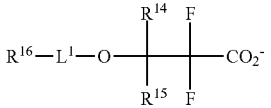  (Z-3)

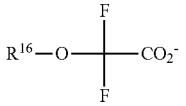  (Z-4)

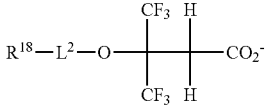  (Z-5)

In formula (Z-1), $R^{11}$ is a $C_1$-$C_4$ perfluoroalkyl group, preferably trifluoromethyl.

In formula (Z-2), $R^{12}$ and $R^{13}$ are each independently hydrogen, fluorine, methyl or trifluoromethyl. At least one of $R^{12}$ and $R^{13}$ is fluorine or trifluoromethyl. The remaining one, if any, is preferably methyl or trifluoromethyl.

In formula (Z-3), $R^{14}$ and $R^{15}$ are each independently hydrogen or a $C_1$-$C_{15}$ hydrocarbyl group which may contain a heteroatom. The hydrocarbyl group may be saturated or unsaturated and straight, branched or cyclic. In the hydrocarbyl group, some or all of the hydrogen atoms may be substituted by a moiety containing a heteroatom such as oxygen, sulfur, nitrogen or halogen, and any constituent —CH₂— may be replaced by a moiety containing a heteroatom such as oxygen, sulfur or nitrogen, so that the group may contain fluorine, chlorine, bromine, iodine, hydroxy moiety, cyano moiety, carbonyl moiety, ether bond, ester bond, sulfonate bond, carbonate bond, lactone ring, sultone ring, carboxylic anhydride or haloalkyl moiety.

Examples of the optionally heteroatom-containing hydrocarbyl group represented by $R^{14}$ and $R^{15}$ include $C_1$-$C_{15}$ alkyl groups such as methyl, ethyl, propyl, isopropyl, n-butyl, sec-butyl, tert-butyl, n-pentyl, n-hexyl, n-octyl, 2-ethylhexyl, n-nonyl, n-decyl; $C_3$-$C_{15}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0²,⁶]decanyl, adamantyl, adamantylmethyl; $C_2$-$C_{15}$ alkenyl groups such as vinyl, allyl, propenyl, butenyl, hexenyl; $C_3$-$C_{15}$ unsaturated alicyclic hydrocarbyl groups such as cyclohexenyl; $C_6$-$C_{15}$ aryl groups such as phenyl, naphthyl, thienyl, 4-hydroxyphenyl, 4-methoxyphenyl, 3-methoxyphenyl, 2-methoxyphenyl, 4-ethoxyphenyl, 4-tert-butoxyphenyl, 3-tert-butoxyphenyl, 2-methylphenyl, 3-methylphenyl, 4-methylphenyl, 4-ethylphenyl, 4-tert-butylphenyl, 4-n-butylphenyl, 2,4-dimethylphenyl, 2,4,6-triisopropylphenyl, methylnaphthyl, ethylnaphthyl, methoxynaphthyl, ethoxynaphthyl, n-propoxynaphthyl, n-butoxynaphthyl, dimethylnaphthyl, diethylnaphthyl, dimethoxynaphthyl, diethoxynaphthyl; $C_7$-$C_{15}$ aralkyl groups such as benzyl, 1-phenylethyl, 2-phenylethyl; and combinations thereof.

$R^{14}$ and $R^{15}$ may bond together to form a ring with the carbon atom to which they are attached. Typical of the ring are cyclopentane, cyclohexane, norbornane and adamantane rings.

Preferably, $R^{14}$ is hydrogen. $R^{15}$ is preferably hydrogen or a $C_1$-$C_{10}$ hydrocarbyl group which may contain oxygen, fluorine or iodine, more preferably hydrogen, isopropyl, cyclohexyl, adamantyl, or optionally substituted phenyl group.

In formulae (Z-3) to (Z-5), $R^{16}$, $R^{17}$ and $R^{18}$ are each independently hydrogen or a $C_1$-$C_{30}$ hydrocarbyl group which may contain a heteroatom. The hydrocarbyl group may be saturated or unsaturated and straight, branched or cyclic. In the hydrocarbyl group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain fluorine, chlorine, bromine, iodine, hydroxy moiety, cyano moiety, carbonyl moiety, ether bond, ester bond, sulfonate bond, carbonate bond, lactone ring, sultone ring, carboxylic anhydride or haloalkyl moiety. Examples of the optionally heteroatom-containing hydrocarbyl group are as exemplified above in conjunction with $R^{14}$ and $R^{15}$. $R^{16}$, $R^{17}$ and $R^{18}$ are preferably hydrogen or a $C_3$-$C_{30}$ cyclic hydrocarbyl group which may contain a heteroatom.

In formulae (Z-3) and (Z-5), $L^1$ and $L^2$ are each independently a single bond, carbonyl group or sulfonyl group, preferably a single bond or carbonyl group.

Of the anions having formulae (Z-1) to (Z-5), anions having the following formulae (Z-1a), (Z-2a), (Z-2b), (Z-3a), (Z-4a), (Z-5a), and (Z-5b) are preferred.

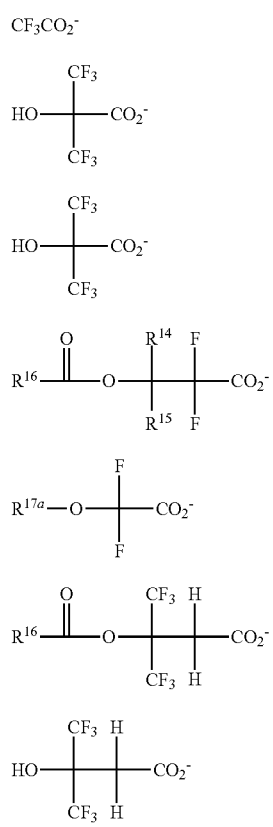

Herein $R^{14}$ and $R^{15}$ are as defined above.

In formulae (Z-3a), (Z-4a), and (Z-5a), $R^{16a}$, $R^{17a}$ and $R^{18a}$ are each independently a $C_3$-$C_{30}$ cyclic hydrocarbyl group which may contain a heteroatom. Examples of the cyclic hydrocarbyl group include cyclic aliphatic hydrocarbyl groups such as cyclopentyl, cyclohexyl, cycloheptyl, cyclooctyl, cyclononyl, cyclodecanyl, norbornyl, tricyclo[5.2.1.0$^{2,6}$]decanyl, adamantyl, cyclohexenyl, norbornenyl; cyclic aromatic hydrocarbyl groups such as phenyl, naphthyl, thienyl, 2-hydroxyphenyl, 4-hydroxyphenyl, 2-methoxyphenyl, 3-methoxyphenyl, 4-methoxyphenyl, 4-fluorophenyl, 4-iodophenyl, 4-tert-butylphenyl, 4-tert-butoxyphenyl, 4-trifluoromethylphenyl, 4-n-butylphenyl, 2,4-dimethylphenyl, 2,4,6-trimethylphenyl, 2,4,6-triisopropylphenyl, methylnaphthyl, methoxynaphthyl, ethoxynaphthyl, isopropoxynaphthyl, tert-butoxynaphthyl, dimethylnaphthyl, dihydroxynaphthyl, dimethoxynaphthyl; spiro-ring hydrocarbyl groups such as spiro[4,5]decanyl; and substituted forms of the foregoing in which some hydrogen is substituted by an alkyl, alkenyl, aryl, aralkyl or alkoxy moiety. In the cyclic hydrocarbyl group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain fluorine, chlorine, bromine, iodine, hydroxy moiety, cyano moiety, carbonyl moiety, ether bond, ester bond, sulfonate bond, carbonate bond, lactone ring, sultone ring, carboxylic anhydride or haloalkyl moiety.

Each of $R^{16a}$, $R^{17a}$ and $R^{18a}$ is preferably an optionally substituted cyclohexyl group, optionally substituted adamantyl group, or optionally substituted phenyl group, more preferably an optionally substituted adamantyl or phenyl group. The preferred substituents include hydroxy, carboxy, fluorine, iodine, and $C_1$-$C_{14}$ hydrocarbyl groups which may contain fluorine or oxygen, $C_1$-$C_{14}$ hydrocarbyloxy groups which may contain fluorine or oxygen, $C_2$-$C_{14}$ hydrocarbyloxyhydrocarbyloxy groups which may contain fluorine or oxygen, $C_2$-$C_{14}$ hydrocarbyloxycarbonyl groups which may contain fluorine or oxygen, or $C_2$-$C_{14}$ hydrocarbyloxycarbonyloxy groups which may contain fluorine or oxygen.

Examples of the anions having formulae (Z-1) to (Z-5) are shown below, but not limited thereto.

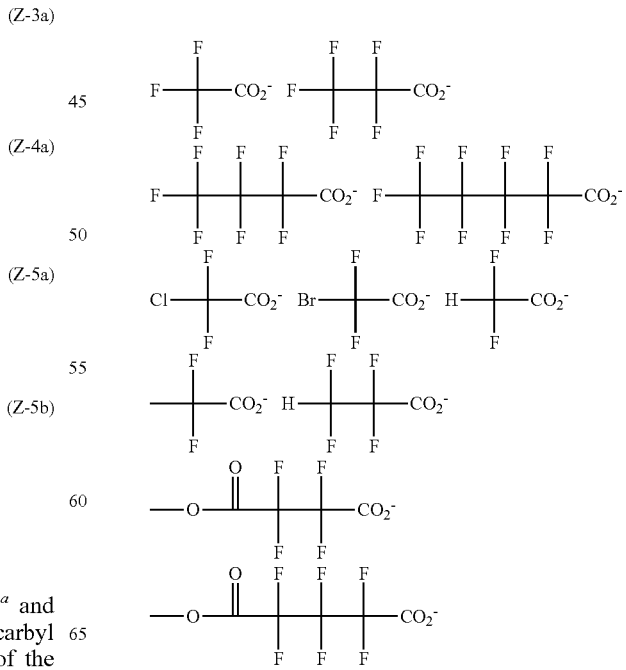

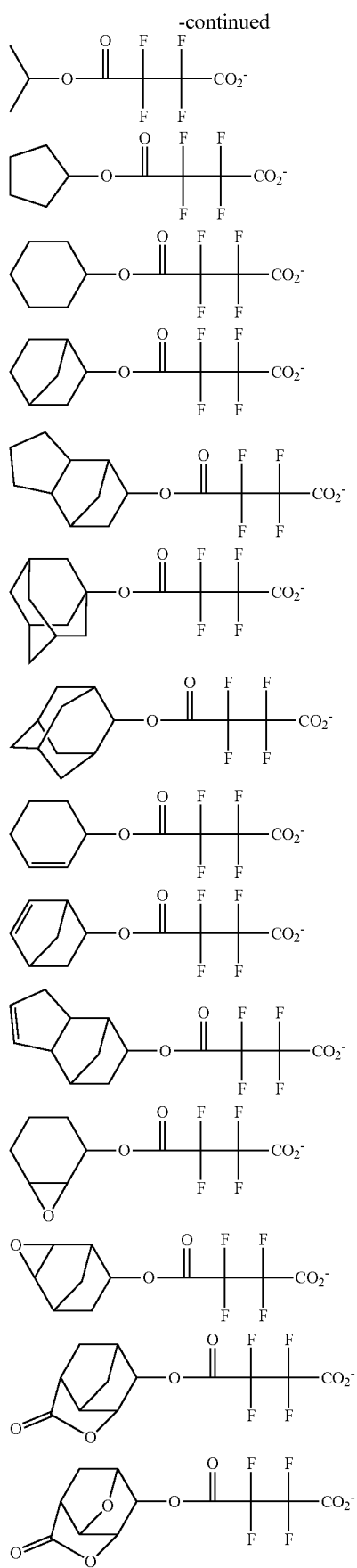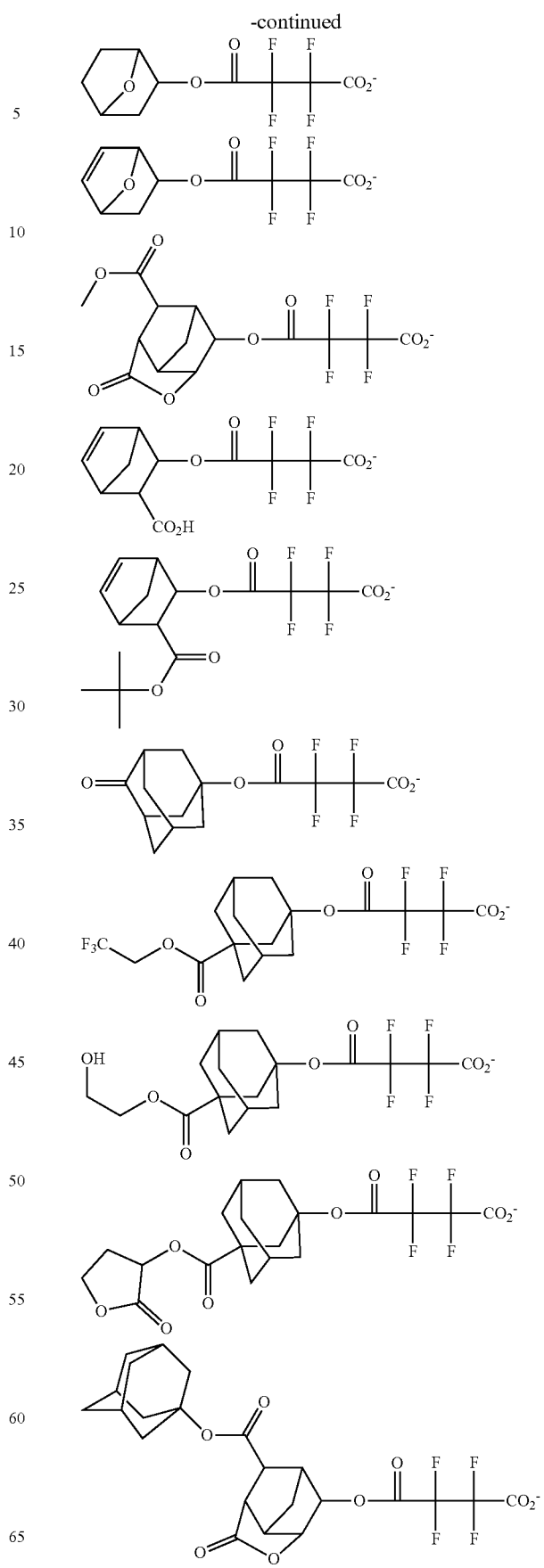

-continued
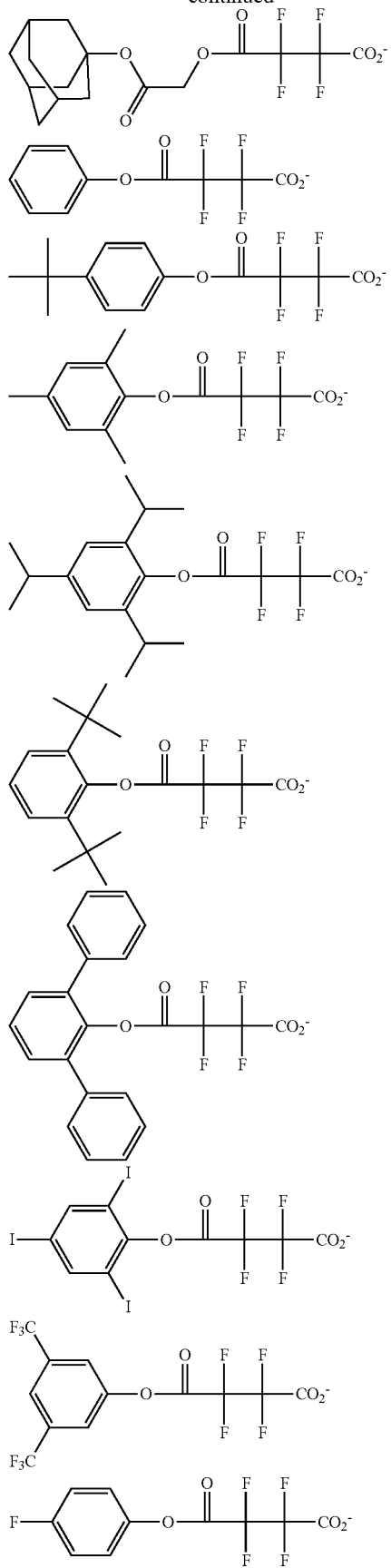
-continued
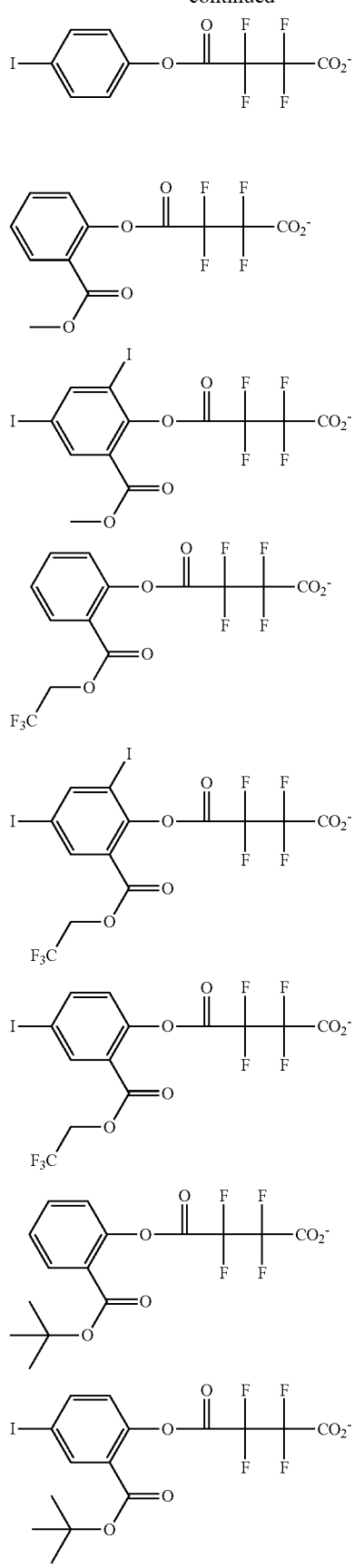

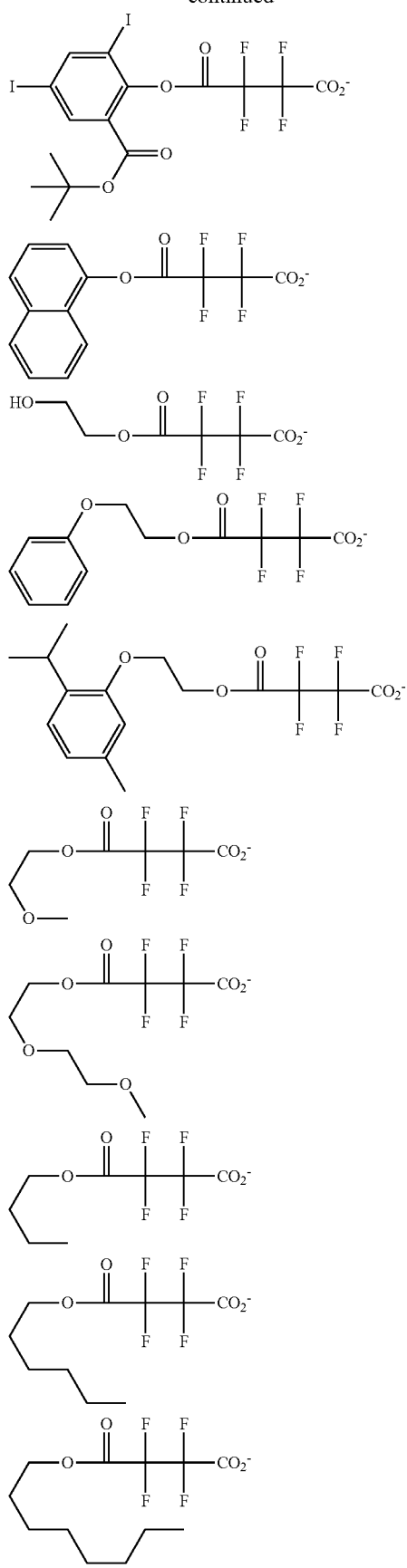
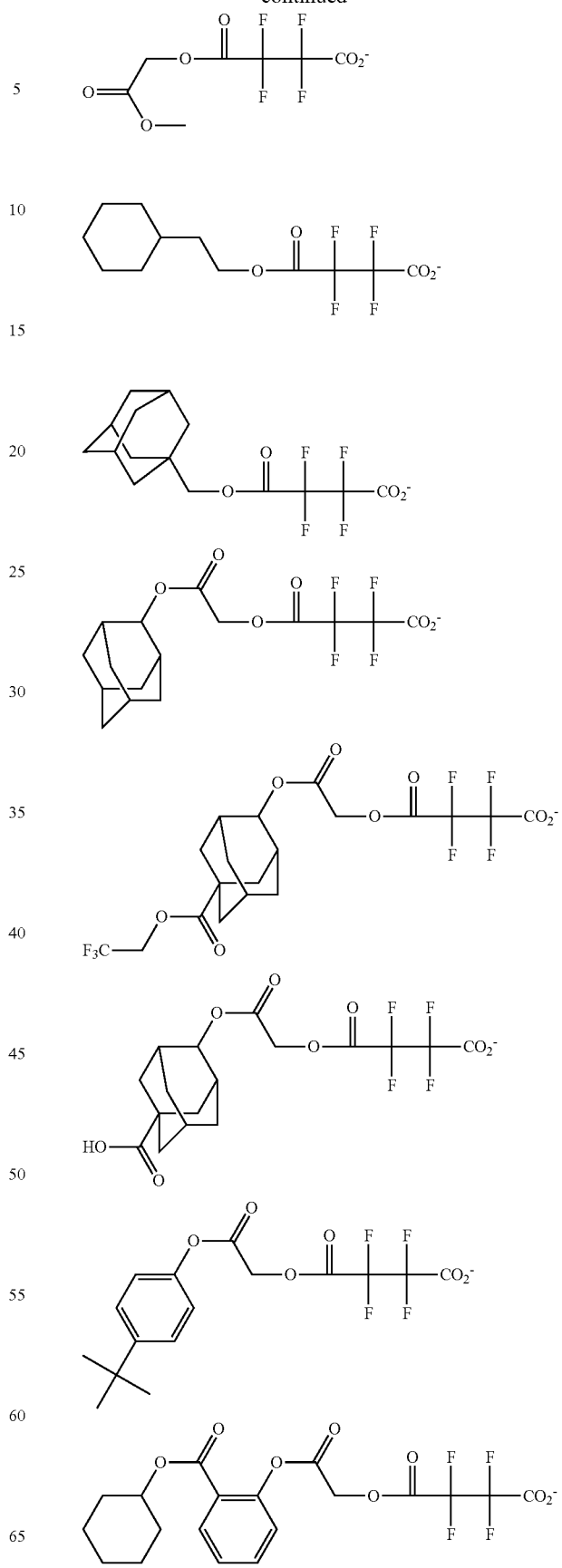

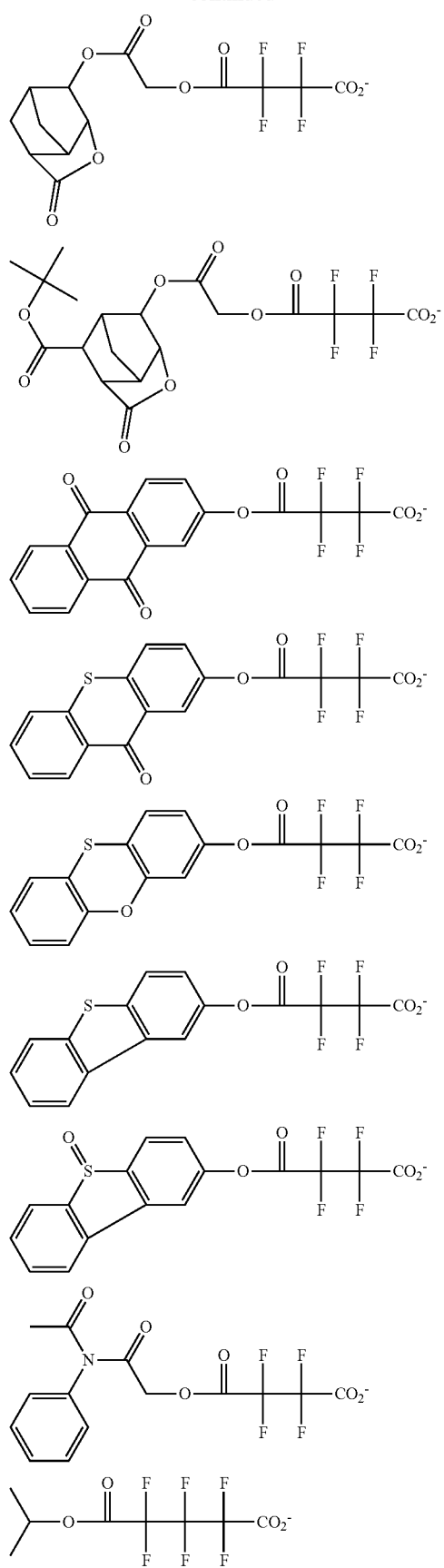
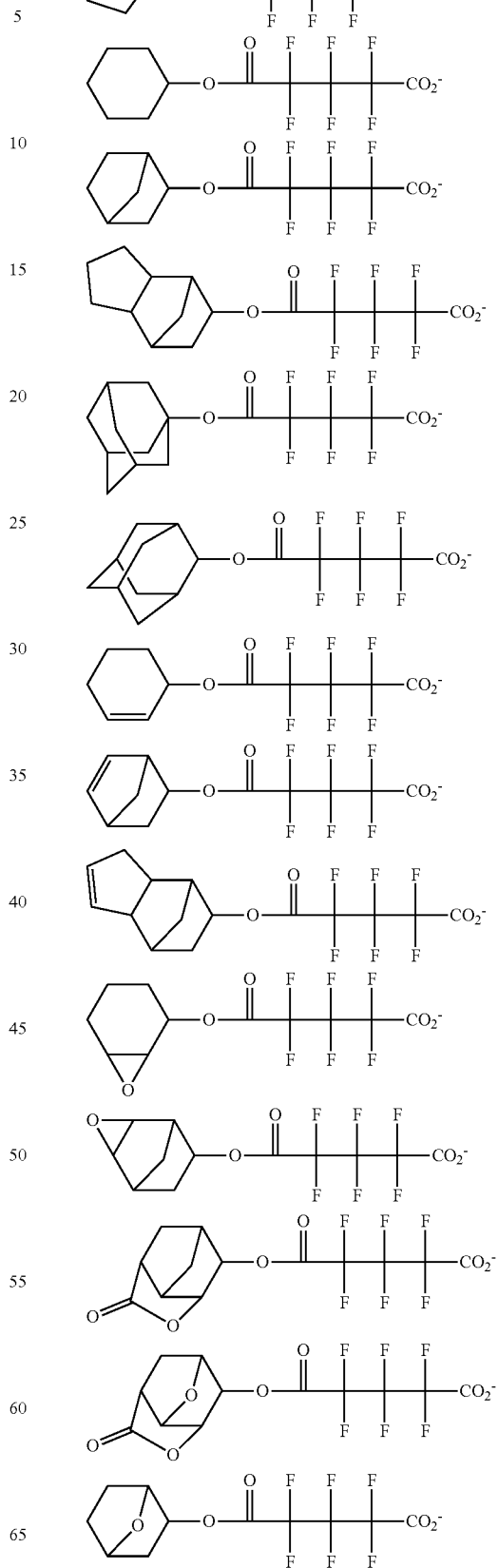

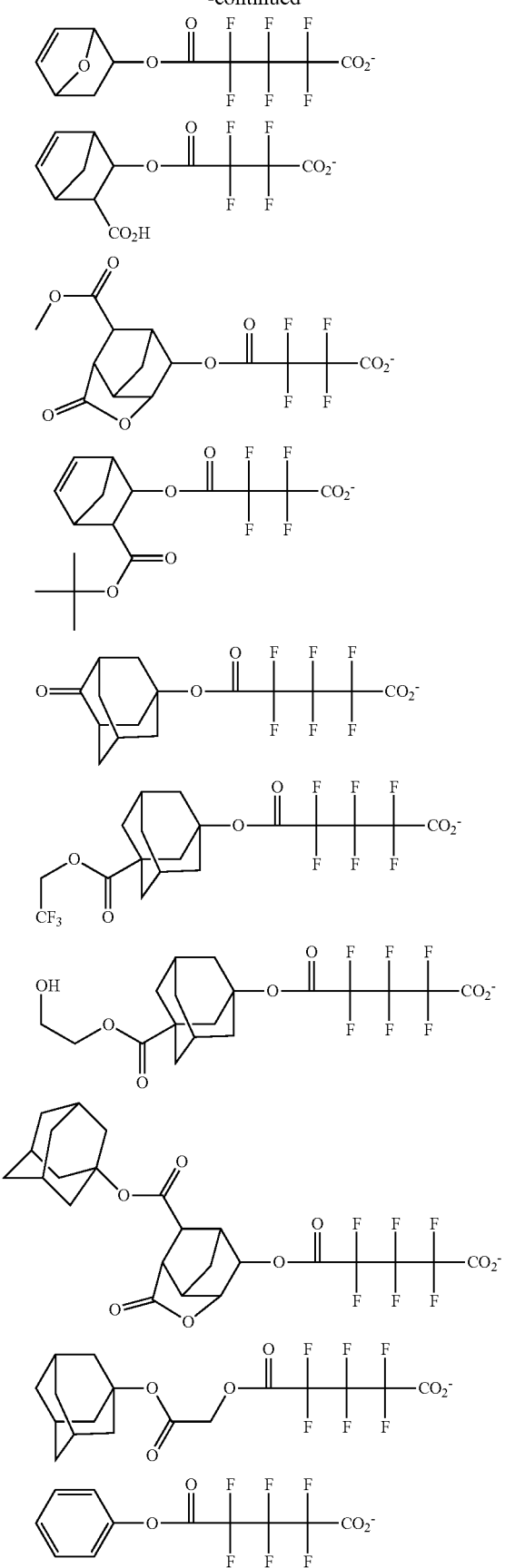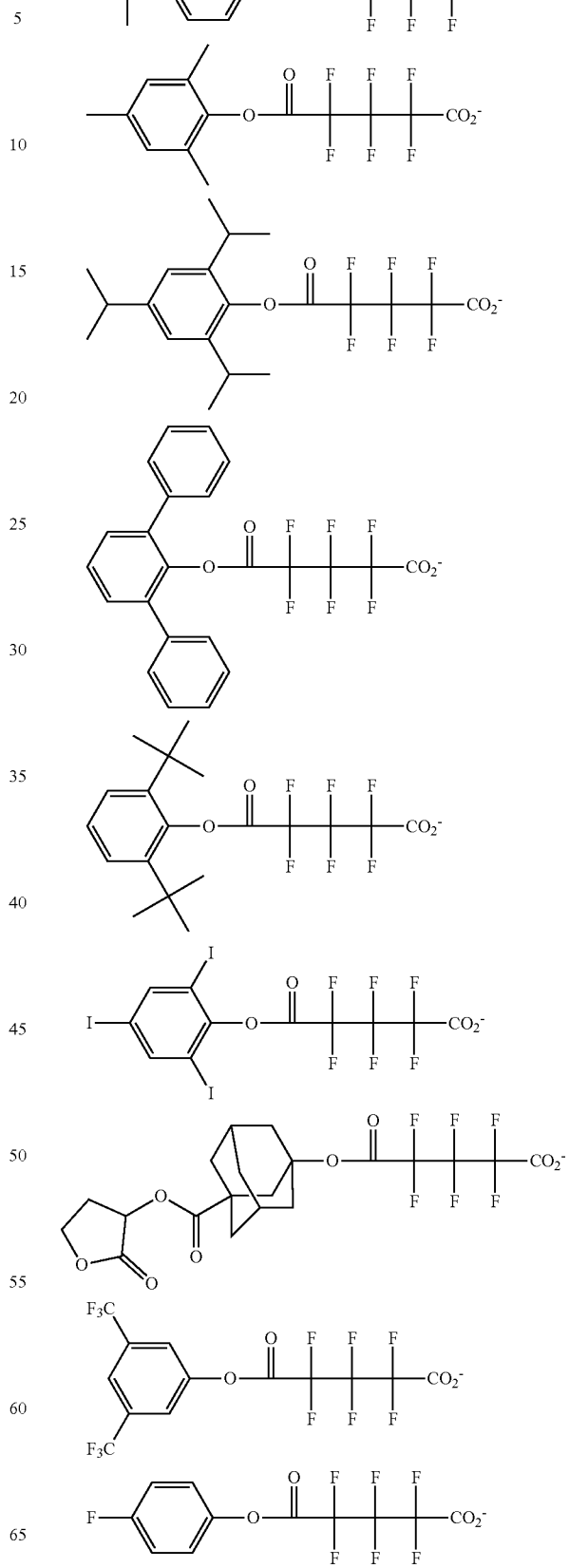

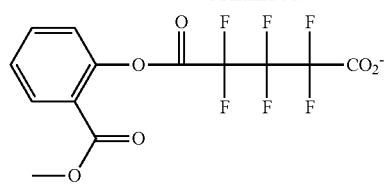
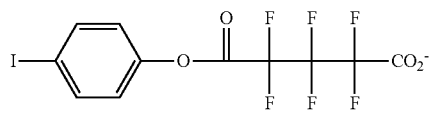
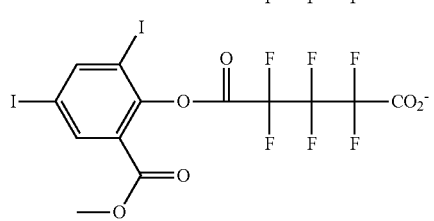
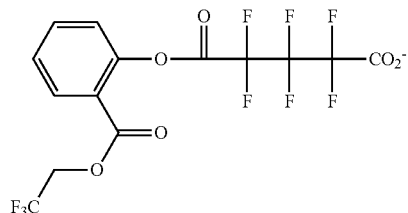
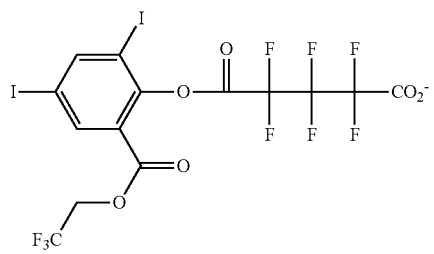
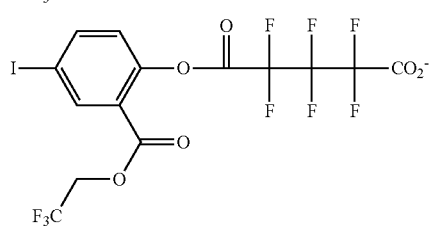
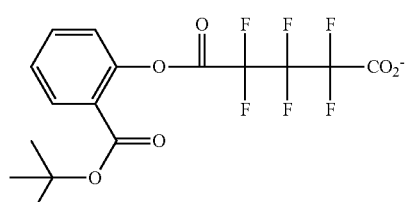
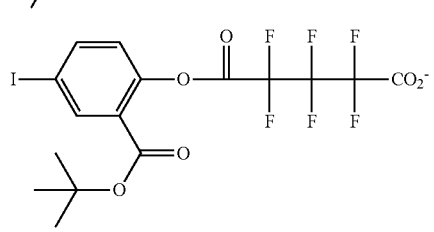
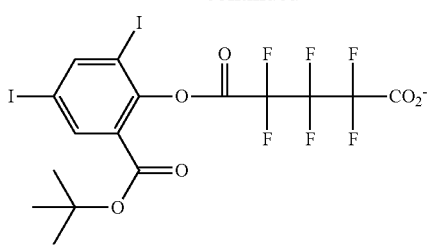
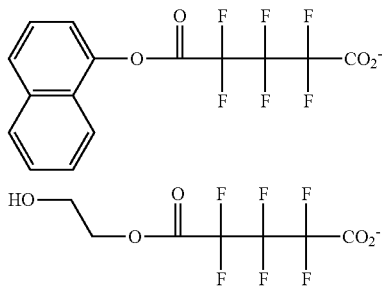
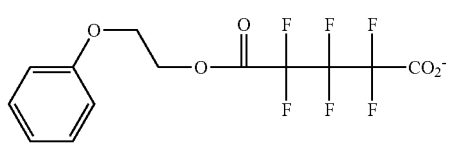
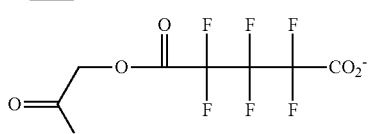
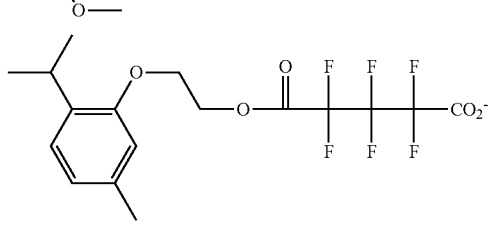
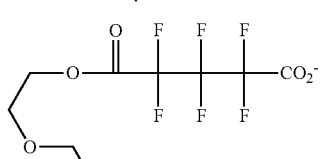
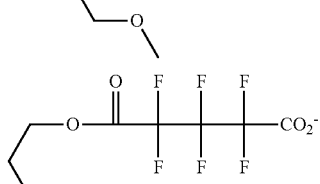
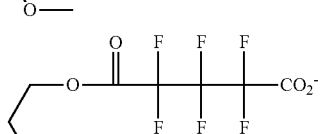
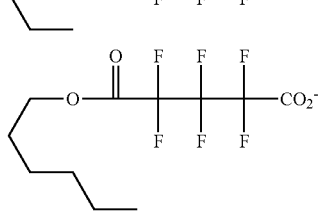

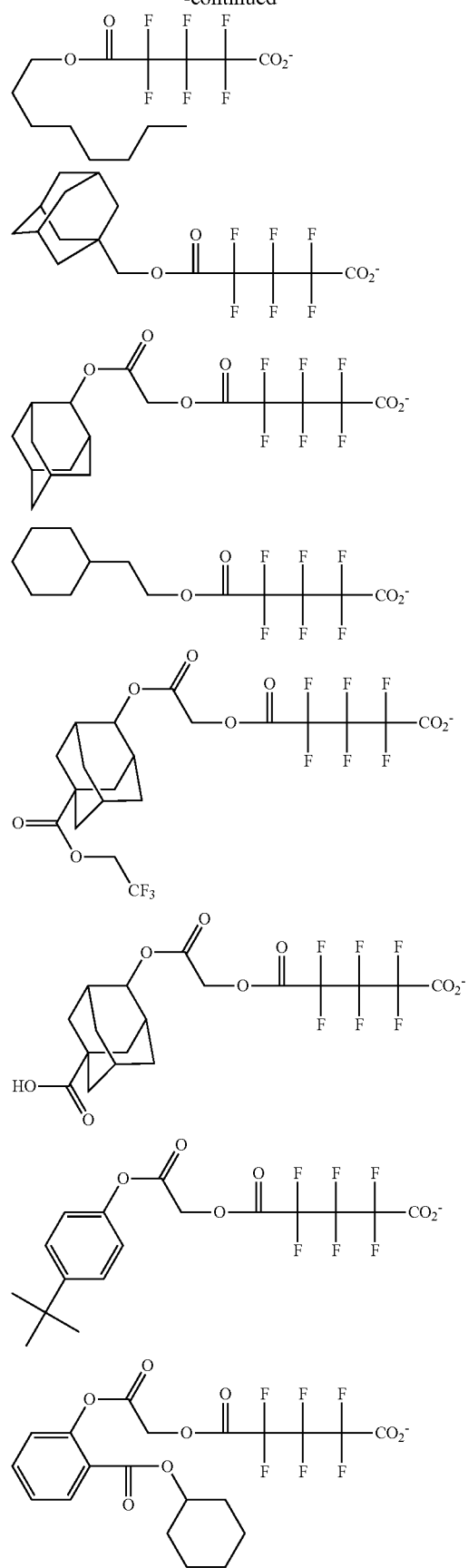
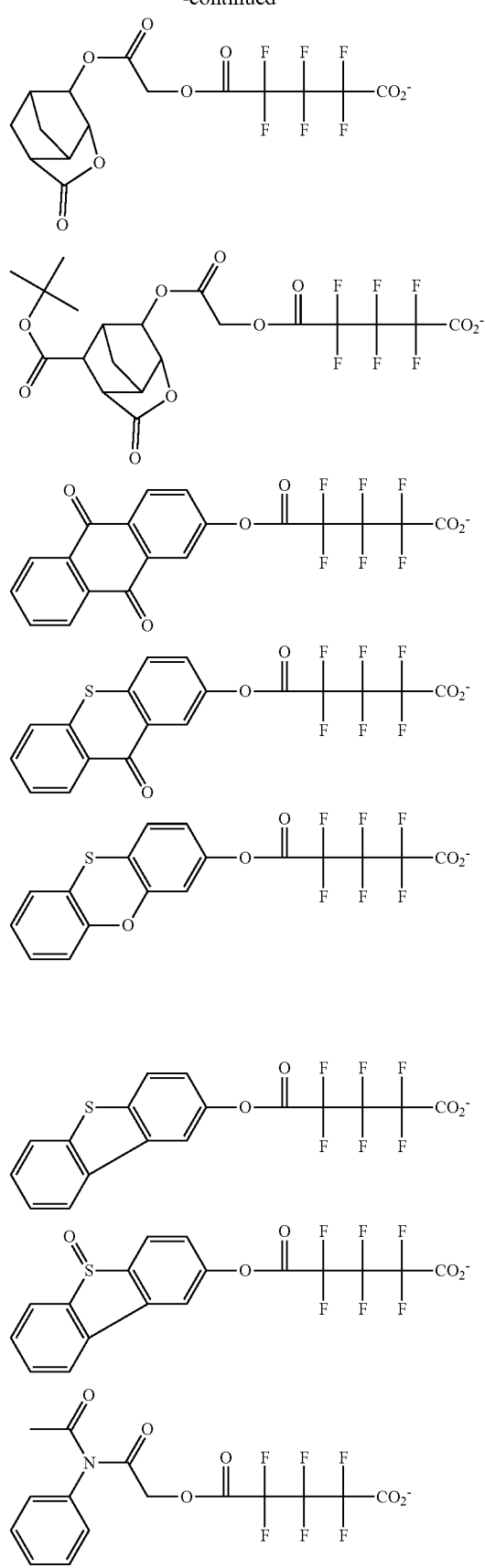

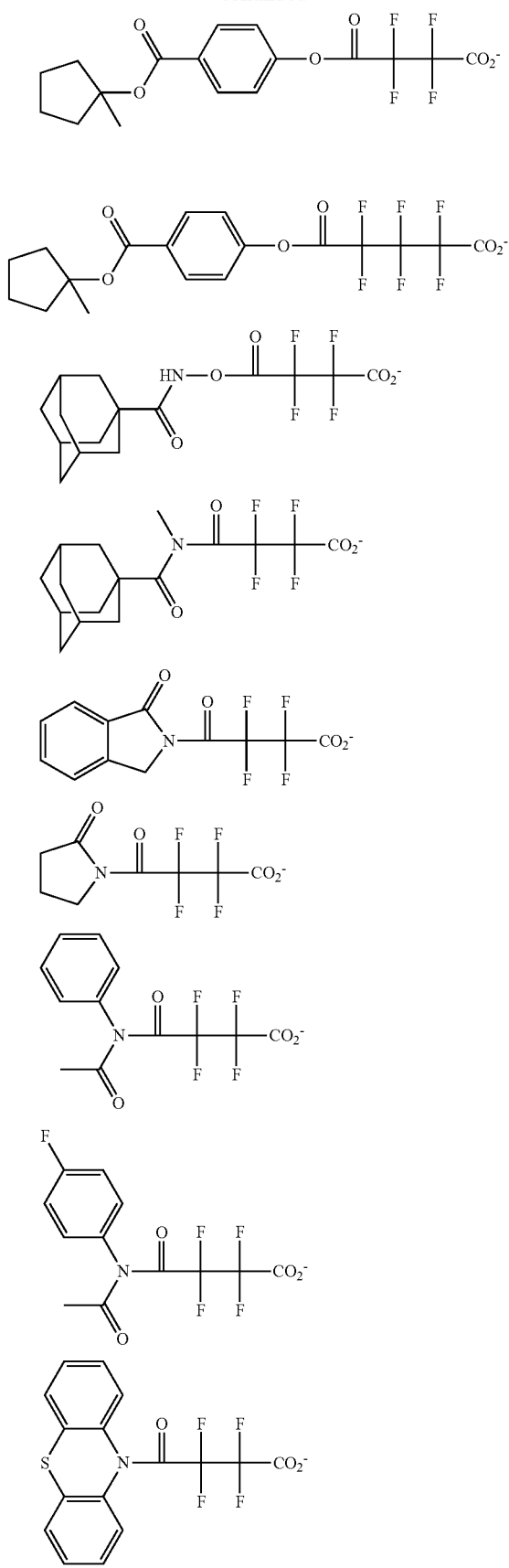
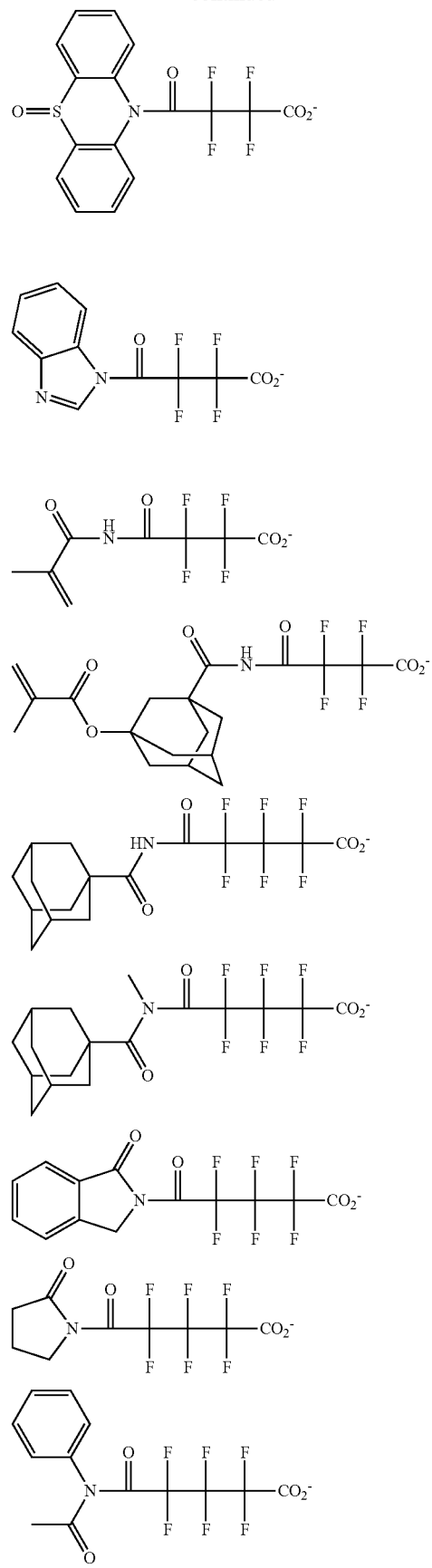

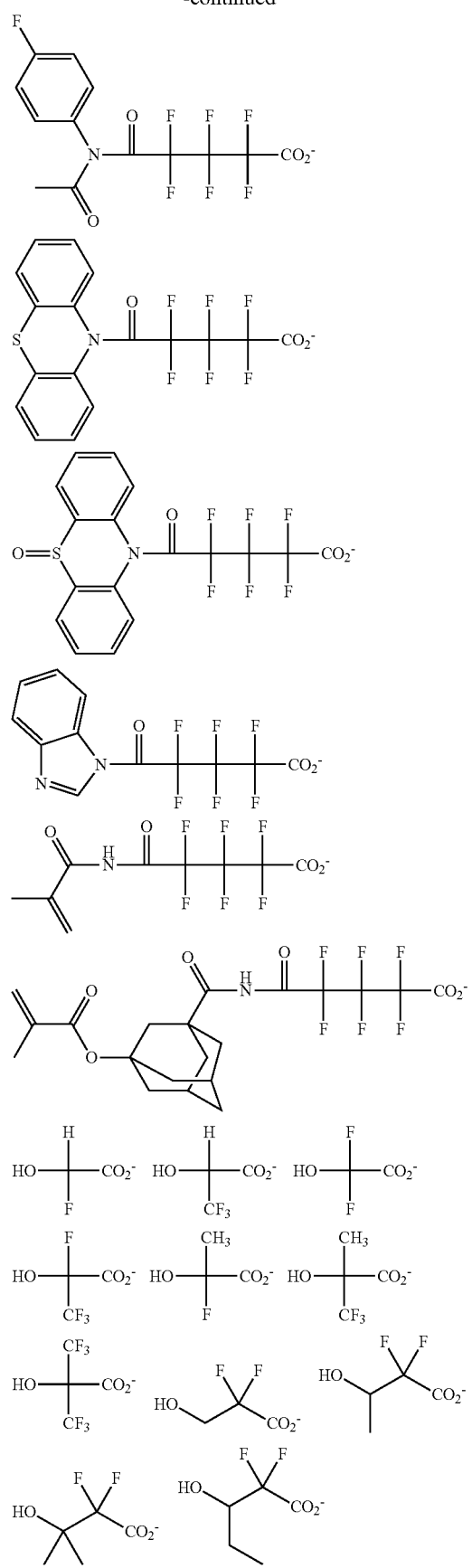
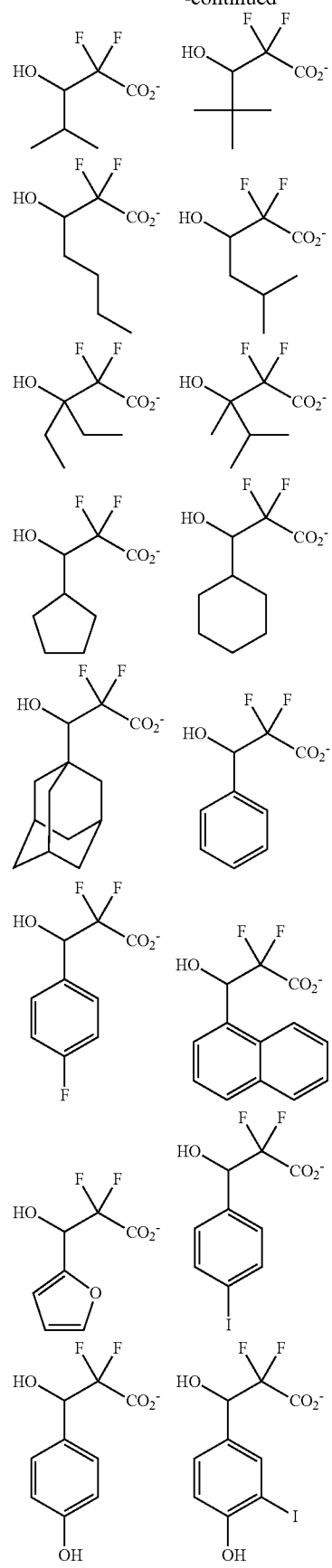

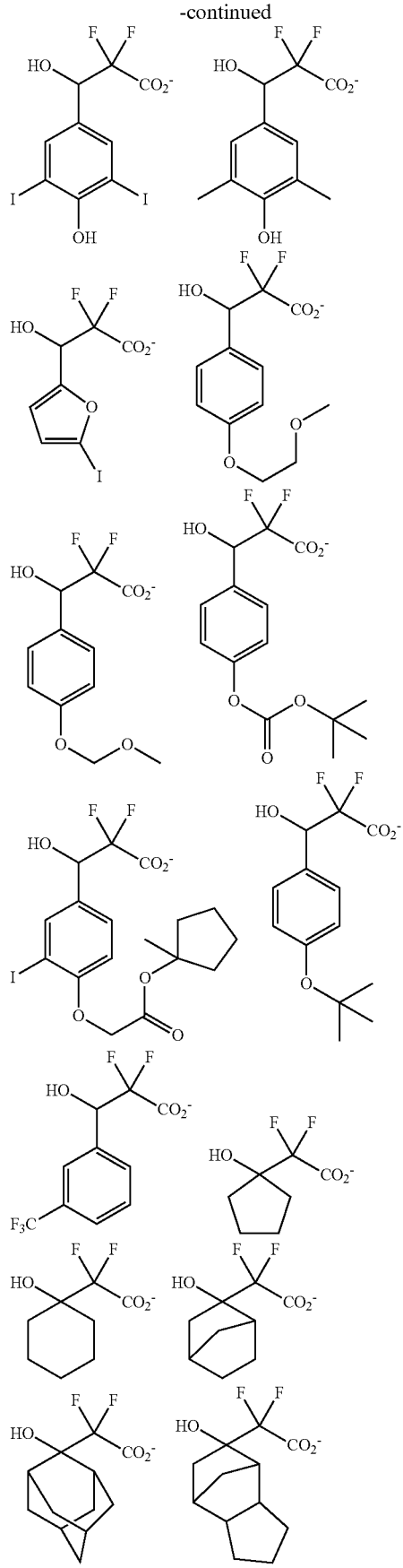
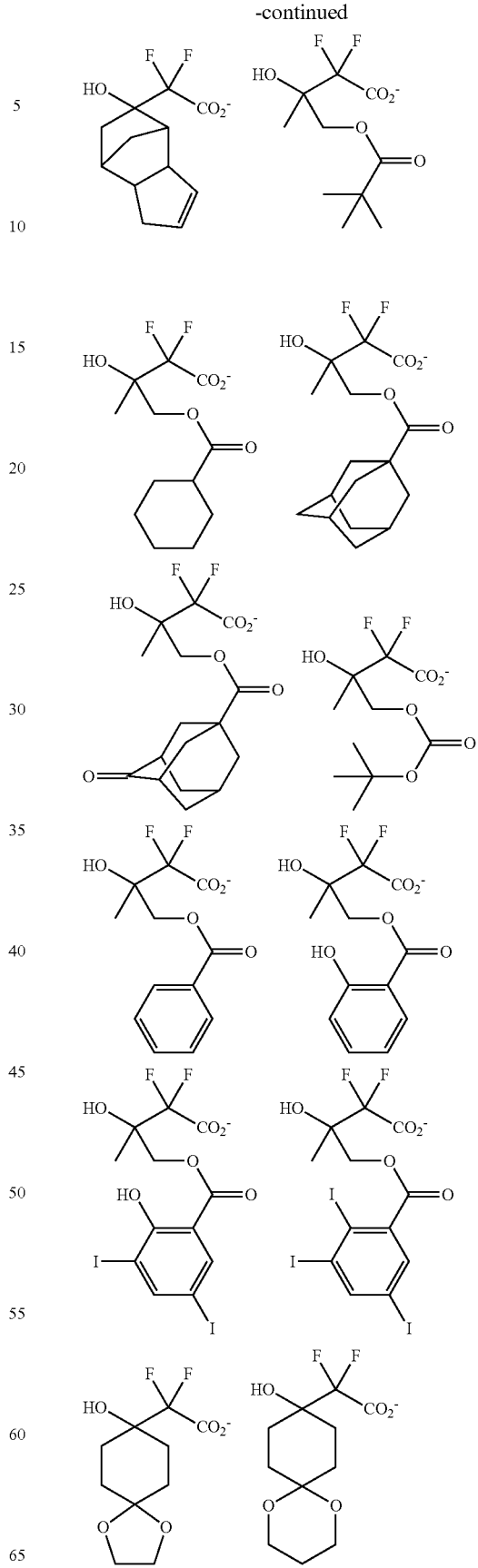

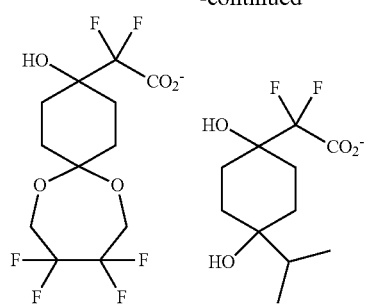
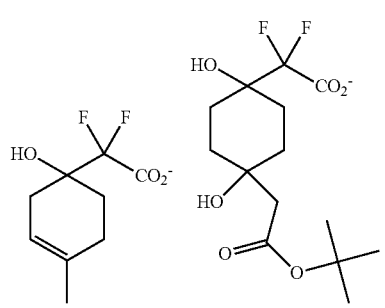
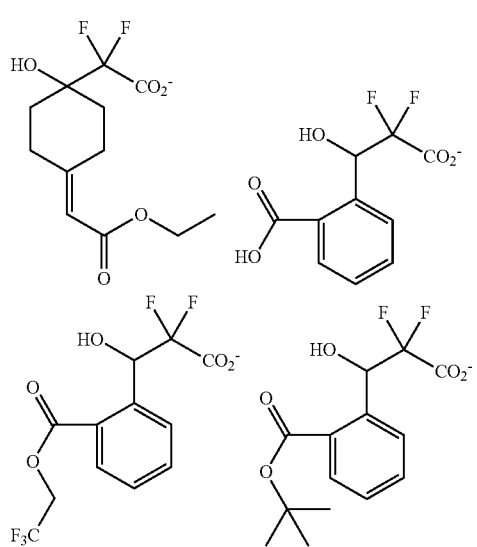
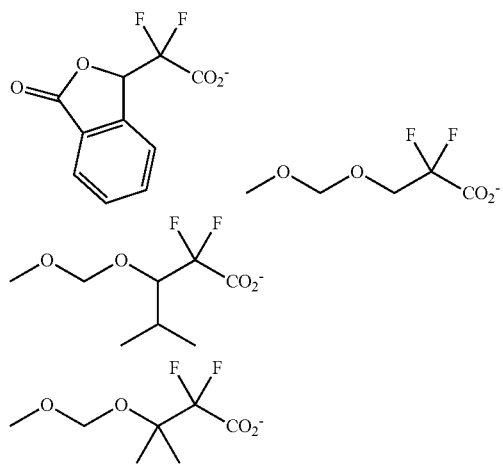
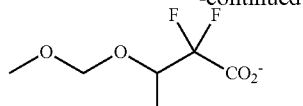
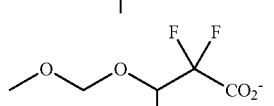
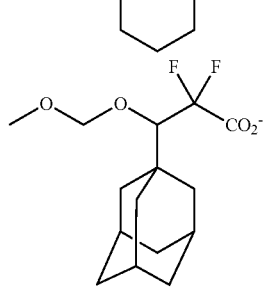
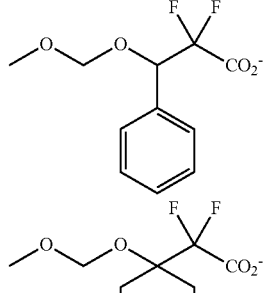
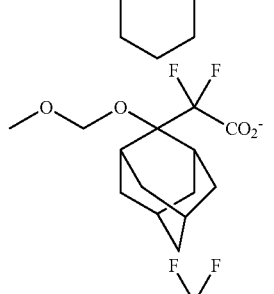
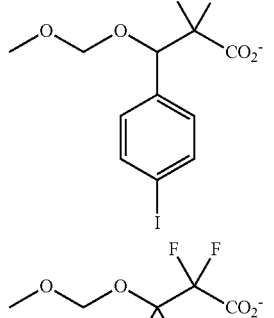
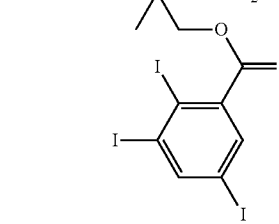
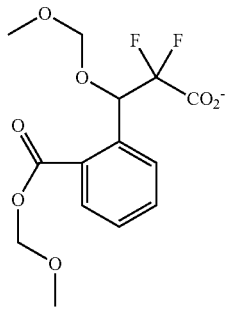

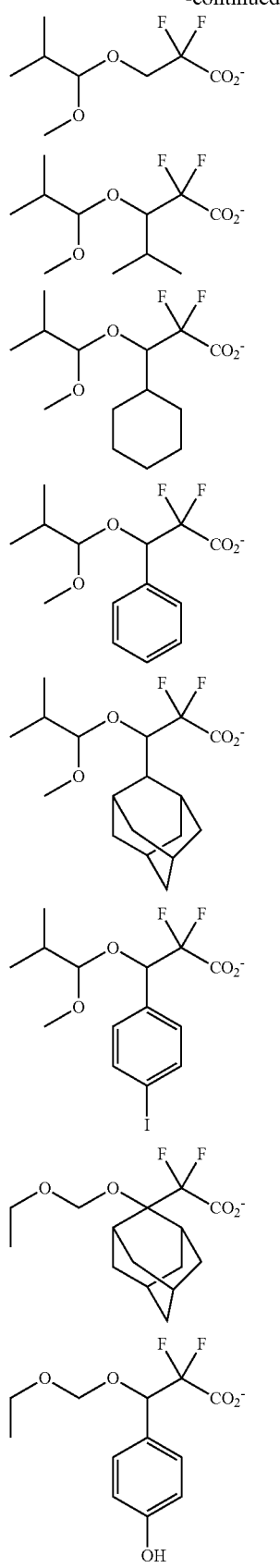
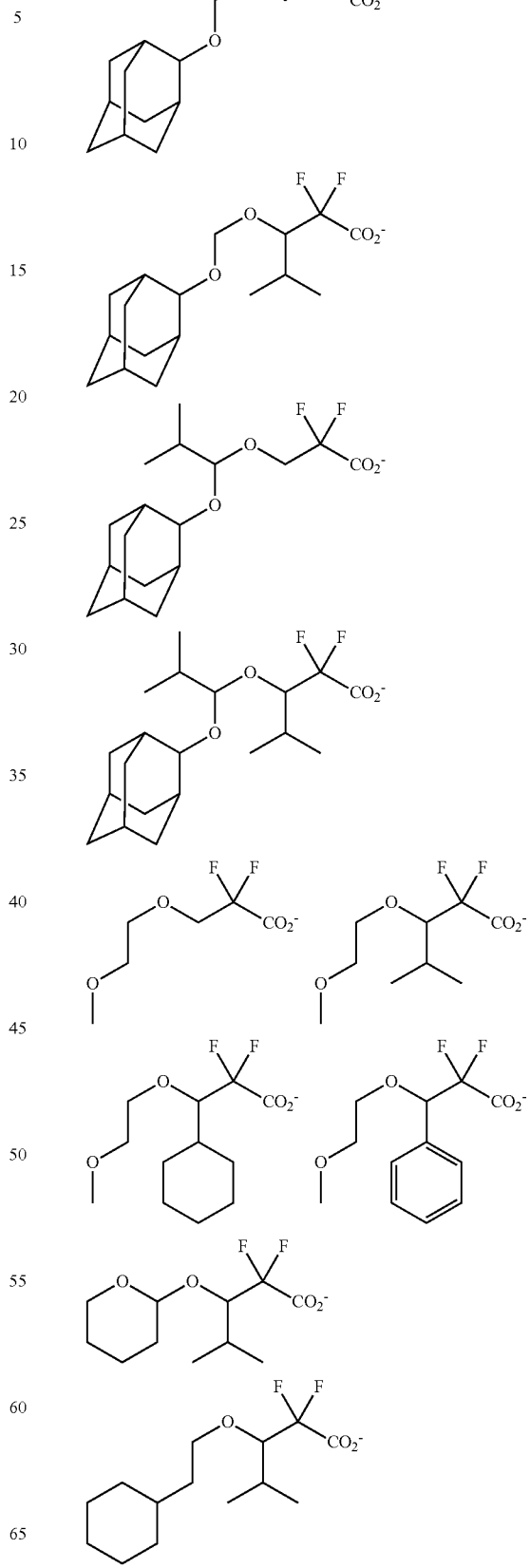

101
-continued
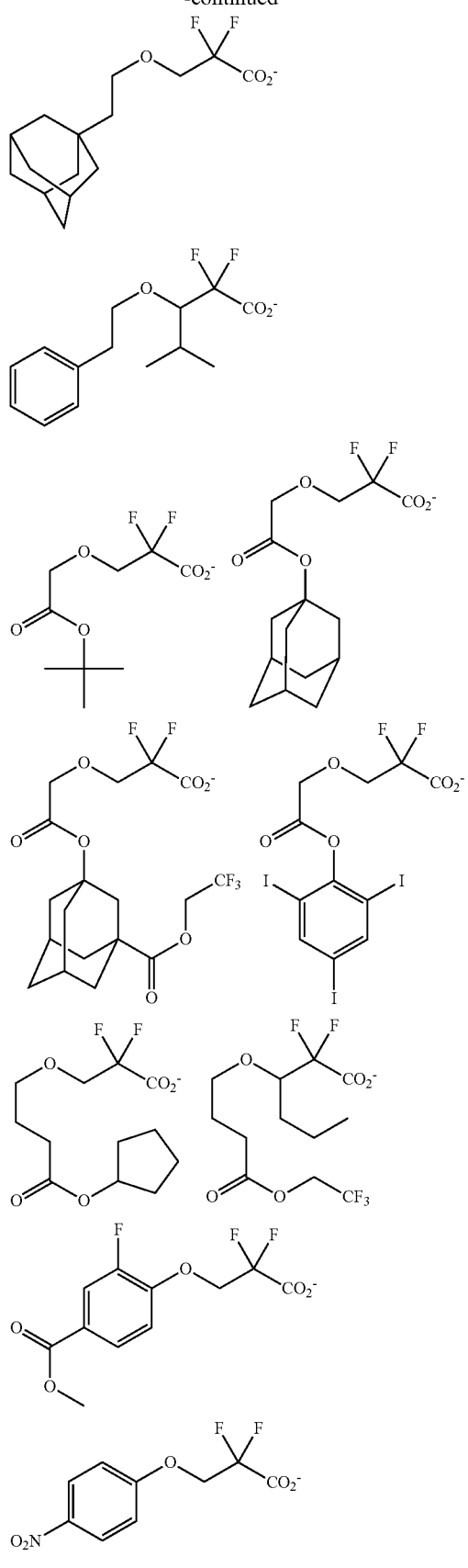
102
-continued
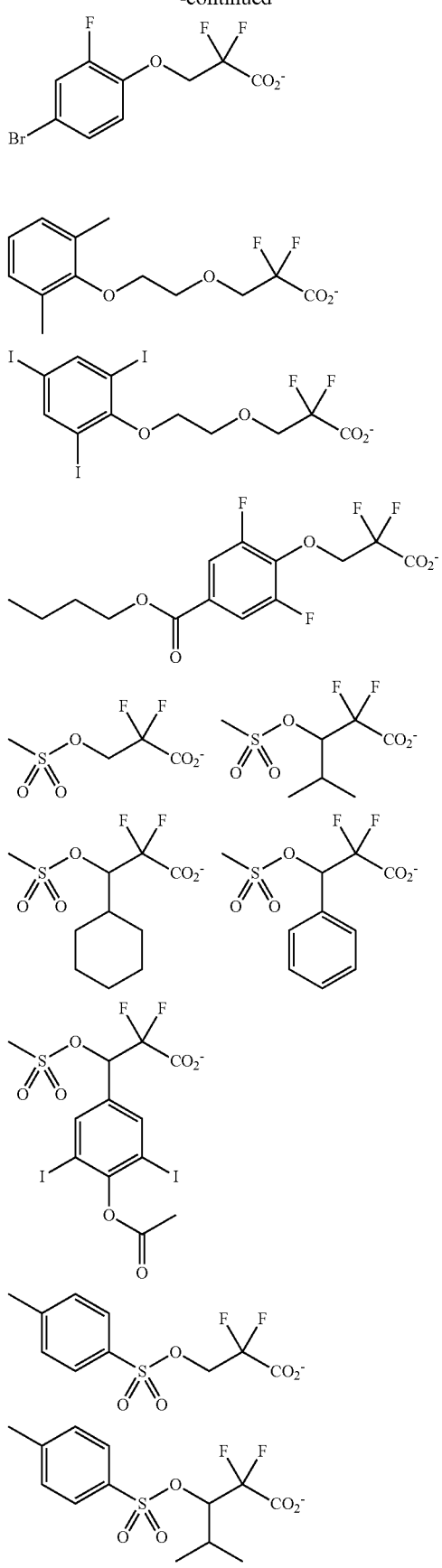

-continued
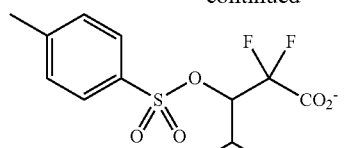
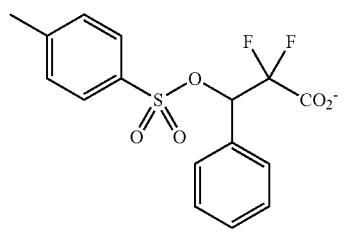
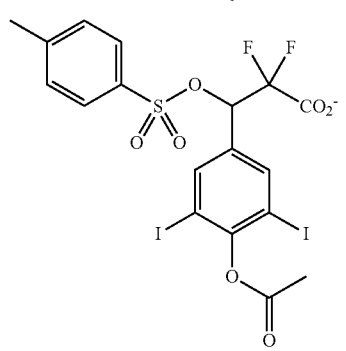
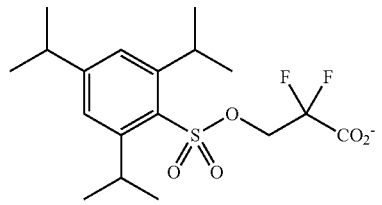
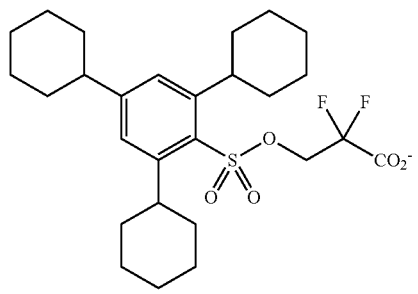
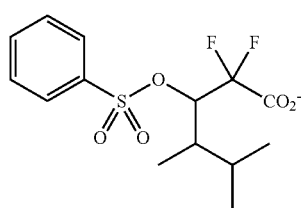
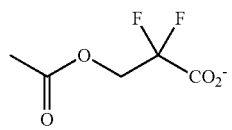
-continued
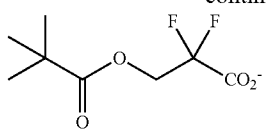
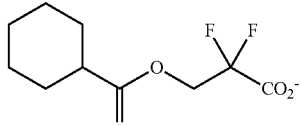
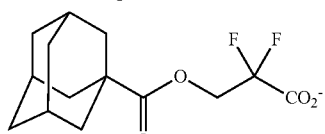
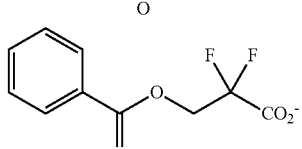
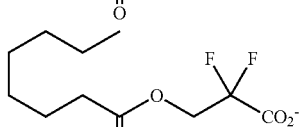
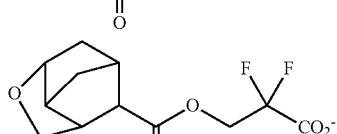
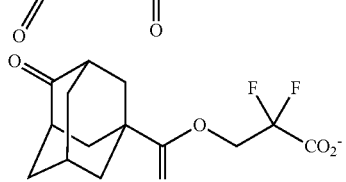
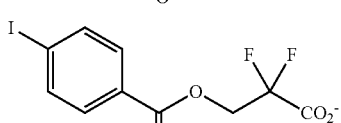
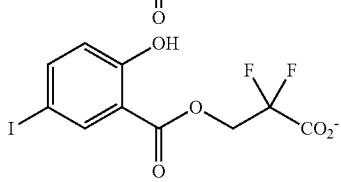
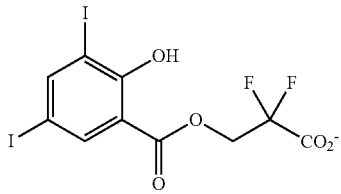
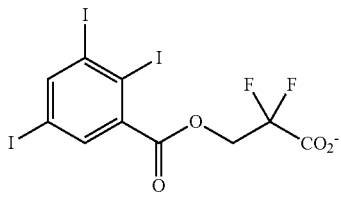

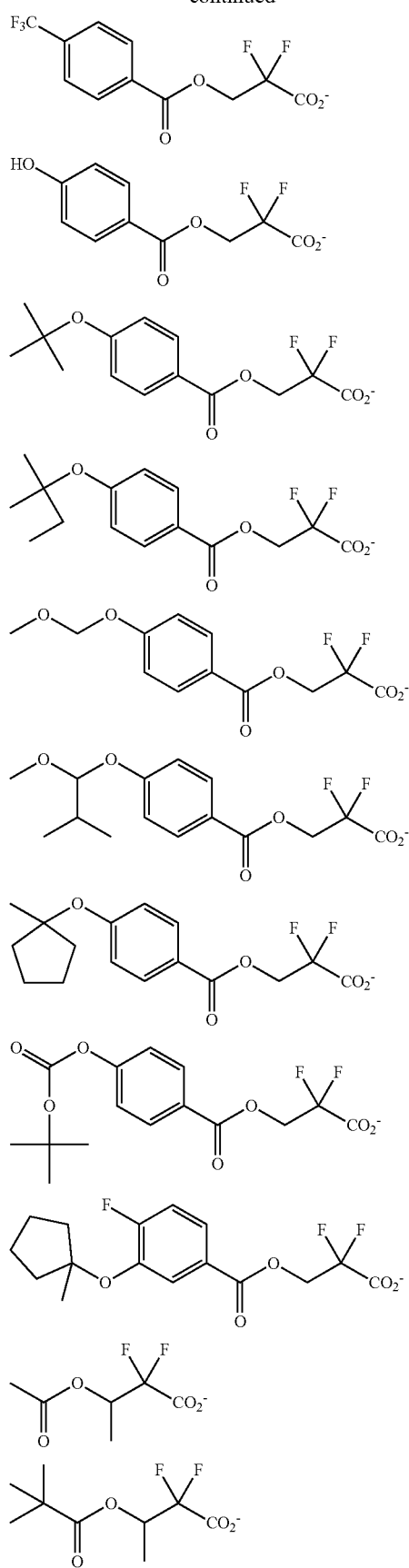
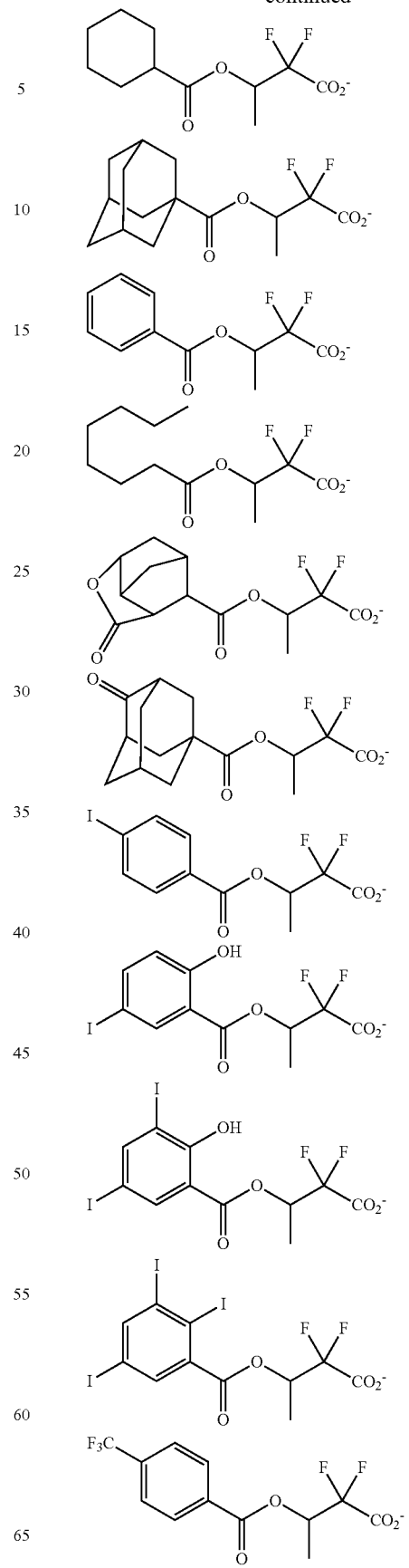

107
-continued
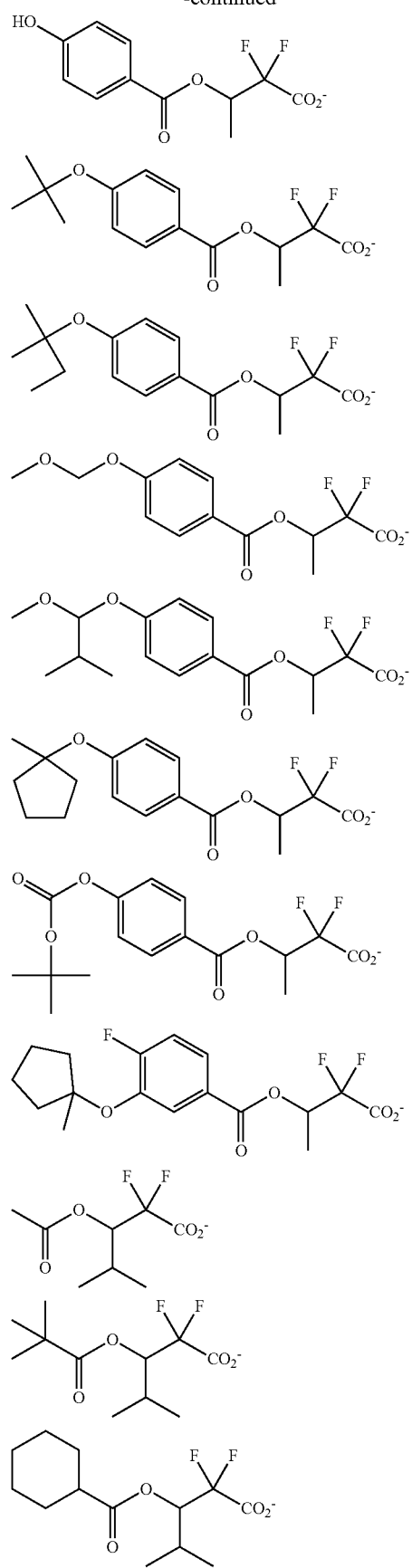
108
-continued
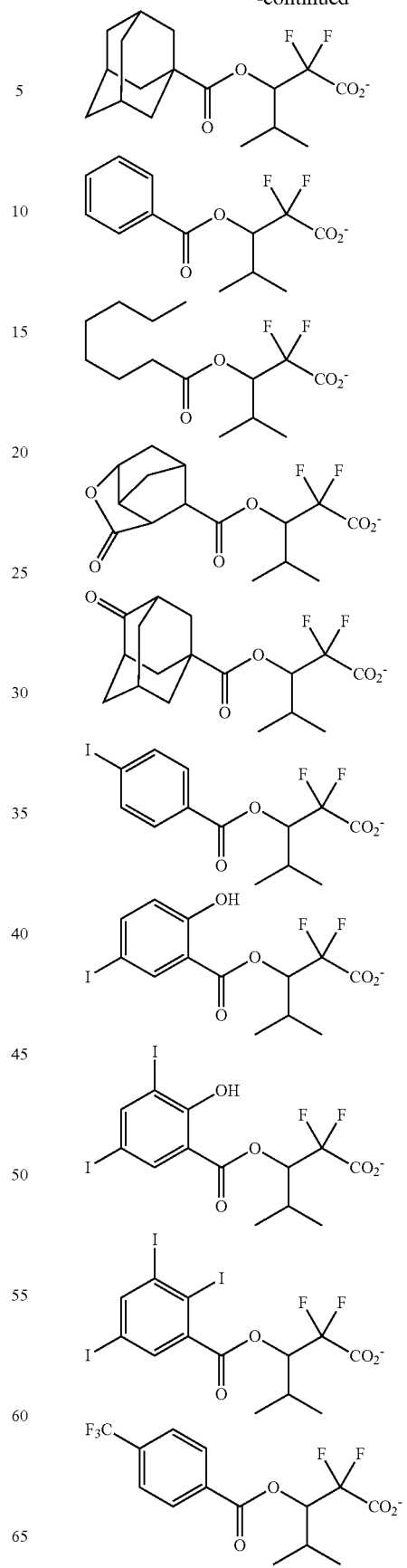

-continued
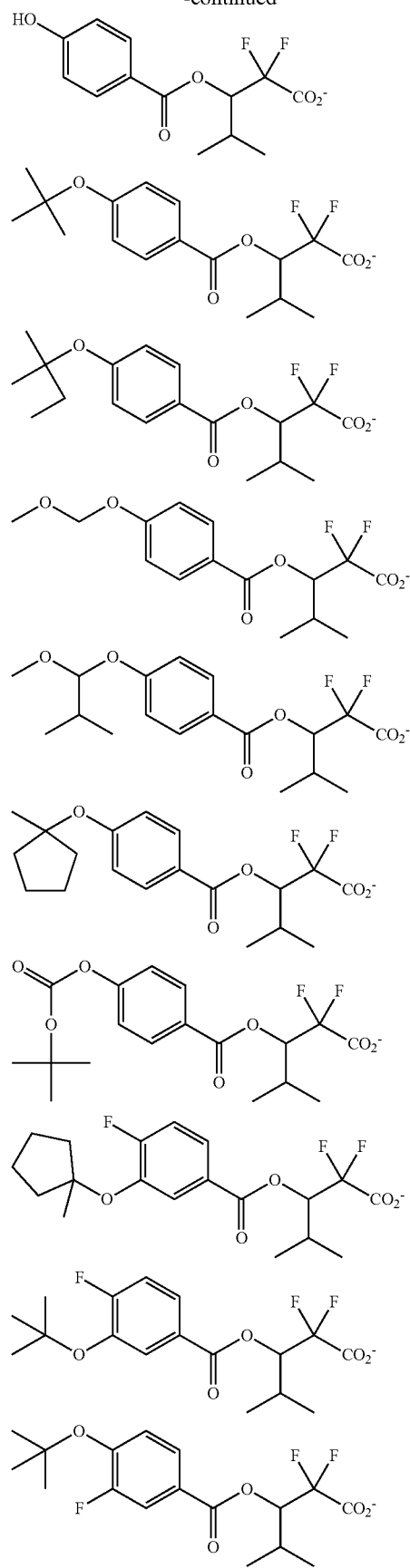
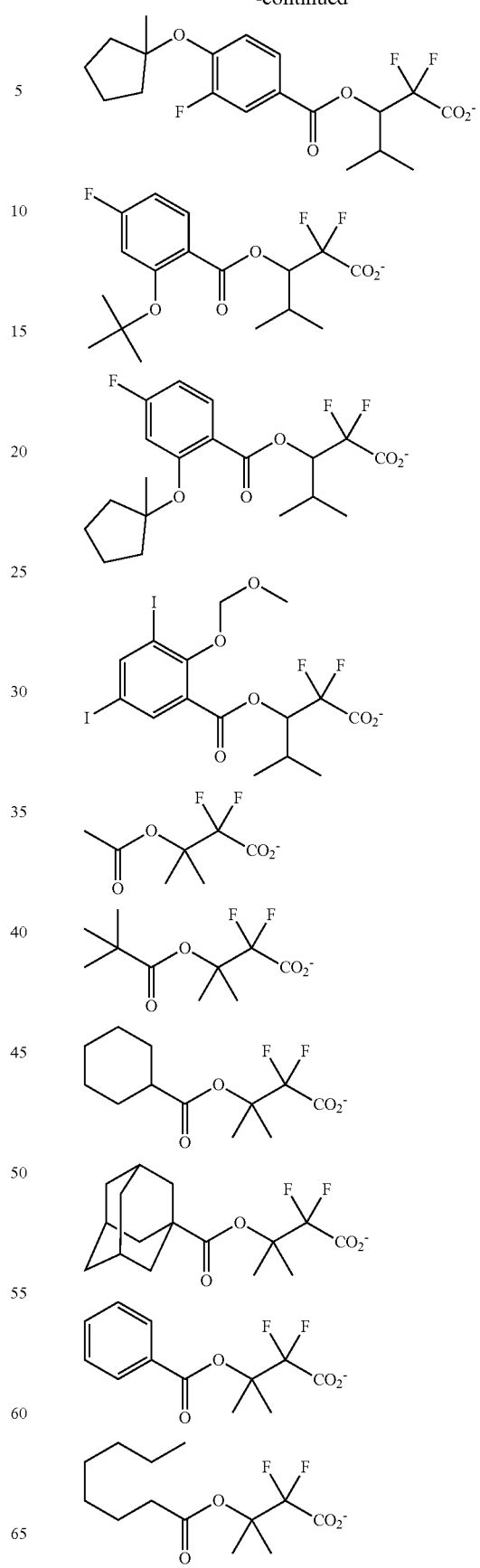

111
-continued
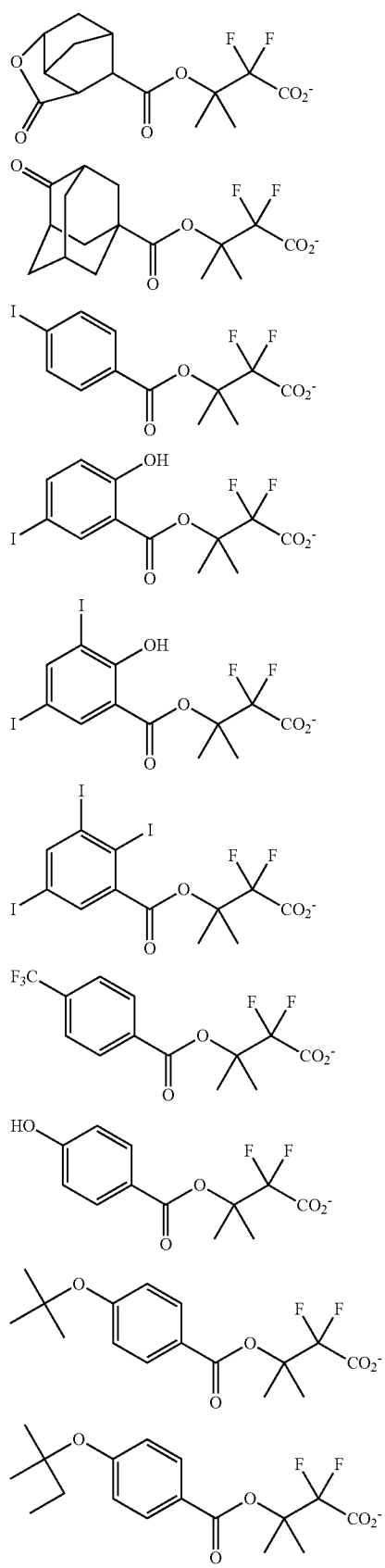
112
-continued
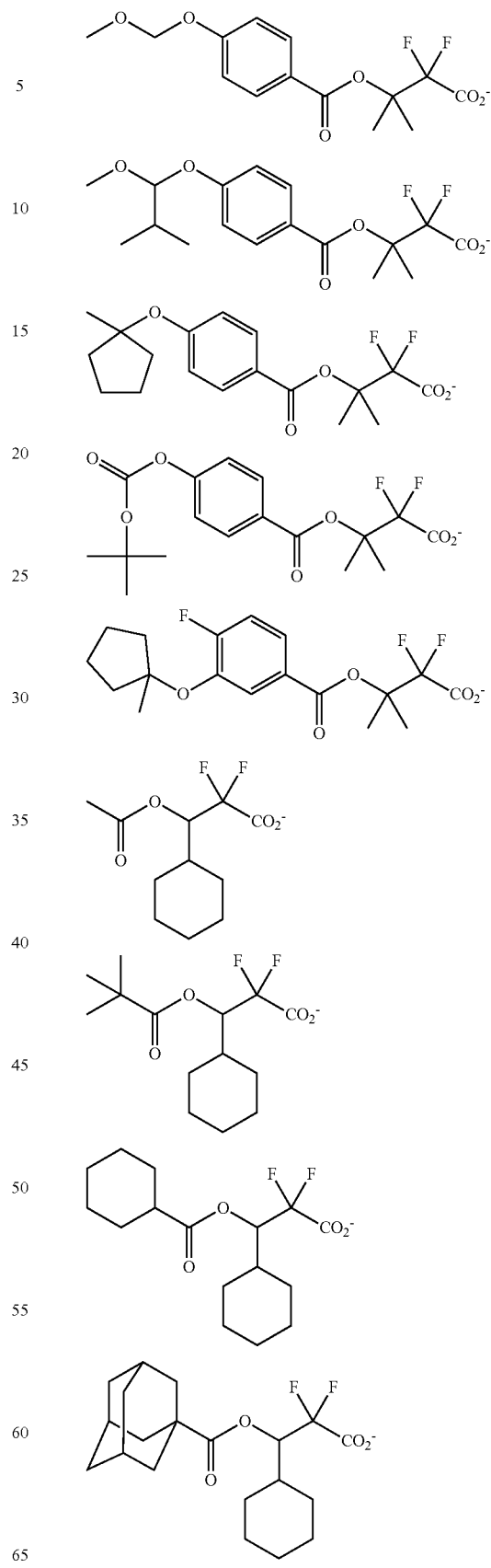

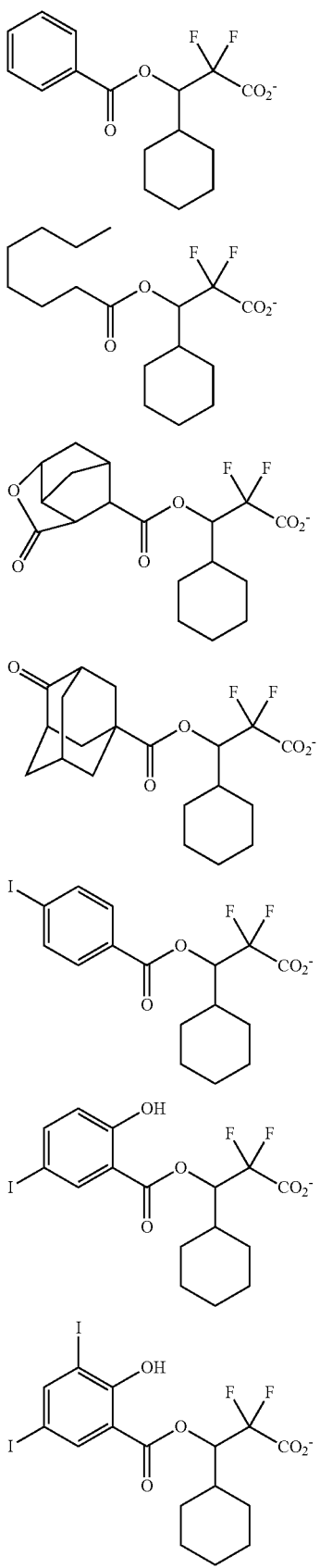
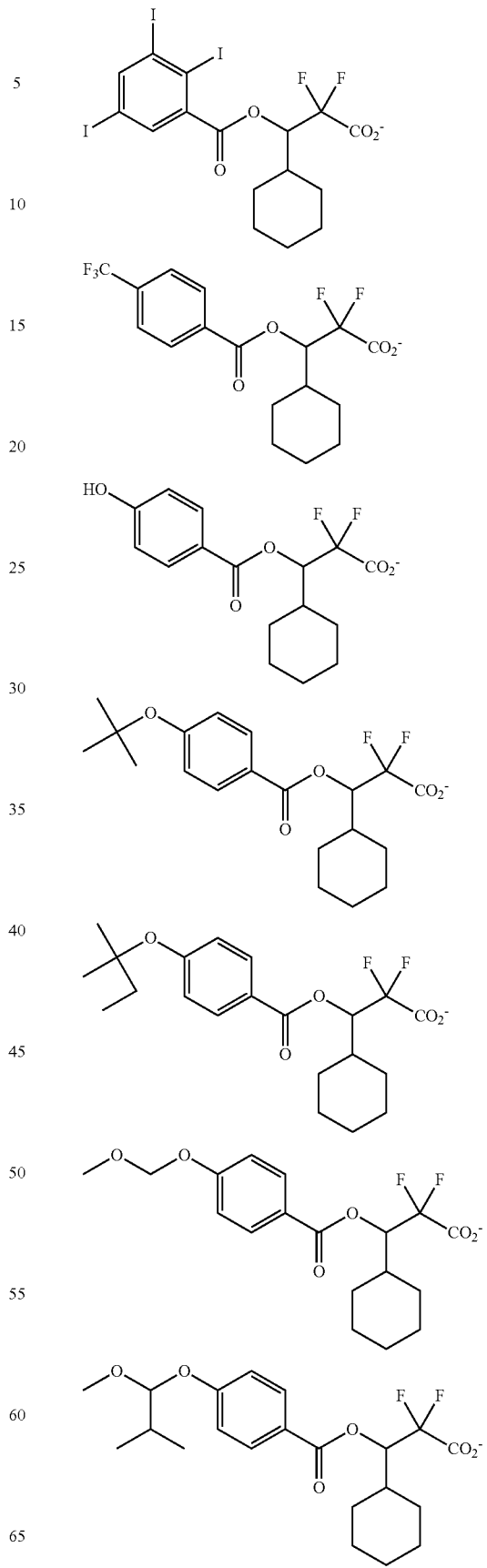

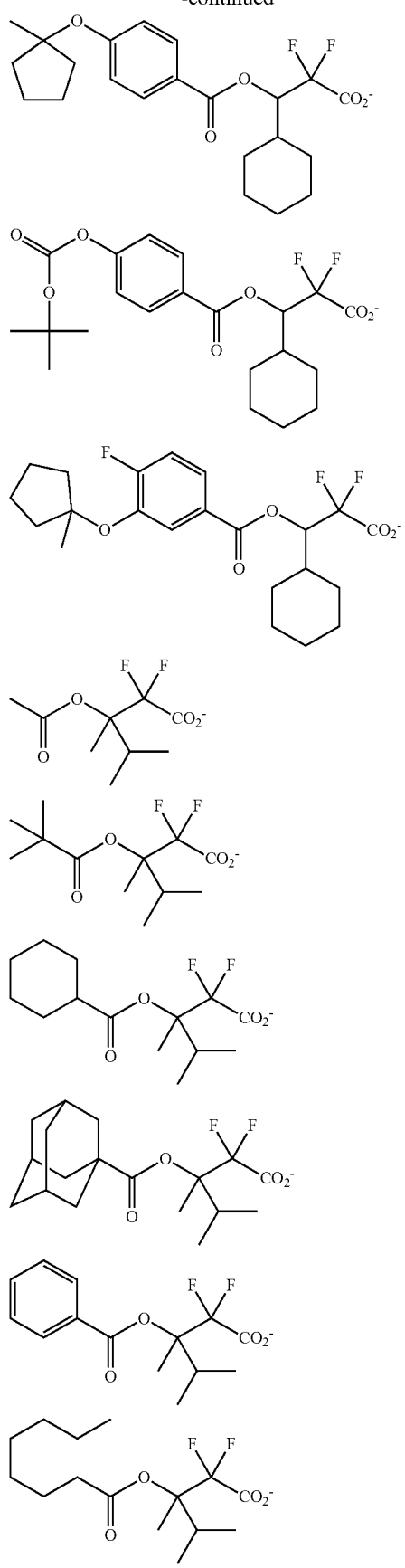
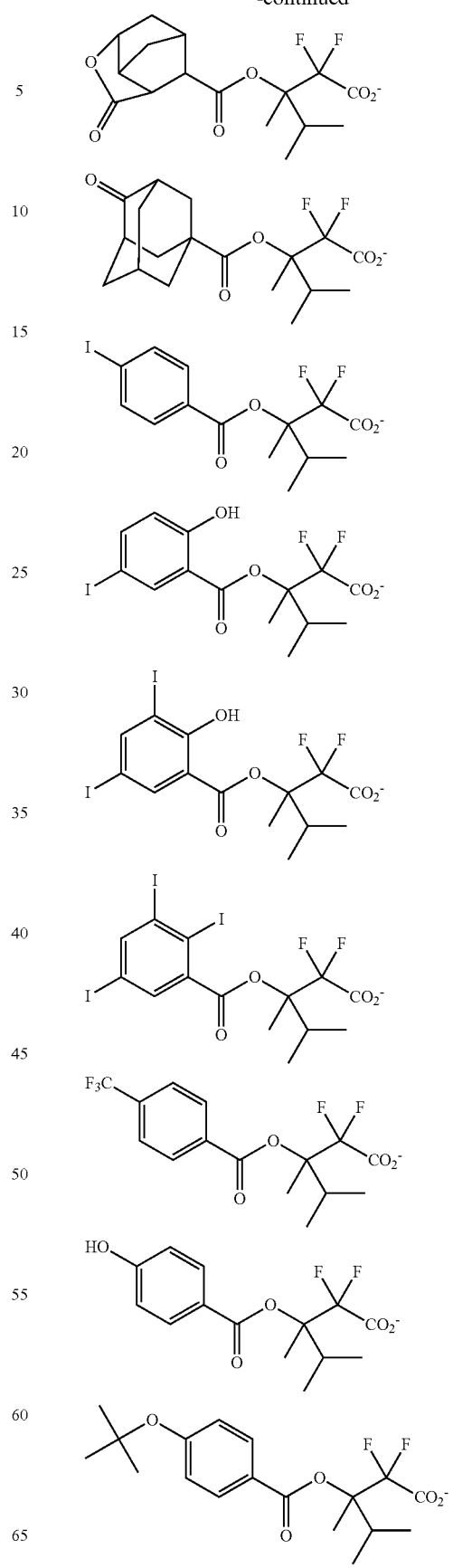

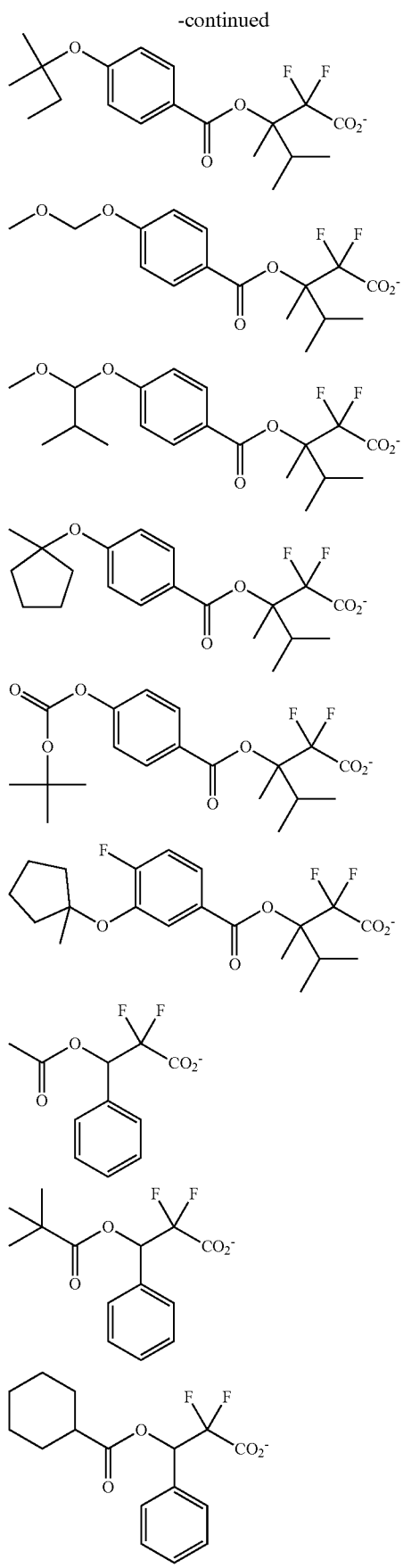
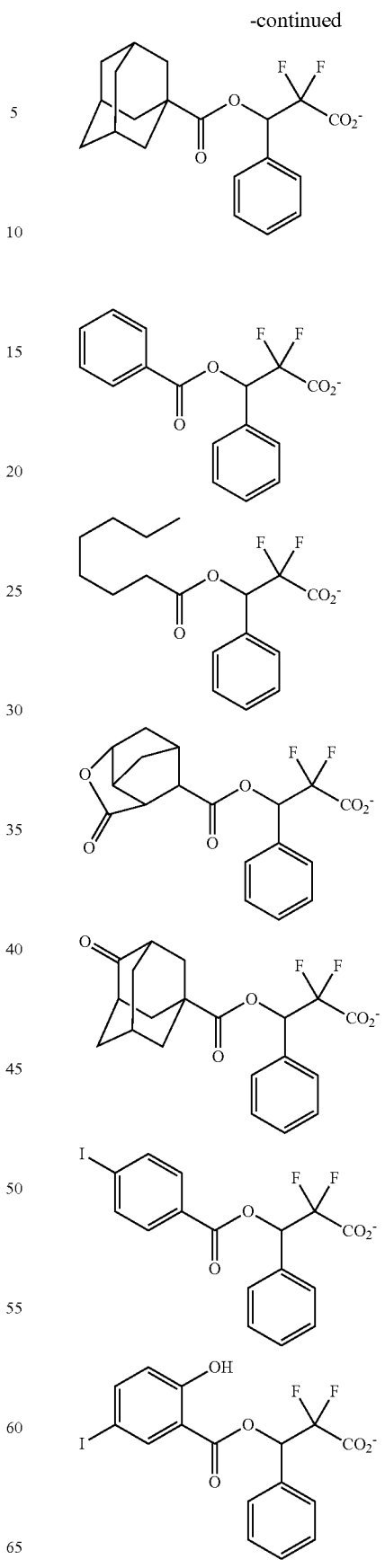

119
-continued
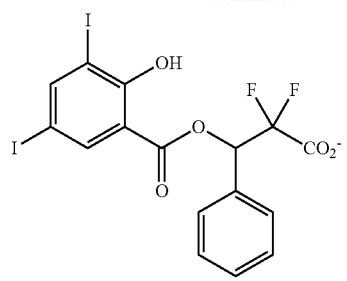
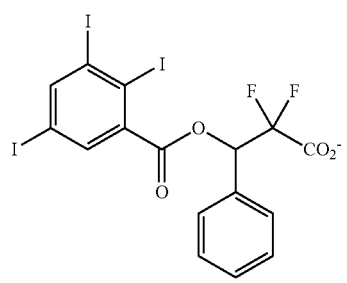
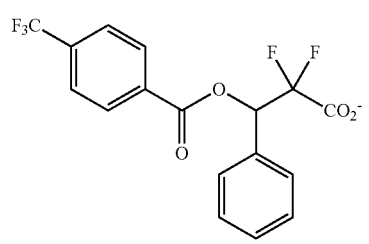
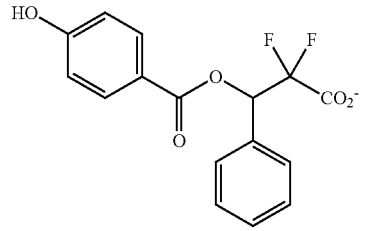
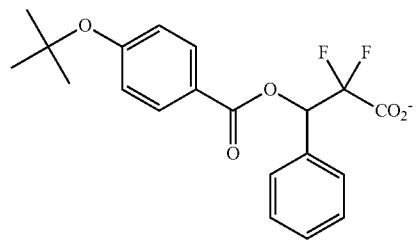
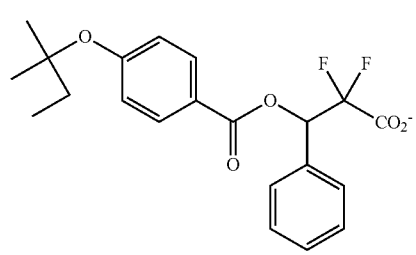
120
-continued
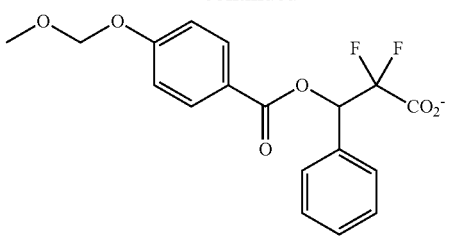
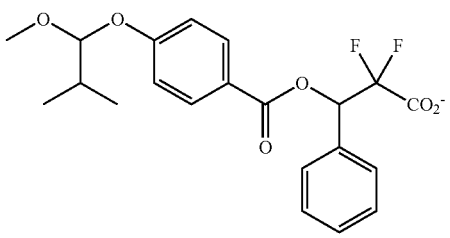
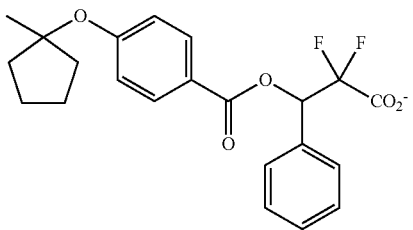
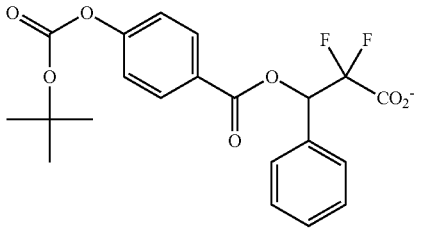
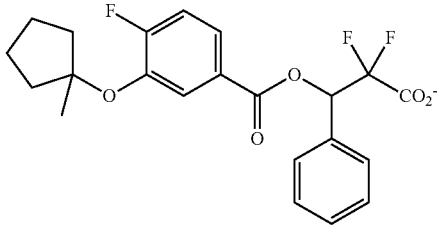
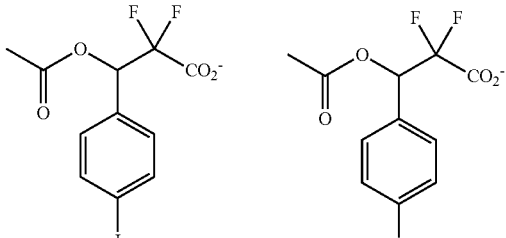
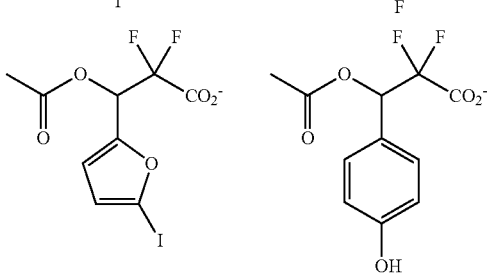

121
-continued
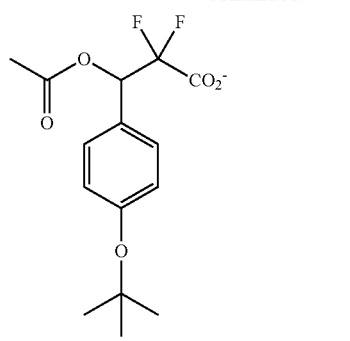
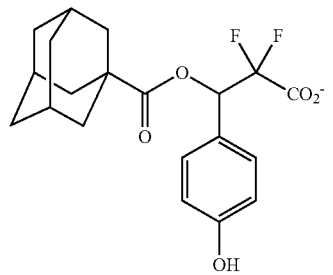
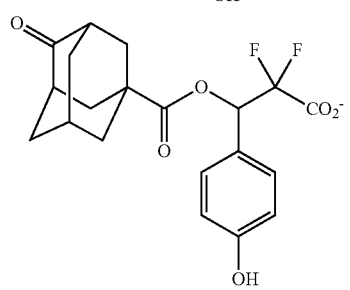
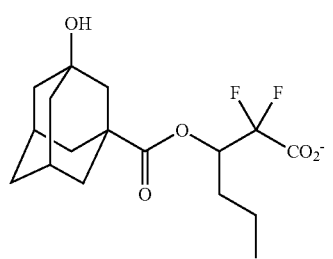
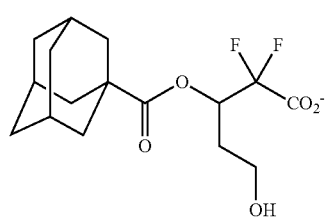
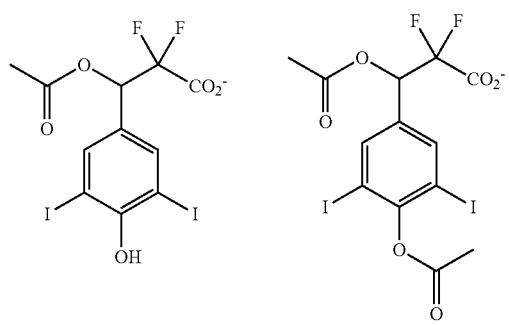
122
-continued
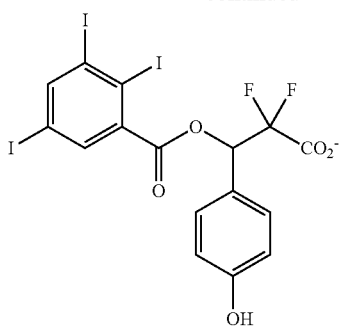
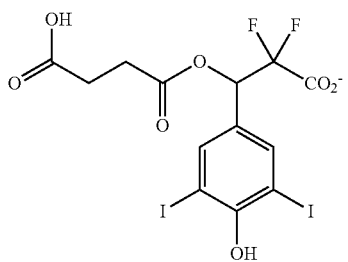
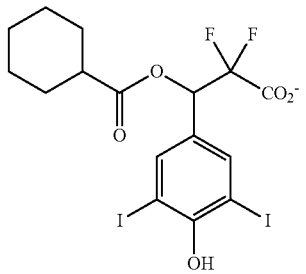
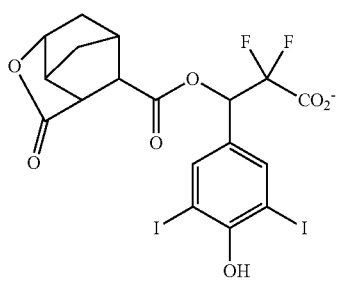
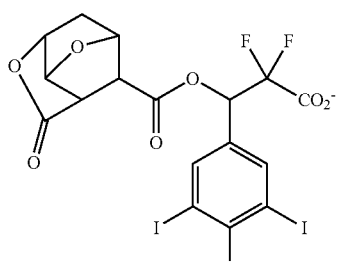
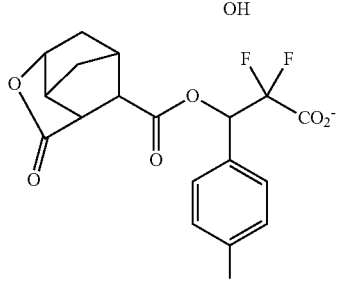

123
-continued
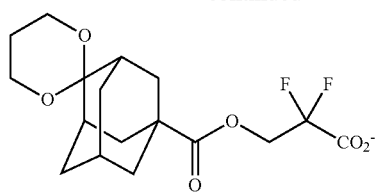
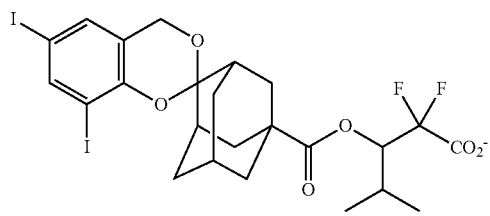
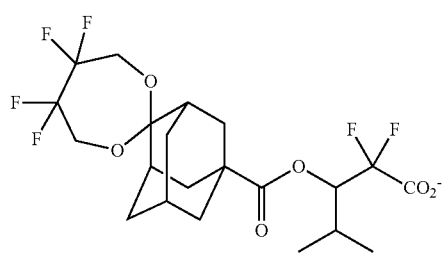
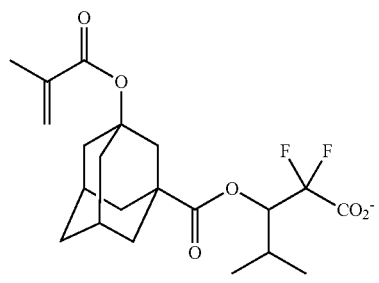
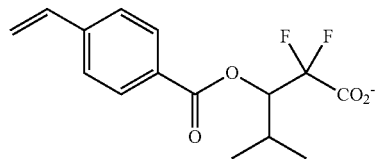
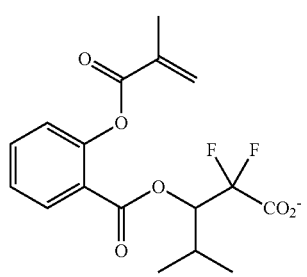
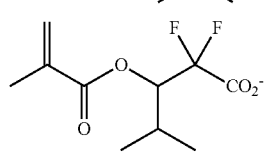
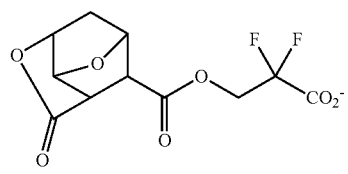
124
-continued
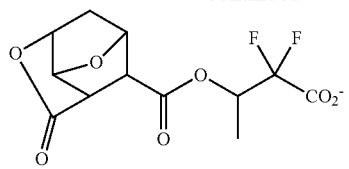
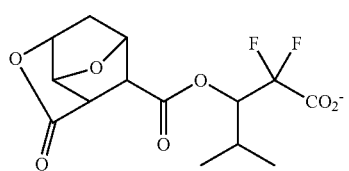
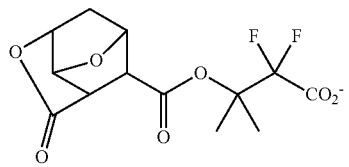
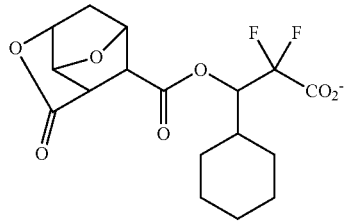
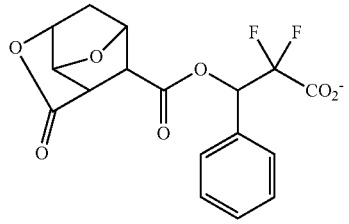
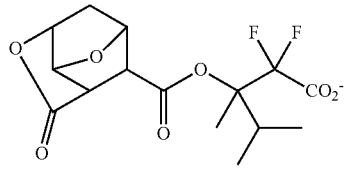
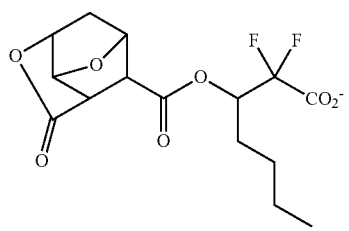
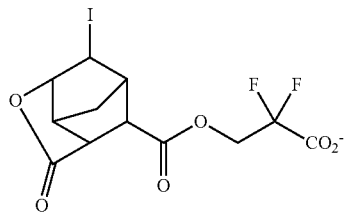

125
-continued
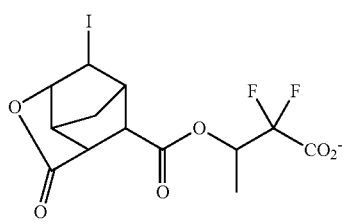
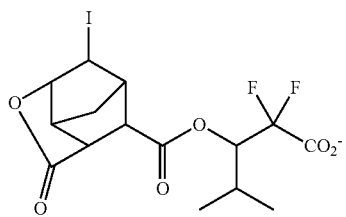
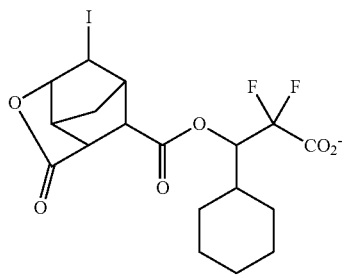
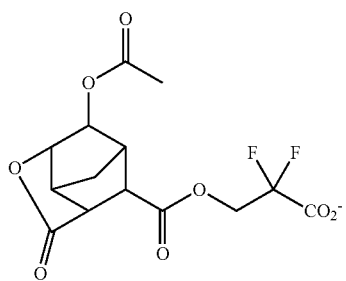
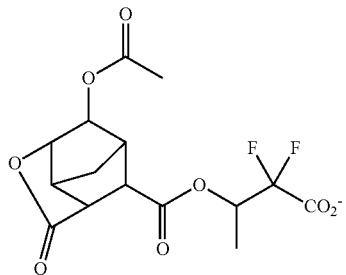
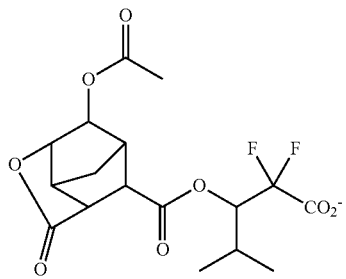
126
-continued
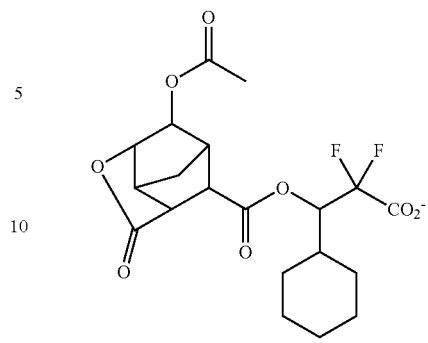
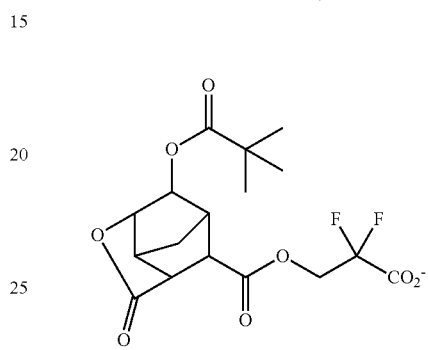
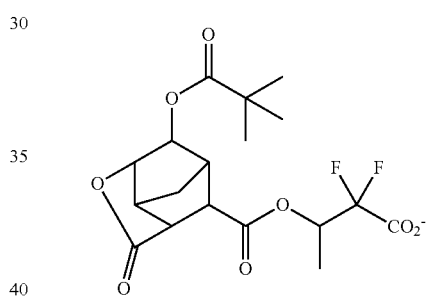
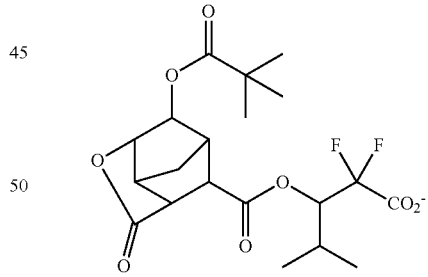
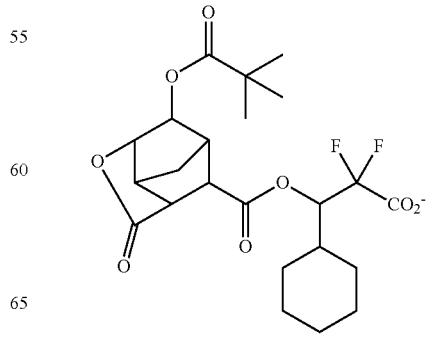

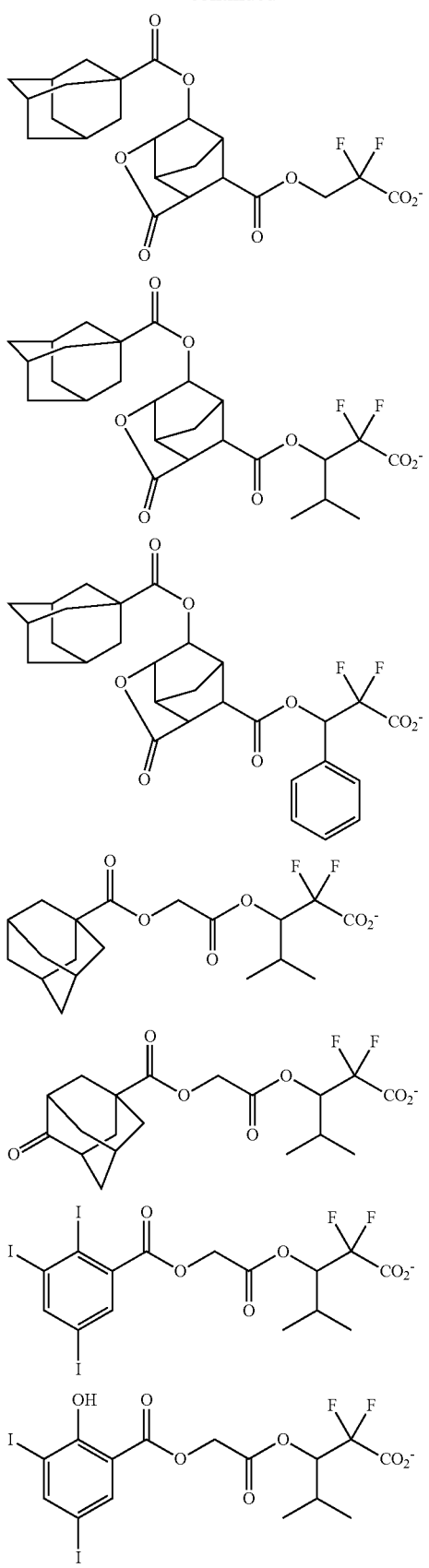
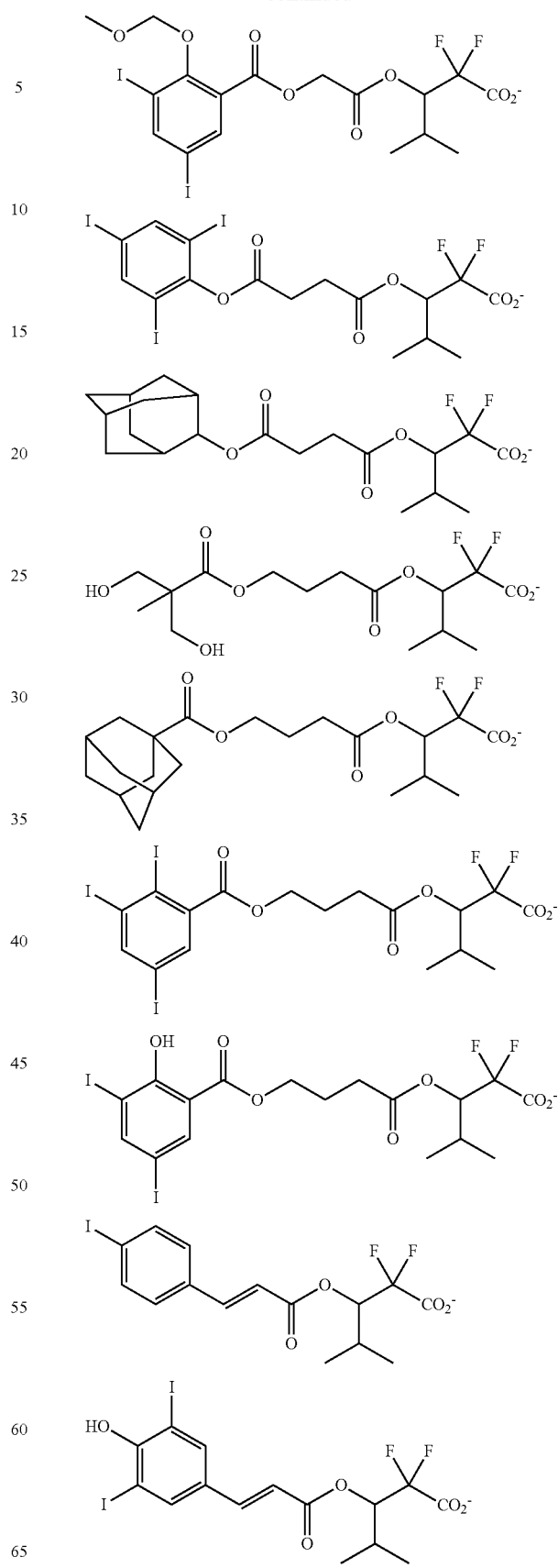

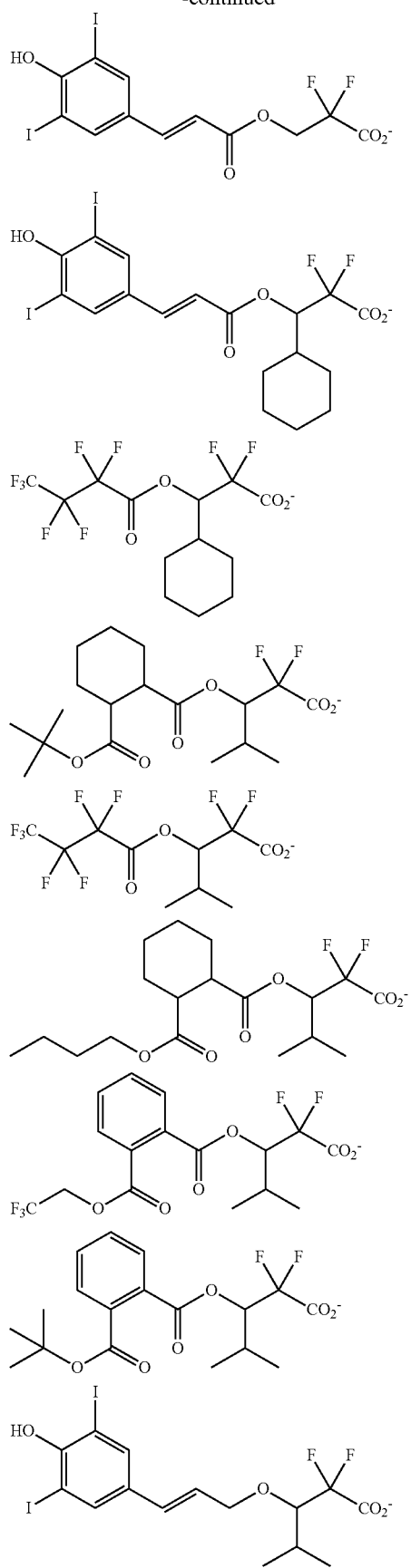
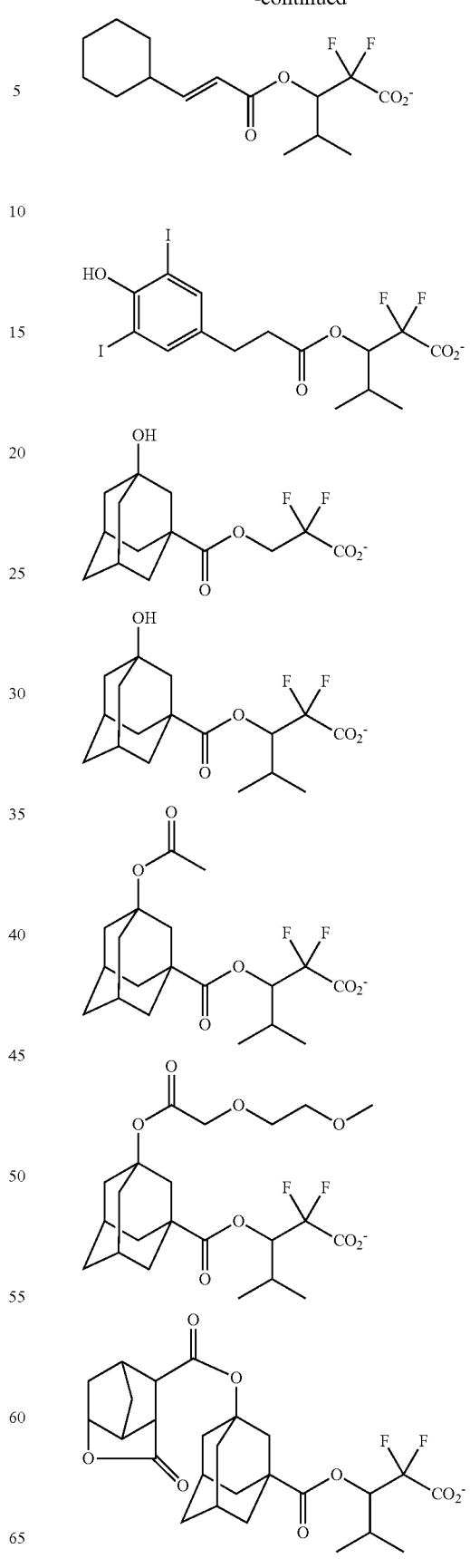

131
-continued
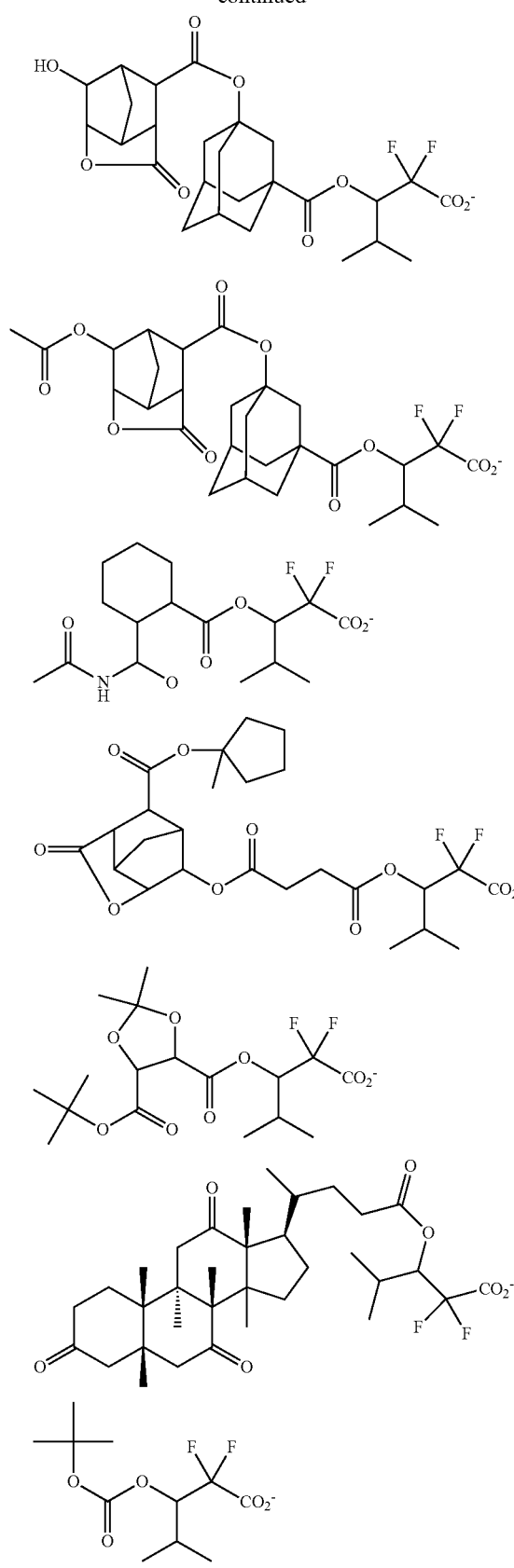
132
-continued
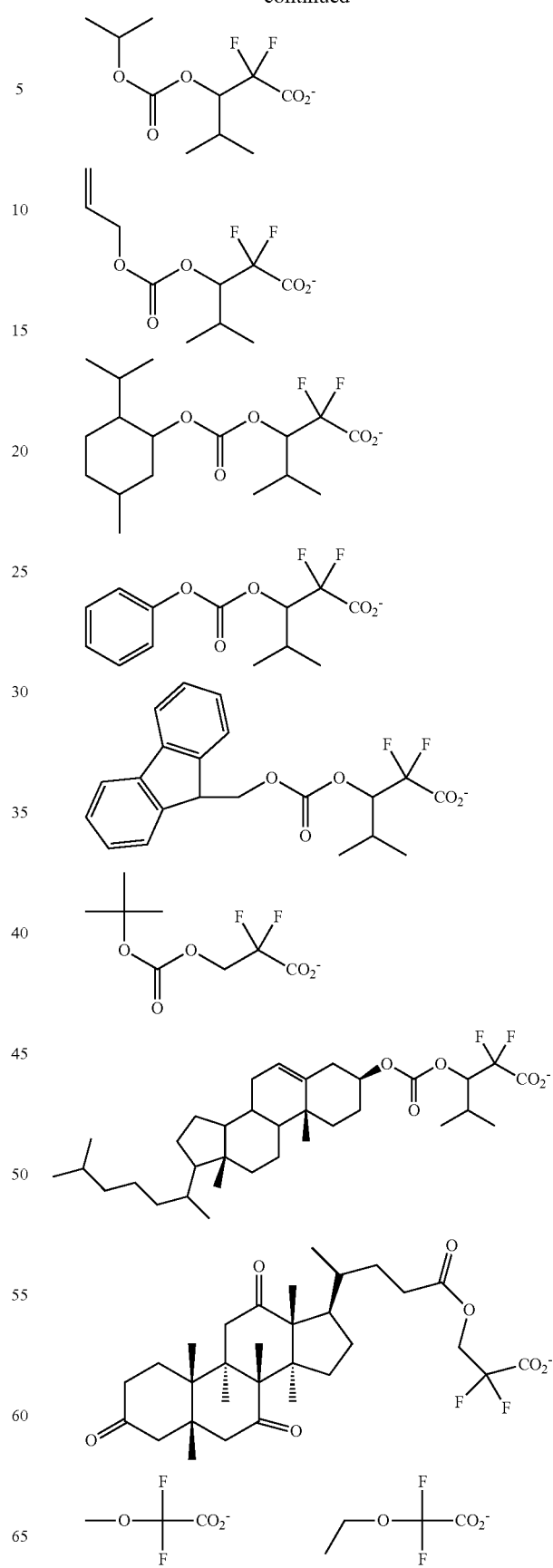

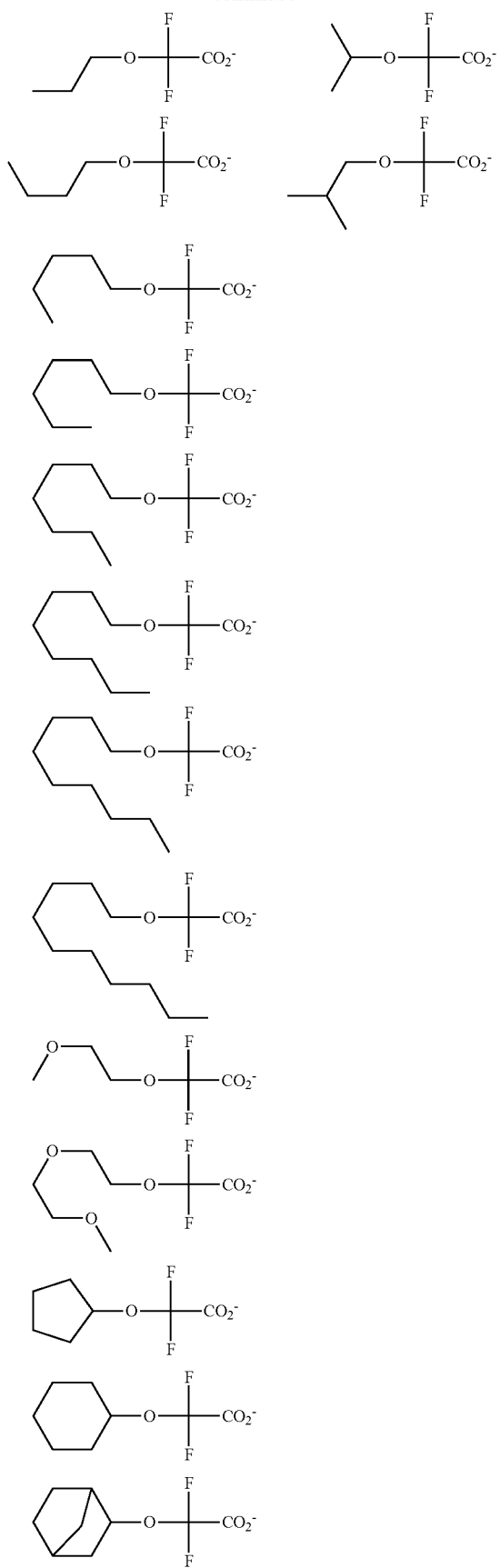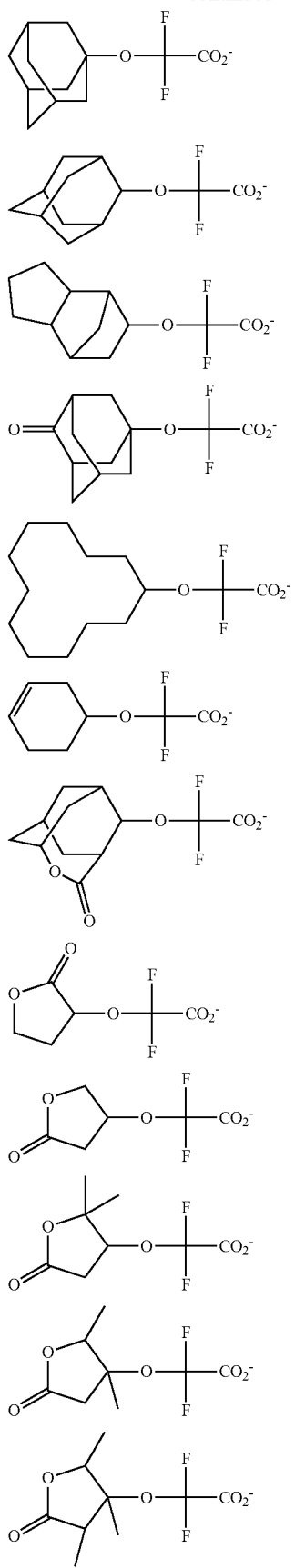

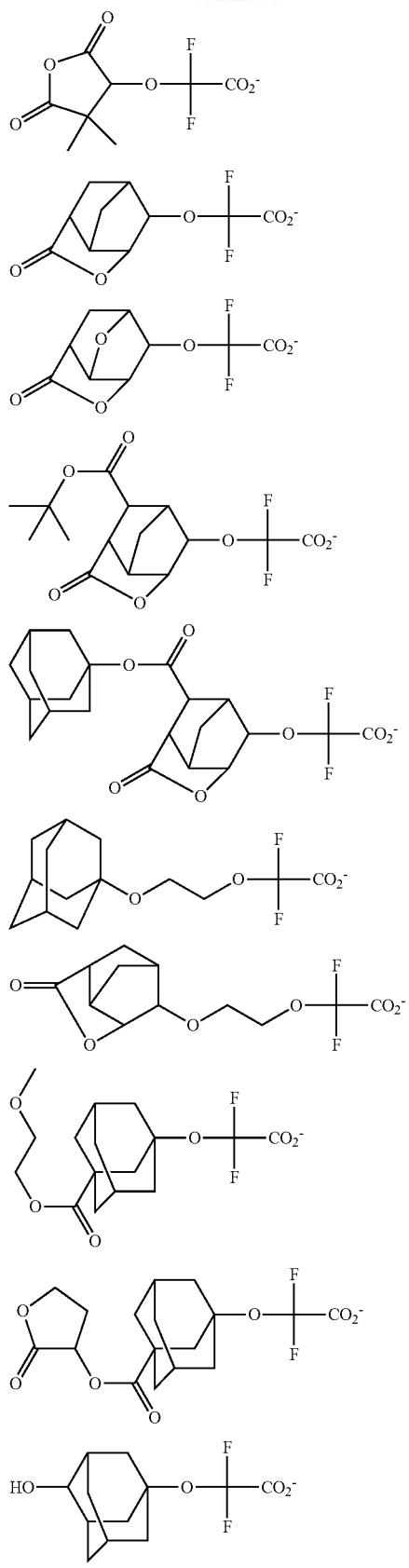
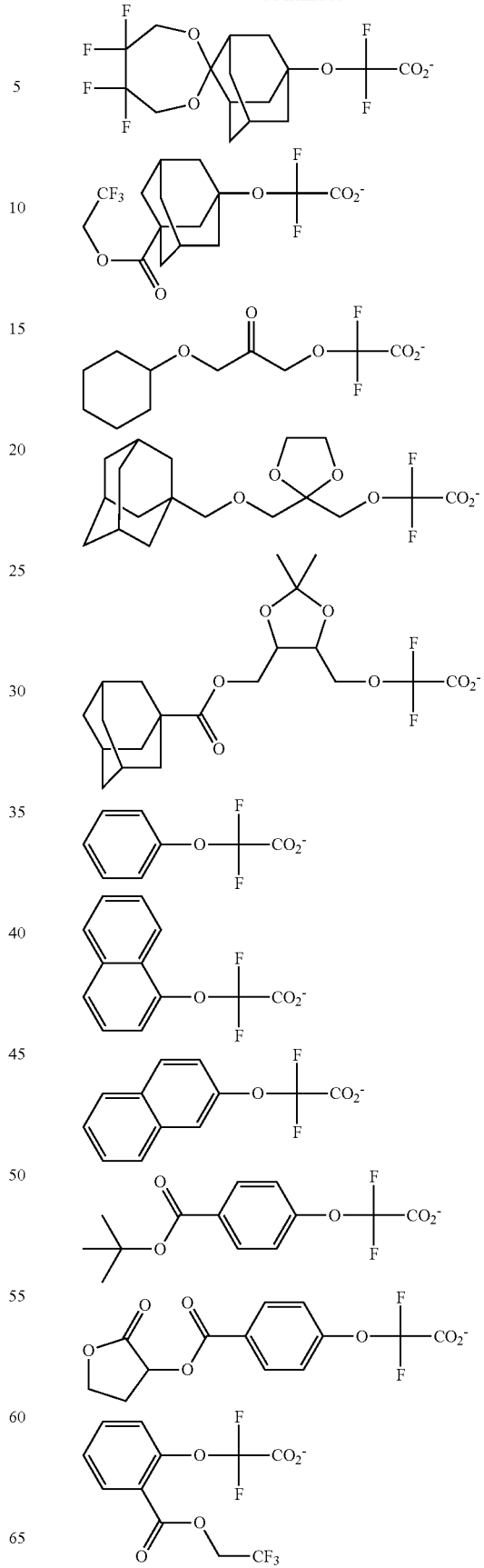

137
-continued
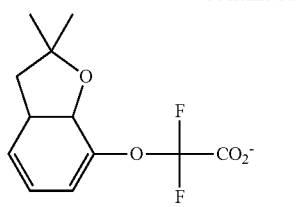
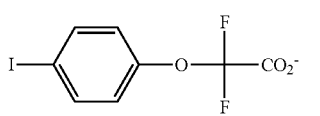
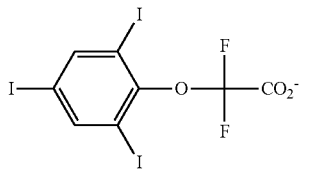
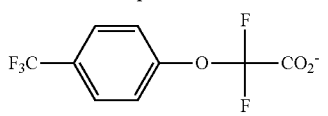
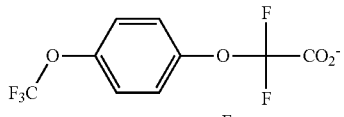
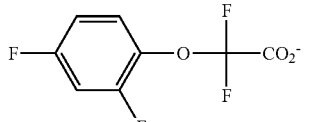
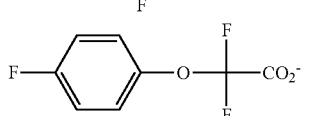
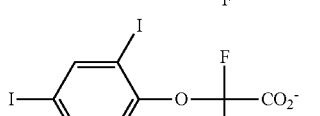
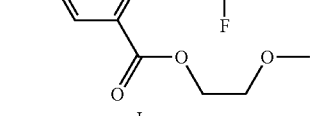
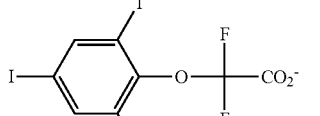
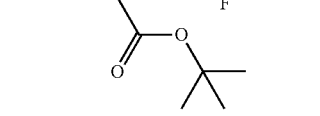
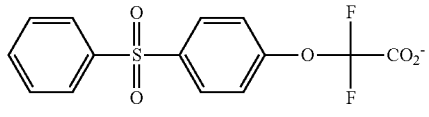
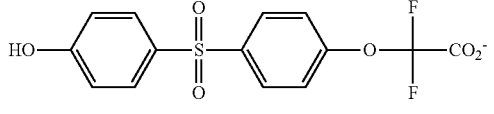
138
-continued
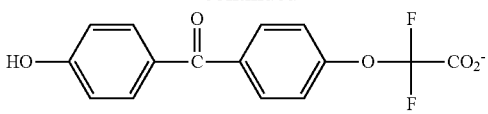
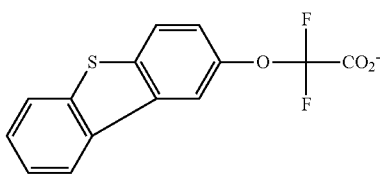
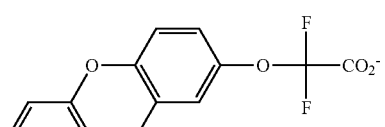
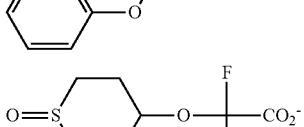
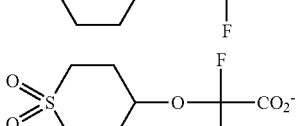
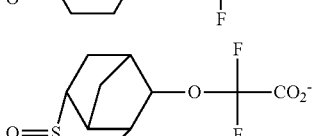
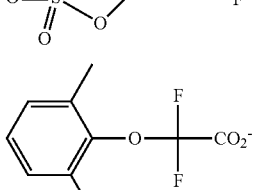
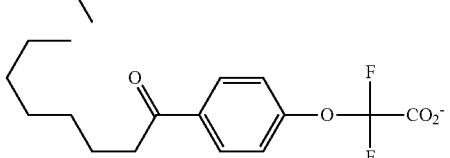
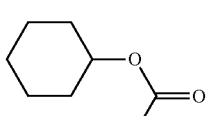
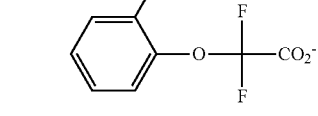
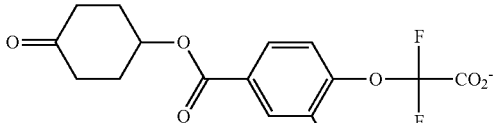
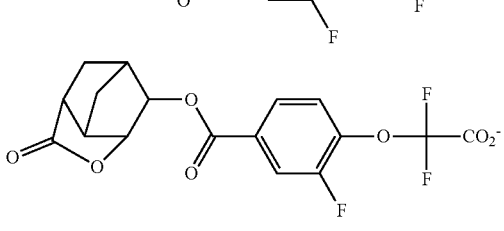

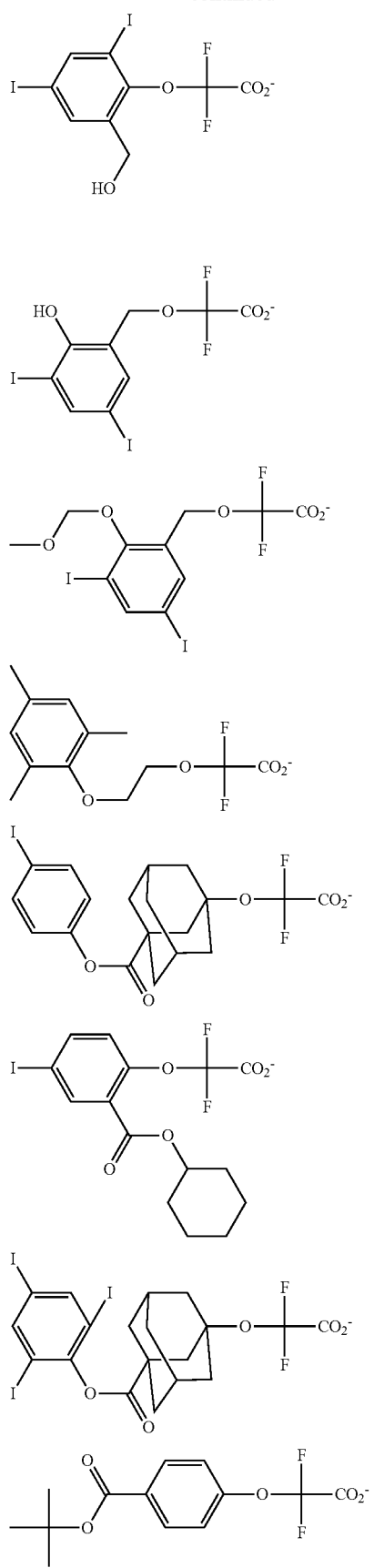
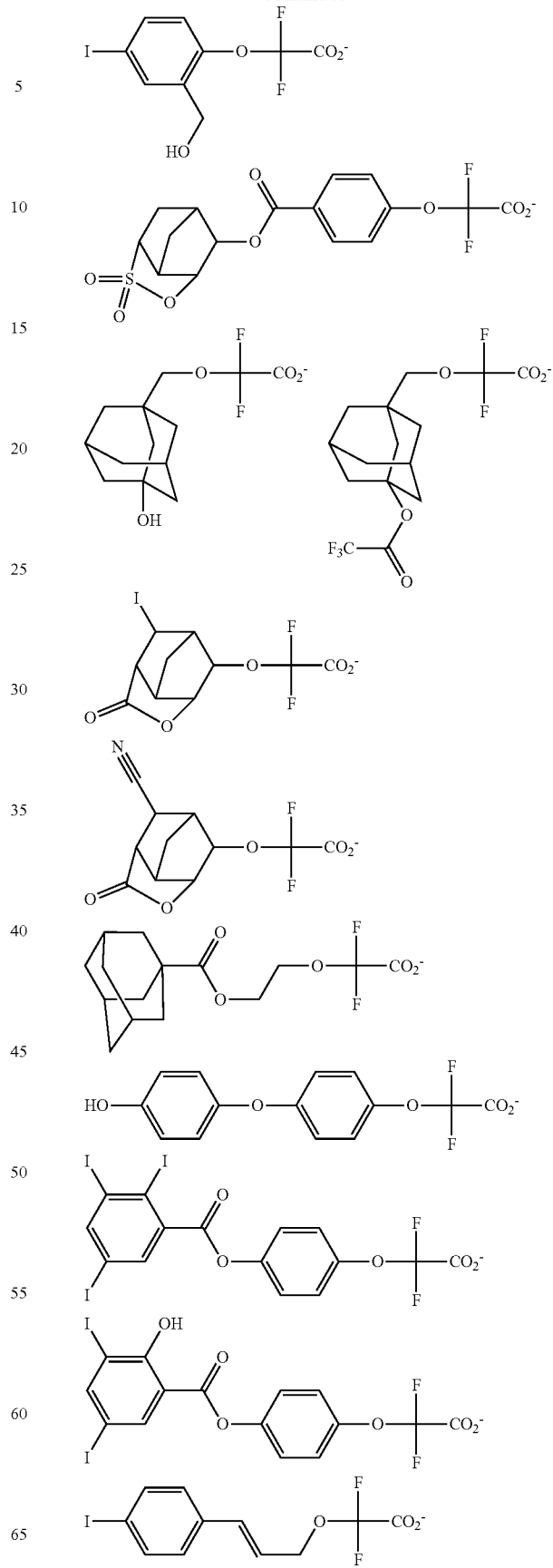

-continued
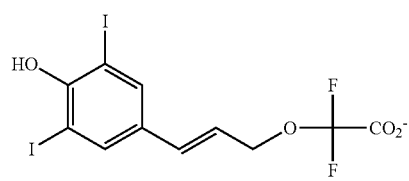
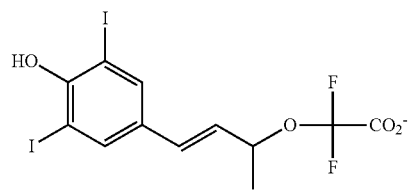
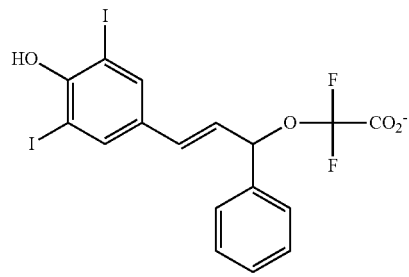
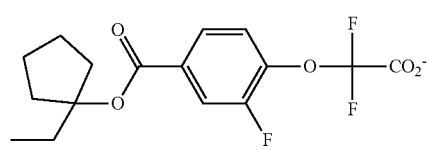
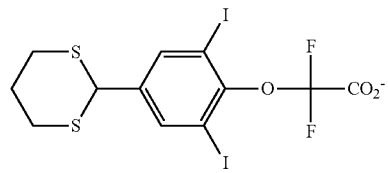
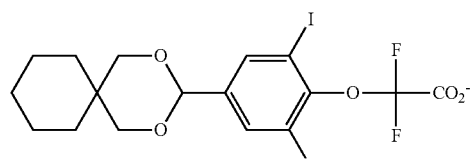
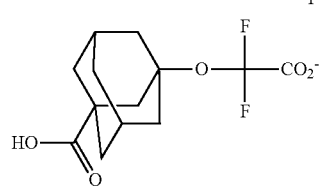
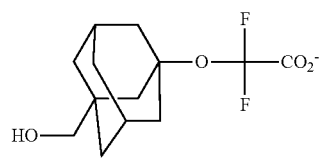
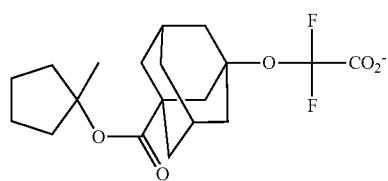
-continued
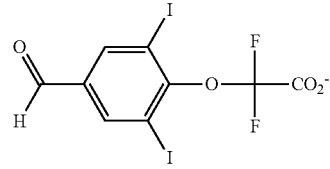
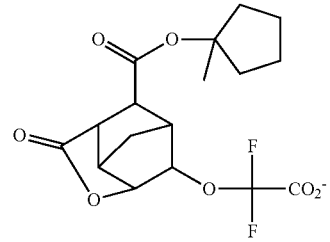
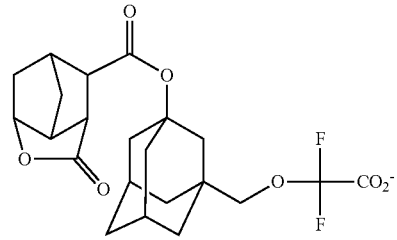
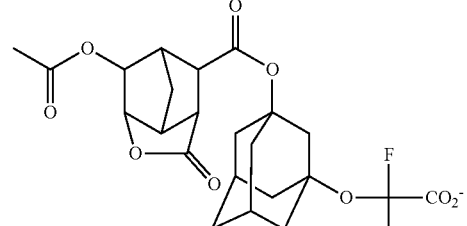
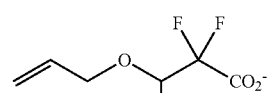
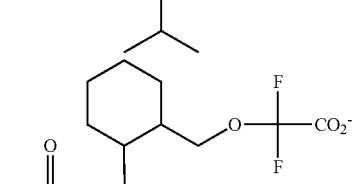
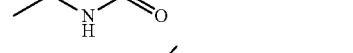
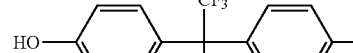
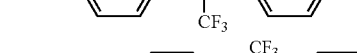

-continued
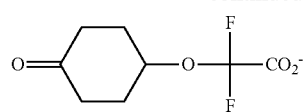
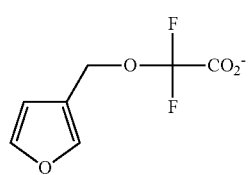
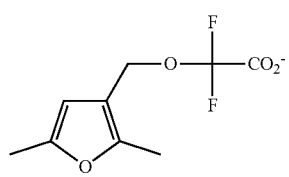
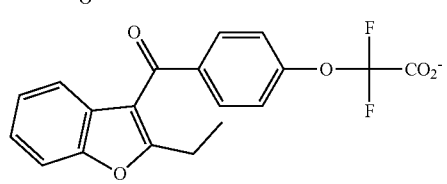
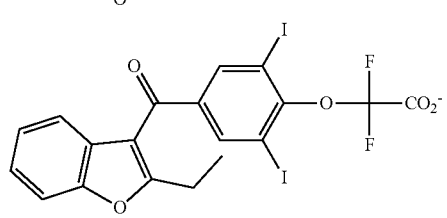
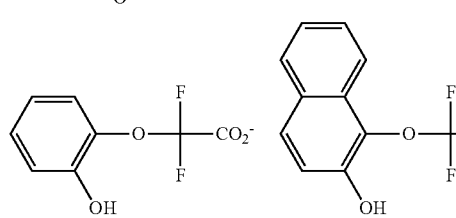
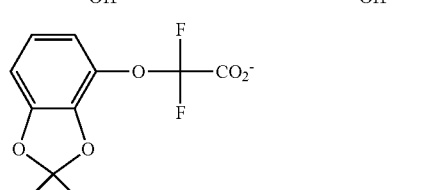
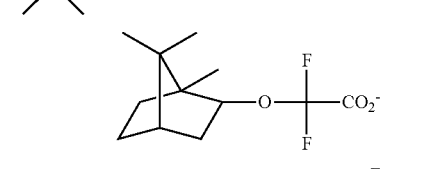
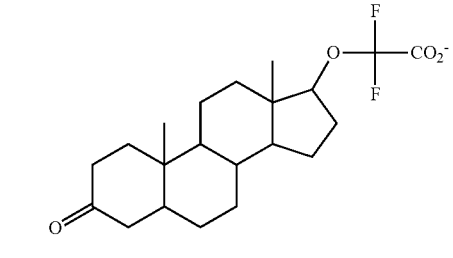
-continued
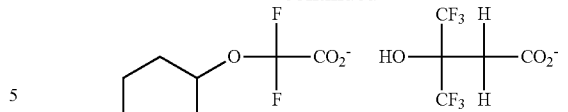
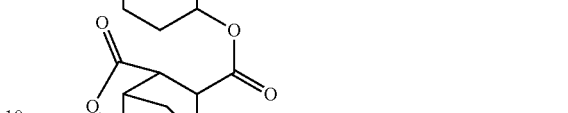
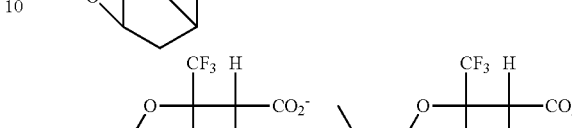
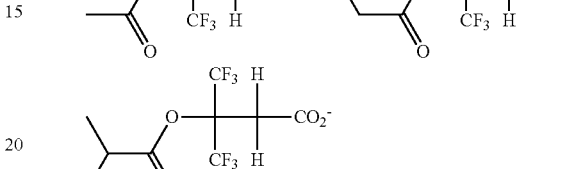
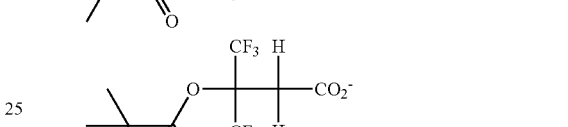
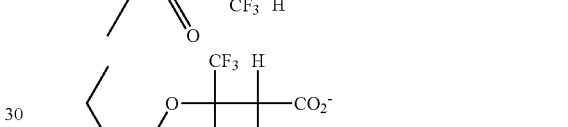
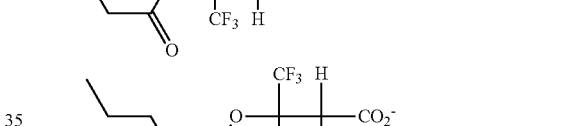
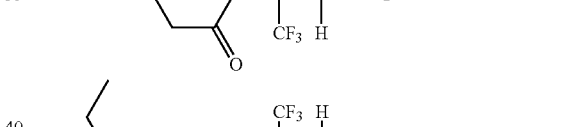
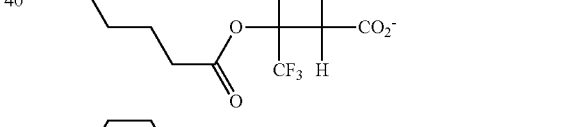
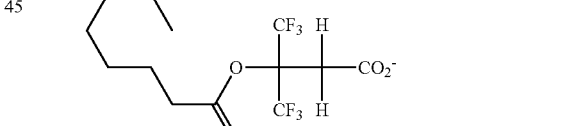
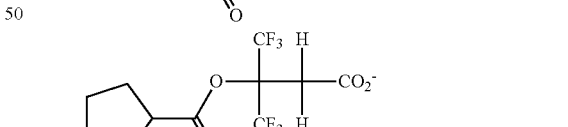
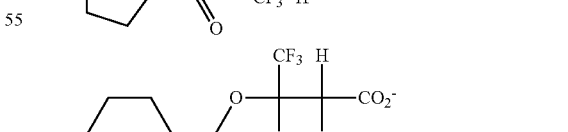
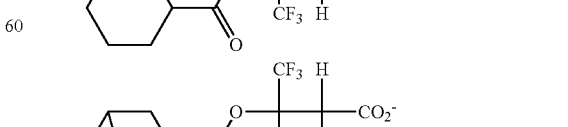
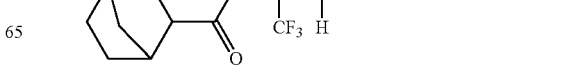

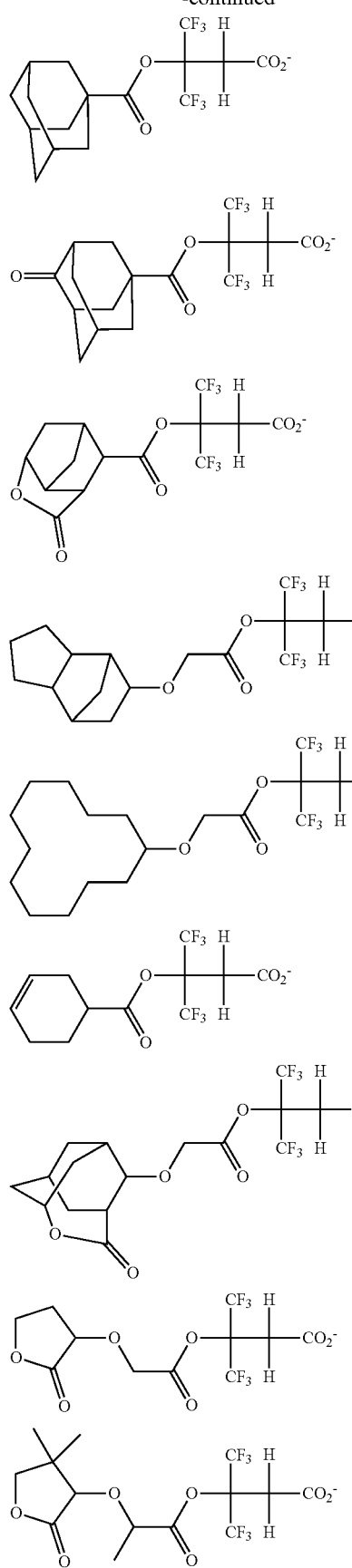
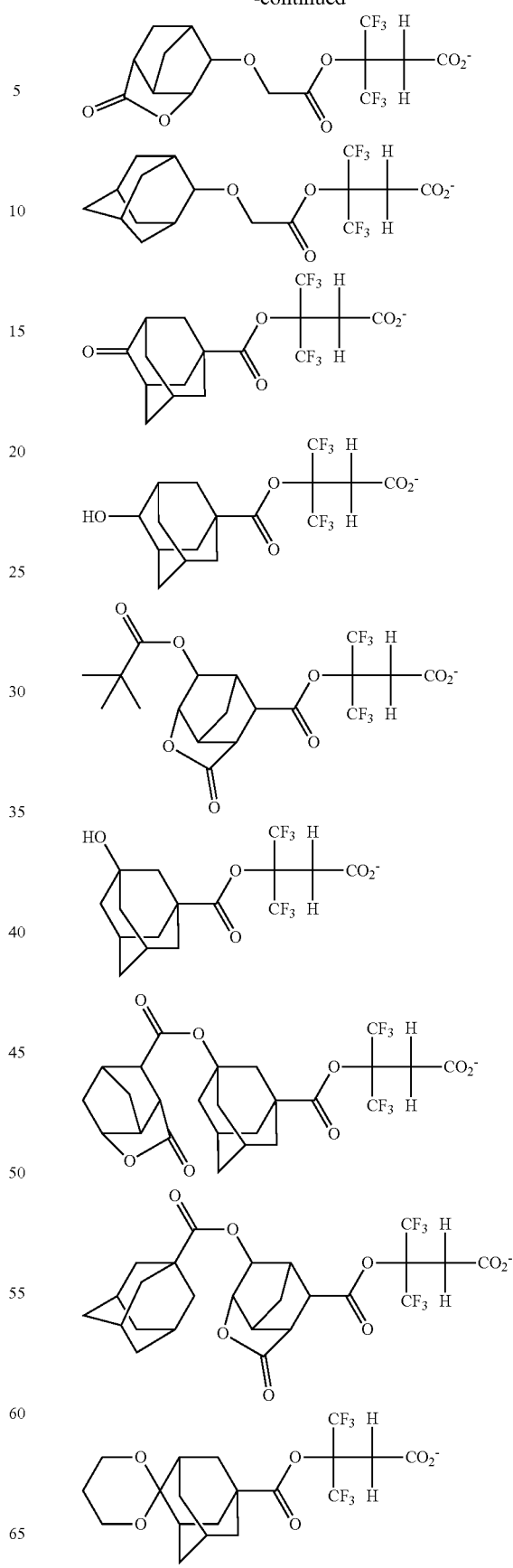

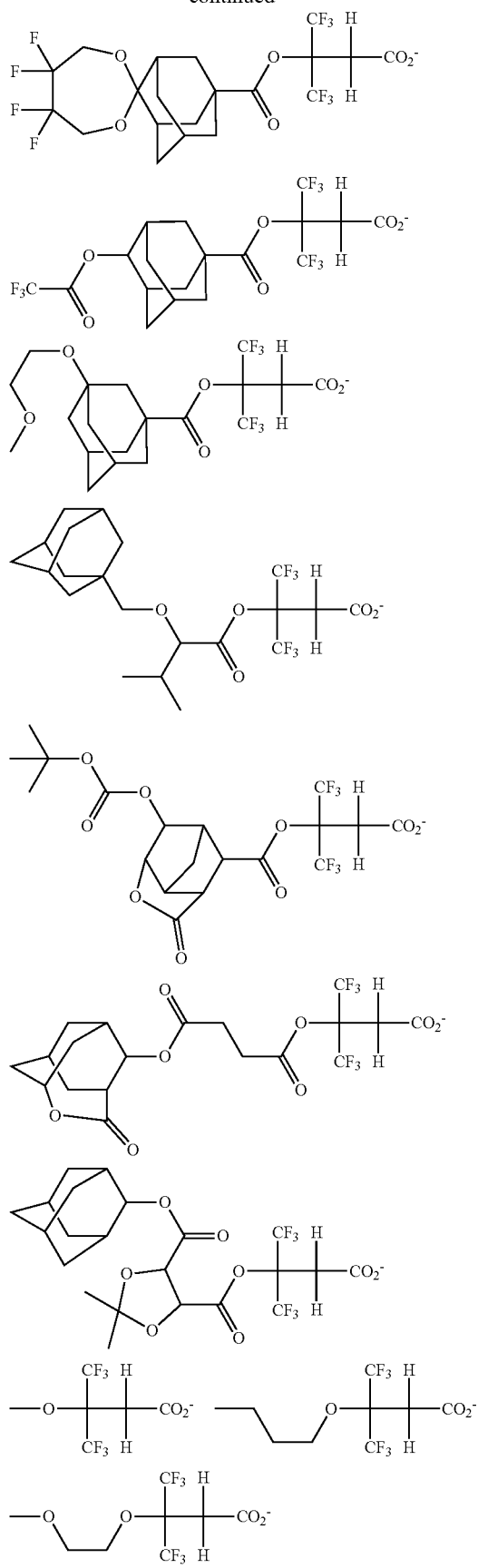
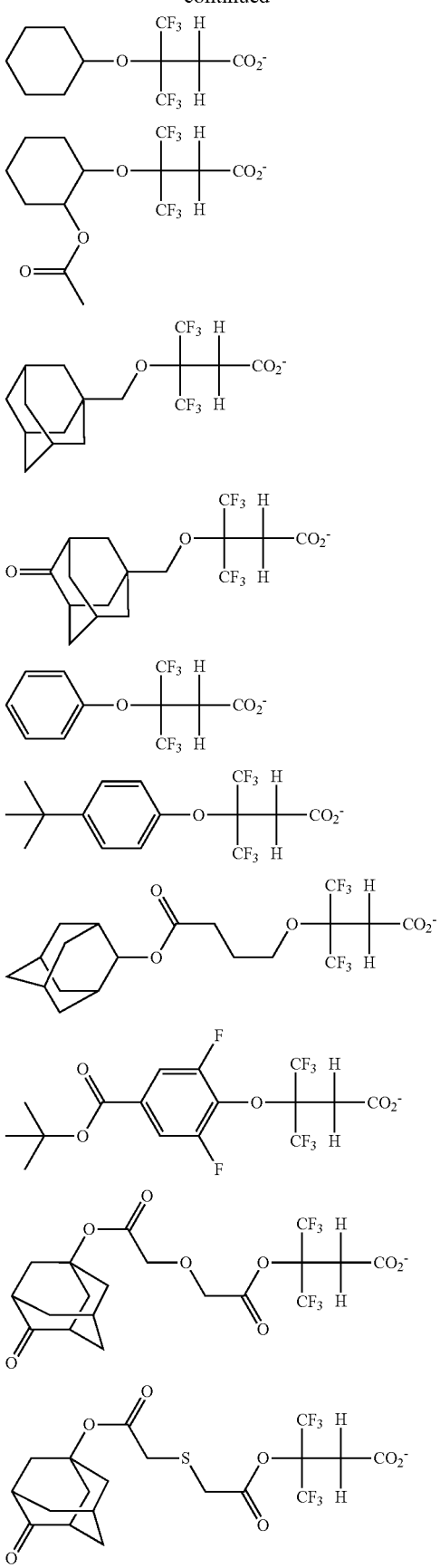

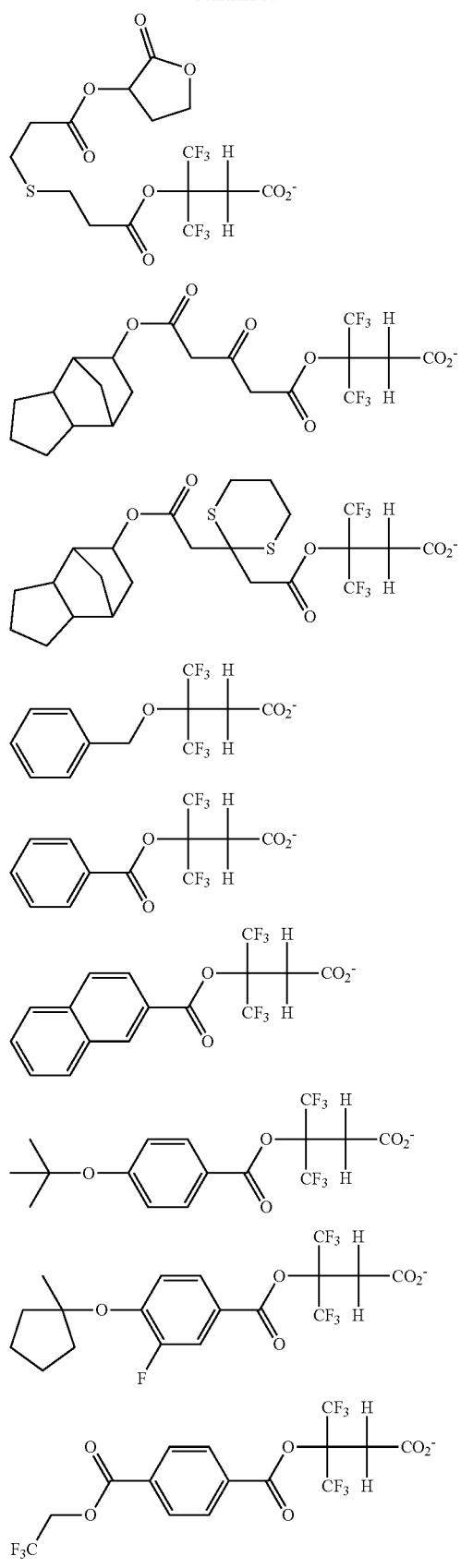
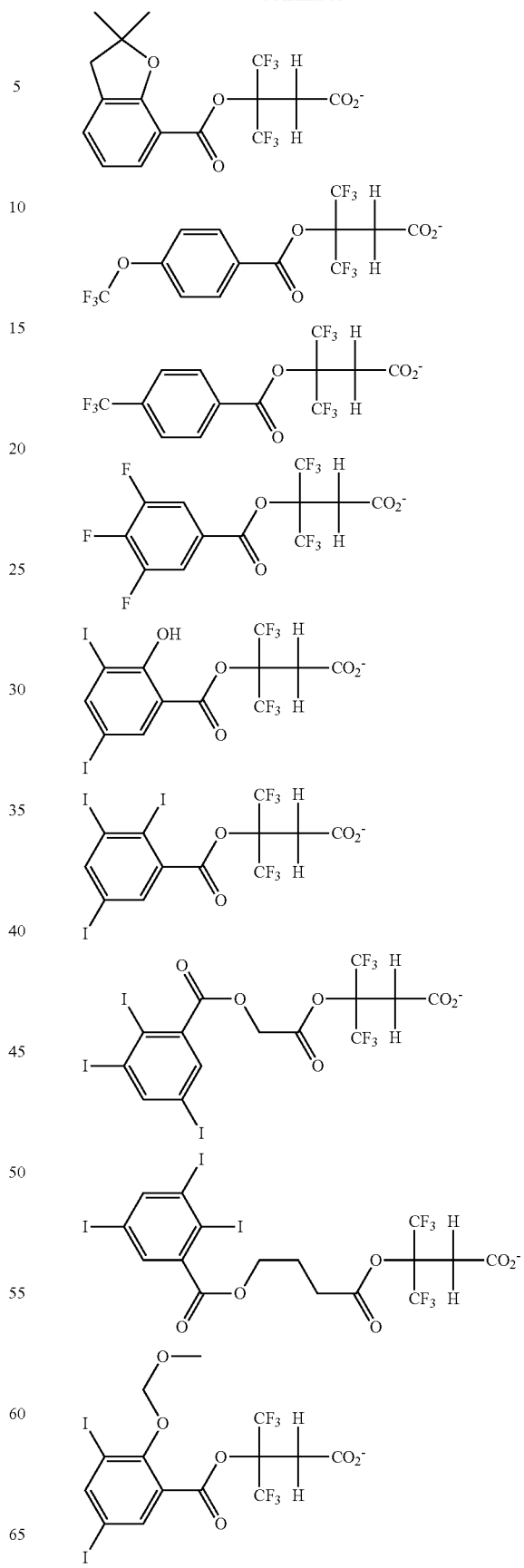

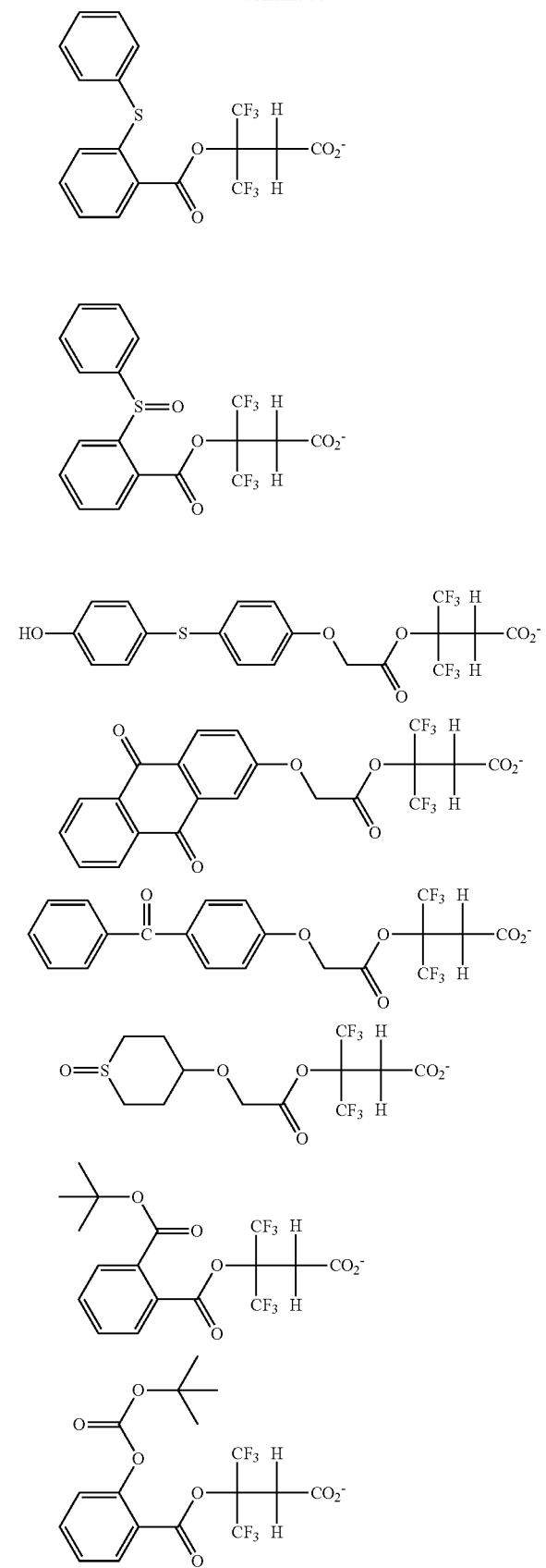
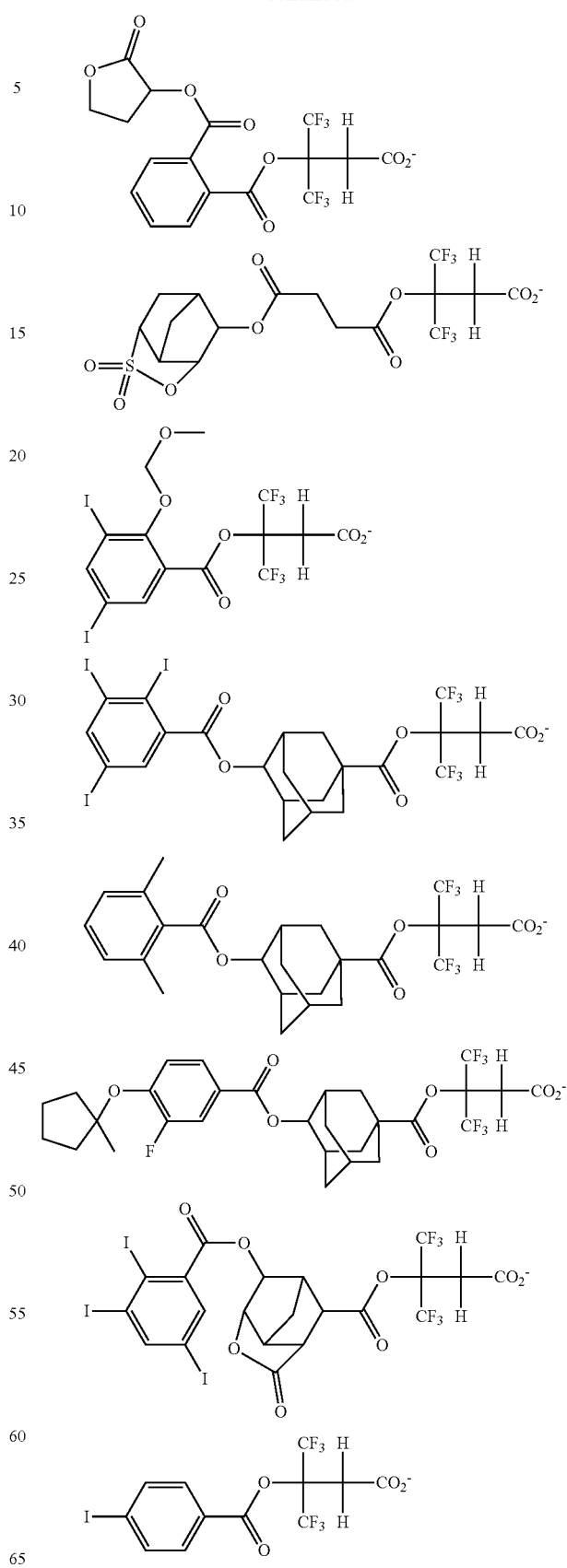

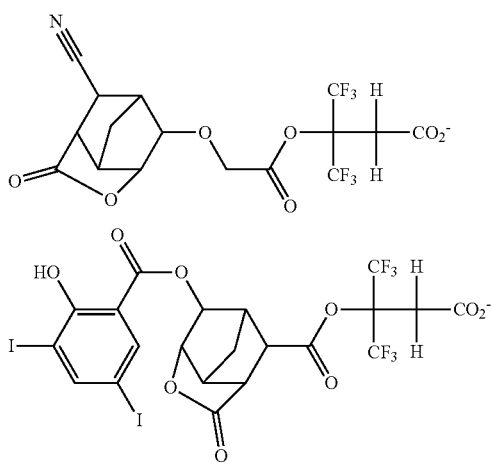

Exemplary structures for the onium salt of the invention include arbitrary combinations of cations with anions, both as exemplified above, but are not limited thereto.

The onium salt of formula (1) may be synthesized, for example, according to the following scheme A.

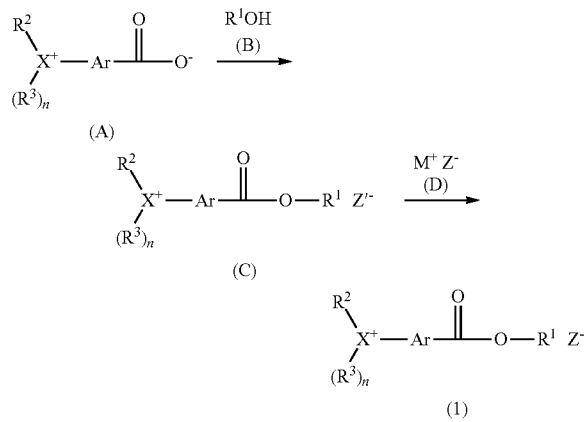

Herein $R^1$, $R^2$, $R^3$, n, X, and $Z^-$ are as defined above. $M^+$ is a cation. $Z'^-$ is an anion.

The first step is an esterification reaction of a betaine compound (A) of carboxylate type with an alcohol (B) to form a salt (C) having a desired cation. This is followed by a salt exchange with a salt compound (D) having a desired anion to synthesize the target onium salt (1).

The first step or esterification may be performed, for example, by converting the compound (A) to an acid chloride with the aid of oxalyl chloride or thionyl chloride, and reacting it with the alcohol (B) under basic conditions. Examples of the base used herein include triethylamine, pyridine, N,N-dimethylaminopyridine, and 2,6-lutidine. The second step or ion exchange may be readily performed by a well-known method, for example, with reference to U.S. Pat. No. 7,511,169 (JP-A 2007-145797).

Alternatively, the onium salt of formula (1) may be synthesized according to the following scheme B.

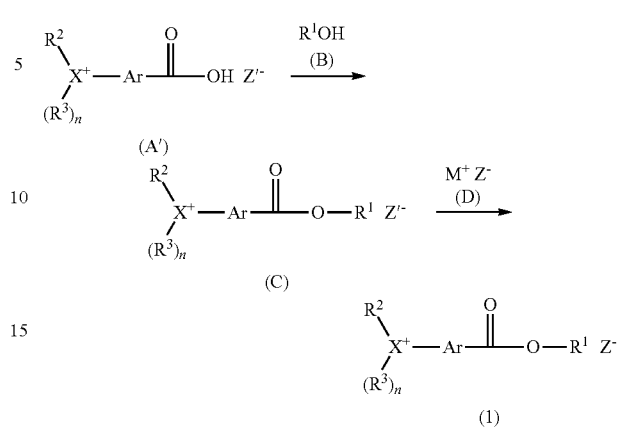

Herein $R^1$, $R^2$, $R^3$, n, X, $Z^-$, $Z'^-$ and $M^+$ are as defined above.

The first step is an esterification reaction of a compound (A') having a carboxy group with an alcohol (B) to form a salt (C) having a desired cation. This is followed by a salt exchange with a salt compound (D) having a desired anion to synthesize the target onium salt (1).

The first step or esterification may be performed, for example, by converting the compound (A') to an acid chloride with the aid of oxalyl chloride or thionyl chloride, and reacting it with the alcohol (B) under basic conditions as in scheme A. The esterification may also be performed using a condensing agent such as diisopropylcarbodiimide instead. The second step or ion exchange may be readily performed by a well-known method.

A resist composition comprising the onium salt having formula (1) is reduced in defectiveness and improved in LWR, CDU and DOF. Although the detail is not well understood, the following reason is presumed. A sulfonium or iodonium cation forms a sulfide or iodobenzene as the decomposition product after exposure. For example, it is known that photo-decomposition of a triphenylsulfonium cation forms diphenyl sulfide and [(2-phenyl)phenyl]phenyl sulfide. Since these photo-decomposition products are poorly soluble in alkaline developer, they become a cause for development defects. The inventive onium salt has an alkali-decomposable group such as chain-like alkyl ester or fluorinated alkyl ester as a partial structure in the cation. Accordingly, the photo-decomposition product also has the alkali-decomposable group. The ester structure is decomposed upon alkaline development so that the photo-decomposition product may turn alkali soluble, which leads to reduction of defects, prevention of pattern dropouts, and improvements in lithography performance factors. The ester structure preferred for preventing a lowering of alkaline decomposition is a straight chain structure. If a quaternary carbon atom originating from tert-butyl or the like is located near the ester, there is a possibility of detracting from alkaline decomposition. Also, the inventive onium salt is decomposed with an alkali to generate a carboxy group on the cation side. When the ester bonding mode is inverse, a phenolic hydroxy group is generated on the cation side. No satisfactory improvements are then obtained because the phenolic hydroxy group has a lower alkaline solubility than the carboxy group.

The use of an alkali-decomposable cation as the cation of the acid diffusion inhibitor leads to improvements in lithography performance factors. Although similar improving effects are expectable from the introduction of an alkali-decomposable group in the cation of a PAG, more lithography performance improvements are achievable from combination with a weak acid anion used in the acid diffusion inhibitor. Although the detail is not well understood, the following reason is presumed. In general, the weak acid anion used in the acid diffusion inhibitor is more hydrophilic than the strong acid anion (e.g., fluorosulfonic acid) used in the PAG. Since the inventive onium salt is a combination of a cation having improved solubility in alkaline developer with an anion which is hydrophilic, i.e., highly soluble in alkaline developer, it is well soluble in alkaline developer as compared with the strong acid anion which is poorly soluble in alkaline developer, leading to reduction of defects and prevention of pattern dropouts.

Although a structure in which a partial structure capable of reacting with alkaline developer is bonded to the cation via a linking group of alkoxyacetate structure or the like may be contemplated as the cation having an alkali-decomposable group, superior lithography performance is achievable using the inventive onium salt as the PAG. The reason is presumed as follows. The inventive onium salt, in which the carboxy group is in direct bond to the benzene ring in the cation, generates a carboxylic acid having a higher acidity. That is, since the decomposition reaction rate of ester site with alkali is high as compared with the cation of non-direct bond type, advantageously effective decomposition is possible even by brief reaction during development.

When the inventive onium salt is used along with a base polymer having a PAG component bound therein, more lithography performance improvements are achievable.

The base polymer having a PAG component bound in its backbone is hydrophilic as compared with a polymer not having a PAG component in its backbone. Although the detail is not well understood, a combination of a hydrophilic polymer with a hydrophilic acid diffusion inhibitor is more effective for reducing defects and preventing pattern dropouts.

Chemically Amplified Resist Composition

Another embodiment of the invention is a chemically amplified resist composition comprising (A) a base polymer comprising repeat units adapted to change solubility in a developer under the action of an acid, (B) a photoacid generator, (C-1) an acid diffusion inhibitor comprising the inventive onium salt, and (D) an organic solvent as essential components, and if necessary, (C-2) an acid diffusion inhibitor other than the inventive onium salt, (E) a surfactant, and (F) other components.

A further embodiment of the invention is a chemically amplified resist composition comprising (A') a base polymer comprising repeat units adapted to change solubility in a developer under the action of an acid and repeat units adapted to generate an acid upon exposure to light, (C-1) an acid diffusion inhibitor comprising the inventive onium salt, and (D) an organic solvent as essential components, and if necessary, (B) a photoacid generator, (C-2) an acid diffusion inhibitor other than the inventive onium salt, (E) a surfactant, and (F) other components.

(A) Base Polymer

Component (A) is a base polymer adapted to change its solubility in a developer under the action of an acid. It is preferably a polymer comprising repeat units having the formula (a) or repeat units having the formula (b), which are also referred to as repeat units (a) and (b), respectively.

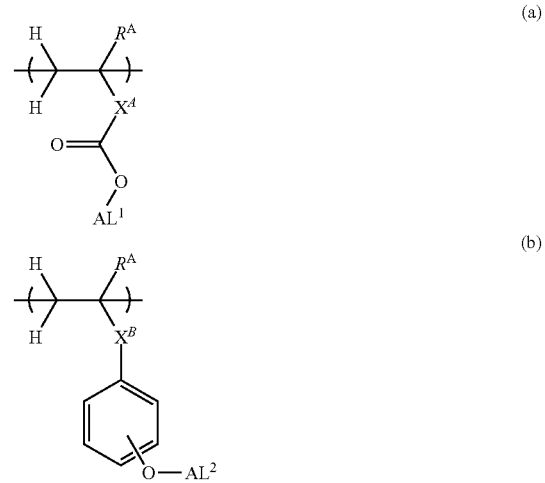

In formulae (a) and (b), $R^A$ is each independently hydrogen or methyl. $X^A$ is a single bond, phenylene group, naphthylene group or (backbone)-C(=O)—O—$X^{A1}$—, wherein $X^{A1}$ is a $C_1$-$C_{15}$ hydrocarbylene group which may contain a hydroxy moiety, ether bond, ester bond or lactone ring. $X^B$ is a single bond or ester bond. $AL^1$ and $AL^2$ are each independently an acid labile group.

While the acid labile groups $AL^1$ and $AL^2$ are not particularly limited, suitable acid labile groups include $C_4$-$C_{20}$ tertiary hydrocarbyl groups, trihydrocarbylsilyl groups in which each hydrocarbyl moiety is $C_1$-$C_6$ alkyl, and $C_4$-$C_{20}$ oxoalkyl groups. With respect to the structure of these acid labile groups, reference should be made to U.S. Pat. No. 9,256,127 (JP-A 2015-214634, paragraphs [0066]-[0100]).

Acid labile groups having the following formula (L1) are preferred as $AL^1$ and $AL^2$.

In formula (L1), $R^{21}$ is a $C_1$-$C_7$ hydrocarbyl group in which —$CH_2$— may be replaced by —O—, and "a" is 1 or 2.

Of the acid labile groups $AL^1$ and $AL^2$, the following groups are most preferred.

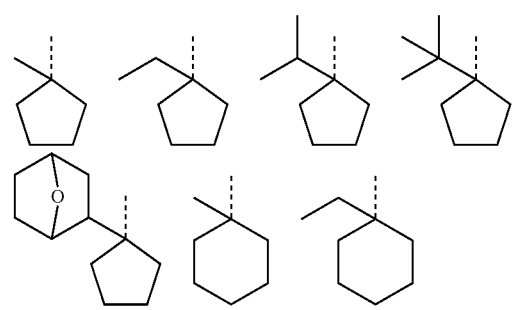

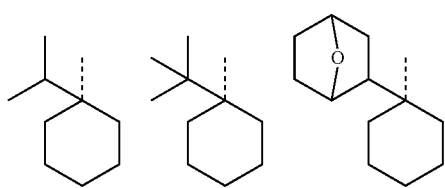
Examples of the structure having formula (a) wherein $X^A$ is a variant include the structures described in U.S. Pat. No. 9,164,384 (JP-A 2014-225005, paragraph [0015]). Of these, preferred structures are shown below. Herein $R^A$ and $AL^1$ are as defined above.
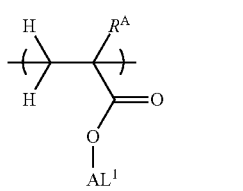 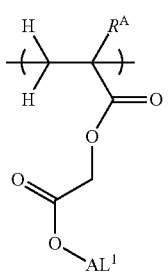
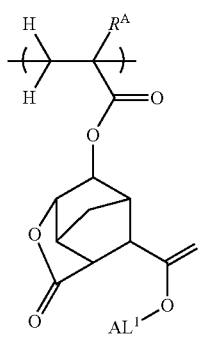 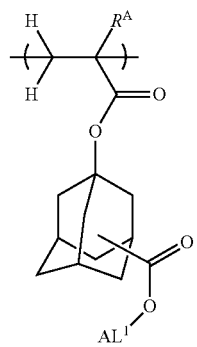
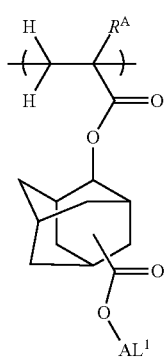 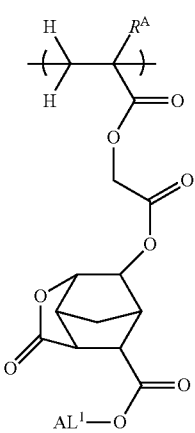
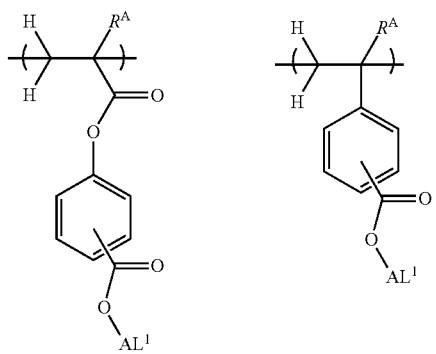
Examples of the repeat unit (a) are given below, but not limited thereto. Herein $R^A$ is as defined above.
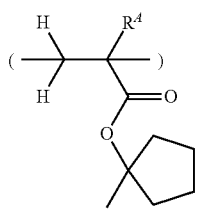 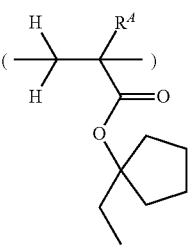
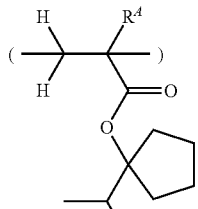 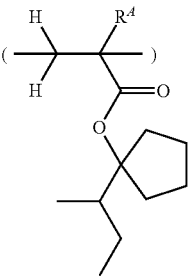
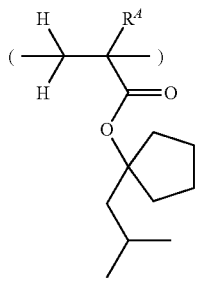 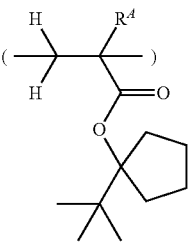
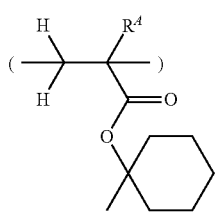 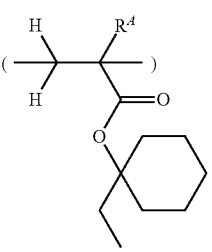

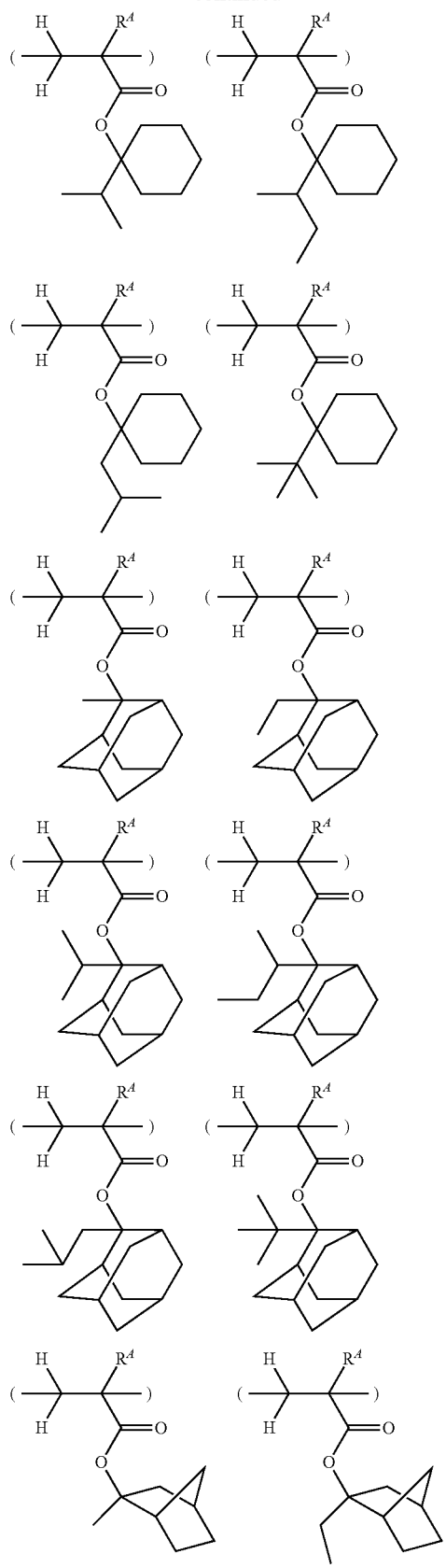
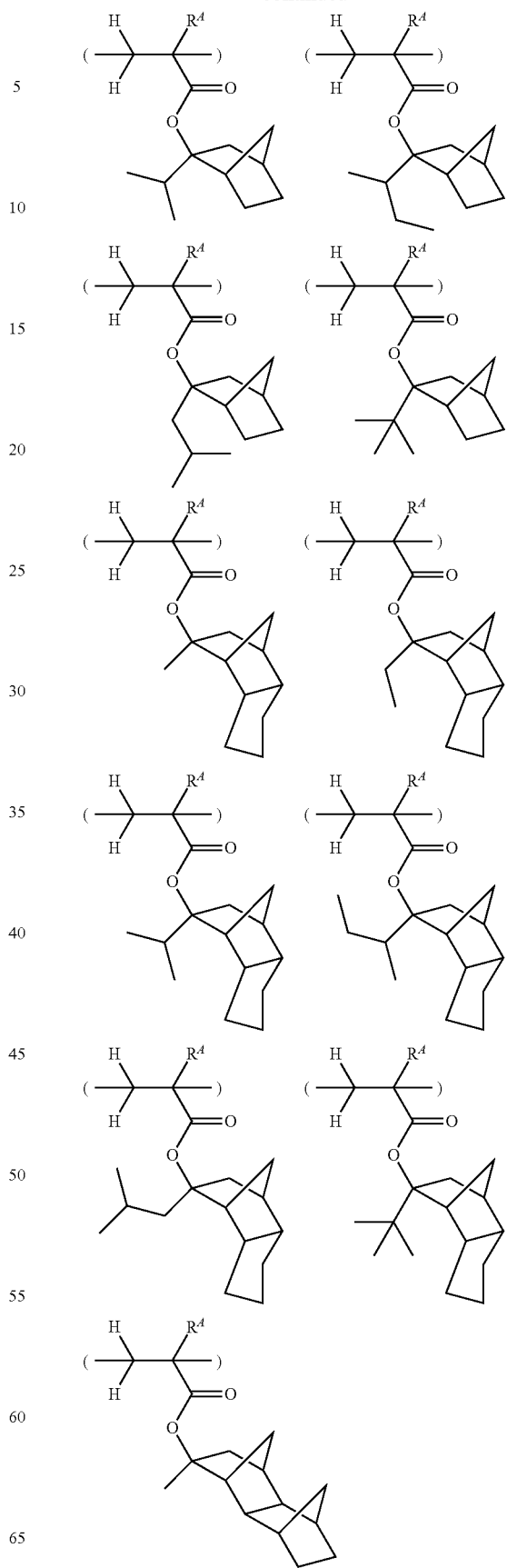

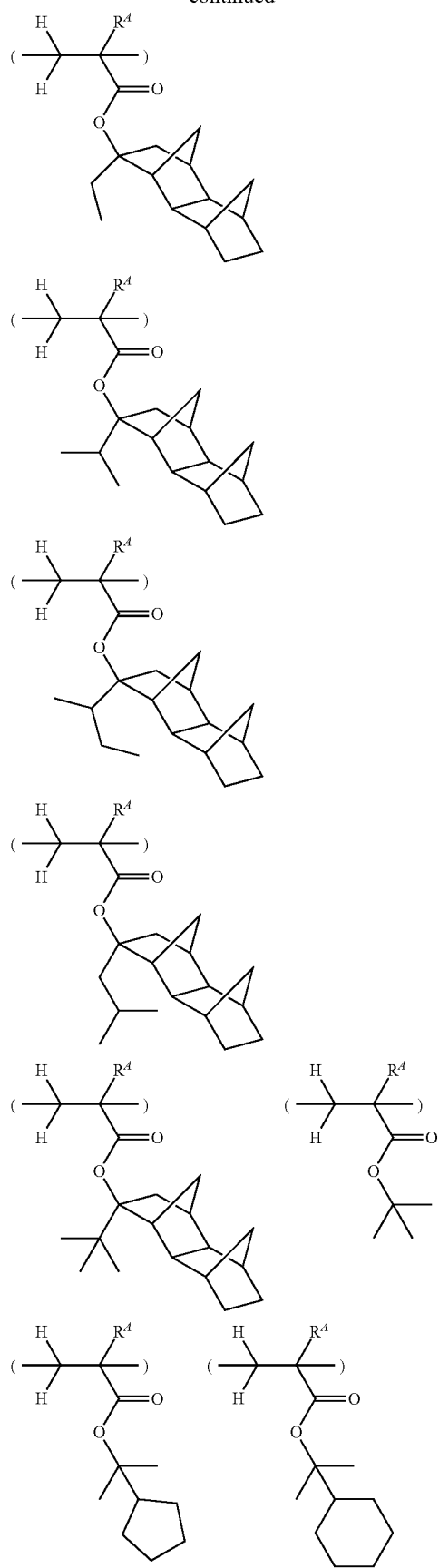
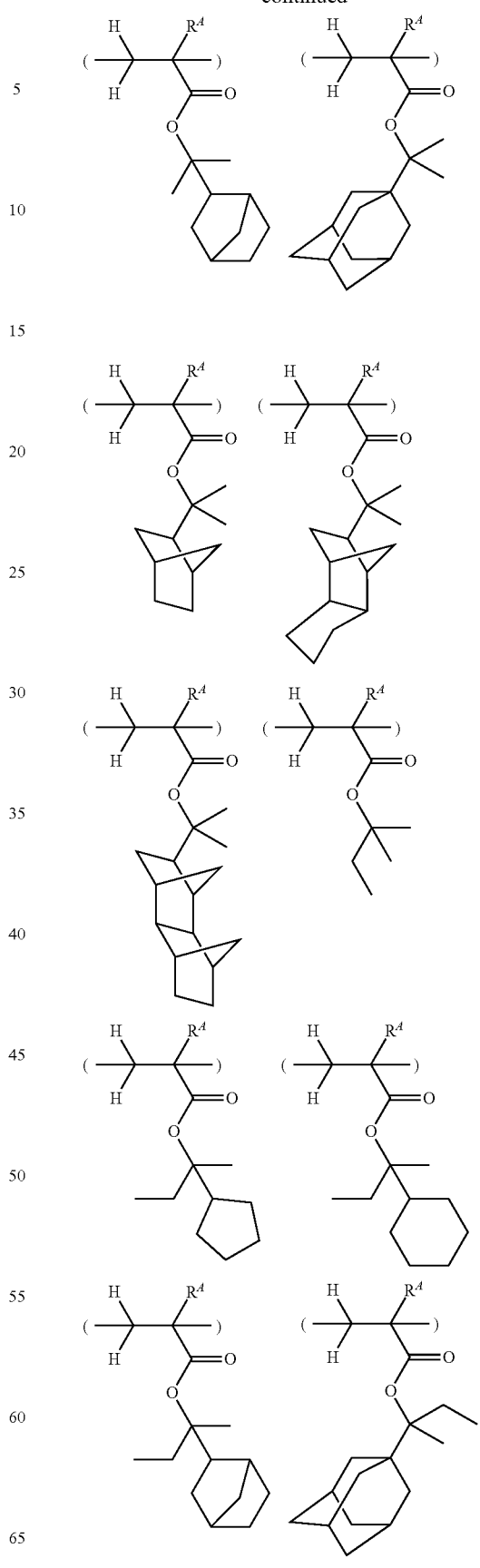

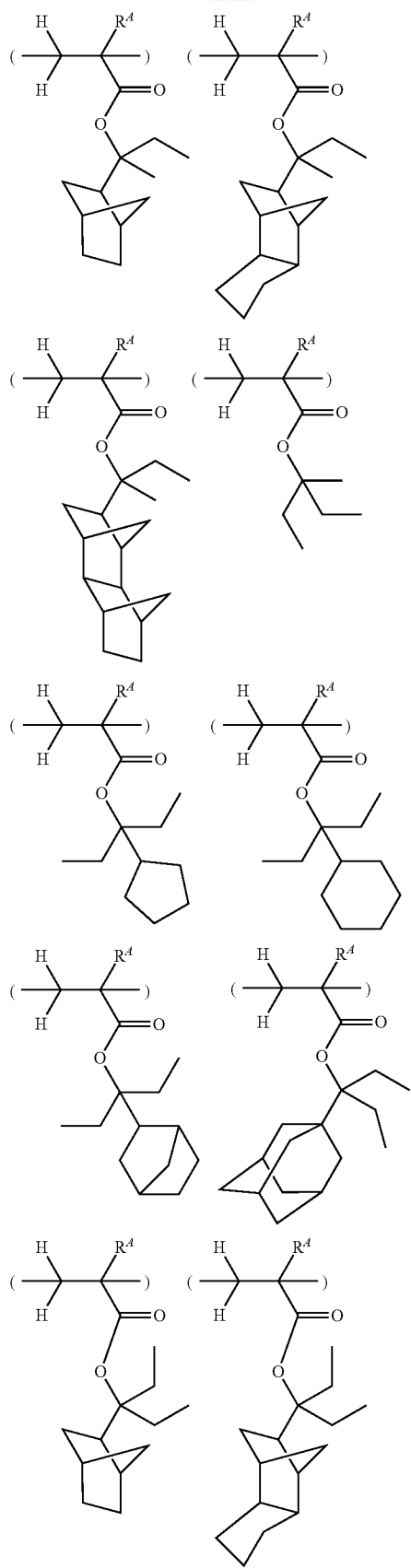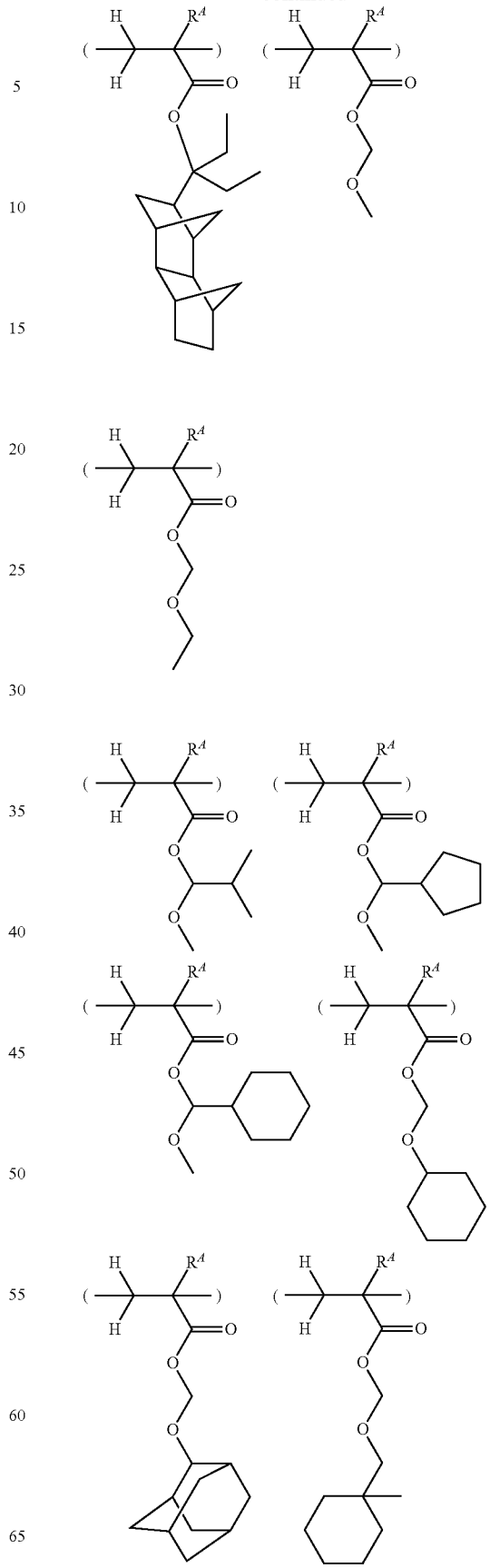

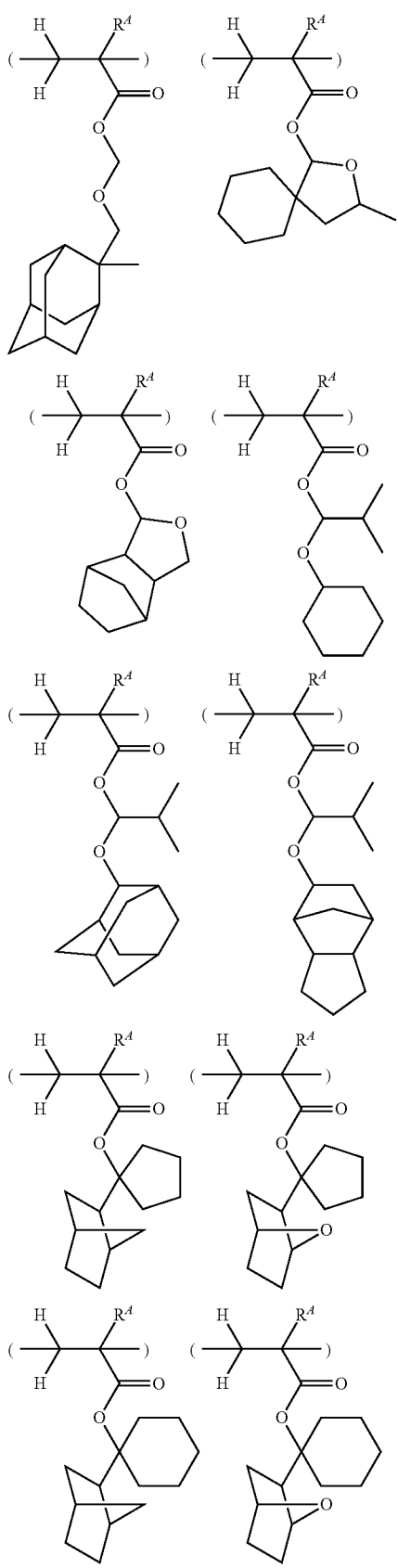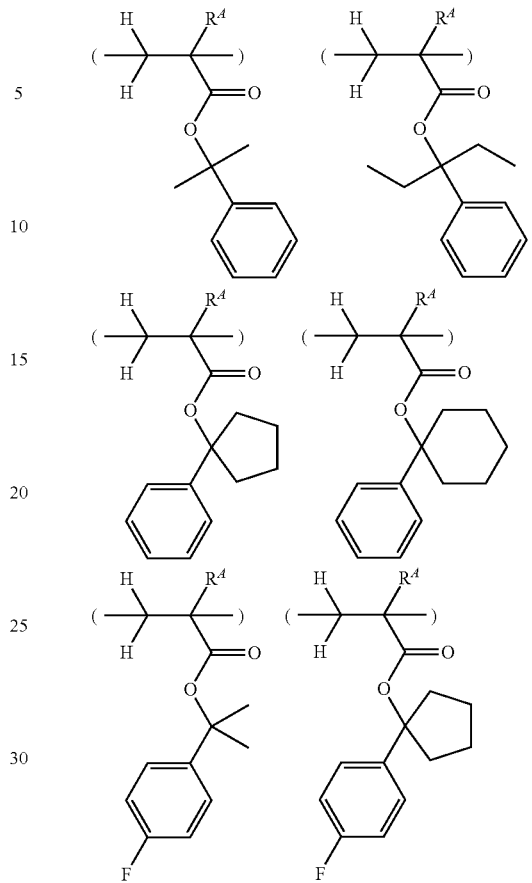
Examples of the repeat unit (b) are given below, but not limited thereto. Herein $R^A$ is as defined above.
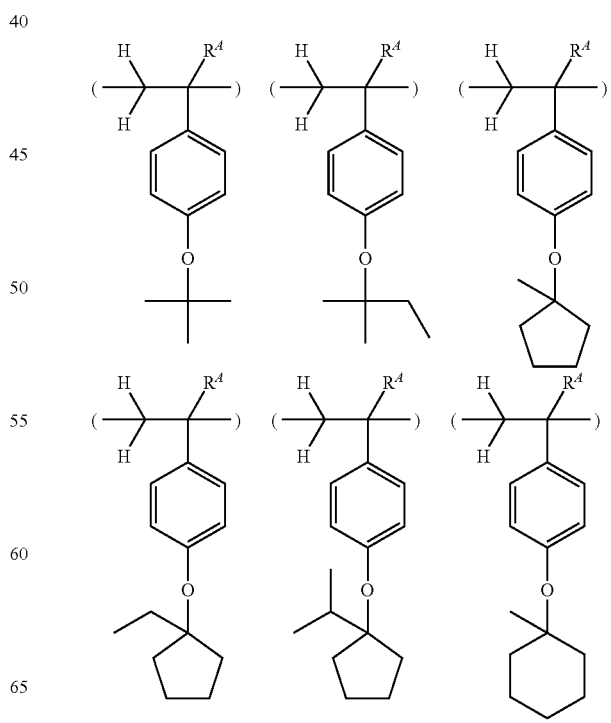

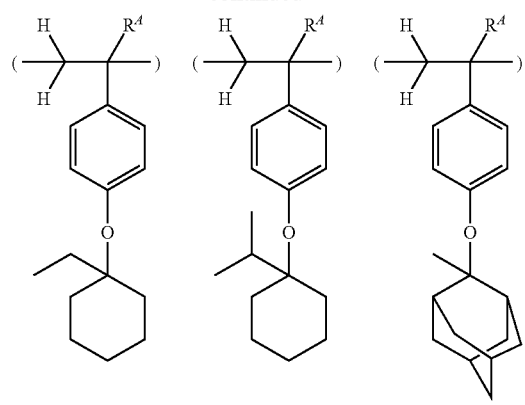
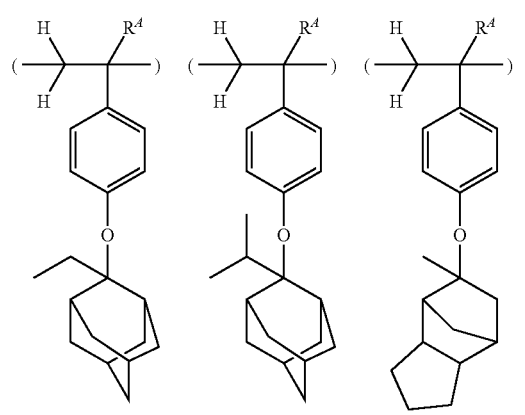
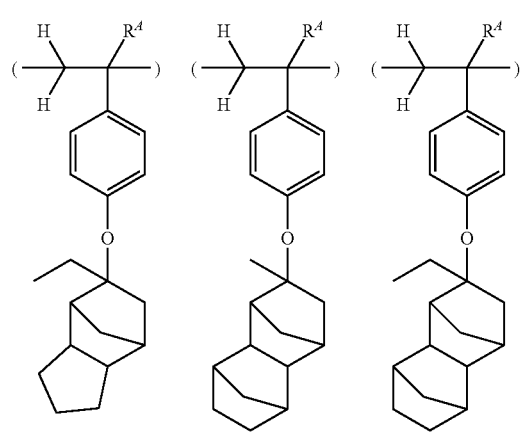
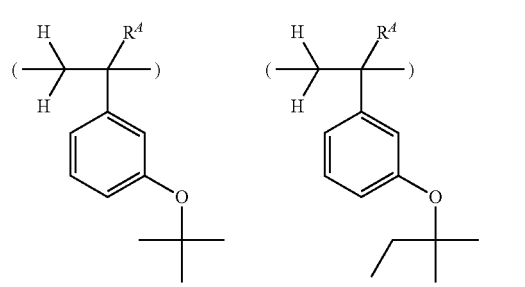
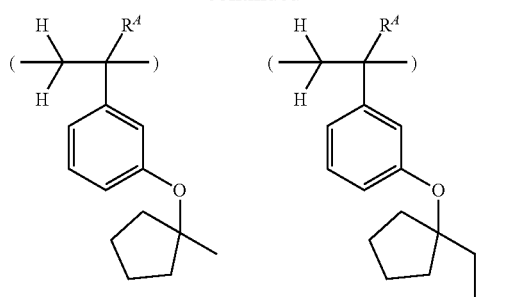
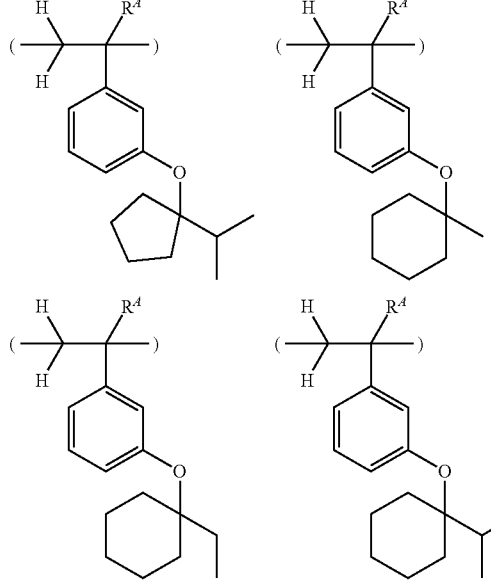
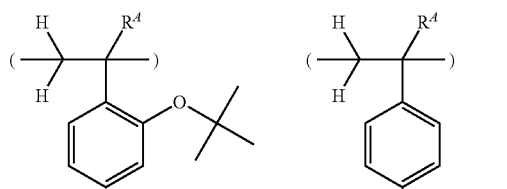
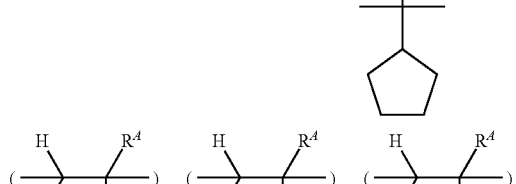
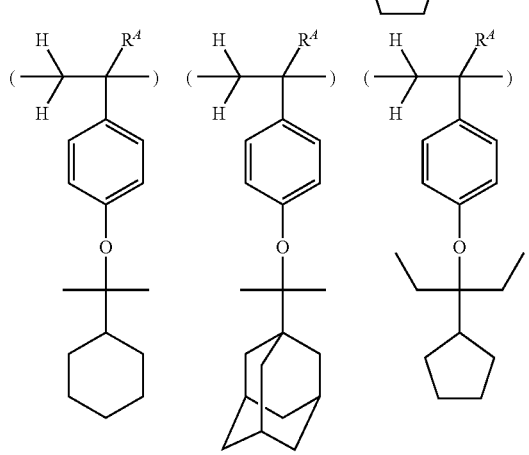

-continued

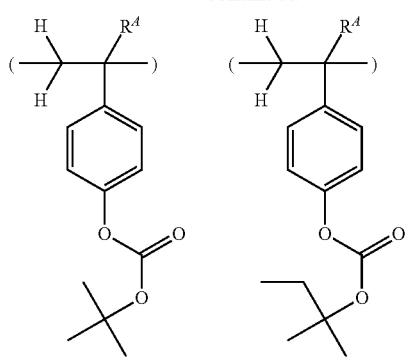
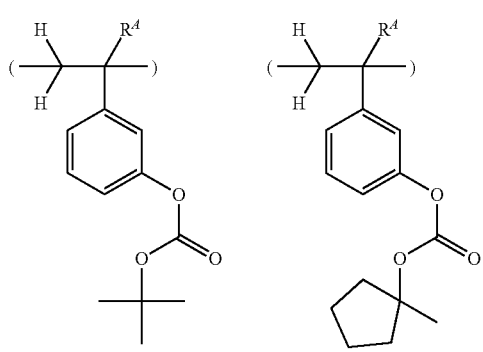
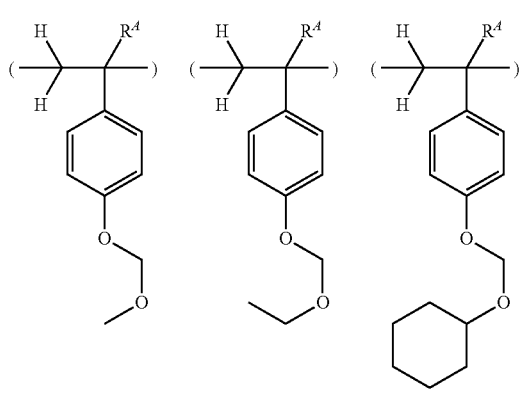
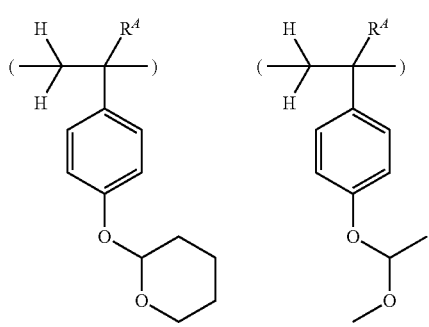

-continued

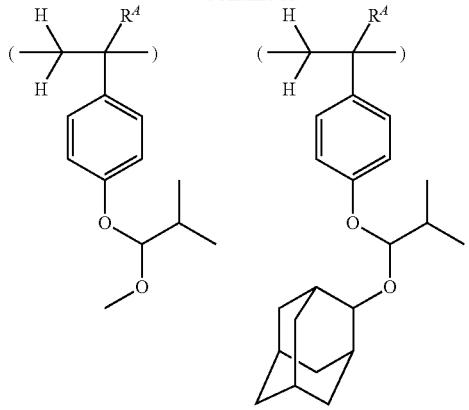
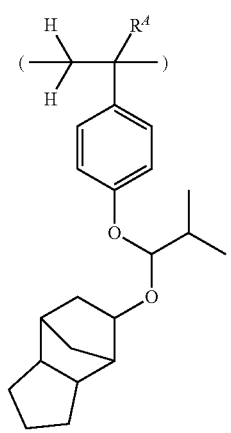
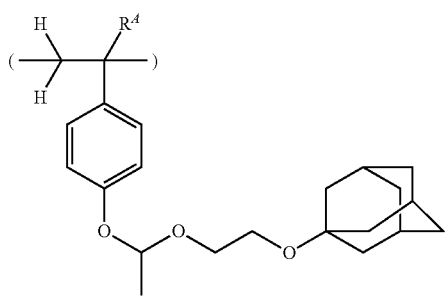

Although the above examples correspond to the unit wherein $X^A$ or $X^B$ is a single bond, combinations with similar acid labile groups are possible where $X^A$ or $X^B$ is other than a single bond. Examples of the units wherein $X^A$ is other than a single bond are as exemplified above. Examples of the units wherein $X^B$ is an ester bond correspond to the above-exemplified units wherein the single bond between the backbone and the benzene ring is replaced by an ester bond.

The base polymer may further comprise repeat units having the formula (c), which are also referred to as repeat units (c).

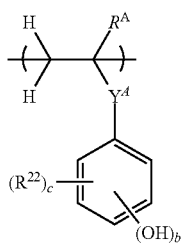
(c)

In formula (c), $R^A$ is hydrogen or methyl. $Y^A$ is a single bond or ester bond.

In formula (c), $R^{22}$ is fluorine, iodine, a carboxy group, formyl group, formyloxy group, a $C_1$-$C_{10}$ hydrocarbyl group which may contain a heteroatom, a $C_1$-$C_{10}$ hydrocarbyloxy group which may contain a heteroatom, $C_2$-$C_{10}$ hydrocarbylcarbonyl group which may contain a heteroatom, a $C_2$-$C_{10}$ hydrocarbylcarbonyloxy group which may contain a heteroatom, or a $C_2$-$C_{10}$ hydrocarbyloxycarbonyloxy group which may contain a heteroatom. The hydrocarbyl group and the hydrocarbyl moiety in the hydrocarbyloxy, hydrocarbylcarbonyl, hydrocarbylcarbonyloxy or hydrocarbyloxycarbonyloxy group may be saturated or unsaturated and straight, branched or cyclic.

Examples of the $C_1$-$C_{10}$ hydrocarbyl group include $C_1$-$C_{10}$ alkyl groups such as methyl, ethyl, propyl, isopropyl, n-butyl, sec-butyl, tert-butyl, n-pentyl, n-hexyl, n-octyl, n-nonyl, and n-decyl; $C_3$-$C_{10}$ cyclic saturated hydrocarbyl groups such as cyclopentyl, cyclohexyl, adamantyl, and norbornyl; $C_2$-$C_{10}$ alkenyl groups such as vinyl and allyl; $C_6$-$C_{10}$ aryl groups such as phenyl, methylphenyl, ethylphenyl, propylphenyl, isopropylphenyl, butylphenyl, isobutylphenyl, sec-butylphenyl, tert-butylphenyl; $C_7$-$C_{10}$ aralkyl groups such as benzyl, and combinations thereof.

Examples of the $C_1$-$C_{10}$ hydrocarbyloxy group include methoxy, ethoxy, propoxy, isopropoxy, n-butoxy, tert-butoxy, phenoxy, and 2-methoxyethoxy. Examples of the $C_2$-$C_{10}$ hydrocarbylcarbonyl group include acetyl, ethylcarbonyl, hexylcarbonyl, and phenylcarbonyl. Examples of the $C_2$-$C_{10}$ hydrocarbylcarbonyloxy group include acetoxy, ethylcarbonyloxy, propylcarbonyloxy, pentylcarbonyloxy, hexylcarbonyloxy, and heptylcarbonyloxy. Examples of the $C_2$-$C_{10}$ hydrocarbyloxycarbonyloxy group include methoxycarbonyloxy, ethoxycarbonyloxy, hexyloxycarbonyloxy, and phenyloxycarbonyloxy.

In the hydrocarbyl group, some or all of the hydrogen atoms may be substituted by a moiety containing oxygen, sulfur, nitrogen or halogen, and any constituent —$CH_2$— may be replaced by a moiety containing oxygen, sulfur, or nitrogen, so that the group may contain fluorine, chlorine, bromine, iodine, hydroxy moiety, carboxy moiety, ether bond, ester bond, or lactone ring. Examples of the substituted hydrocarbyl group include, but are not limited to, alkoxyalkoxy groups such as methoxymethoxy, ethoxymethoxy, 1-ethoxyethoxy, 1-methoxy-2-methylpropyloxy; alkoxyalkylcarbonyloxy groups such as methoxymethylcarbonyloxy and (2-methoxyethoxy)methylcarbonyloxy; and alkoxycarbonyloxy groups such as methoxycarbonyloxy, ethoxycarbonyloxy, and tert-butoxycarbonyloxy.

Preferably $R^{22}$ is fluorine, iodine, methyl, acetyl or methoxy.

In formula (c), b is an integer of 1 to 5, c is an integer of 0 to 4, and b+c is 1 to 5. Preferably b is 1, 2 or 3, and c is 0, 1 or 2.

The repeat unit (c) serves to improve the adhesion to the substrate or the underlay film. Since the repeat unit (c) has a phenolic hydroxy group with high acidity, it promotes the action of an acid generated upon exposure, contributing to a higher sensitivity, and becomes a proton source to the acid generated upon EUV exposure, from which an improvement in sensitivity is expectable.

Examples of the repeat unit (c) are given below, but not limited thereto. Herein $R^4$ is as defined above.

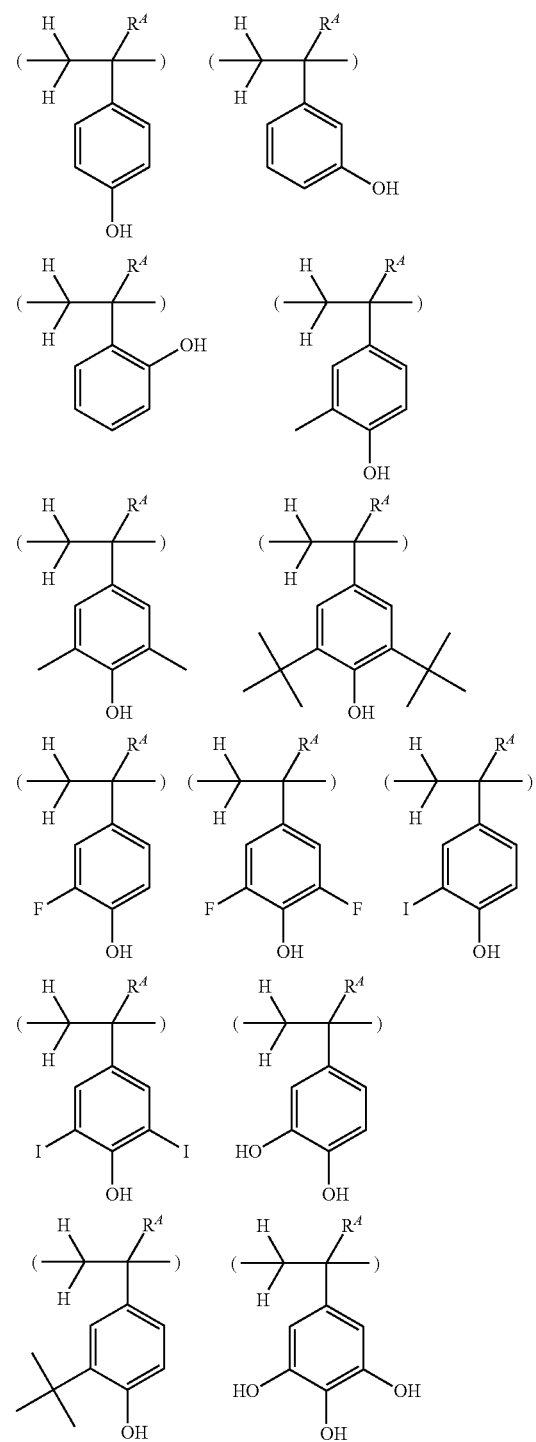

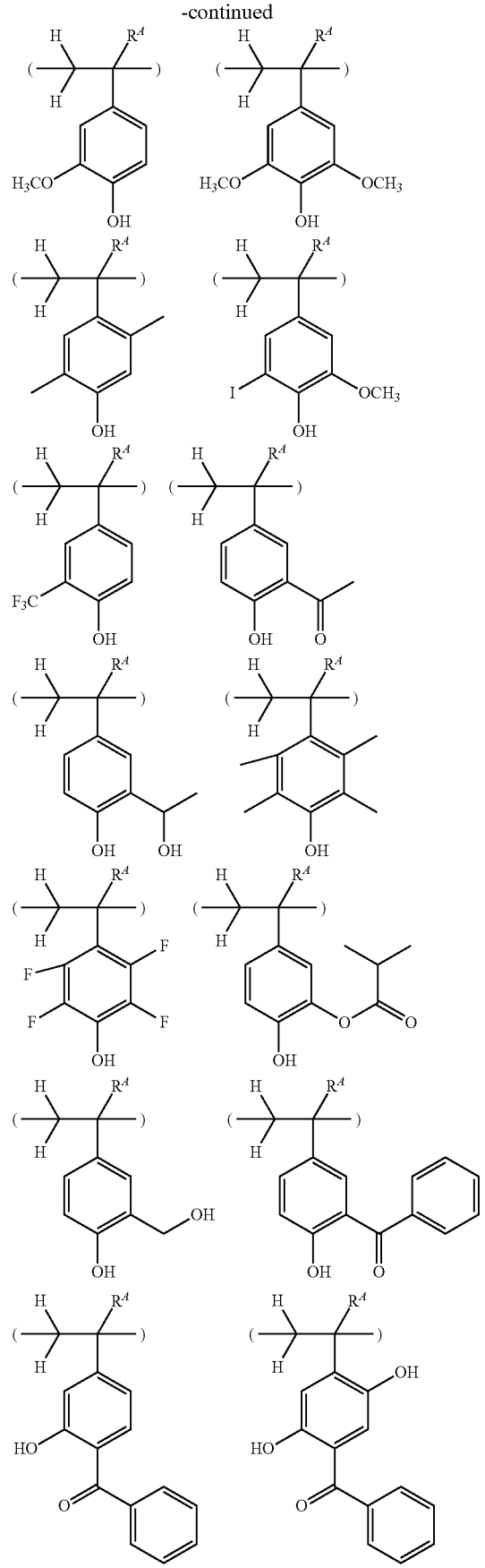
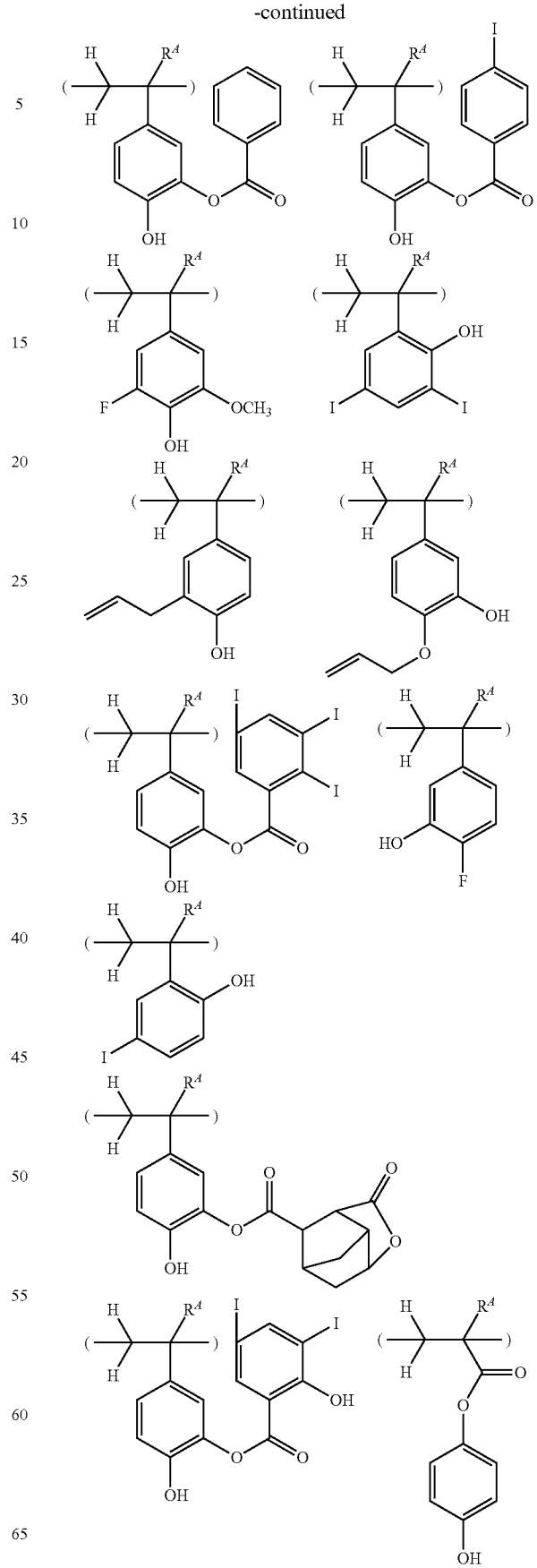

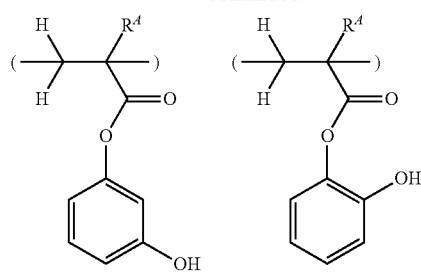
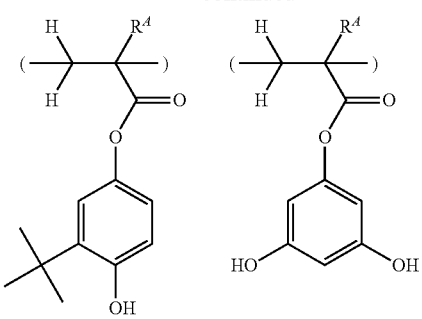
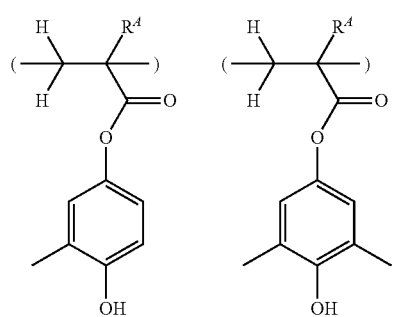
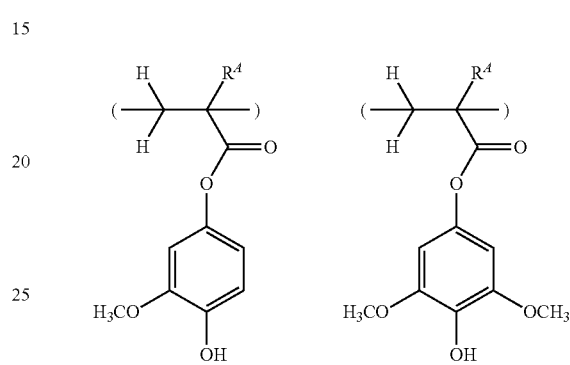
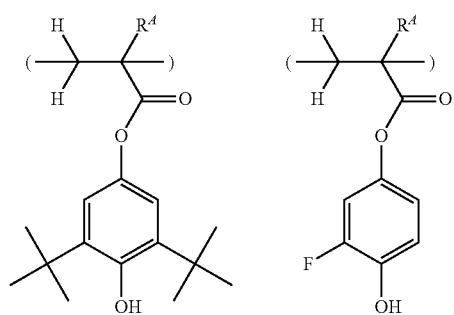
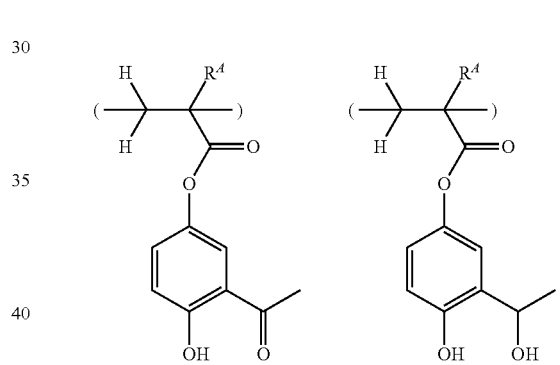
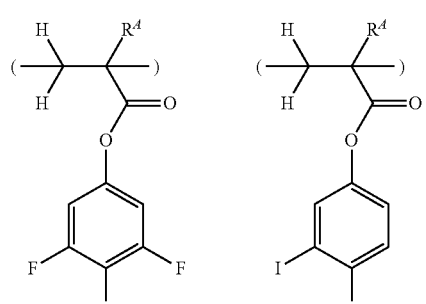
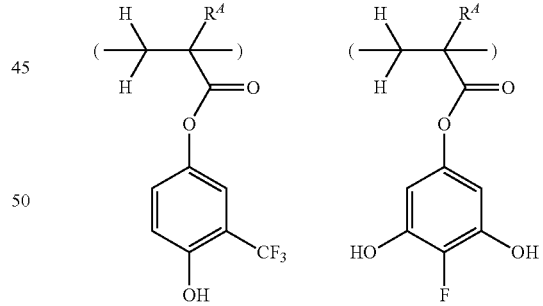
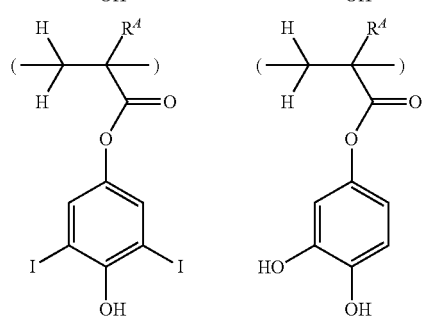
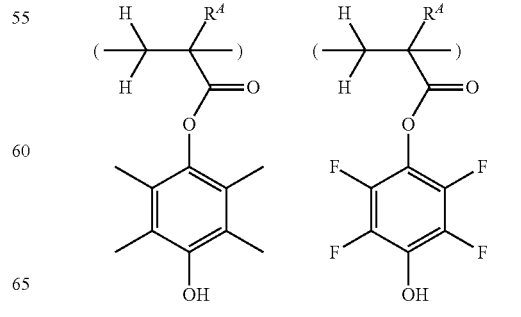

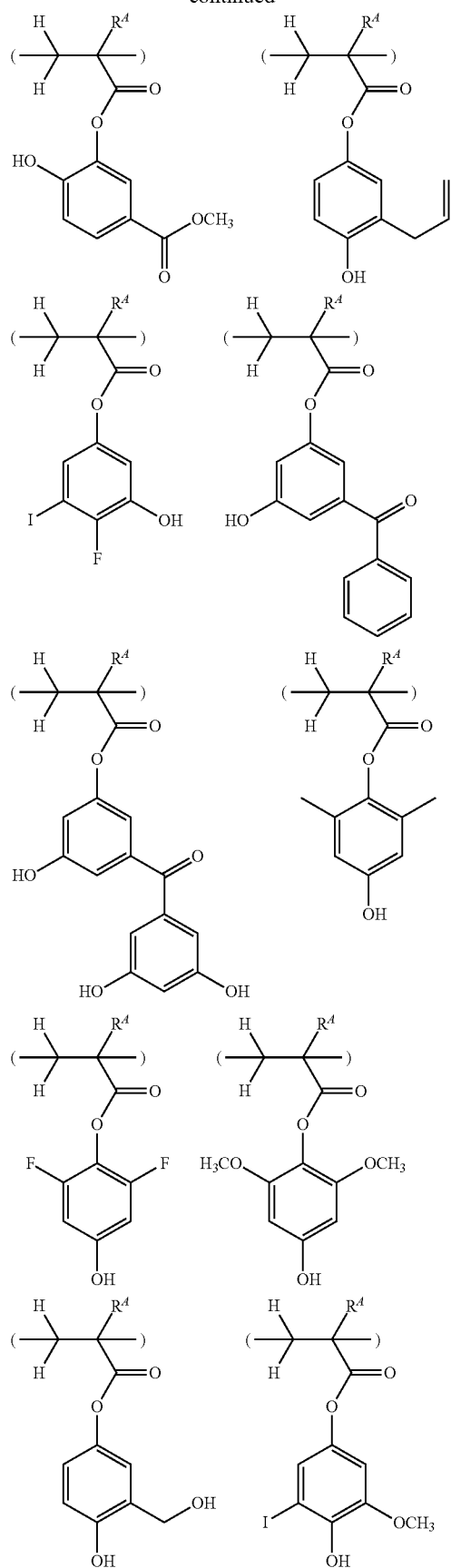
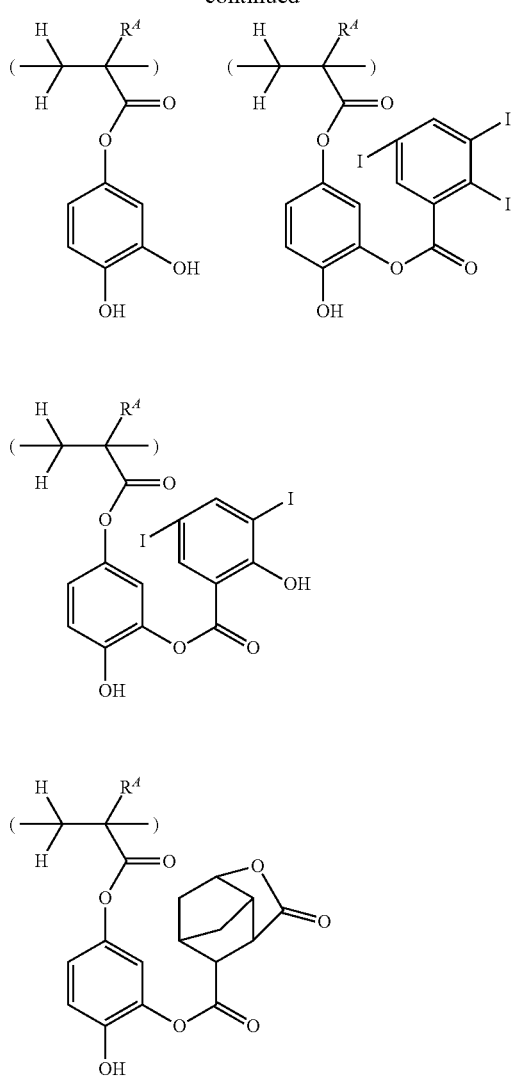
Of the above repeat units (c), the following units are preferred. Herein $R^A$ is as defined above.
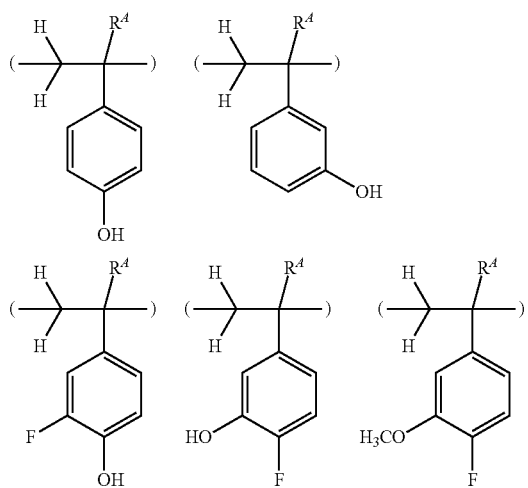

-continued

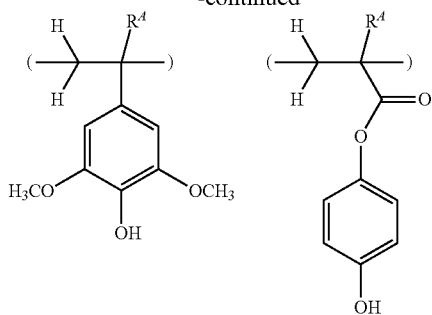

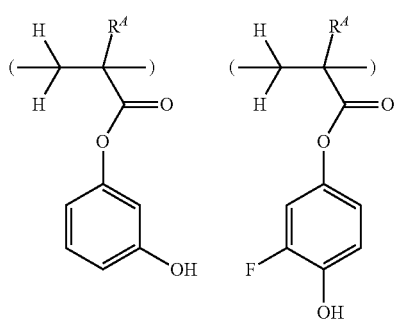

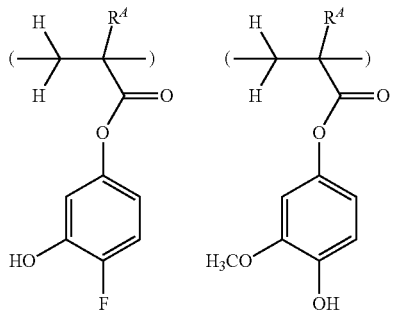

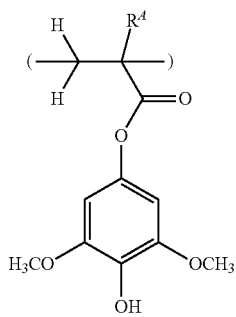

The base polymer may further comprise repeat units having the formula (d1), (d2), (d3) or (d4), which are also referred to as repeat units (d1), (d2), (d3) or (d4), respectively.

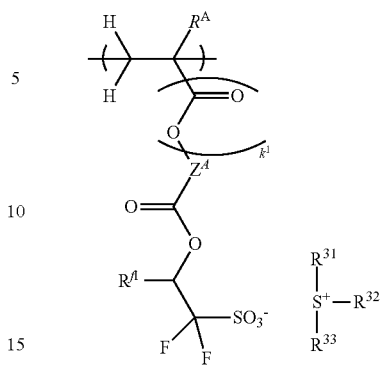

(d1)

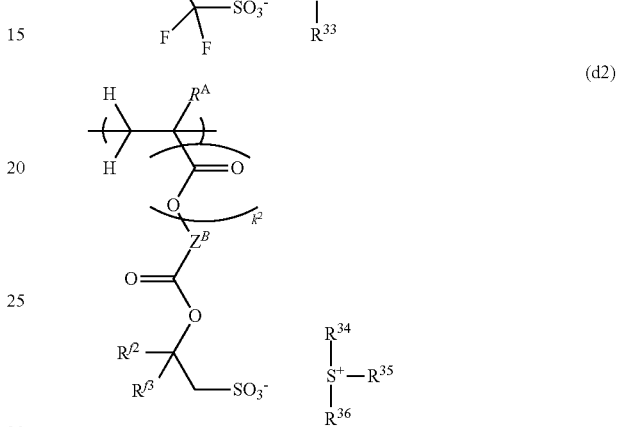

(d2)

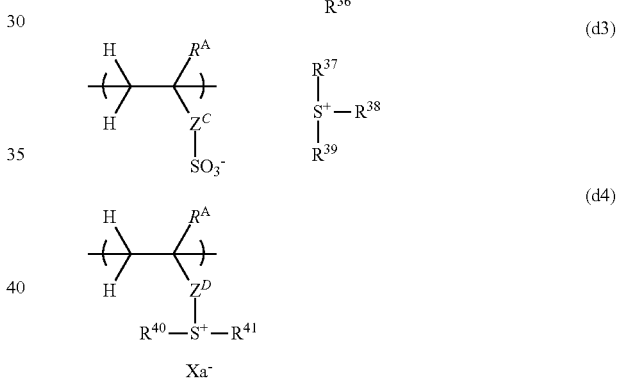

(d3)

(d4)

In formulae (d1) to (d4), $R^A$ is each independently hydrogen or methyl. $R^{f1}$, $R^{f2}$ and $R^{f3}$ are each independently hydrogen or trifluoromethyl. $Z^A$ and $Z^B$ are each independently a single bond or a $C_1$-$C_{20}$ hydrocarbylene group which may contain a heteroatom. $Z^C$ is a single bond, $—Z^{C1}—$, $—O—Z^{C1}—$, or $—C(=O)—O—Z^{C1}—$, wherein $Z^{C1}$ is a phenylene group which may be substituted with a substituent selected from a hydroxy group, fluorine, iodine, trifluoromethyl group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, and $C_2$-$C_{10}$ hydrocarbylcarbonyloxy group which may contain a heteroatom. $Z^D$ is a single bond, phenylene group, $—O—Z^{D1}—$, $—C(=O)—O—Z^{D1}—$ or $—C(=O)—NH—Z^{D1}—$, wherein $Z^{D1}$ is a hydrocarbylene group which may contain a heteroatom.

The hydrocarbylene group represented by $Z^A$ and $Z^B$ may be saturated or unsaturated and straight, branched or cyclic. Examples thereof include $C_1$-$C_{20}$ alkanediyl groups such as methanediyl, ethane-1,1-diyl, ethane-1,2-diyl, propane-1,2-diyl, propane-1,3-diyl, butane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, and 2,2-dimethylpropane-1,3-diyl; cyclic saturated hydrocarbylene groups such as cyclopentanediyl, cyclohexanediyl, norbornanediyl, and adamantanediyl; $C_2$-$C_{20}$ alkenediyl groups such as ethene-1,2-diyl, 1-propene-1,3-diyl, 2-butene-1,4-diyl, and 1-methyl-1-butene-1,4-diyl; unsaturated alicyclic hydrocarbylene groups such as 2-cyclohexene-1,4-diyl; aromatic hydrocarbylene groups such as phenylene, naphthylene, $C_1$-$C_{10}$ alkyl-substituted phenylene, and $C_1$-$C_{10}$ alkyl-substituted naphthylene, and combinations thereof. In the hydrocarbylene groups, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain fluorine, chlorine, bromine, iodine, hydroxy moiety, cyano moiety, carbonyl moiety, ether bond, ester bond, sulfonate ester bond, carbonate bond, lactone ring, sultone ring, carboxylic anhydride or haloalkyl moiety. $Z^A$ and $Z^B$ are preferably selected from a single bond, adamantanediyl, phenylene, and substituted phenylene.

The hydrocarbylene group represented by $Z^{D1}$ may be saturated or unsaturated and straight, branched or cyclic. Examples thereof are as exemplified above for the hydrocarbylene groups $Z^A$ and $Z^B$. $Z^D$ is preferably a structure containing a phenyl group bonded to $S^+$ in the formula.

In formulae (d1) to (d4), $R^{31}$ to $R^{41}$ are each independently a $C_1$-$C_{30}$ hydrocarbyl group which may contain a heteroatom. The hydrocarbyl group may be saturated or unsaturated and straight, branched or cyclic. In the hydrocarbyl group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain fluorine, chlorine, bromine, iodine, hydroxy moiety, cyano moiety, carbonyl moiety, ether bond, ester bond, sulfonate ester bond, carbonate bond, lactone ring, sultone ring, carboxylic anhydride or haloalkyl moiety. A pair of $R^{31}$ and $R^{32}$, $R^{34}$ and $R^{35}$, $R^{37}$ and $R^{38}$, or $R^{40}$ and $R^{41}$ may bond together to form a ring with the sulfur atom to which they are attached.

Examples of the optionally heteroatom-containing hydrocarbyl groups $R^{31}$ to $R^{41}$ include alkyl groups such as methyl, ethyl, n-propyl, isopropyl, n-butyl, sec-butyl, tert-butyl, n-pentyl, n-hexyl, n-octyl, 2-ethylhexyl, n-nonyl, n-decyl; cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, adamantylmethyl; alkenyl groups such as vinyl, allyl, propenyl, butenyl, and hexenyl; unsaturated alicyclic hydrocarbyl groups such as cyclohexenyl; $C_6$-$C_{30}$ aryl groups such as phenyl, naphthyl, 4-hydroxyphenyl, 2-hydroxyphenyl, 4-methoxyphenyl, 3-methoxyphenyl, 2-methoxyphenyl, 4-ethoxyphenyl, 4-tert-butoxyphenyl, 3-tert-butoxyphenyl, 2-methylphenyl, 3-methylphenyl, 4-methylphenyl, 4-ethylphenyl, 4-tert-butylphenyl, 4-n-butylphenyl, 4-n-butoxyphenyl, 4-fluorophenyl, 3-fluorophenyl, 4-iodophenyl, 4-fluoro-3-hydroxyphenyl, 3-fluoro-4-hydroxyphenyl, 4-fluoro-3-tert-butoxyphenyl, 3-fluoro-4-tert-butoxyphenyl, 2,4-dimethylphenyl, 2,6-dimethylphenyl, 2,4,6-trimethylphenyl, 2,4,6-triisopropylphenyl, methylnaphthyl, ethylnaphthyl, methoxynaphthyl, ethoxynaphthyl, n-propoxynaphthyl, n-butoxynaphthyl, dimethylnaphthyl, diethylnaphthyl, dimethoxynaphthyl, diethoxynaphthyl; aralkyl groups such as benzyl, 1-phenylethyl and 2-phenylethyl, $C_3$-$C_{30}$ heteroaryl groups such as thienyl, and combinations thereof.

In formulae (d1) to (d4), $R^{31}$ to $R^{41}$ each are preferably a structure containing a phenyl group bonded to $S^+$ in the formula.

In formula (d1), $k^1$ is 0 or $k^1$ is 0 when $Z^A$ is a single bond.
In formula (d2), $k^2$ is 0 or 1, $k^2$ is 0 when $Z^B$ is a single bond.

In formula (d4), Xa$^-$ is a non-nucleophilic counter ion. Examples of the non-nucleophilic counter ion include, but are not limited to, halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl)imide and bis(perfluorobutylsulfonyl)imide; and methide ions such as tris(trifluoromethylsulfonyl)methide and tris(perfluoroethylsulfonyl)methide. Preferred are anions having the formulae (d4-1) and (d4-2).

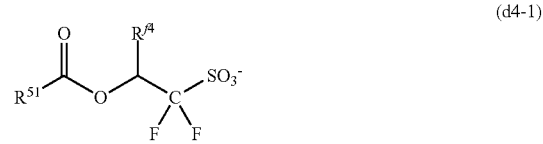

(d4-1)

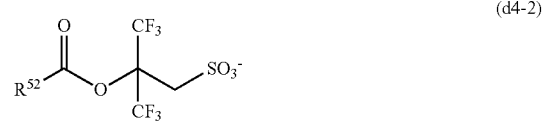

(d4-2)

In formulae (d4-1) and (d4-2), $R^{51}$ and $R^{52}$ are each independently a $C_1$-$C_{40}$ hydrocarbyl group which may contain a heteroatom. $R^{fA}$ is hydrogen or trifluoromethyl.

Examples of the anion having formula (d4-1) include the anions described in JP-A 2014-225005, paragraphs [0108]-[0109] and JP-A 2016-040598, paragraphs [0123]-[0129] and the anions shown below, but are not limited thereto. Herein $R^{f1}$ is as defined above.

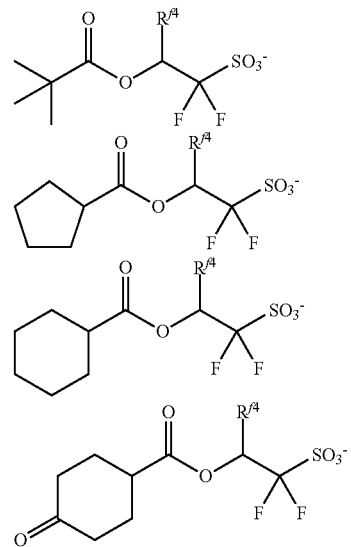

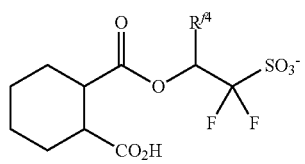
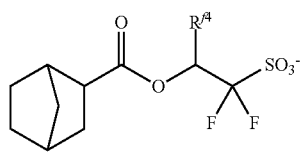
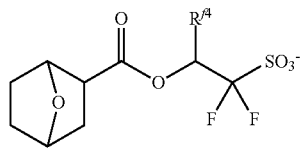
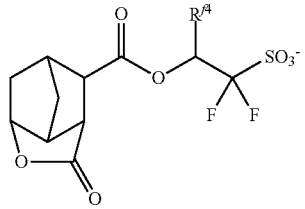
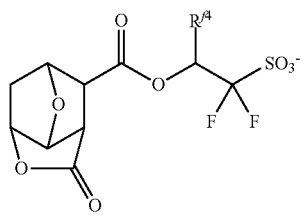
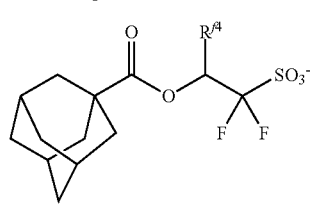
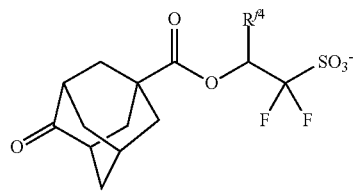
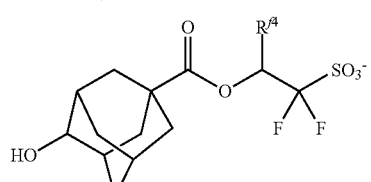
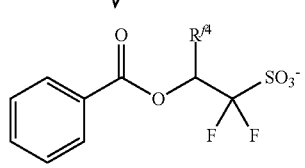
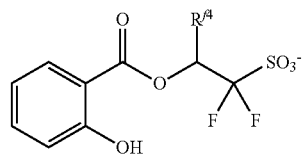
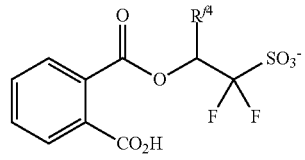
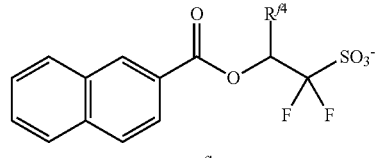
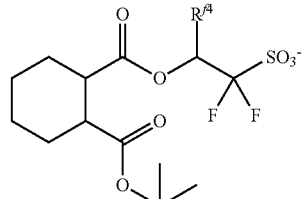
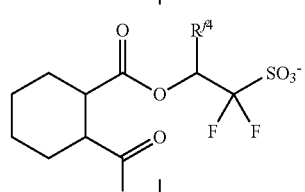
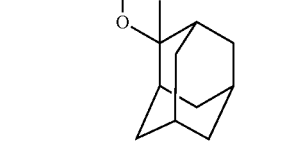
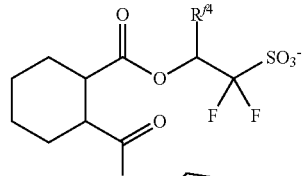
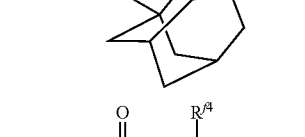
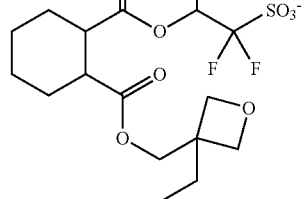

185
-continued
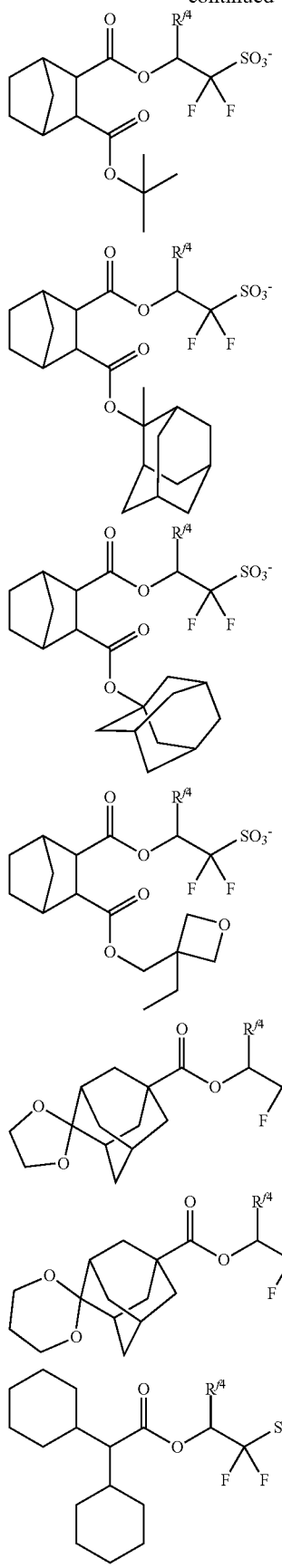
186
-continued
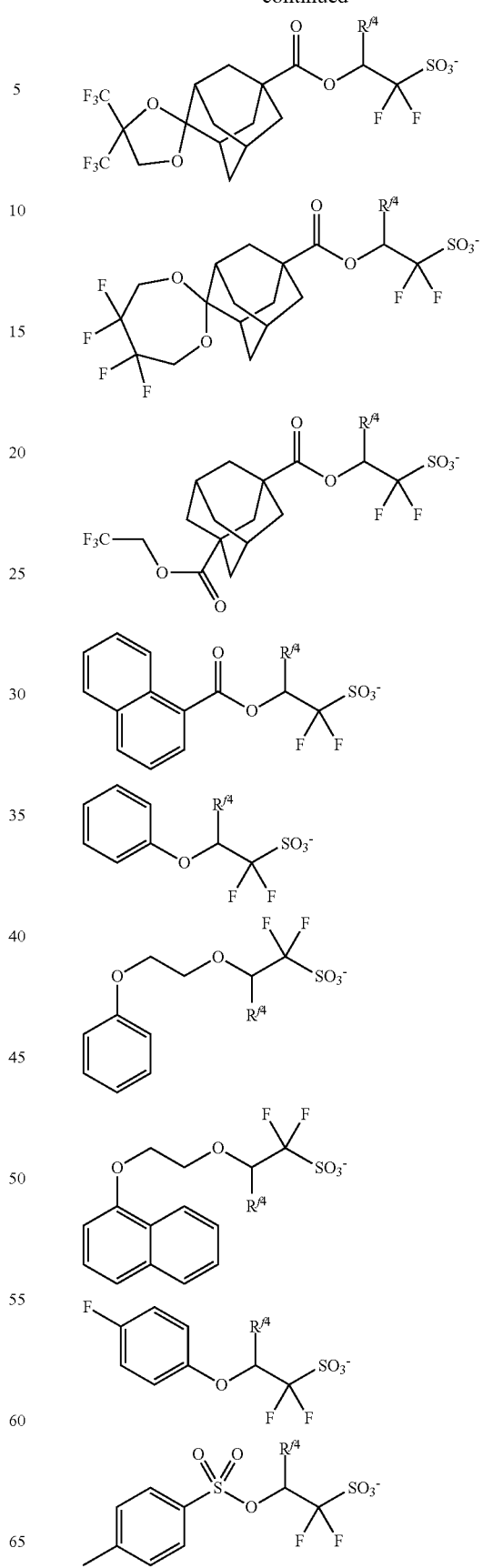

187
-continued
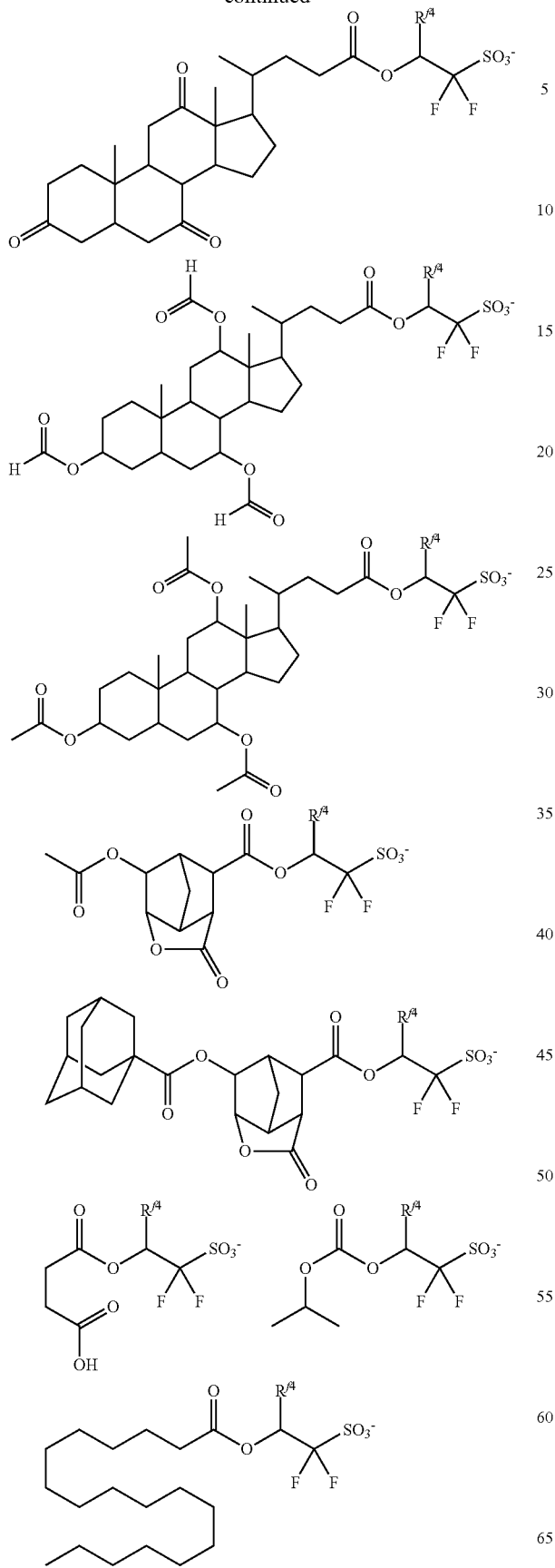
188
-continued
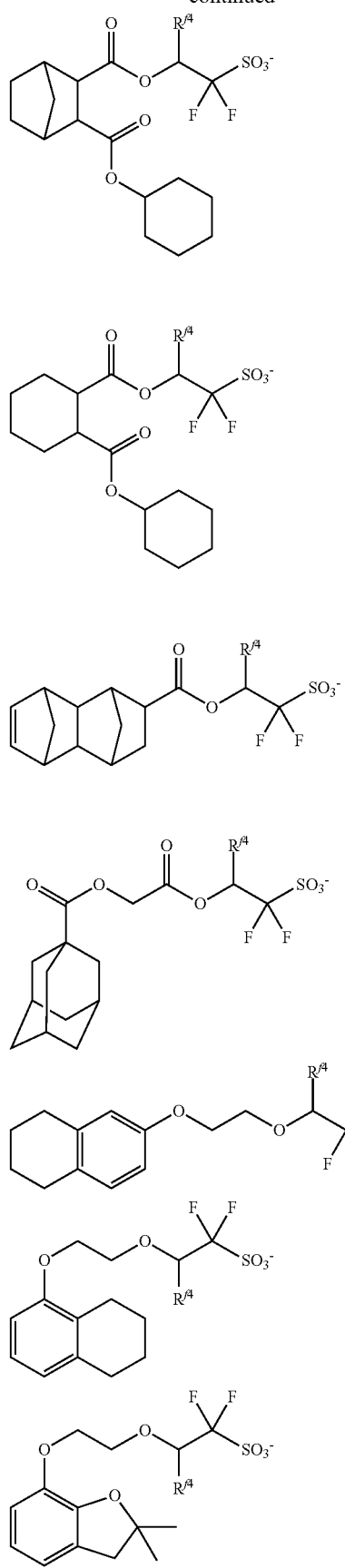

189
-continued
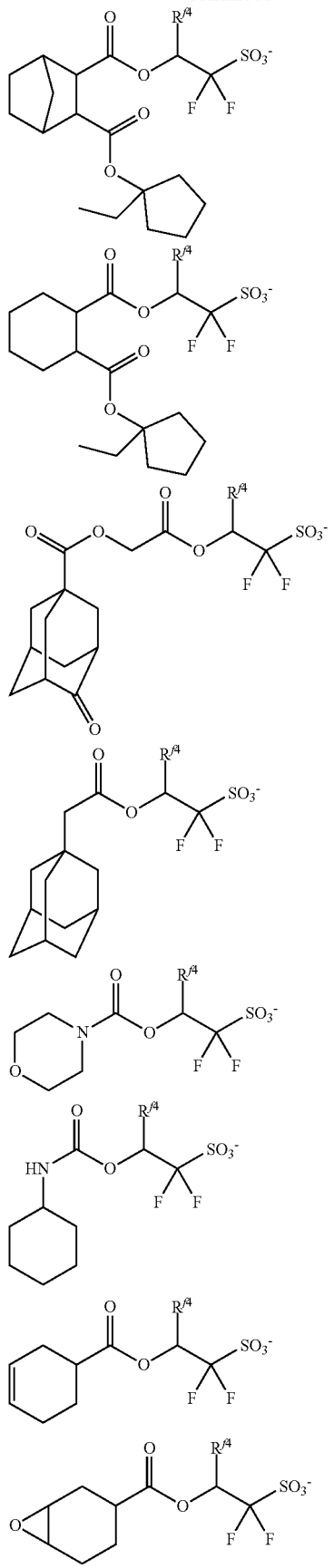
190
-continued
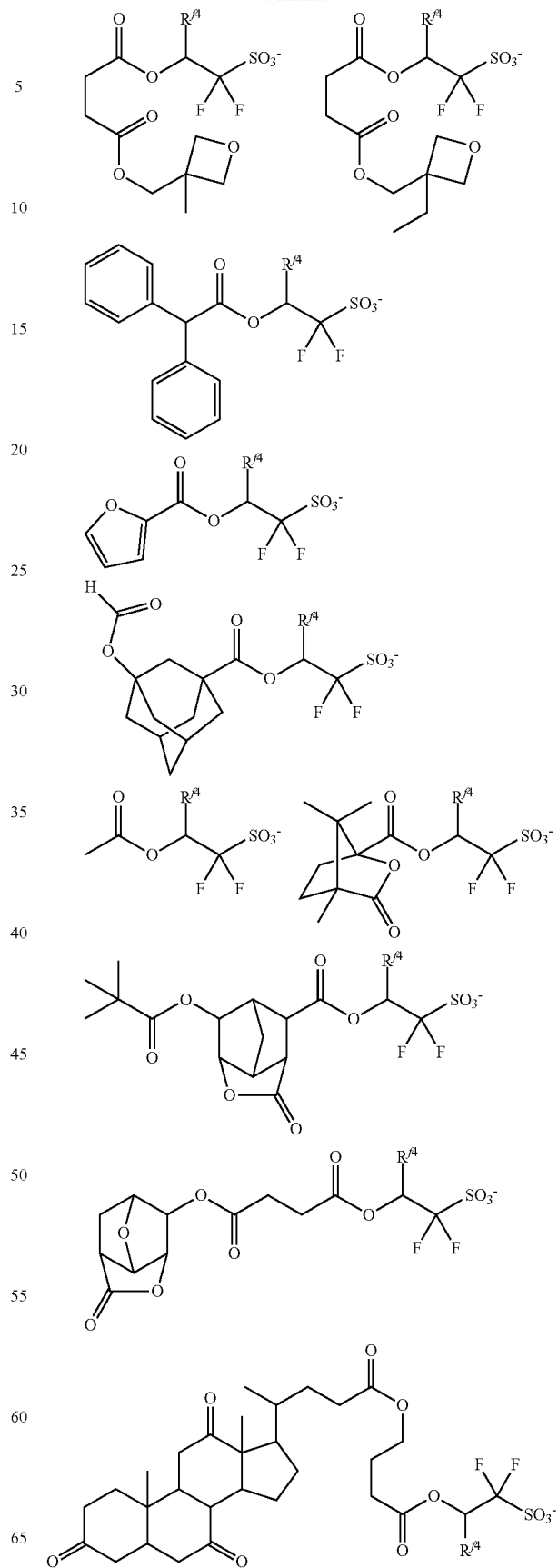

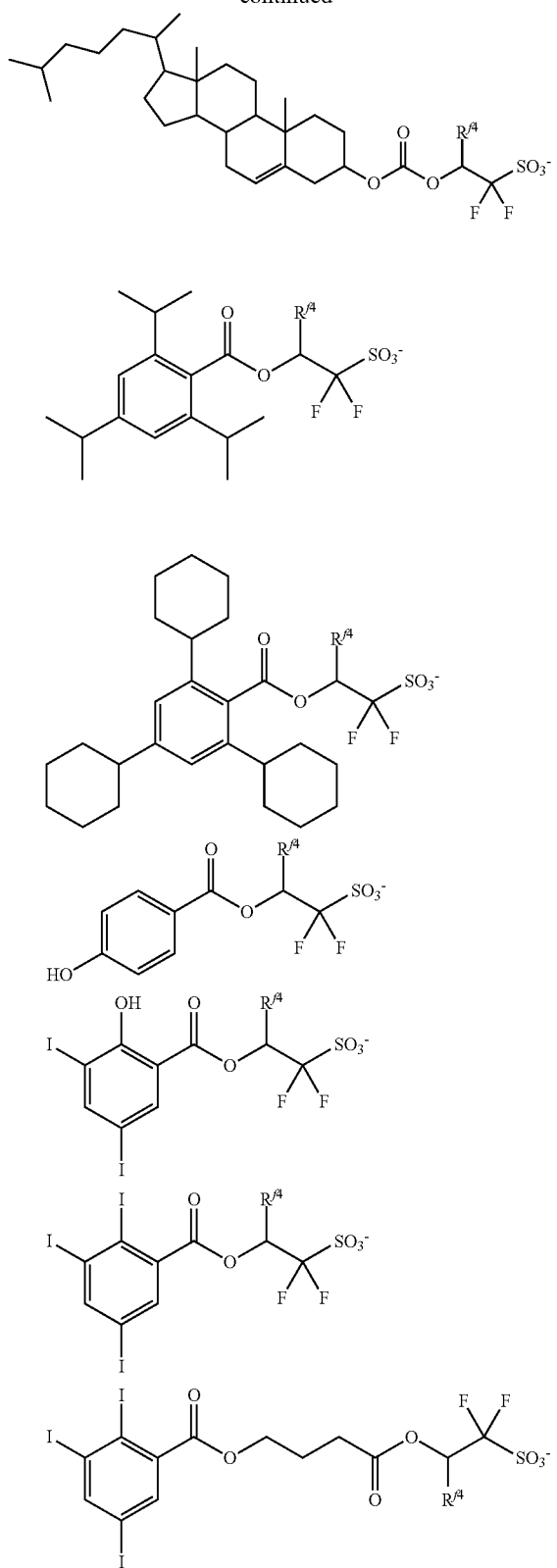
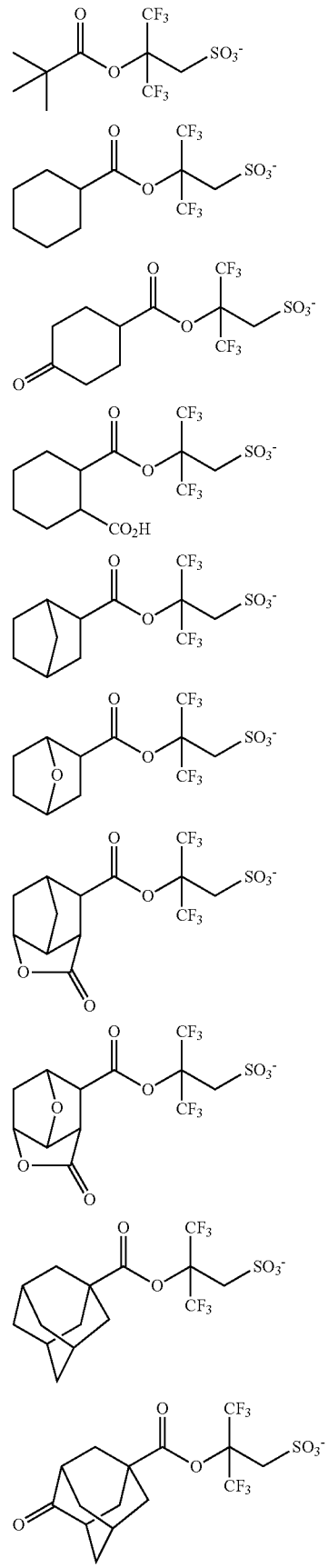
Examples of the anion having formula (d4-2) include the anions described in JP-A 2010-215608, paragraphs [0080]-[0081] and the anions shown below, but are not limited thereto.

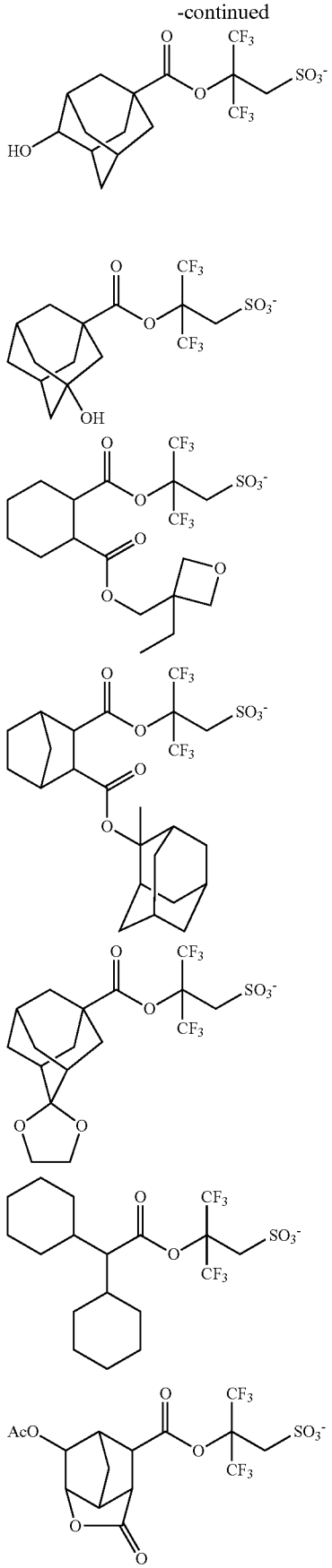
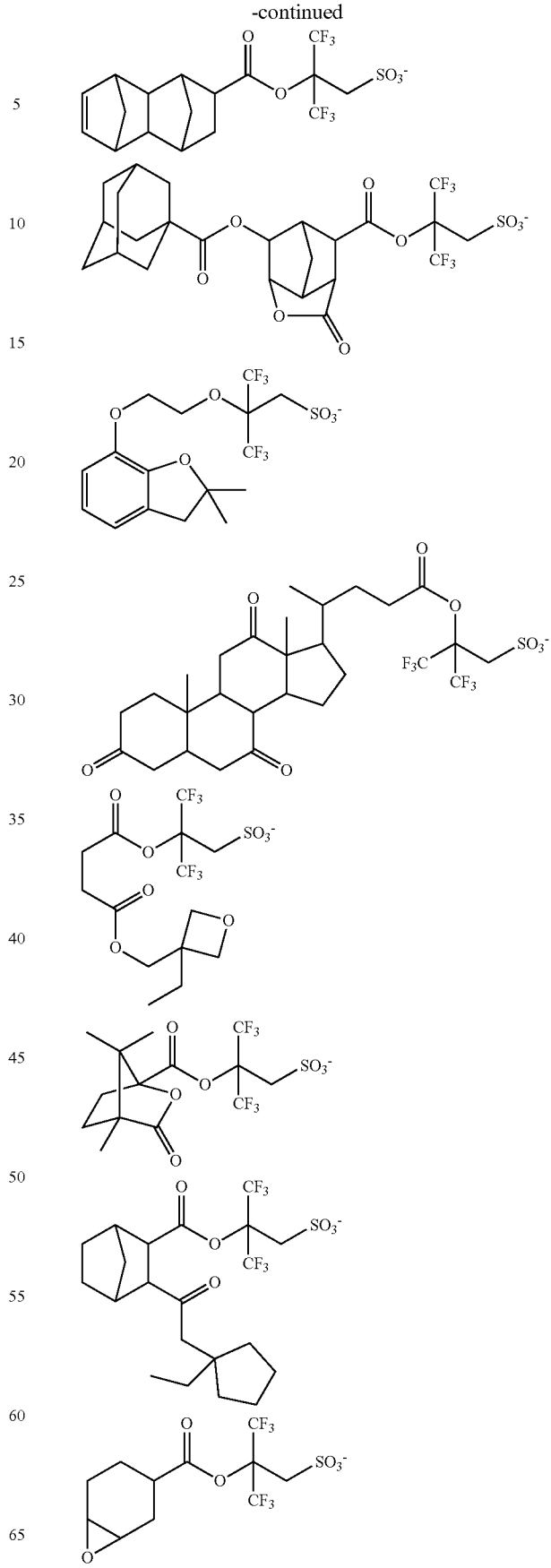

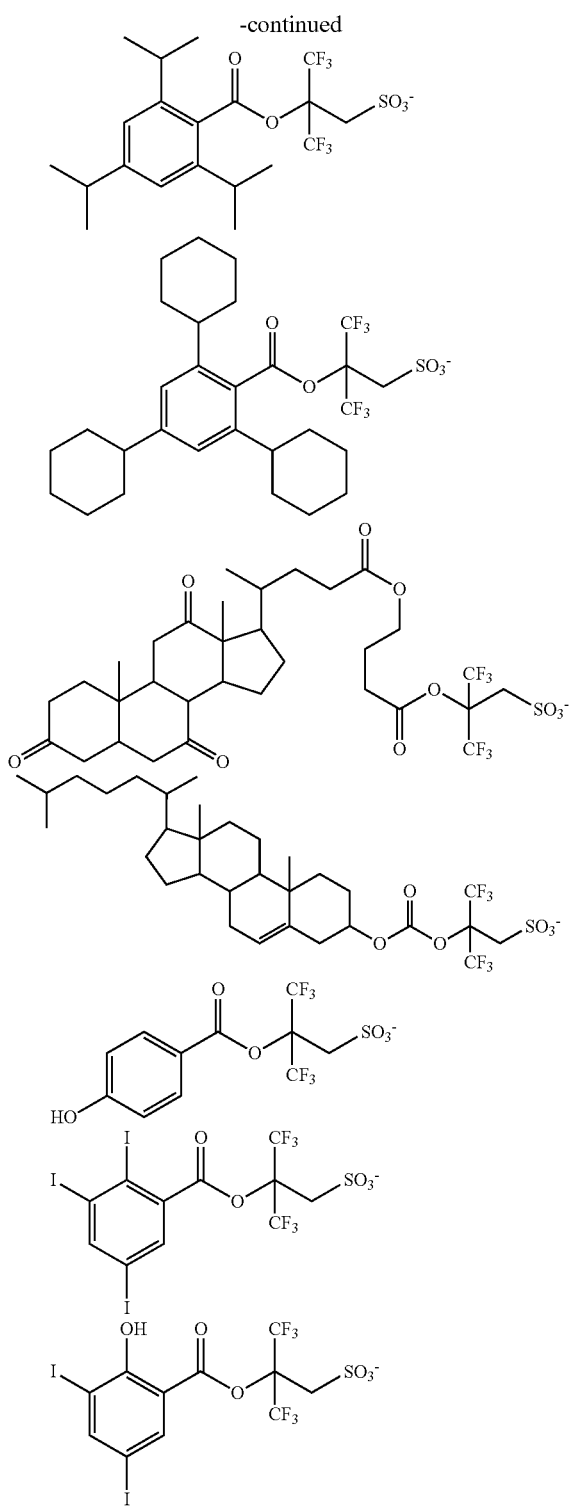

With respect to repeat unit (d1) wherein $R^{f1}$ is hydrogen, reference is made to JP-A 2010-116550. With respect to repeat unit (d1) wherein $R^{f1}$ is trifluoromethyl, reference is made to JP-A 2010-077404. Examples of the anion in repeat unit (d1) include the anions described in these patent documents and JP-A 2014-177407, paragraphs [0021]-[0026].

With respect to repeat unit (d2) wherein $R^{f2}$ and $R^{f3}$ are trifluoromethyl, reference is made to JP-A 2017-031377. Examples of the anion in repeat unit (d2) include the anions described in these patent documents and correspond to the examples of the anion in repeat unit (d1) wherein —CH($R^{f1}$)CF$_2$SO$_3^-$ is replaced by —C(CF$_3$)$_2$CH$_2$SO$_3^-$ or —CH$_2$CH$_2$SO$_3^-$.

Preferred examples of the anion in repeat units (d1) to (d3) are given below, but not limited thereto. Herein $R^A$ is as defined above.

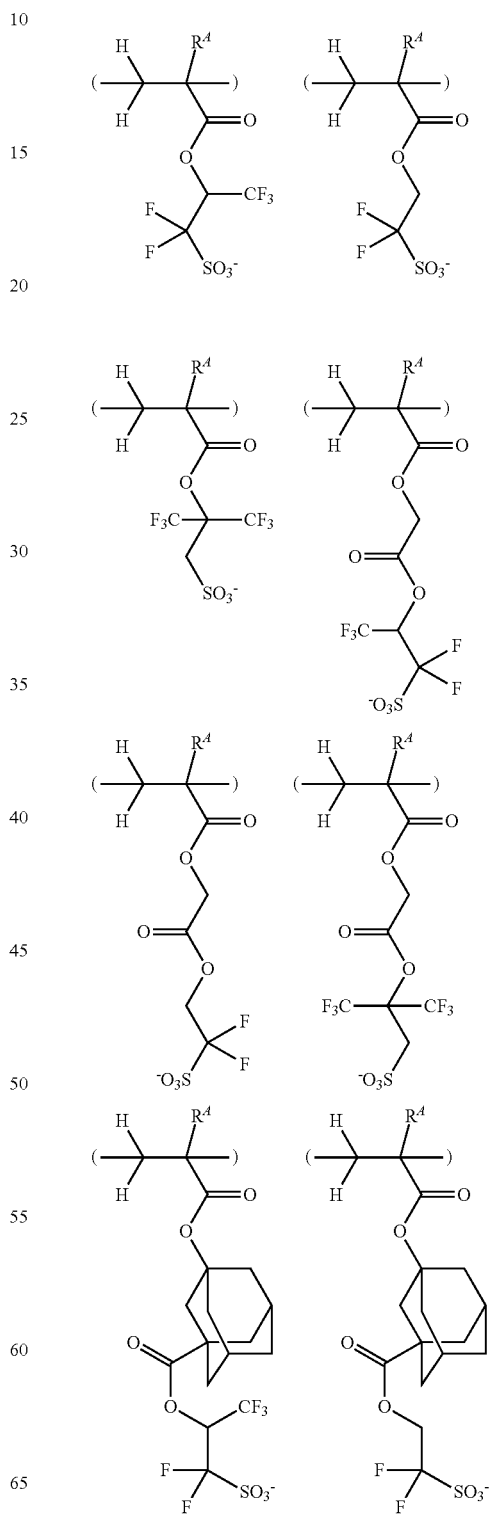

-continued
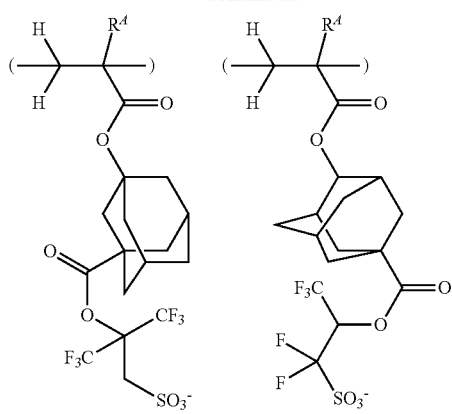
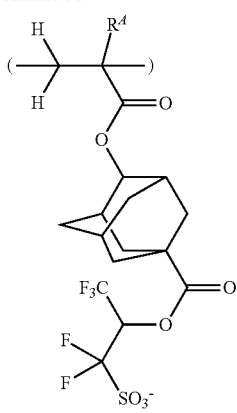
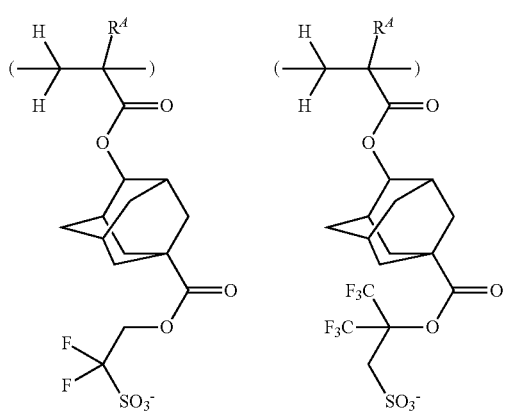
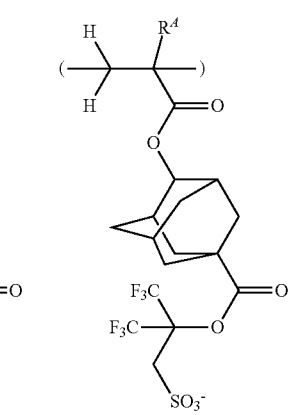
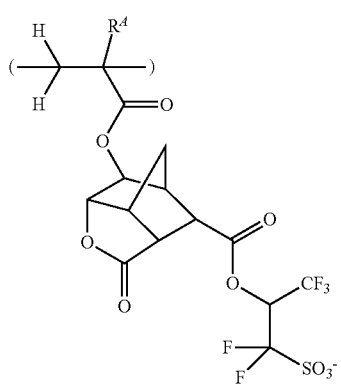
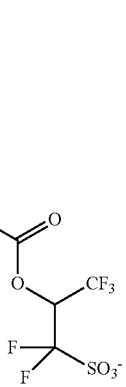
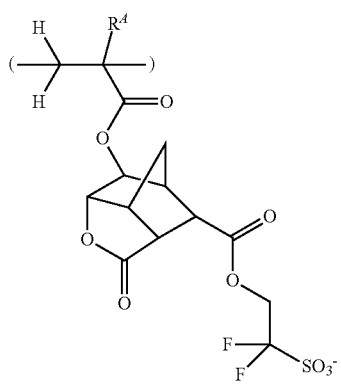
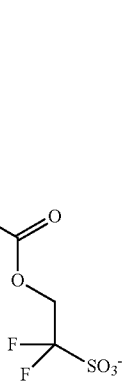
-continued
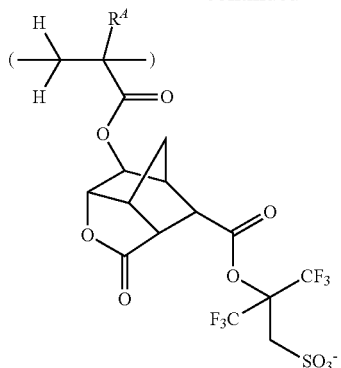
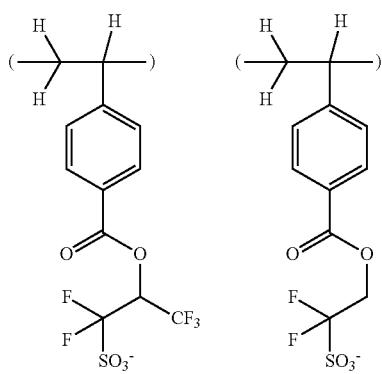
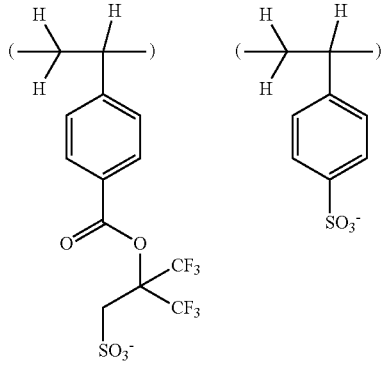
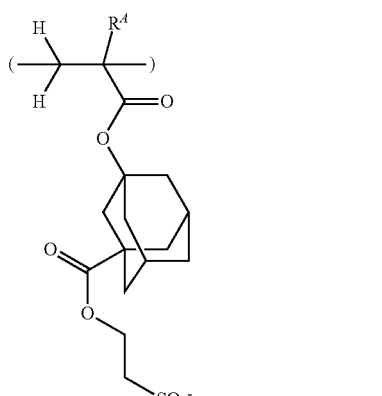
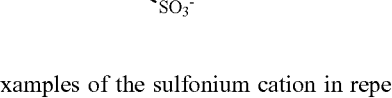
Examples of the sulfonium cation in repeat units (d1) to (d3) are shown below, but not limited thereto.

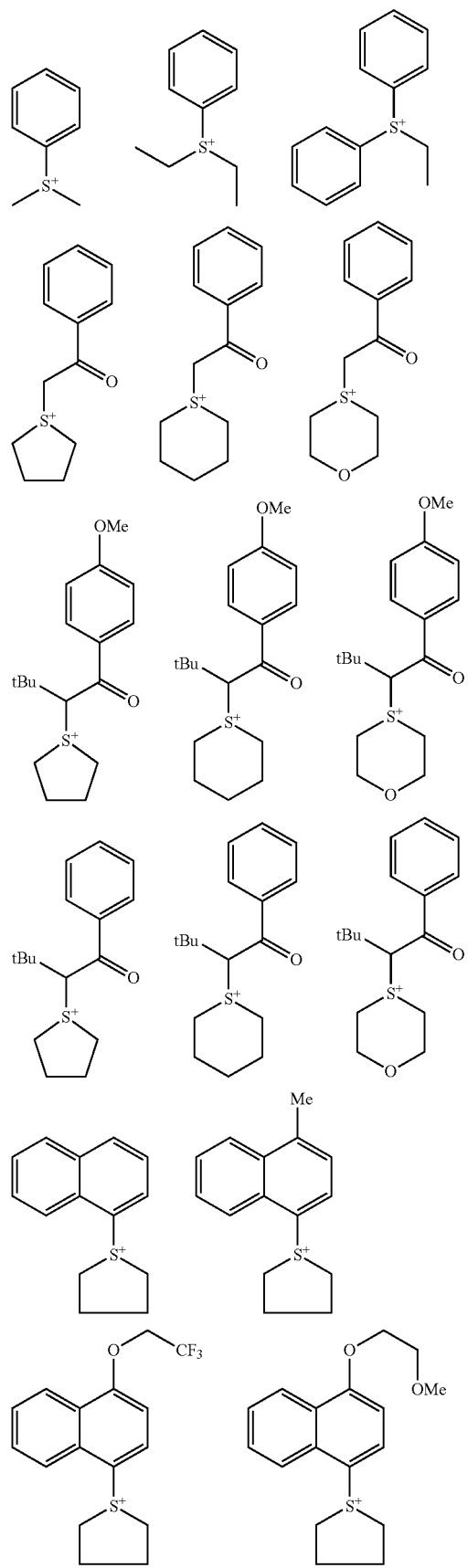
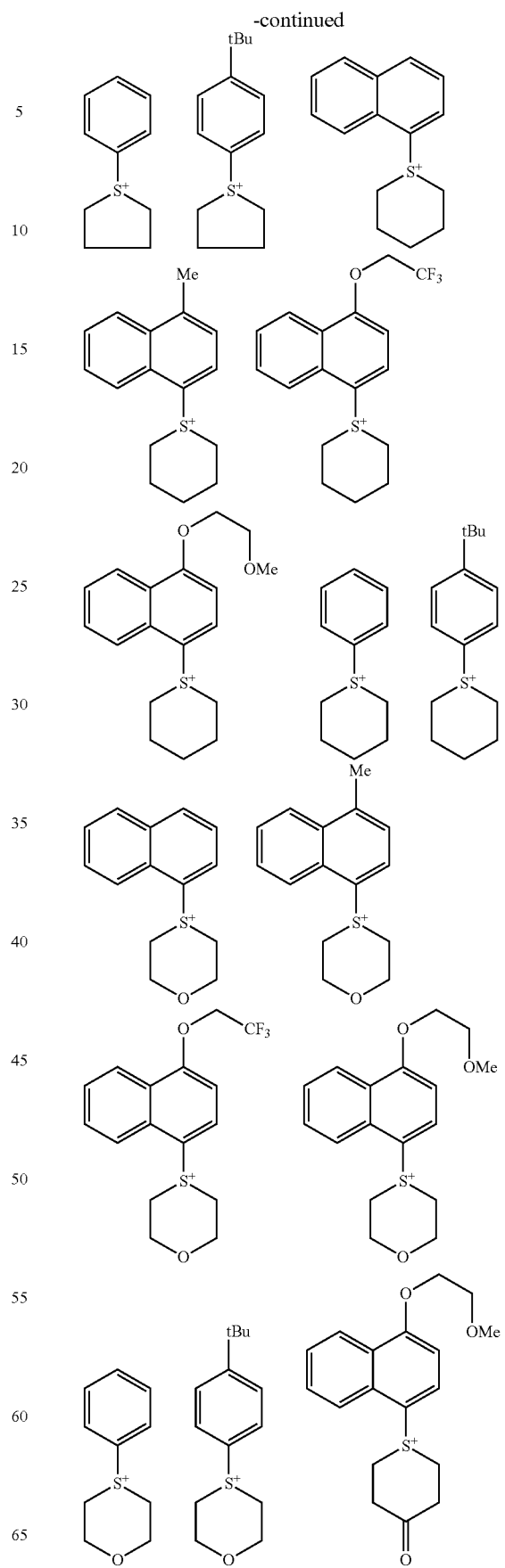

201
-continued
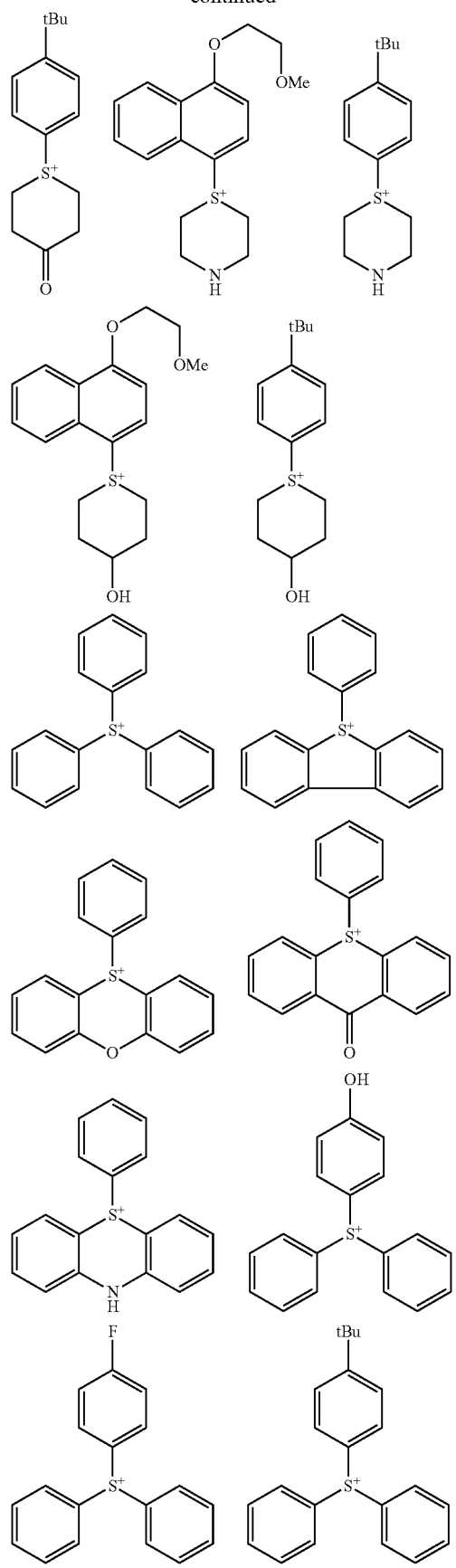
202
-continued
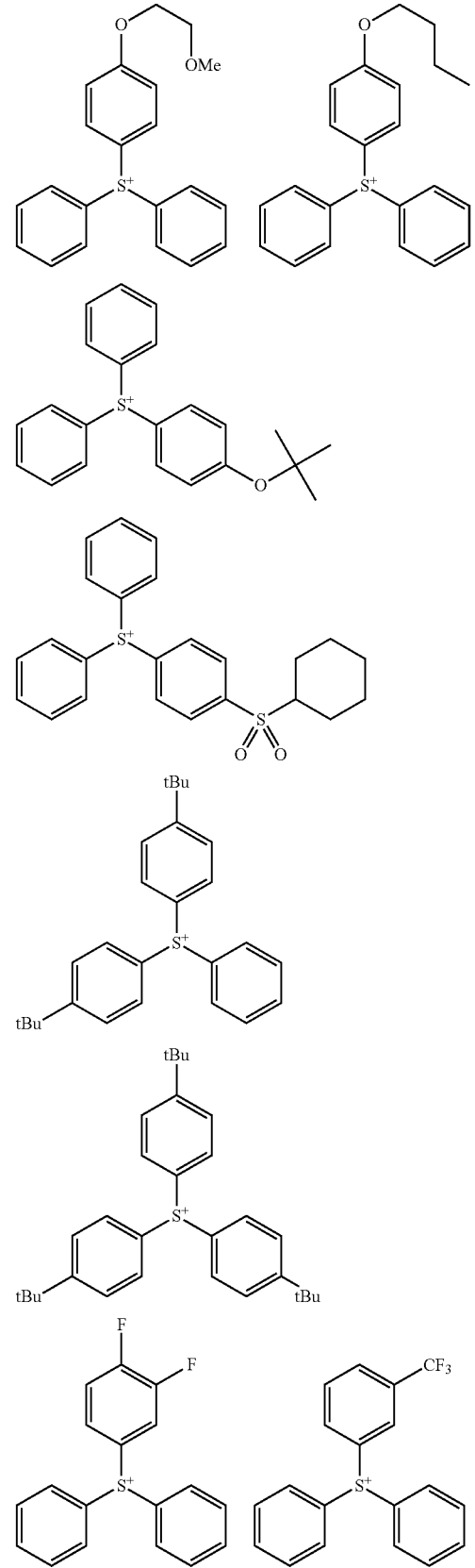

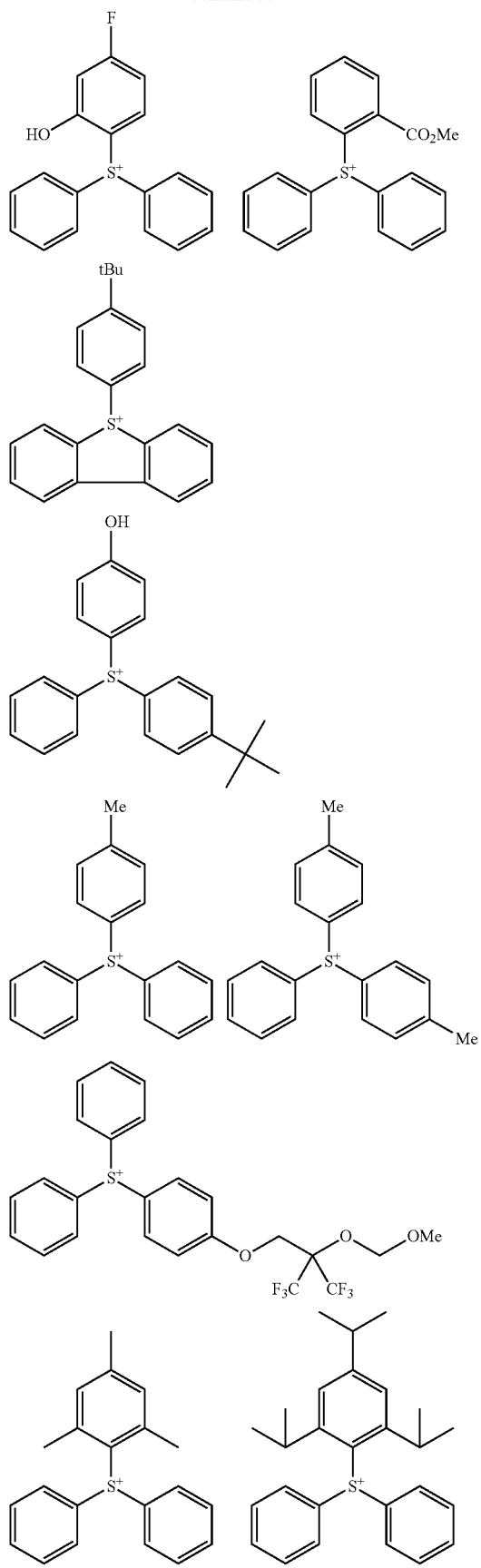
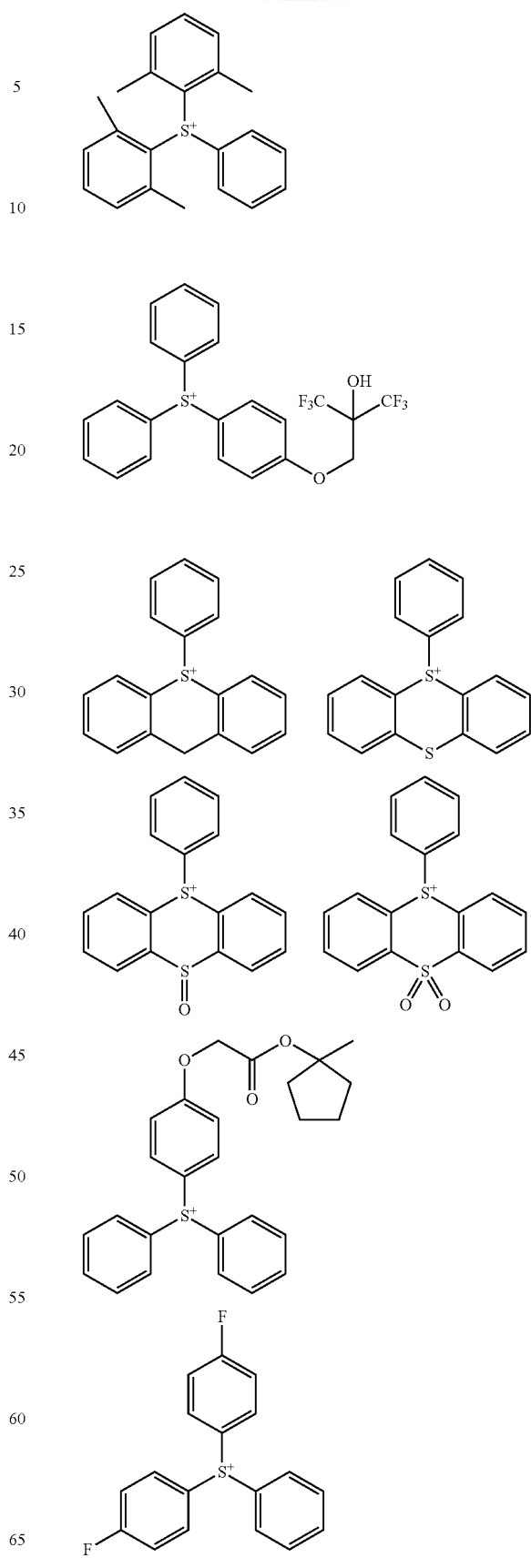

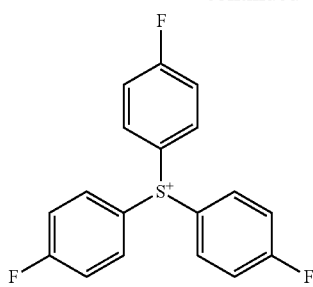
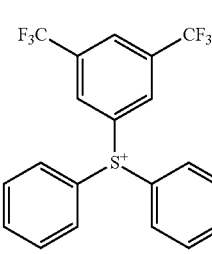
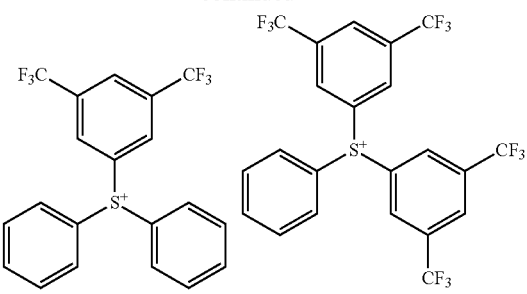
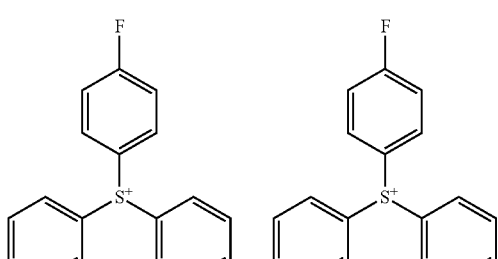
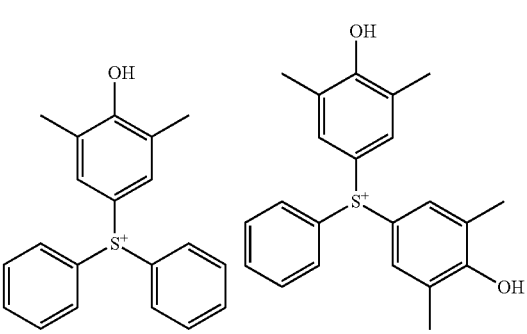
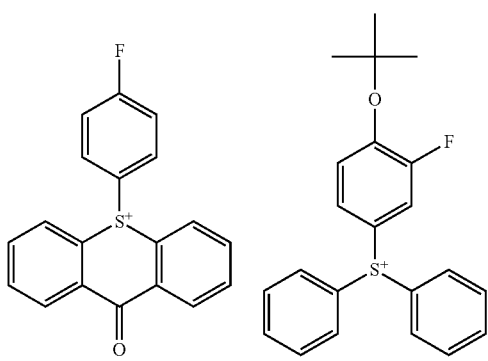
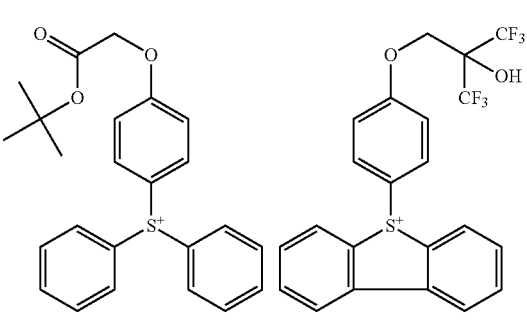
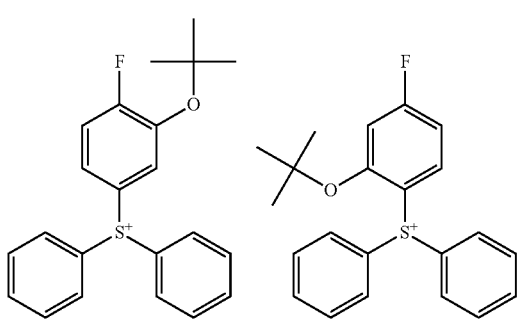
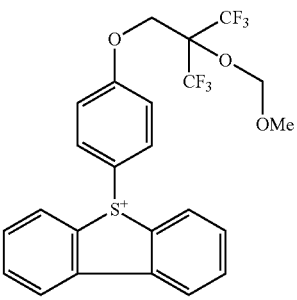
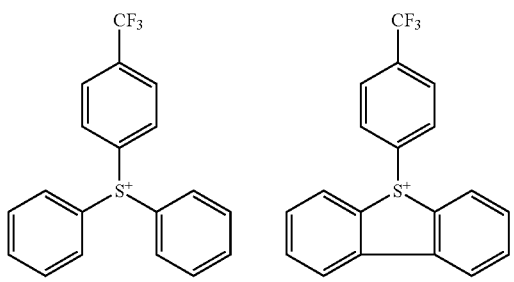
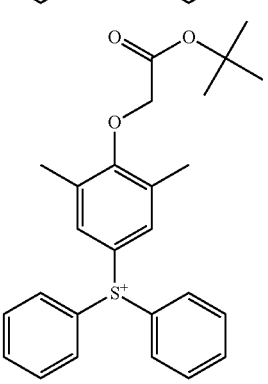

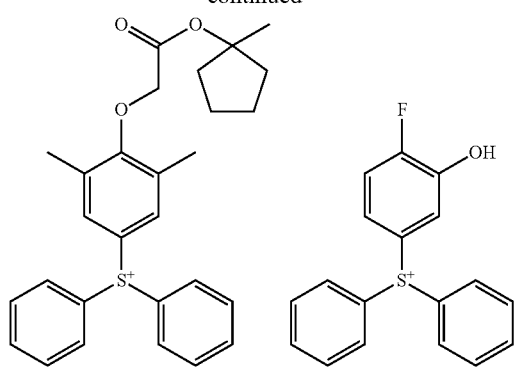
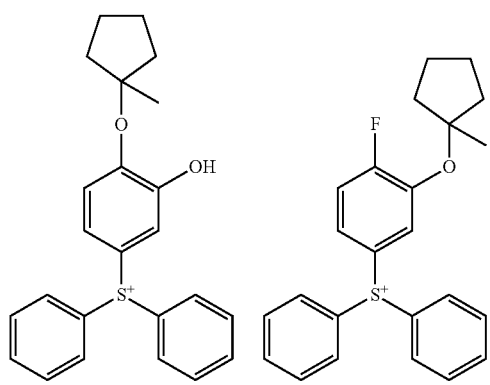
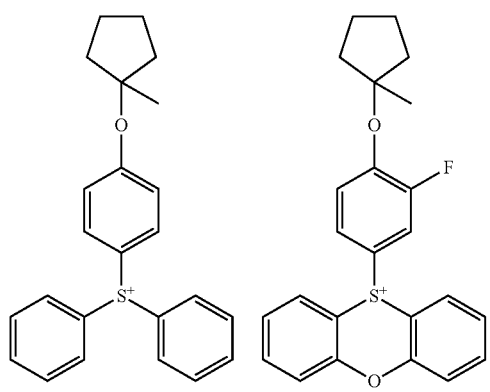
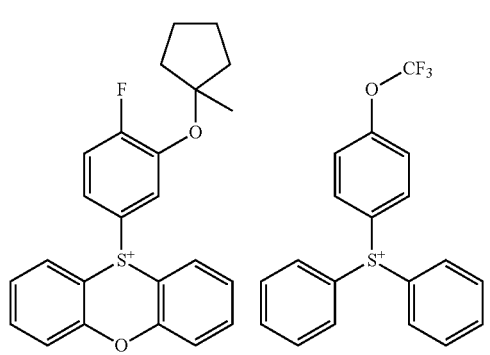
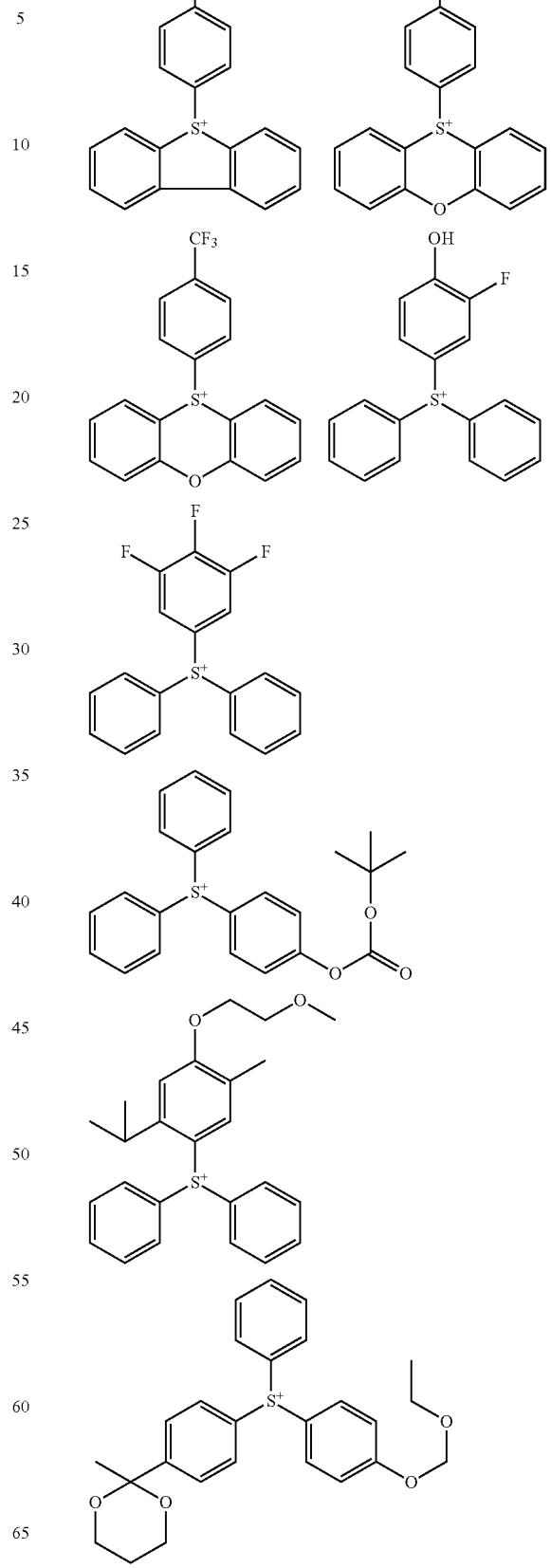

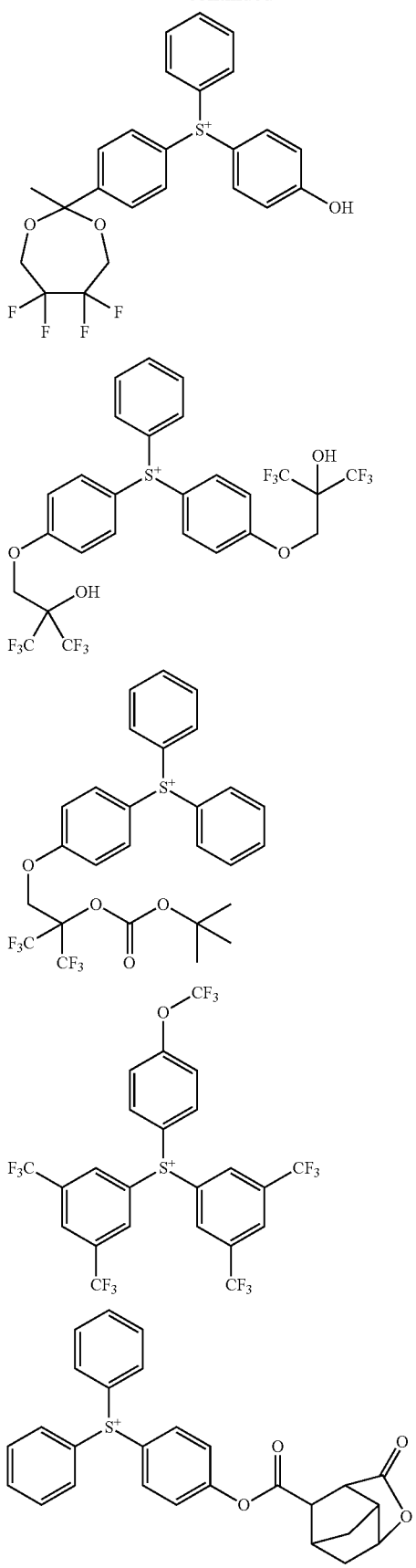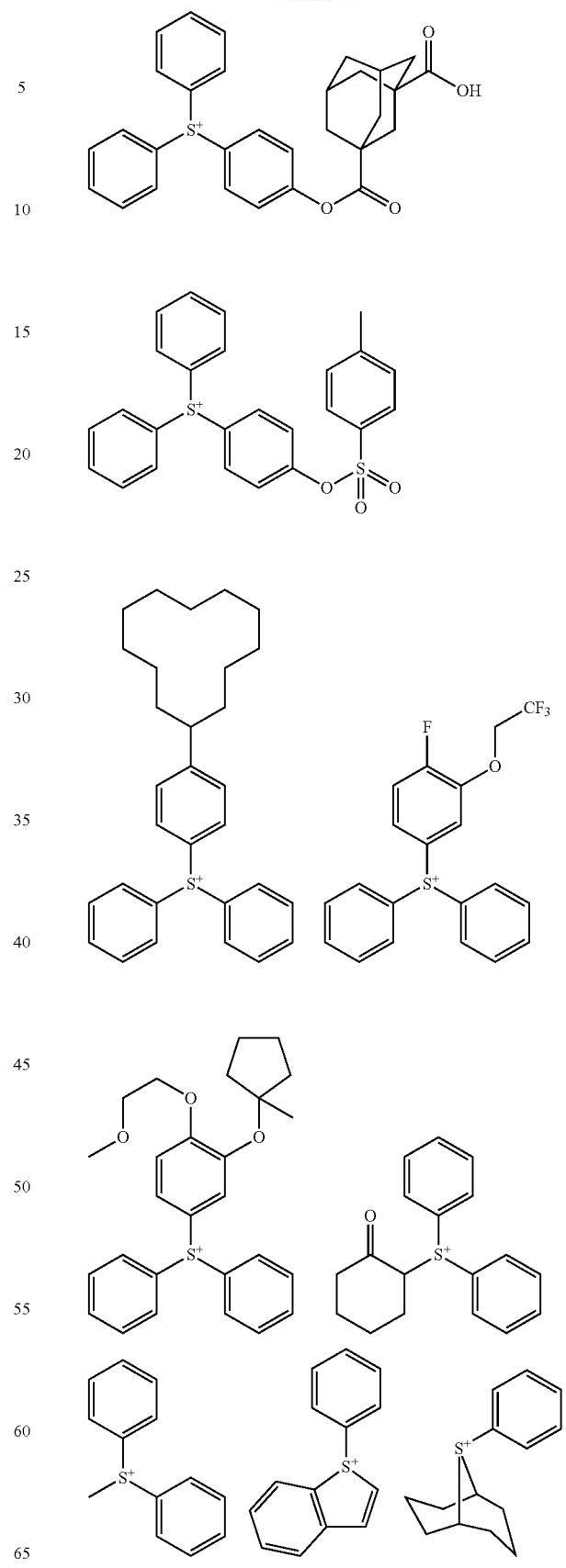

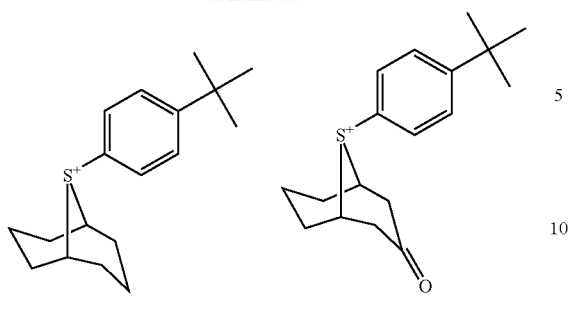
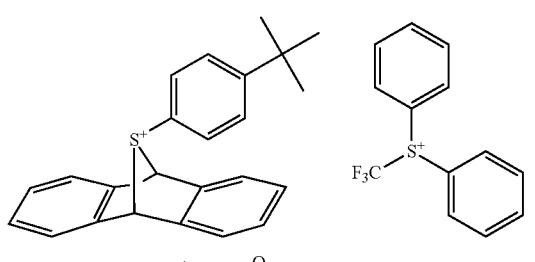
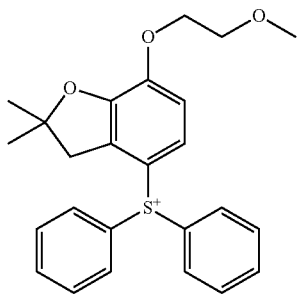
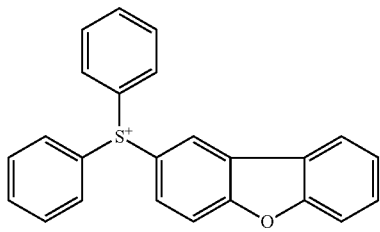
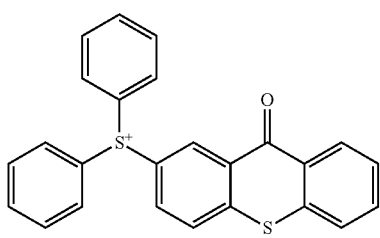
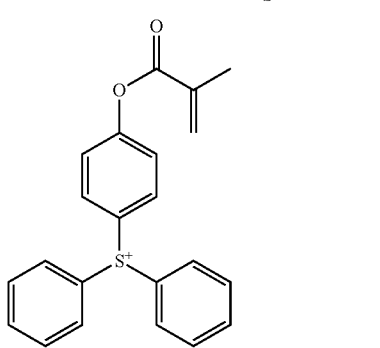
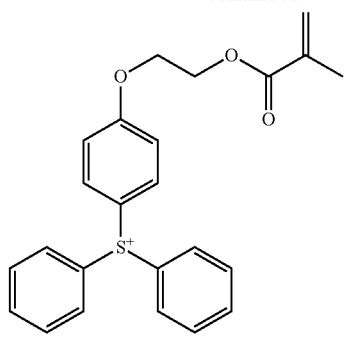
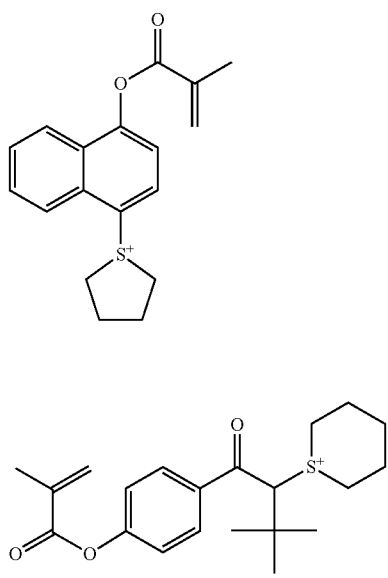
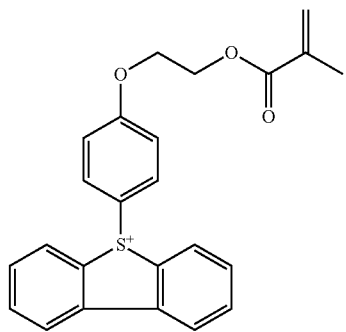
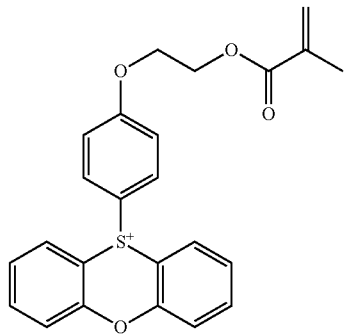

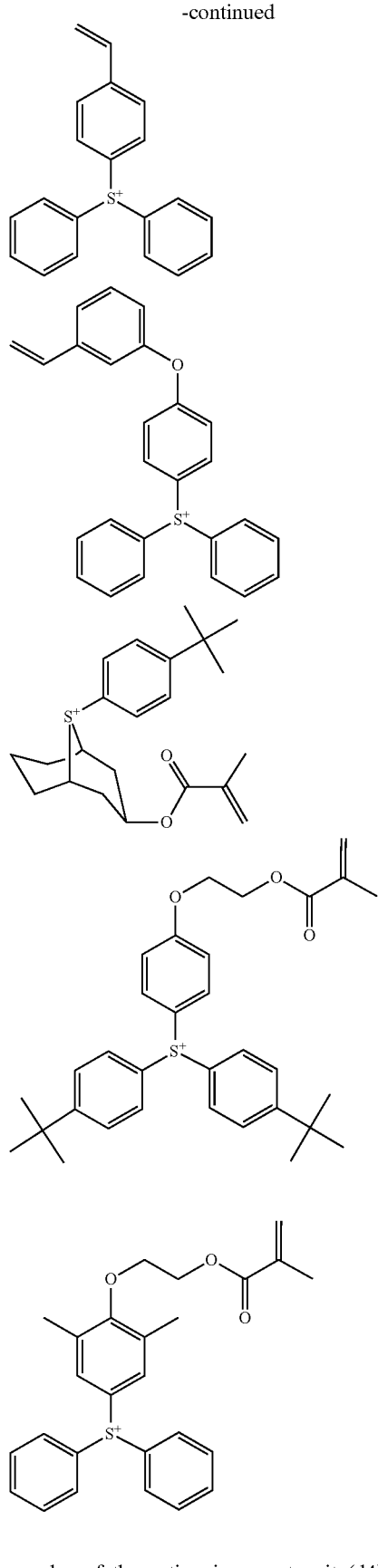
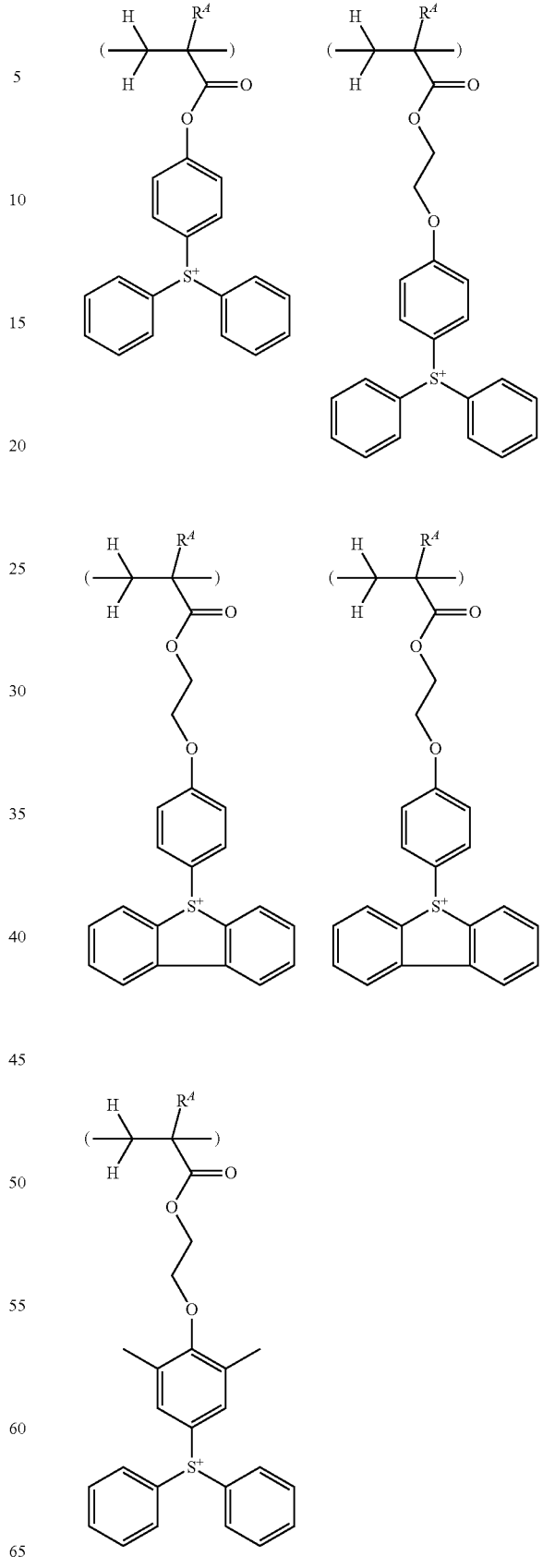
Examples of the cation in repeat unit (d4) are shown below, but not limited thereto. $R^A$ is as defined above.

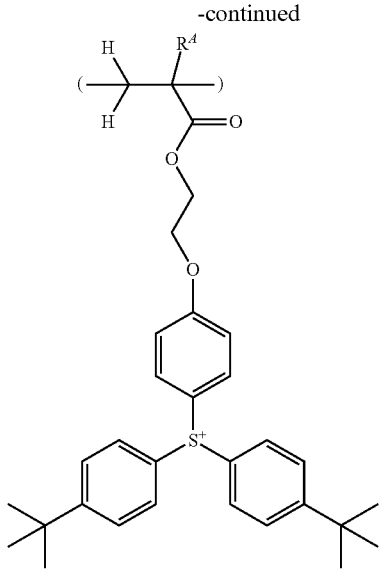

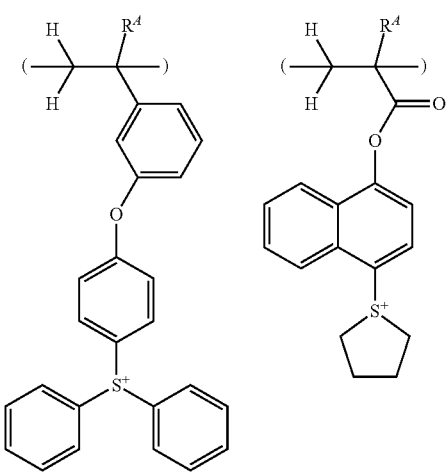

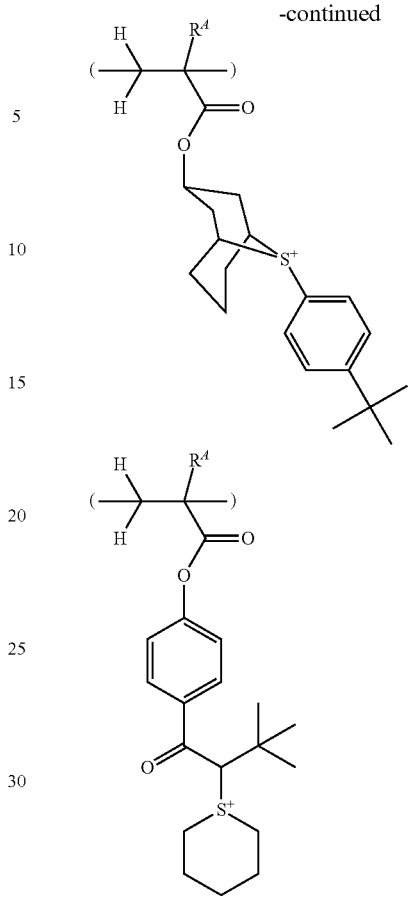

Of the sulfonium cations in repeat units (d1) to (d3), cations having the formulae (M-1) and (M-2) are preferred.

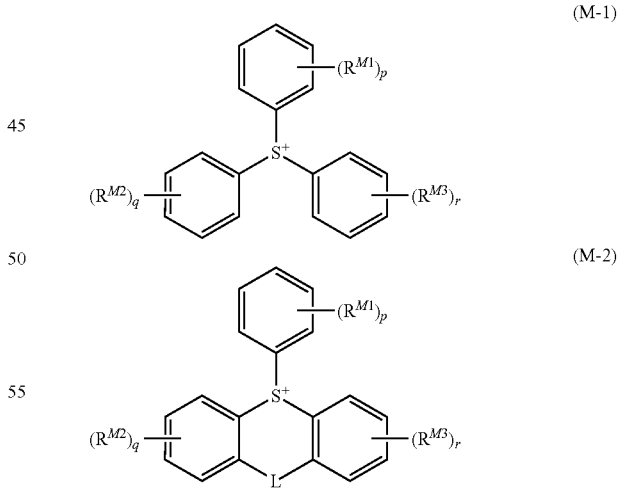

In formulae (M-1) and (M-2), $R^{M1}$, $R^{M2}$ and $R^{M3}$ are each independently halogen, hydroxy, or a $C_1$-$C_{15}$ hydrocarbyl group which may contain a heteroatom, p, q and r are each independently an integer of 0 to 4. In formula (M-2), L is a single bond, ether bond or carbonyl bond.

Examples of the sulfonium cations having formulae (M-1) and (M-2) are shown below, but not limited thereto.

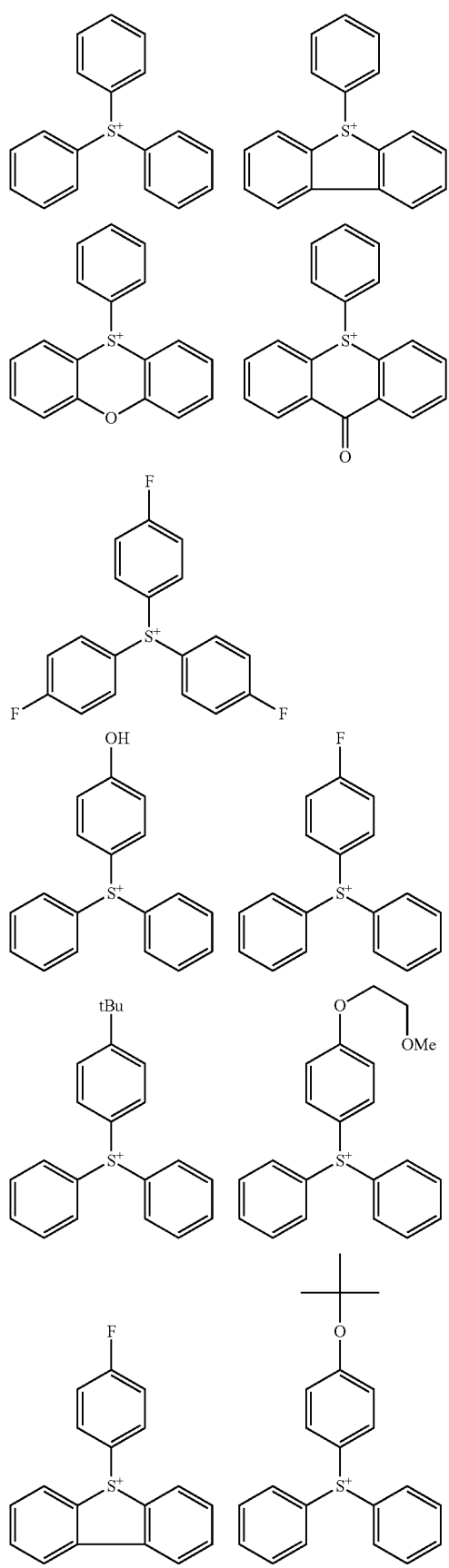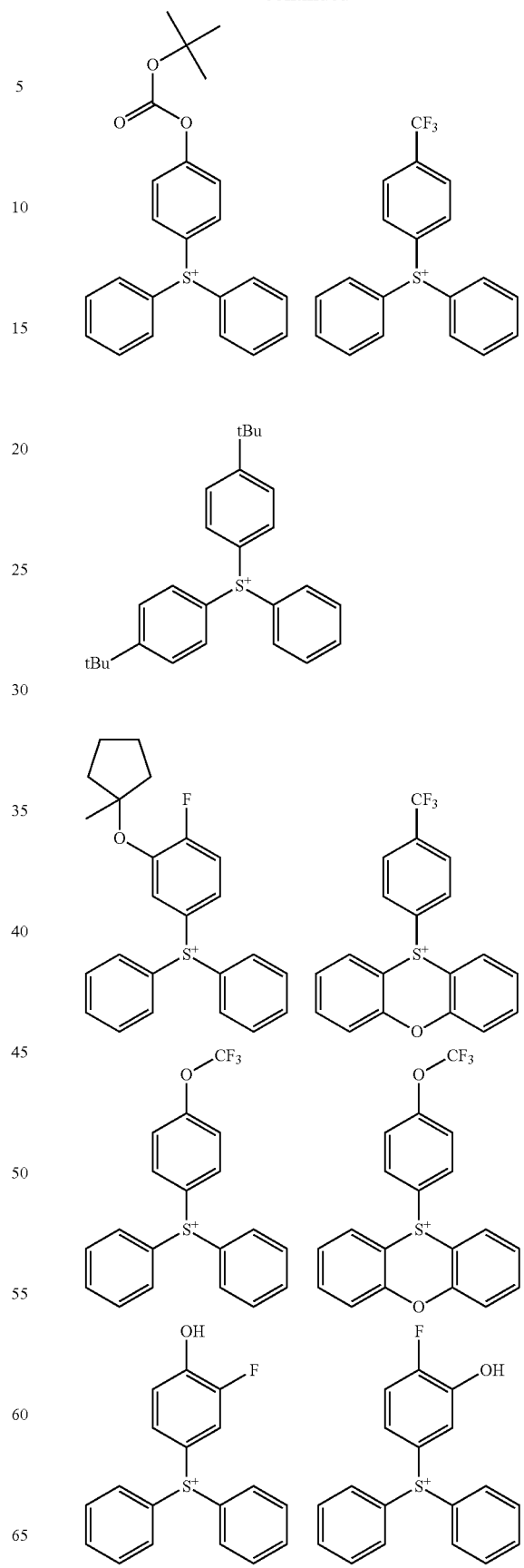

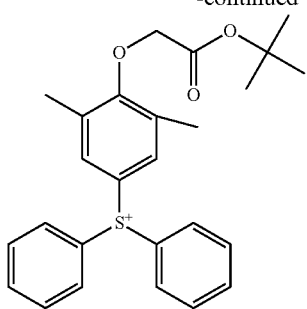

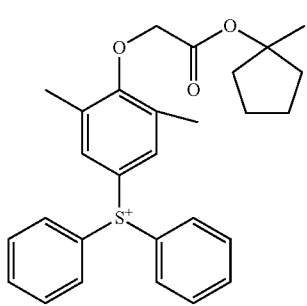

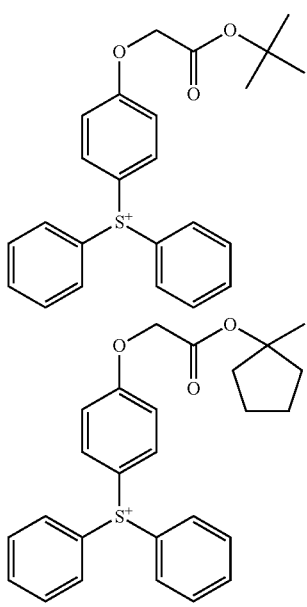

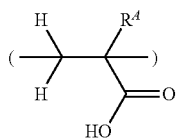 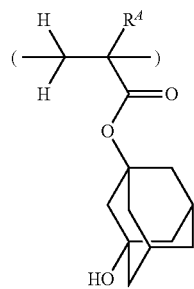

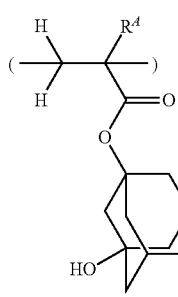 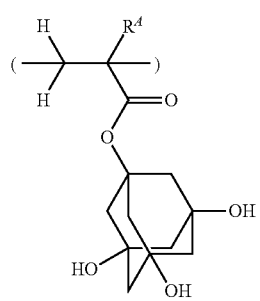

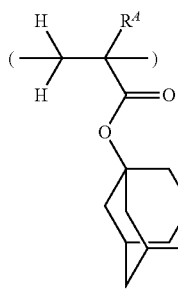 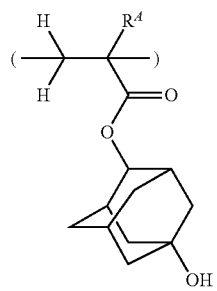

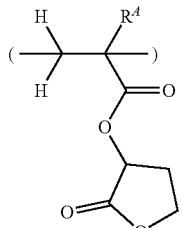 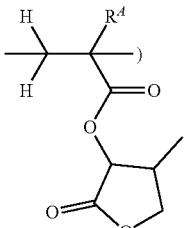

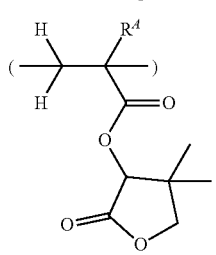 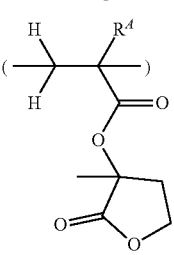

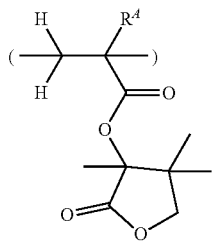 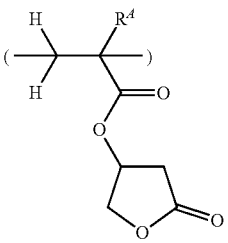

The repeat units (d1) to (d4) have the function of a photoacid generator. On use of a base polymer comprising repeat units (d1) to (d4), a photoacid generator of addition type to be described later may be omitted. Of the repeat units (d1) to (d4), units (d1) are preferred.

The base polymer may further comprise repeat units (e) containing a hydroxy group (other than phenolic hydroxy group), lactone ring, sultone ring, ether bond, ester bond, amide group, imide group, carbonyl group, sulfinyl group, sulfonyl group, cyano group or carboxy group as another adhesive group.

Examples of the repeat units (e) are given below, but not limited thereto. Herein $R^4$ is as defined above.

221
-continued
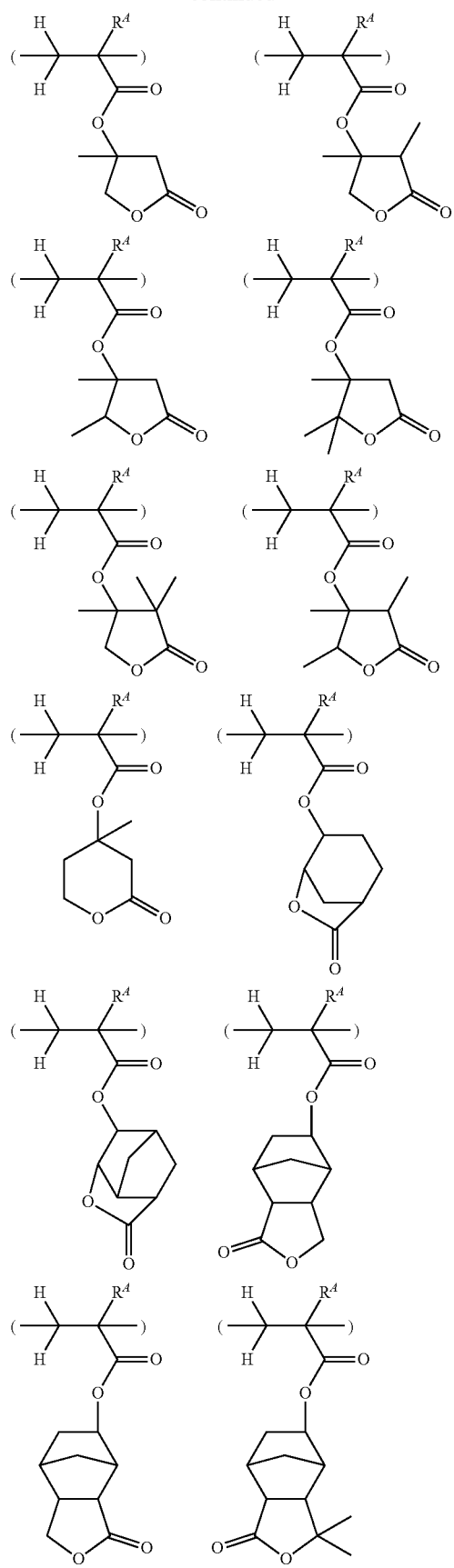
222
-continued
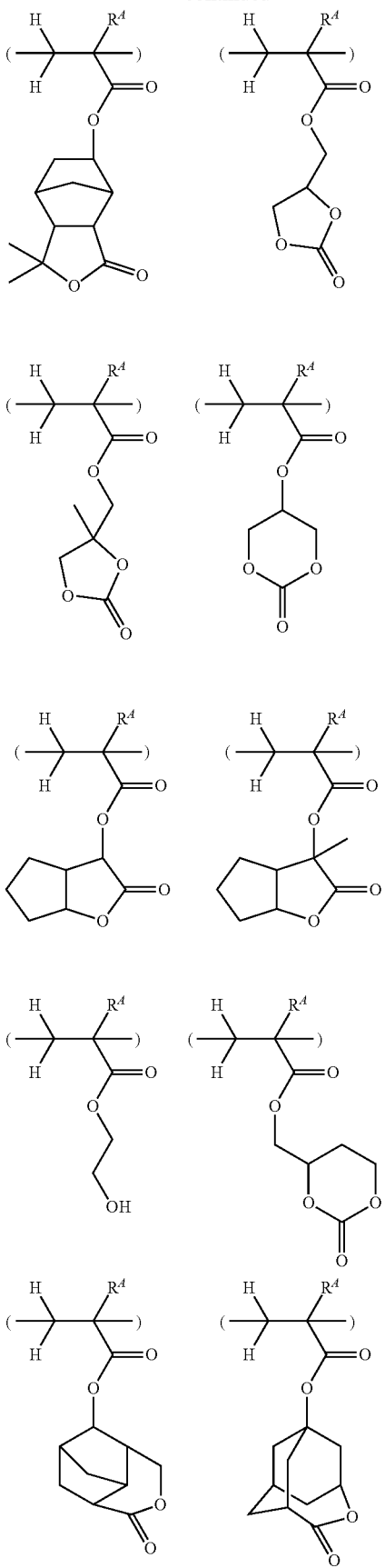

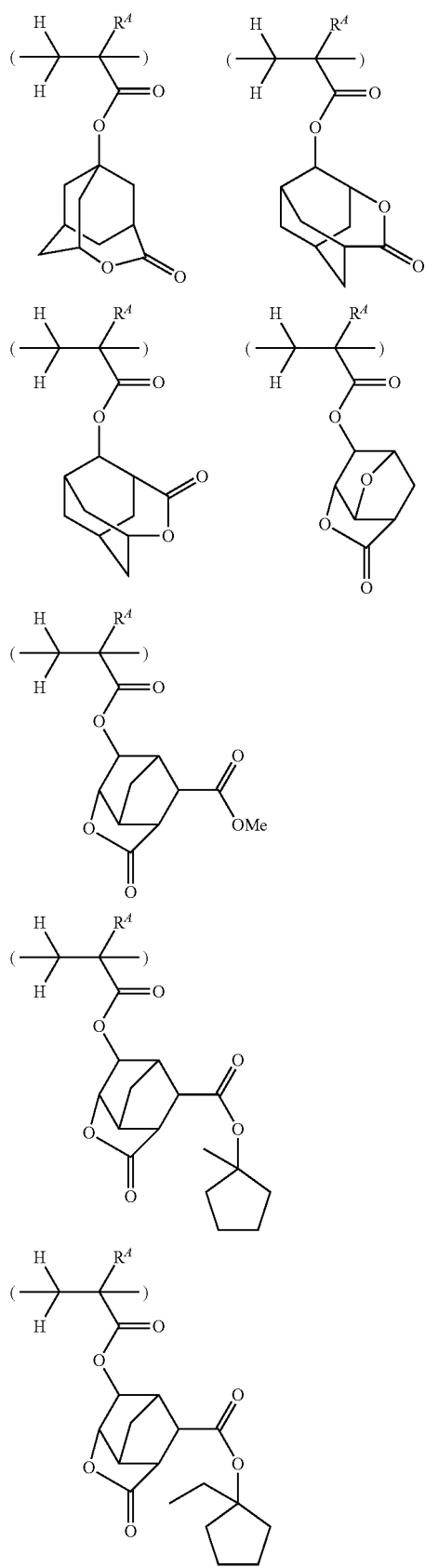
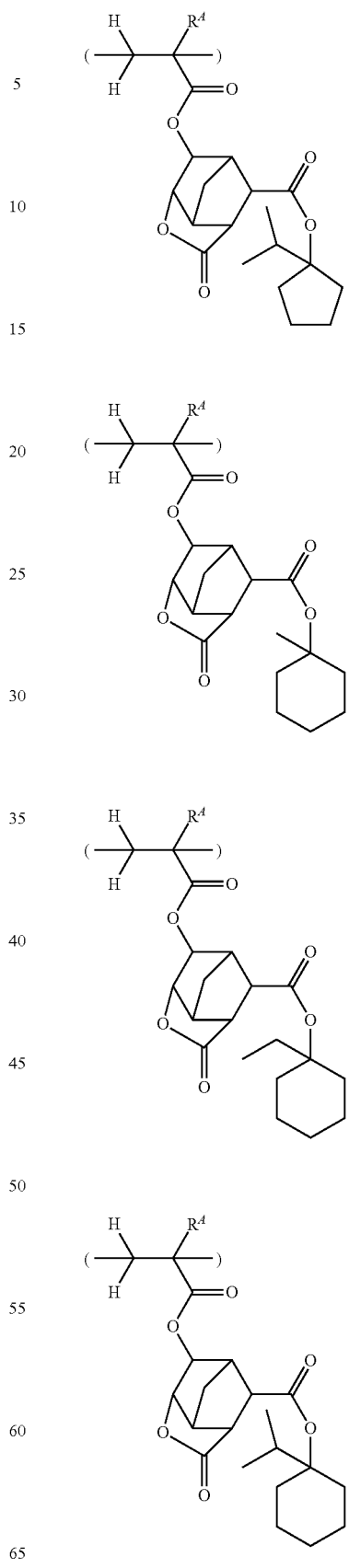

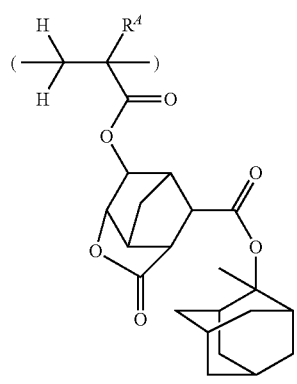
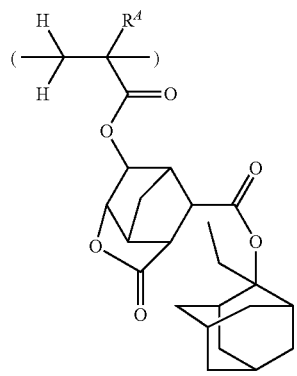
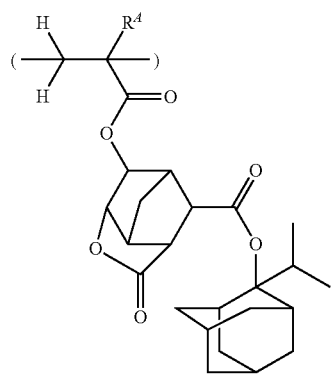
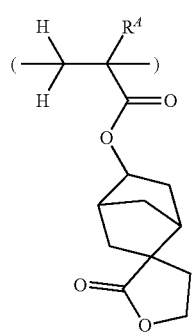
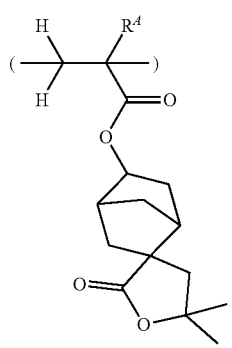
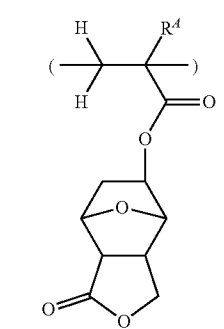
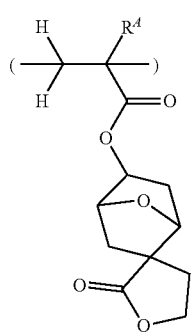
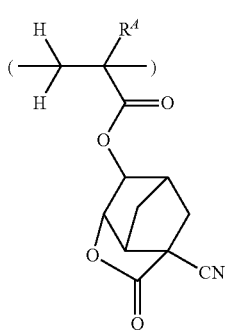
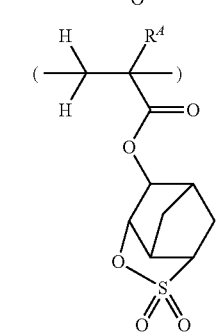
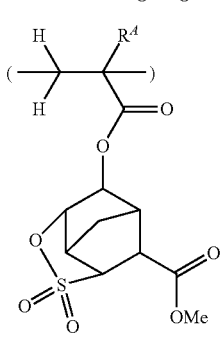
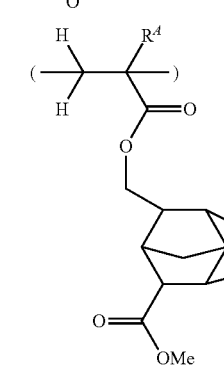

227
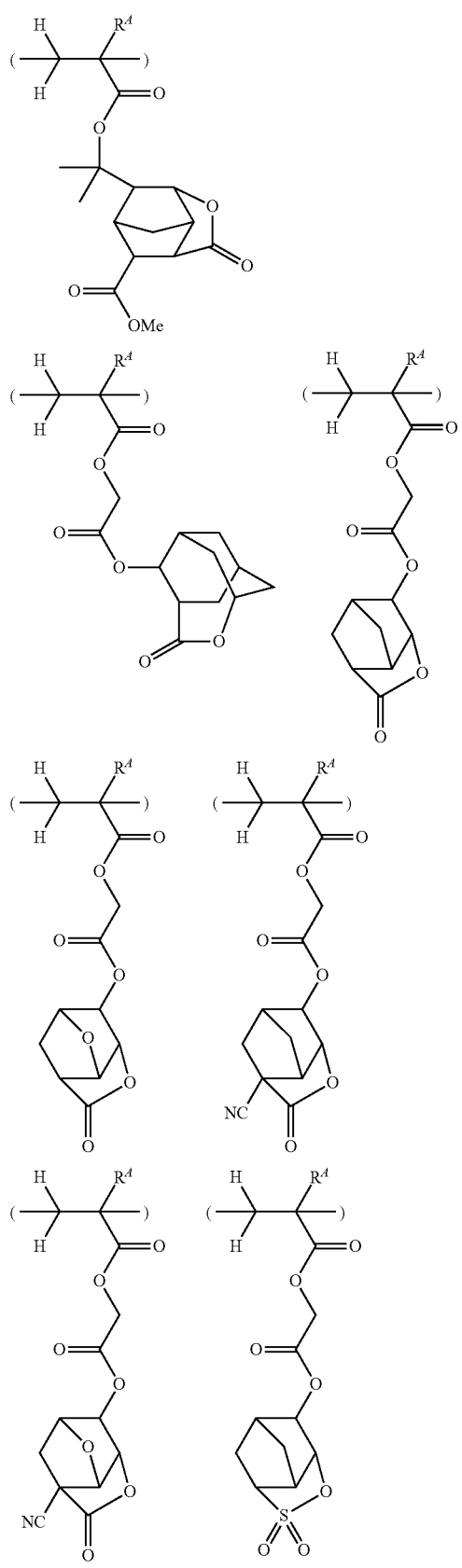
228
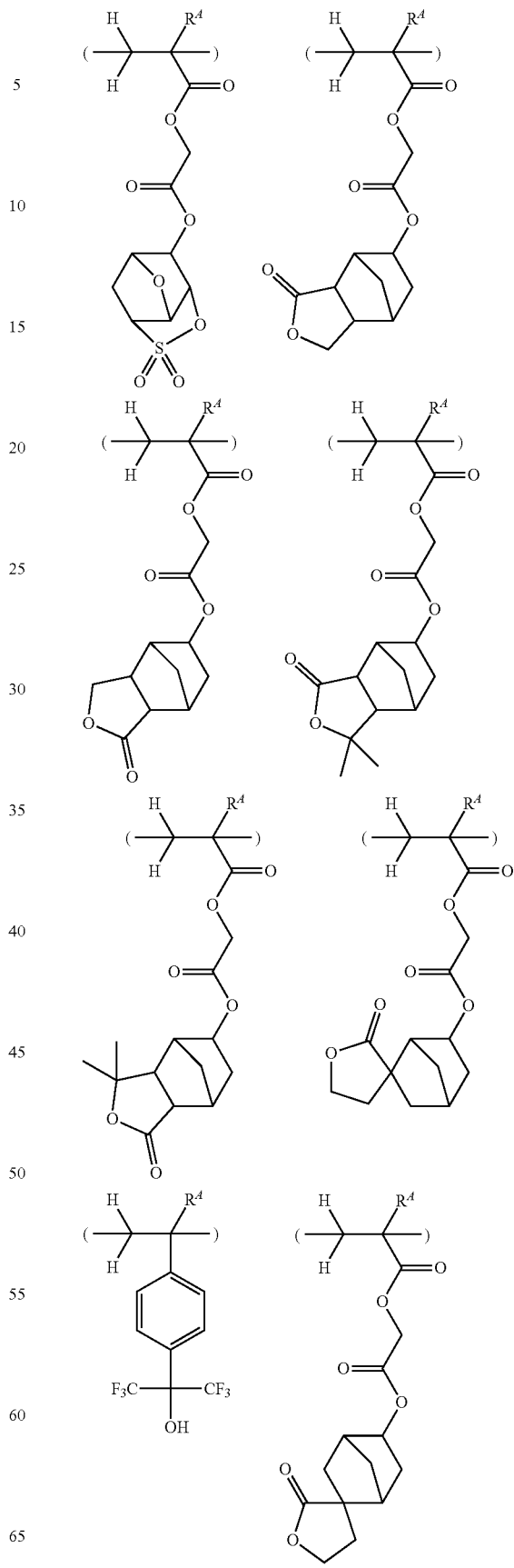

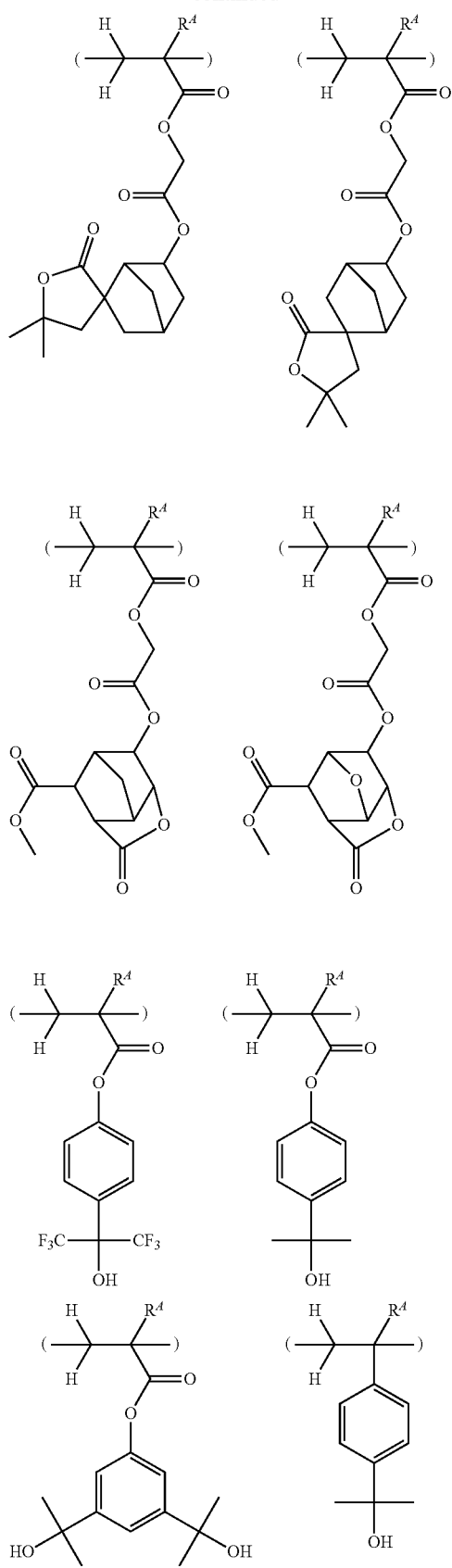
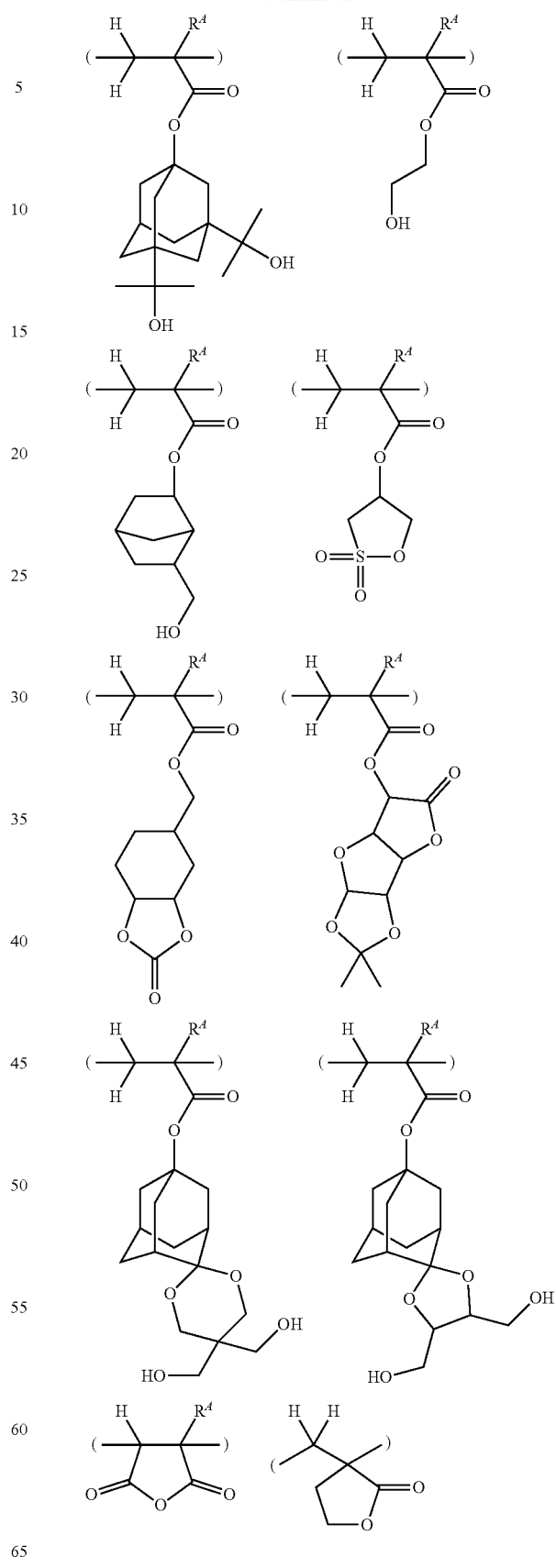

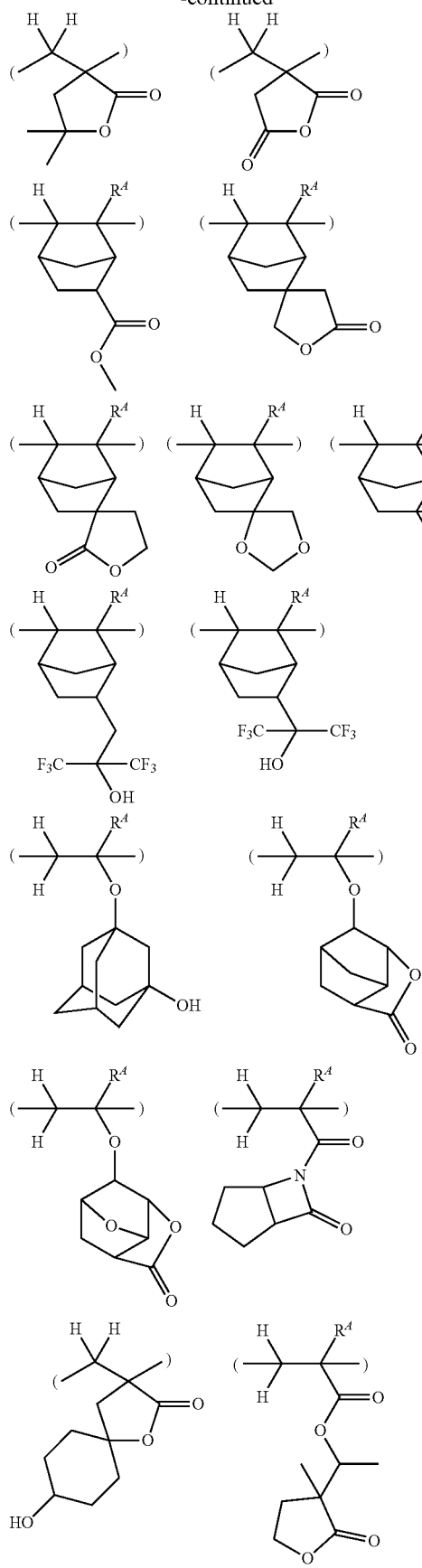
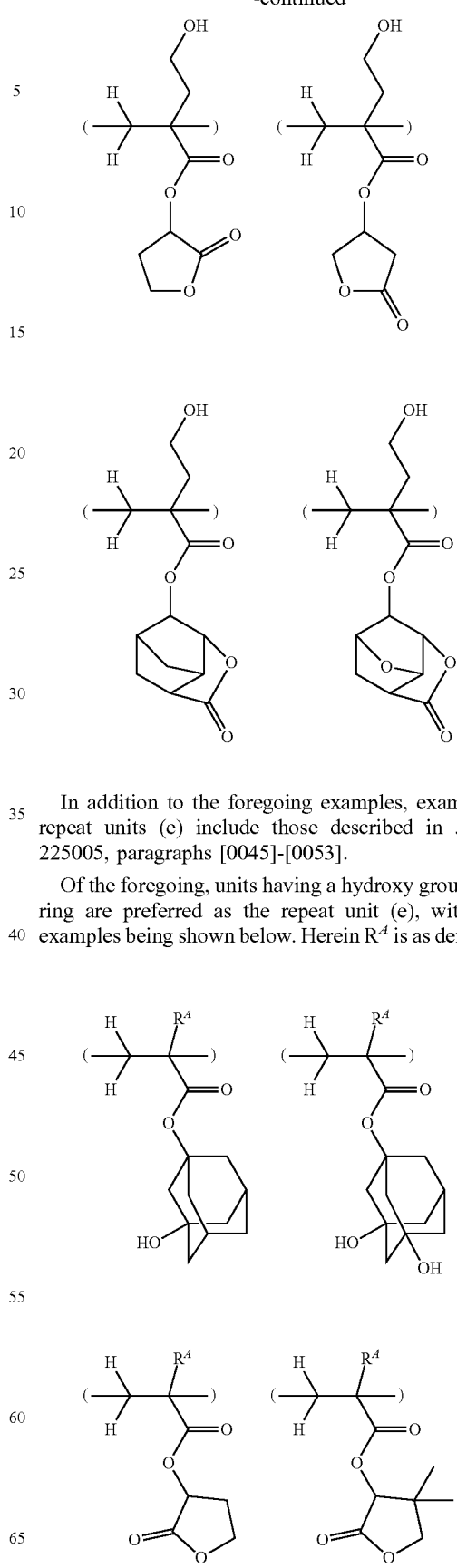
In addition to the foregoing examples, examples of the repeat units (e) include those described in JP-A 2014-225005, paragraphs [0045]-[0053].
Of the foregoing, units having a hydroxy group or lactone ring are preferred as the repeat unit (e), with preferred examples being shown below. Herein $R^A$ is as defined above.
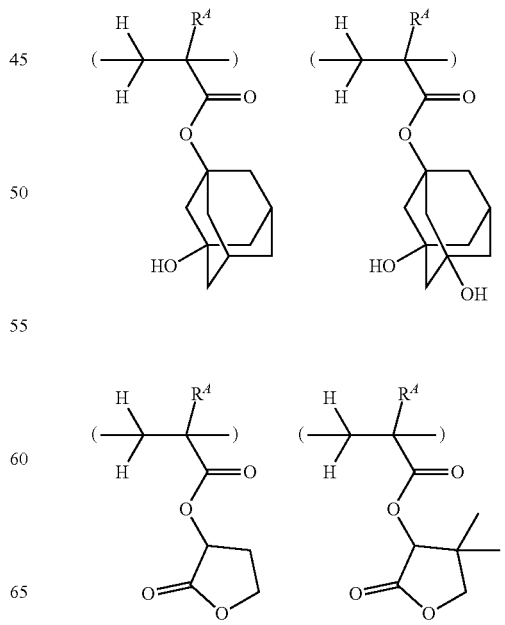

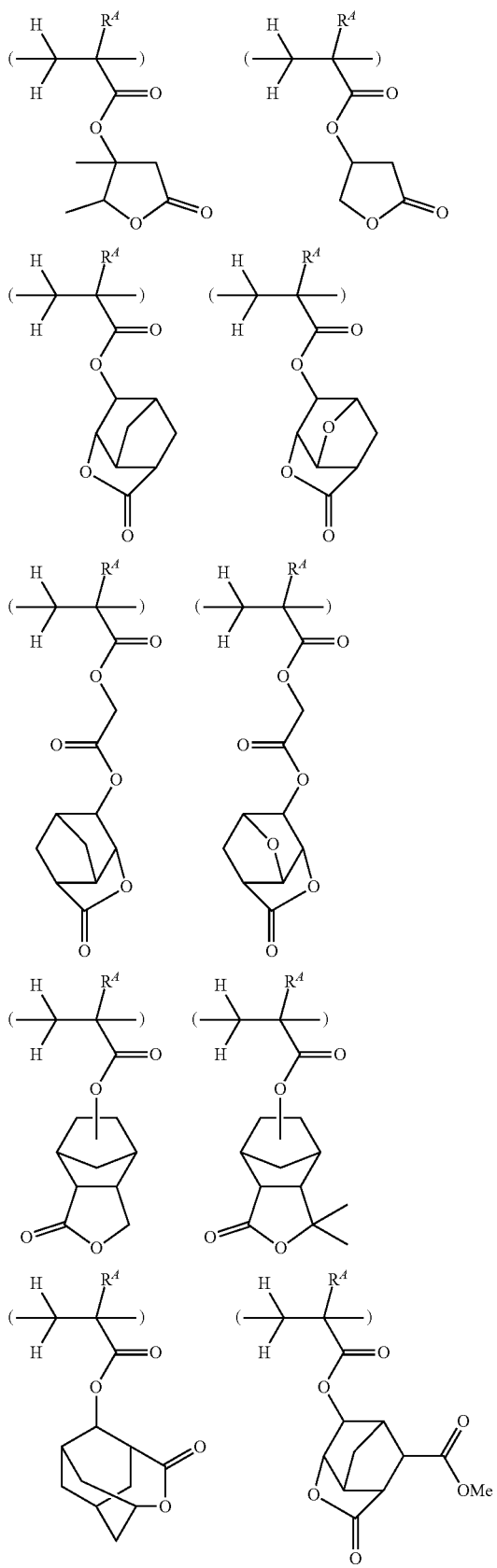

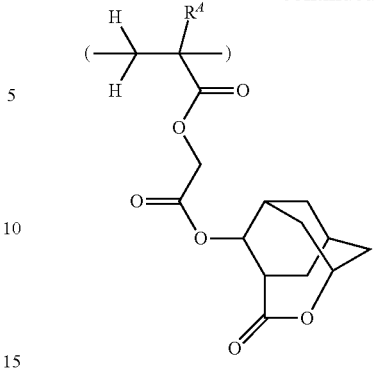

The base polymer may further comprise repeat units of the structure having a hydroxy group protected with an acid labile group. The repeat unit of the structure having a hydroxy group protected with an acid labile group is not particularly limited as long as the unit has at least one protected hydroxy structure wherein a hydroxy group is resumed as a result of decomposition of the protective group under the action of acid. Such repeat units are described in JP-A 2014-225005, paragraphs [0055]-[0065] and JP-A 2015-214634, paragraphs [0110]-[0115].

The base polymer may further comprise other repeat units. Typical of the other repeat units are repeat units having an oxirane or oxetane ring. A polymer comprising repeat units having an oxirane or oxetane ring is crosslinked in exposed regions, leading to improvements in retention and etching resistance of a resist film in exposed regions. Such repeat units are described in JP-A 2015-214634, paragraphs [0120]-[0122]

The base polymer may further comprise still other repeat units, for example, units derived from substituted acrylates such as methyl crotonate, dimethyl maleate, and dimethyl itaconate, unsaturated carboxylic acids such as maleic acid, fumaric acid, and itaconic acid, cyclic olefins such as norbornene, norbornene derivatives, tetracyclo[6.2.1.1$^{3,6}$.0$^{2,7}$]dodecene derivatives, unsaturated acid anhydrides such as itaconic anhydride, aromatics such as styrene, tert-butylstyrene, vinylnaphthalene, acetoxystyrene, methoxystyrene, acenaphthylene, phenyl methacrylate, benzyl methacrylate, and phenyl vinyl ether, and other monomers.

The base polymer should preferably have a Mw of 1,000 to 500,000, more preferably 3,000 to 100,000, and even more preferably 4,000 to 20,000. A Mw within the range eliminates an extreme drop of etching resistance and provides satisfactory resolution due to a difference in dissolution rate before and after exposure. As used herein, Mw is measured versus polystyrene standards by GPC. Also preferably the polymer has a dispersity (Mw/Mn) of 1.20 to 2.50, more preferably 1.30 to 2.00.

The polymer may be synthesized by any method, for example, by using one or more monomers corresponding to the desired repeat units in an organic solvent, adding a radical polymerization initiator, and heating for polymerization. For the polymerization method, reference should be made to U.S. Pat. No. 9,256,127 (JP-A 2015-214634, paragraphs [0134]-[0137]). The acid labile group that has been incorporated in the monomer may be kept as such, or polymerization may be followed by protection or partial protection.

While the base polymer comprises repeat units derived from monomers, the molar fractions of respective units preferably fall in the following range (mol %), but are not limited thereto:

(I) 10 to 70 mol %, more preferably 20 to 65 mol %, even more preferably 30 to 60 mol % of repeat units of at least one type selected from repeat units (a) and (b), (II) 0 to 90 mol %, more preferably 15 to 80 mol %, even more preferably 30 to 60 mol % of repeat units (c) of at least one type, and optionally, (III) 0 to 30 mol %, more preferably 0 to 20 mol %, and even more preferably 5 to 20 mol % of repeat units of at least one type selected from repeat units (d1) to (d4), and optionally, (IV) 0 to 80 mol %, more preferably 0 to 70 mol %, and even more preferably 0 to 50 mol % of repeat units of at least one type selected from repeat units (e) and other repeat units.

The base polymer (A) may be used alone or in a combination of two or more polymers which are different in compositional ratio, Mw and/or Mw/Mn. In addition to the polymer, a hydrogenated product of ring-opening metathesis polymerization (ROMP) polymer may be used. The hydrogenated ROMP polymer is as described in JP-A 2003-066612.

(B) Photoacid Generator

The resist composition should comprise (B) a photoacid generator, which is sometimes referred to as PAG of addition type, when the base polymer does not contain any of repeat units (d1) to (d4). It is noted that a PAG of addition type may be added even when the base polymer contains repeat units of at least one type selected from repeat units (d1) to (d4).

The PAG of addition type may be any compound capable of generating an acid upon exposure to high-energy radiation. Suitable PAGs include sulfonium salts, iodonium salts, sulfonyldiazomethanes, N-sulfonyloxydicarboxyimides, O-arylsulfonyloximes, and O-alkylsulfonyloximes, which may be used alone or in admixture. Suitable examples are described in JP-A 2007-145797, paragraphs [0102]-[0113], JP-A 2008-111103, paragraphs [0122]-[0142], JP-A 2014-001259, paragraphs [0081]-[0092], JP-A 2012-041320, JP-A 2012-153644, and JP-A 2012-106986, and JP-A 2016-018007. The PAGs capable of generating partially fluorinated sulfonic acids described in the foregoing patent documents are preferably used in a resist composition because the strength and diffusion length of the generated acid are appropriate in the ArF lithography.

Preferred as the PAG (B) are sulfonium salts having the formula (3A) and iodonium salts having the formula (3B).

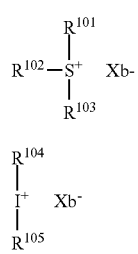

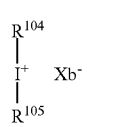

In formulae (3A) and (3B), $R^{101}$ to $R^{105}$ are each independently a $C_1$-$C_{30}$ hydrocarbyl group which may contain a heteroatom. Examples of the hydrocarbyl group are as exemplified above for $R^{31}$ to $R^{41}$ in formulae (d1) to (d4). A pair of $R^{101}$ and $R^{102}$ to may bond together to form a ring with the sulfur atom to which they are attached, and $R^{104}$ and $R^{105}$ may bond together to form a ring with the iodine atom to which they are attached.

The sulfonium cation of the sulfonium salt having formula (3A) is described in JP-A 2014-001259, paragraphs [0082]-[0085]. Exemplary sulfonium cations include those described in JP-A 2007-145797, paragraphs [0027]-[0033], JP-A 2010-113209, paragraph [0059], JP-A 2012-041320, JP-A 2012-153644, and JP-A 2012-106986, as well as those exemplified above for the cation in formulae (d1) to (d3).

Preferred examples of the cation of the sulfonium salt having formula (3A) are given below, but not limited thereto.

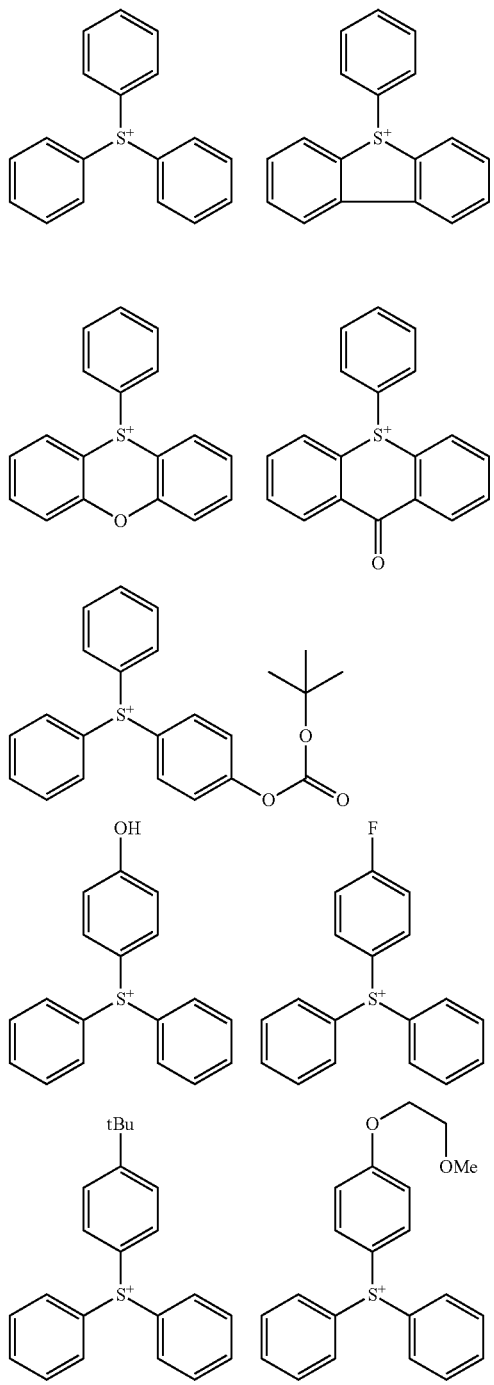

-continued
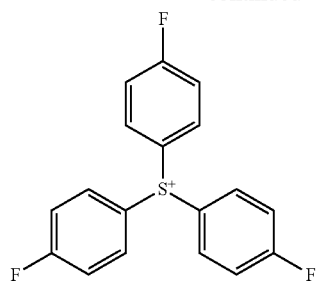
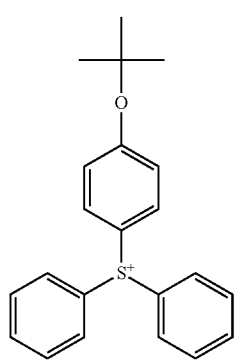
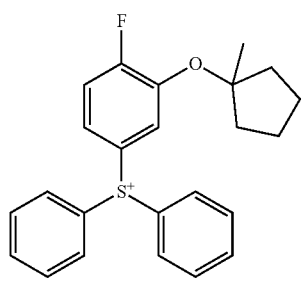
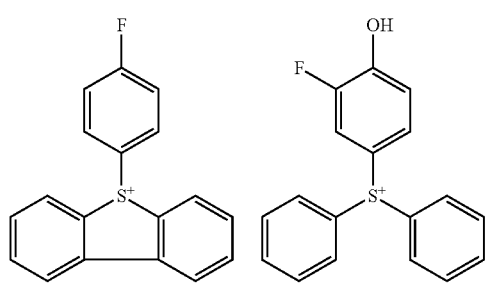
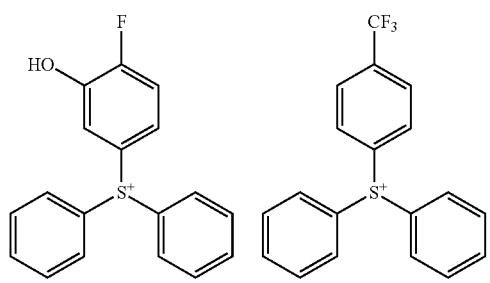
-continued
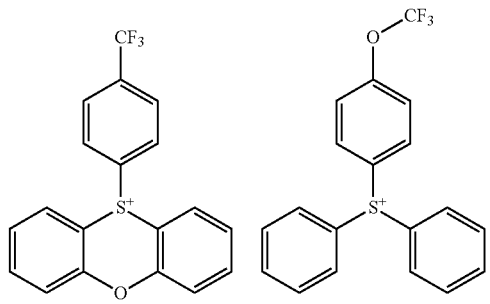
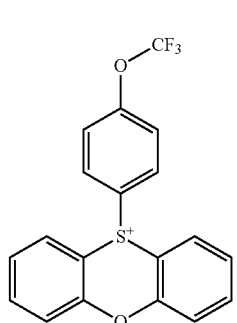
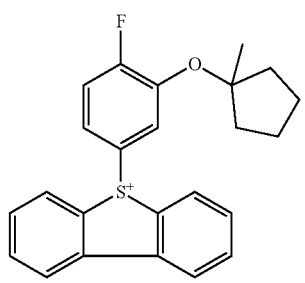
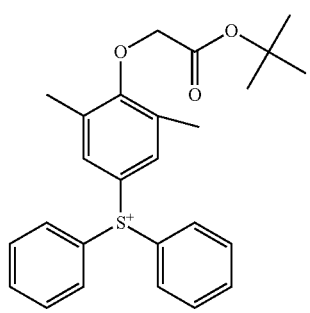
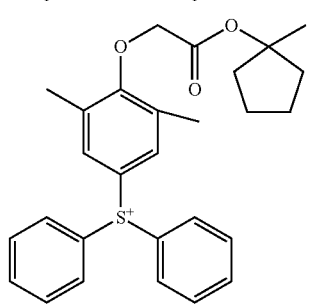

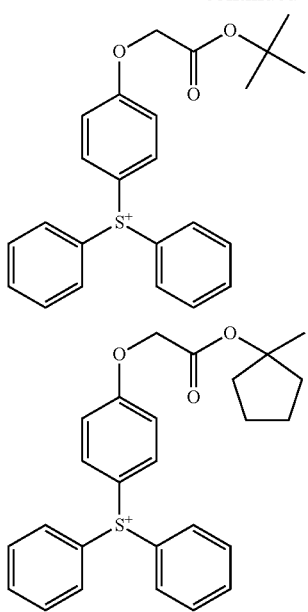

Specific examples of the cation of the sulfonium salt having formula (3A) include triphenylsulfonium, S-phenyldibenzothiophenium, (4-tert-butylphenyl)diphenylsulfonium, (4-fluorophenyl)diphenylsulfonium, and (4-hydroxyphenyl)diphenylsulfonium cations.

Preferred examples of the cation of the iodonium salt having formula (3B) are given below, but not limited thereto.

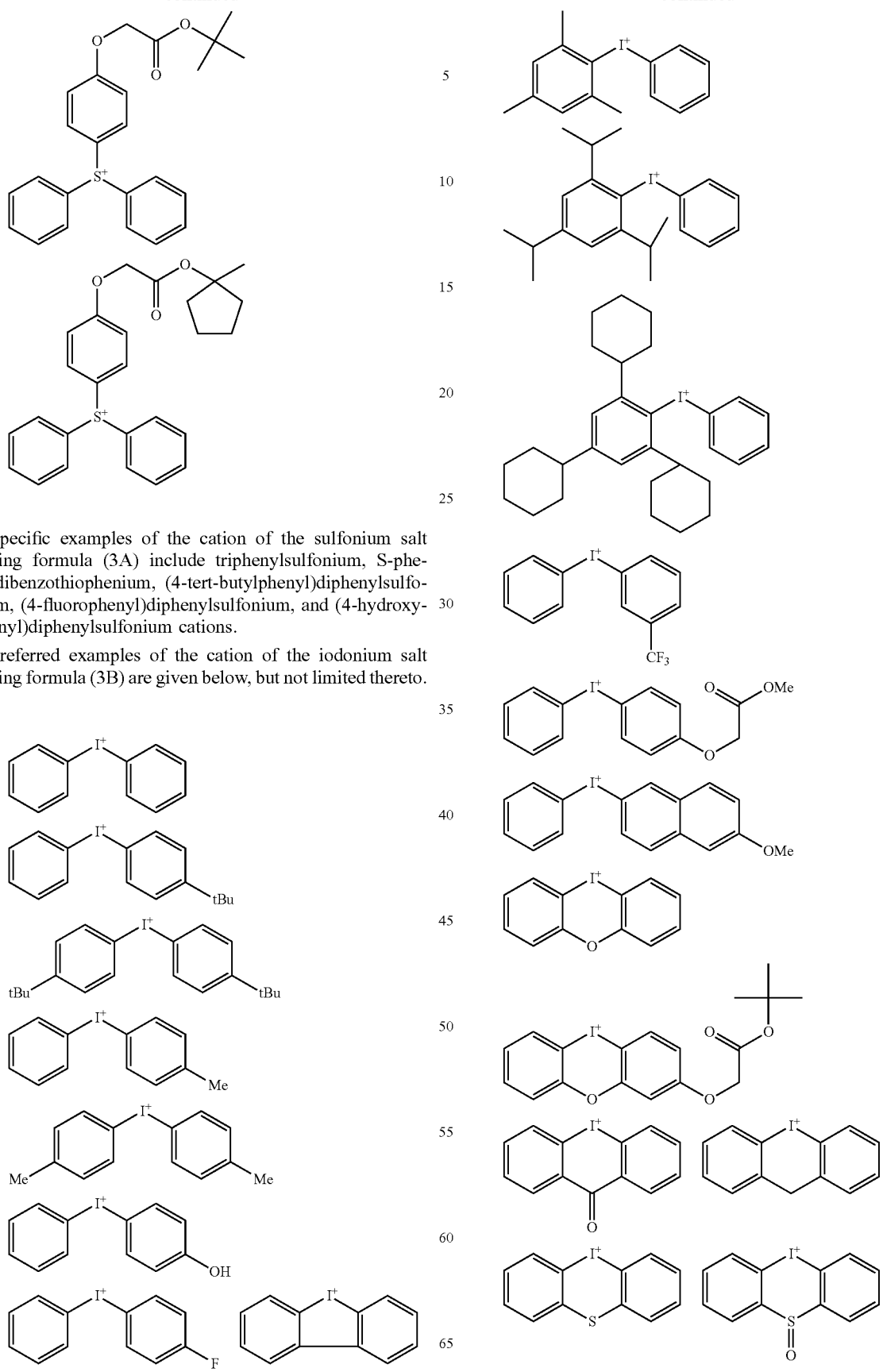

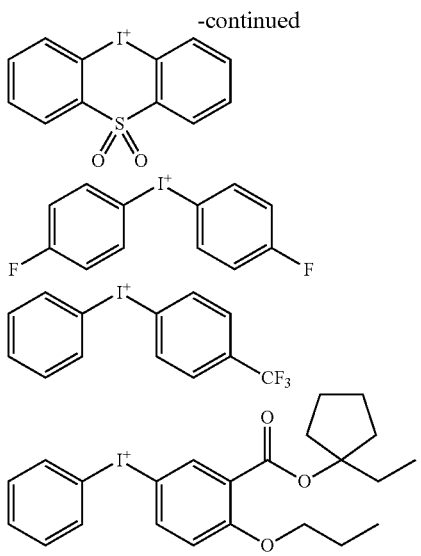

As the cation of the iodonium salt having formula (3B), diphenyliodonium and di-tert-butylphenyliodonium cations are preferred.

In formulae (3A) and (3B), $Xb^-$ is an anion having the formula (3C) or (3D).

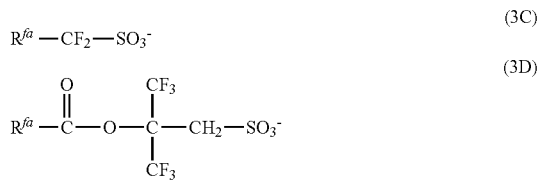

In formula (3C), $R^{fa}$ is fluorine, a $C_1$-$C_4$ perfluoroalkyl group, or a $C_1$-$C_{40}$ hydrocarbyl group which may contain a heteroatom.

Preferred examples of the anion having formula (3C) include trifluoromethanesulfonate and nonafluorobutanesulfonate anions, and anions having the formula (3C').

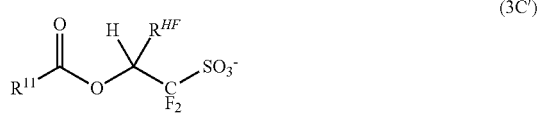

In formula (3C'), $R^{HF}$ is hydrogen or trifluoromethyl.

$R^{111}$ is a $C_1$-$C_{35}$ hydrocarbyl group which may contain a heteroatom. The hydrocarbyl group may be saturated or unsaturated and straight, branched or cyclic. Examples thereof include alkyl groups such as methyl, ethyl, propyl, isopropyl, n-butyl, sec-butyl, tert-butyl, n-pentyl, n-hexyl, n-octyl, n-nonyl, n-decyl; $C_3$-$C_{35}$ cyclic saturated hydrocarbyl groups such as cyclopentyl, cyclohexyl, cyclooctyl, norbornyl, tricyclo[5.2.1.0$^{2,6}$]decanyl, adamantyl; alkenyl groups such as vinyl, allyl, propenyl, butenyl, hexenyl; unsaturated alicyclic hydrocarbyl groups such as cyclohexenyl; aryl groups such as phenyl, naphthyl, thienyl; aralkyl groups such as benzyl, 1-phenylethyl, 2-phenylethyl, and combinations thereof. Some or all of the hydrogen atoms in the hydrocarbyl group may be substituted by a moiety containing a heteroatom such as oxygen, sulfur, nitrogen or halogen, and any constituent —CH$_2$-in the hydrocarbyl group may be replaced by a moiety containing a heteroatom such as oxygen, sulfur, or nitrogen, so that the group may contain fluorine, chlorine, bromine, iodine, a hydroxy moiety, cyano moiety, carbonyl moiety, ether bond, ester bond, sulfonic ester bond, carbonate bond, lactone ring, sultone ring, carboxylic anhydride or haloalkyl moiety.

The anion having formula (3C') is described in JP-A 2007-145797, JP-A 2008-106045, JP-A 2009-007327, JP-A 2009-258695, and JP-A 2012-181306. Examples of the anion having formula (3C') include those described in these patent documents.

In formula (3D), $R^{fb}$ is a $C_1$-$C_{40}$ hydrocarbyl group which may contain a heteroatom. The hydrocarbyl group $R^{fb}$ may be saturated or unsaturated and straight, branched or cyclic. Examples thereof are as exemplified above for $R^{111}$ in formula (3C').

The anion having formula (3D) is described in JP-A 2010-215608 and JP-A 2014-133723. Examples of the anion having formula (3D) include those described in these patent documents. Notably, the compound having the anion of formula (3D) does not have fluorine at the α-position relative to the sulfo group, but two trifluoromethyl groups at the β-position. For this reason, it has a sufficient acidity to sever the acid labile groups in the base polymer. The compound is thus an effective PAG.

Preferred examples of the anion $Xb^-$ are shown below, but not limited thereto. Herein $R^{HF}$ is hydrogen or trifluoromethyl.

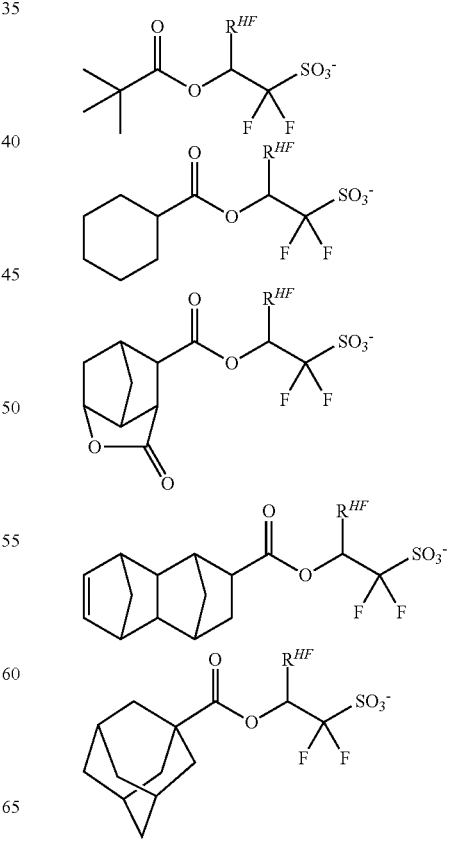

-continued
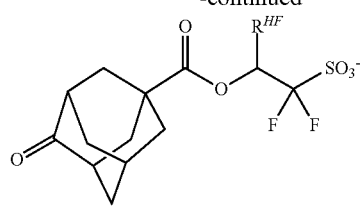
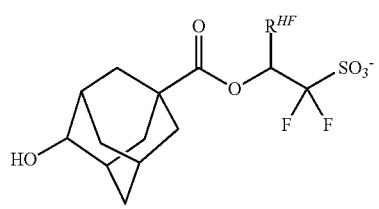
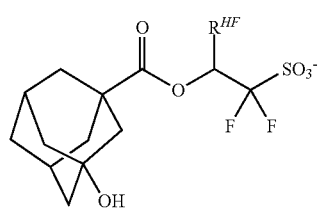
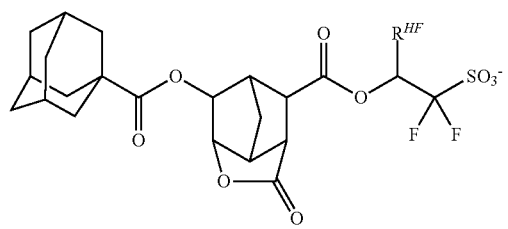
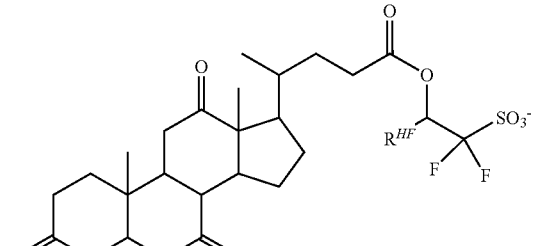
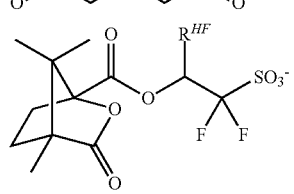
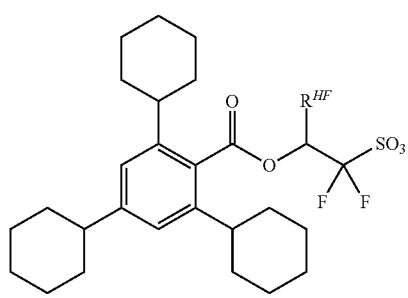
-continued
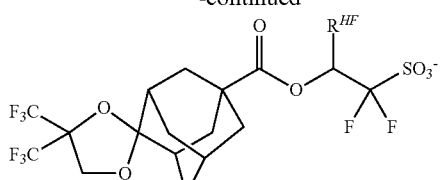
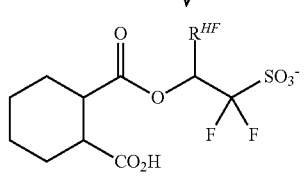
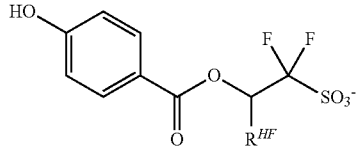
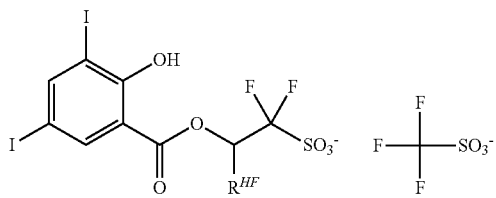
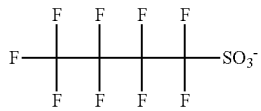
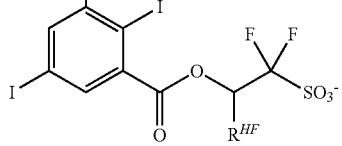
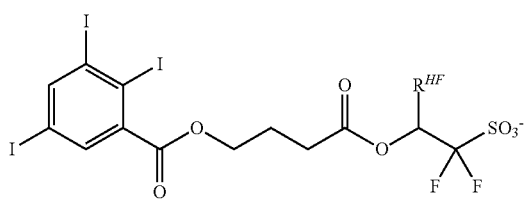
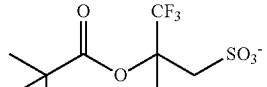
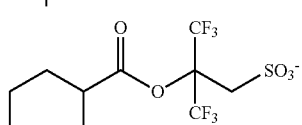
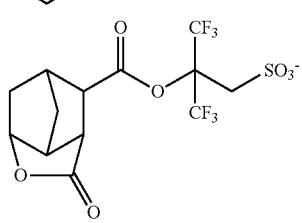

-continued

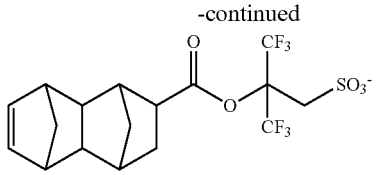

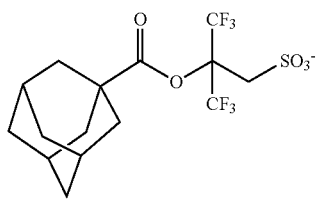

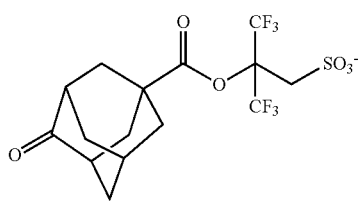

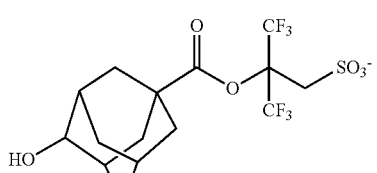

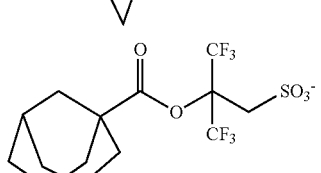

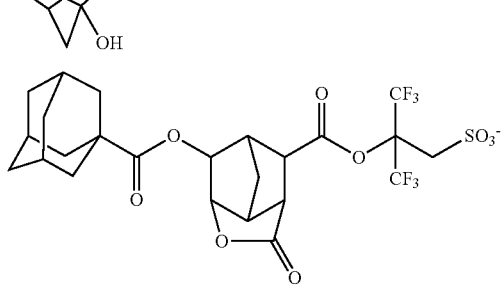

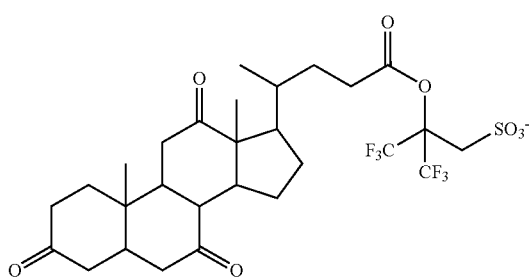

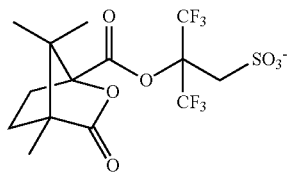

-continued

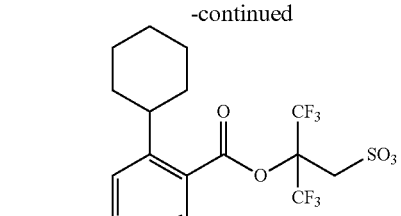

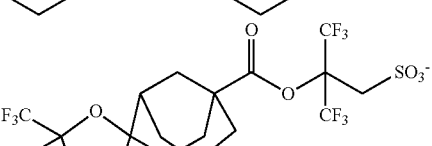

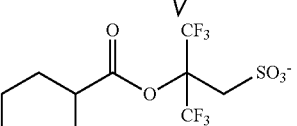

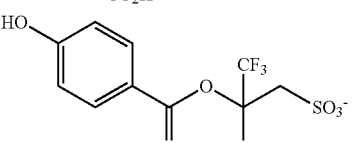

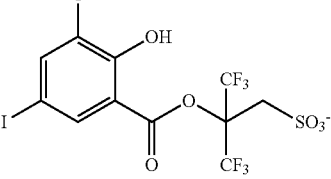

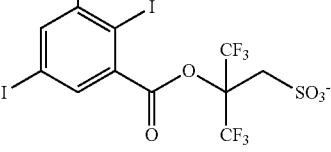

Exemplary structures for the PAG having formula (3A) or (3B) include arbitrary combinations of cations with anions, both as exemplified above, but are not limited thereto.

Another preferred example of the PAG (B) is a compound having the formula (4).

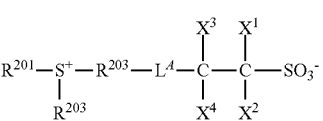

(4)

In formula (4), $R^{201}$ and $R^{202}$ are each independently a $C_1$-$C_{30}$ hydrocarbyl group which may contain a heteroatom. $R^{203}$ is a $C_1$-$C_{30}$ hydrocarbylene group which may contain a heteroatom. Any two of $R^{201}$, $R^{202}$ and $R^{203}$ may bond together to form a ring with the sulfur atom to which they are attached.

The hydrocarbyl groups $R^{201}$ and $R^{202}$ may be saturated or unsaturated and straight, branched or cyclic. Examples thereof are as exemplified above for $R^{111}$ in formula (3C').

The hydrocarbylene group $R^{203}$ may be saturated or unsaturated and straight, branched or cyclic. Examples thereof include $C_1$-$C_{30}$ alkanediyl groups such as methanediyl, ethane-1,2-diyl, propane-1,3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, and tetradecane-1,14-diyl; $C_3$-$C_{30}$ cyclic saturated hydrocarbylene groups such as cyclopentanediyl, cyclohexanediyl, norbornanediyl, and adamantanediyl; arylene groups such as phenylene, methylphenylene, ethylphenylene, n-propylphenylene, isopropylphenylene, n-butylphenylene, isobutylphenylene, sec-butylphenylene, tert-butylphenylene, dimethylphenylene, diethylphenylene, naphthylene, methylnaphthylene, ethylnaphthylene, n-propylnaphthylene, isopropylnaphthylene, n-butylnaphthylene, isobutylnaphthylene, sec-butylnaphthylene, tert-butylnaphthylene, dimethylnaphthylene, diethylnaphthylene, and combinations thereof. In the hydrocarbylene group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain fluorine, chlorine, bromine, iodine, a hydroxy moiety, cyano moiety, carbonyl moiety, ether bond, ester bond, sulfonate bond, carbonate bond, lactone ring, sultone ring, carboxylic anhydride or haloalkyl moiety.

In formula (4), $L^A$ is a single bond, ether bond, ester bond, or a $C_1$-$C_{20}$ hydrocarbylene group which may contain a heteroatom, in which —$CH_2$— may be replaced by —O— or —C(=O)—. The constituent —$CH_2$-in the hydrocarbyl group may be one bonding to the carbon atom and/or $R^{203}$ on the benzene ring in formula (4). The hydrocarbylene group $L^A$ may be saturated or unsaturated and straight, branched or cyclic. Examples thereof are as exemplified above for $R^{203}$.

In formula (4), $X^1$, $X^2$, $X^3$ and $X^4$ are each independently hydrogen, fluorine or trifluoromethyl, with at least one thereof being fluorine or trifluoromethyl.

Of the compounds having formula (4), those having formula (4') are more preferred.

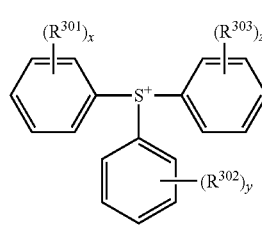

(4')

In formula (4'), R' is hydrogen or trifluoromethyl, preferably trifluoromethyl. $R^{301}$, $R^{302}$ and $R^{303}$ to are each independently a $C_1$-$C_{20}$ hydrocarbyl group which may contain a heteroatom. In the hydrocarbyl group, some or all of the hydrogen atoms may be substituted by a moiety containing a heteroatom such as oxygen, sulfur, nitrogen or halogen, and —$CH_2$— may be replaced by —O— or —C(=O)—. The constituent —$CH_2$-in the hydrocarbyl group may be one bonding to a carbon atom on the benzene ring in formula (4'). The hydrocarbyl groups $R^{301}$, $R^{302}$ and $R^{303}$, may be saturated or unsaturated and straight, branched or cyclic. Examples thereof are as exemplified above for $R^{111}$ in formula (3C'). The subscripts x and y are each independently an integer of 0 to 5, and z is an integer of 0 to 4.

The PAG having formula (4) or (4') is described in JP-A 2011-016746. Examples thereof include those exemplified for the sulfonium salt in the same patent document and those exemplified for the sulfonium salt in JP-A 2015-214634, paragraphs [0149]-[0150].

Specific examples of the PAG having formula (4) are given below, but not limited thereto. Herein $R^{HF}$ is as defined above.

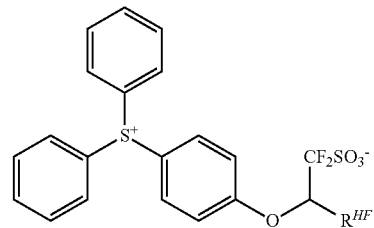

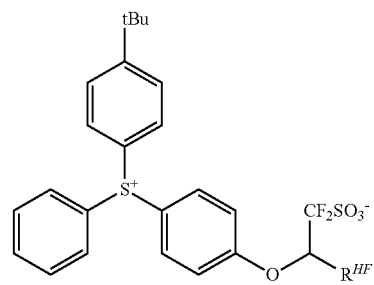

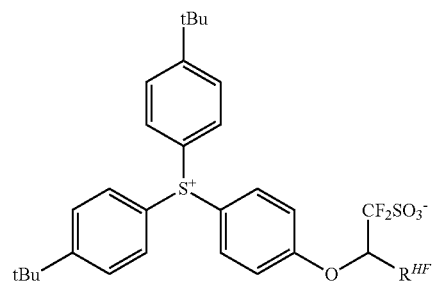

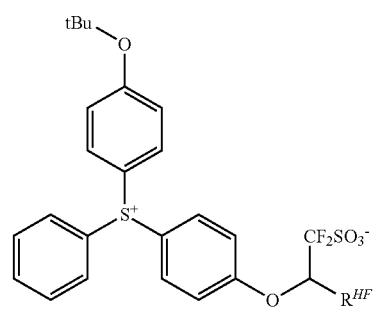

-continued
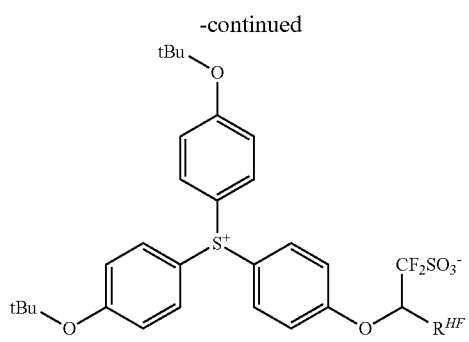
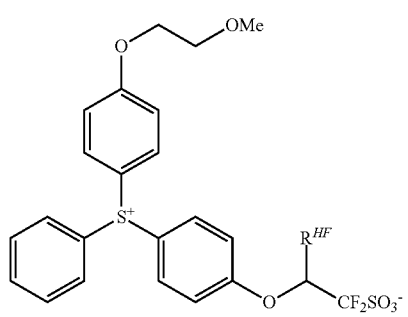
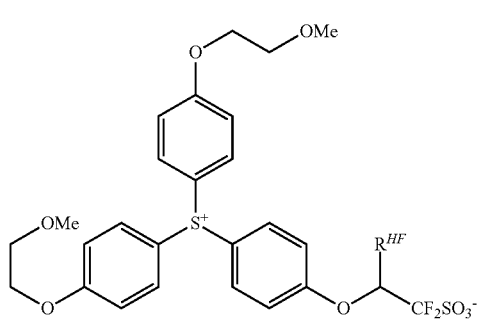
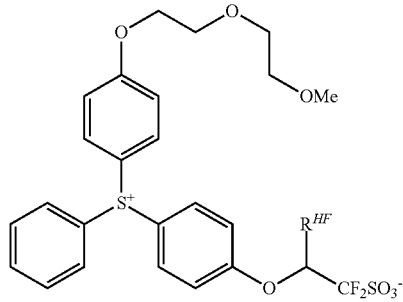
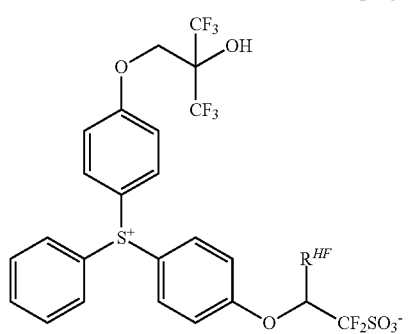
-continued
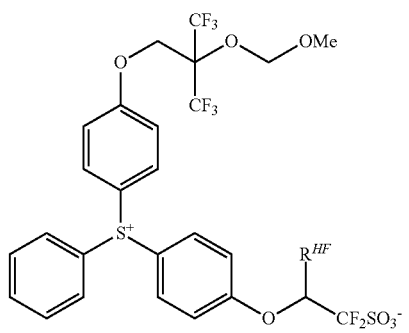
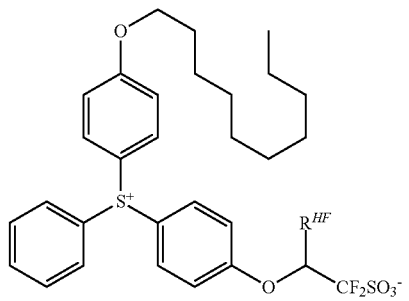
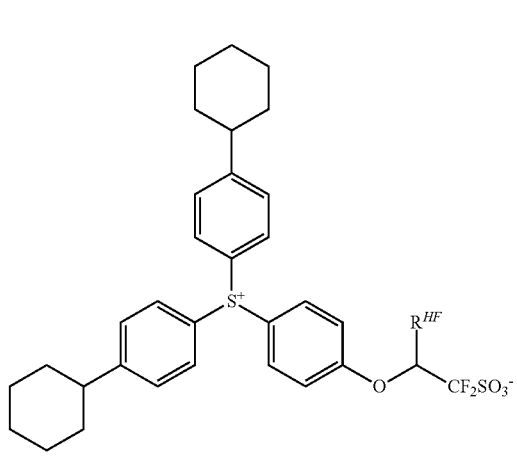
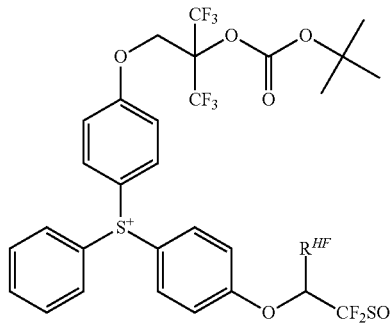

251
-continued

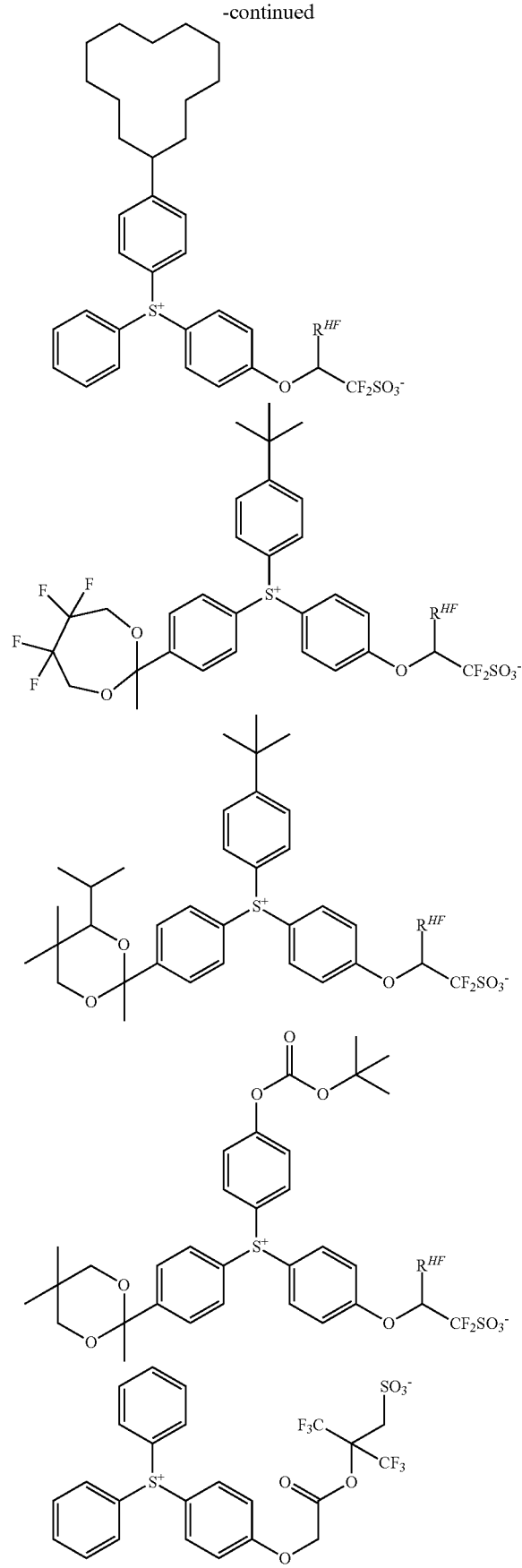

252
-continued

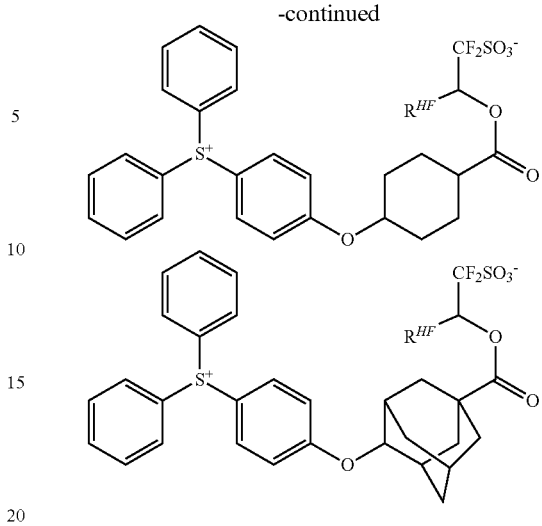

The PAG (B) is preferably added in an amount of 1 to 30 parts by weight, more preferably 2 to 25 parts by weight, even more preferably 4 to 20 parts by weight per 100 parts by weight of the base polymer (A). The PAG in the range eliminates the problems of degradation of resolution and formation of foreign matter after development or during stripping. The PAG may be used alone or in admixture.

(C) Acid Diffusion Inhibitor

The resist composition further comprises (C) an acid diffusion inhibitor or quencher. Component (C) should contain (C-1) the onium salt having formula (1) as an essential component and may contain (C-2) an acid diffusion inhibitor other than the onium salt having formula (1). As used herein, the "acid diffusion inhibitor" refers to a compound capable of holding down the diffusion rate when the acid generated by the PAG diffuses in the resist film.

The acid diffusion inhibitor (C-2) is typically selected from amine compounds and onium salts of weak acids such as α-non-fluorinated sulfonic acids and carboxylic acids.

Examples of the amine compound include primary, secondary, and tertiary amine compounds, specifically amine compounds having a hydroxy group, ether bond, ester bond, lactone ring, cyano group or sulfonate bond. Primary and secondary amine compounds protected with a carbamate group are also included. Such protected amine compounds are effective when the resist composition contains a base labile component. Suitable acid diffusion inhibitors include the compounds described in JP-A 2008-111103, paragraphs [0146]-[0164], and JP 3790649 as well as the following compounds, but are not limited thereto.

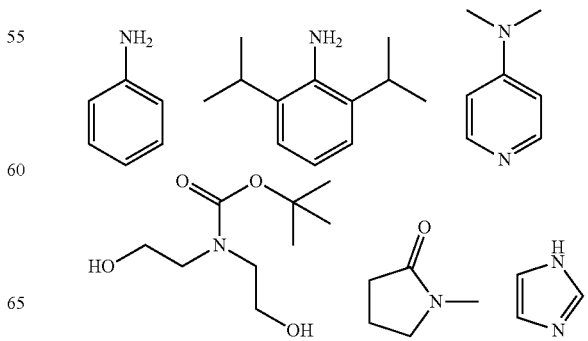

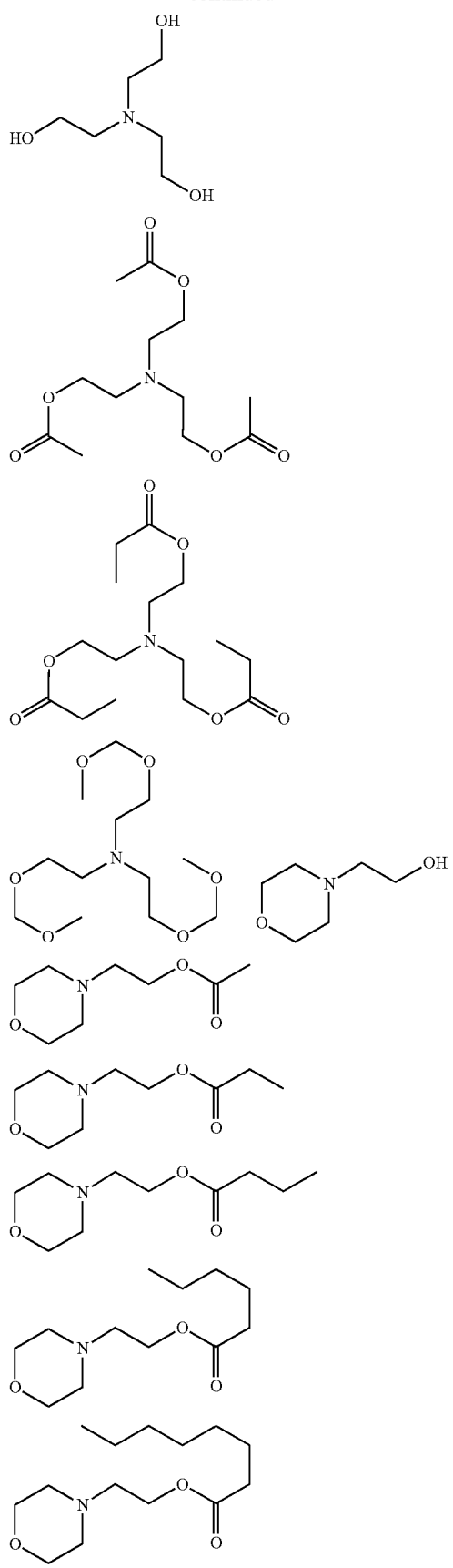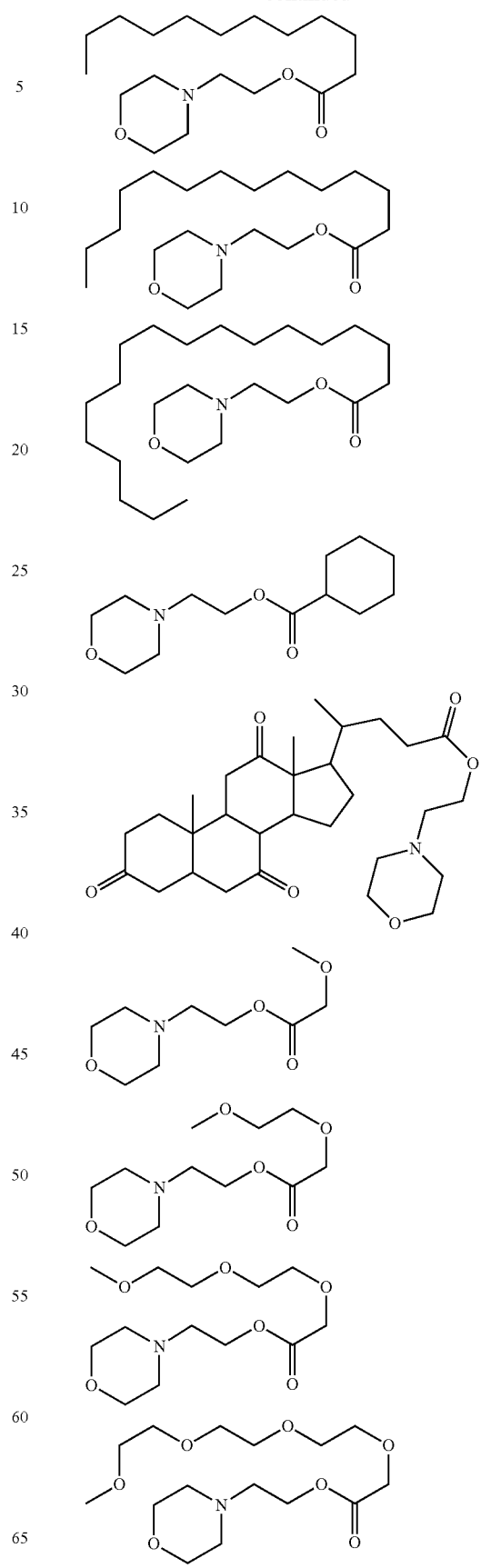

255
-continued
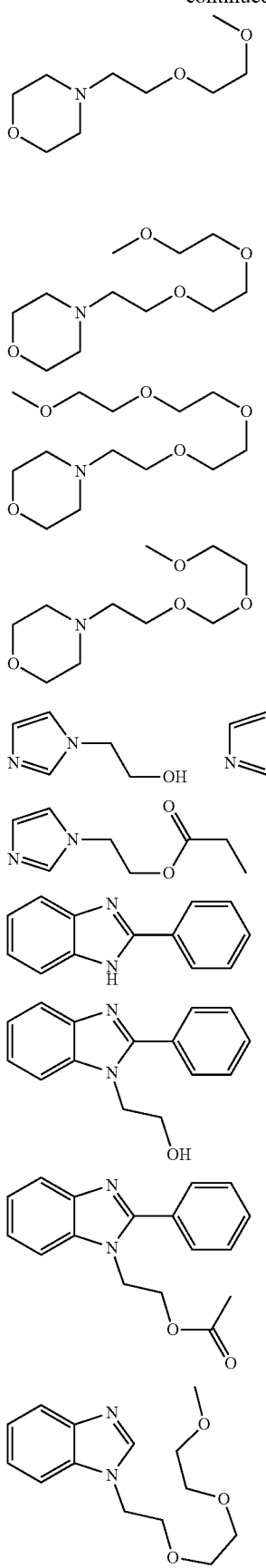
256
-continued
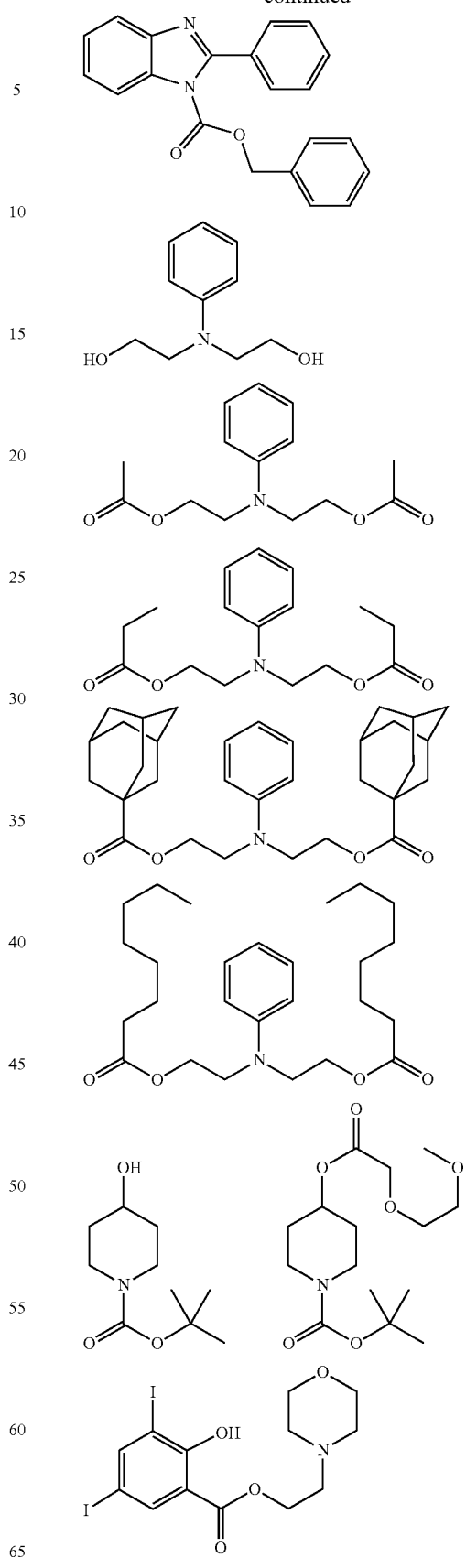

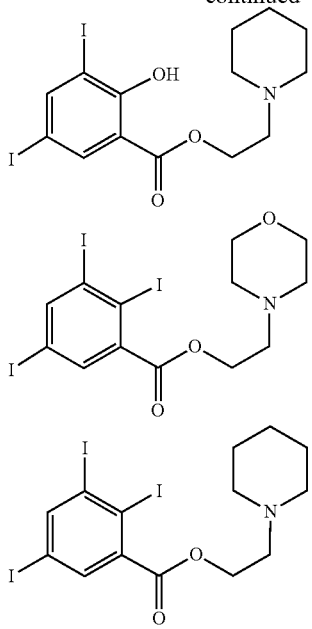

Suitable onium salts of α-non-fluorinated sulfonic acids and carboxylic acids include onium salts having the formulae (5A) and (5B).

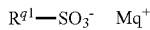

(5A)

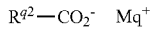

(5B)

In formula (5A), $R^{q1}$ is hydrogen, methoxy, or a $C_1$-$C_{40}$ hydrocarbyl group which may contain a heteroatom, exclusive of the group wherein hydrogen bonded to the carbon atom at α-position relative to the sulfo group is substituted by fluorine or fluoroalkyl.

The optionally heteroatom-containing $C_1$-$C_{40}$ hydrocarbyl group, represented by $R^{q1}$, may be saturated or unsaturated and straight, branched or cyclic. In the hydrocarbyl group, some or all of the hydrogen atoms may be substituted by a moiety containing a heteroatom such as oxygen, sulfur, nitrogen or halogen, and any constituent —$CH_2$— may be replaced by a moiety containing a heteroatom such as oxygen, sulfur or nitrogen, so that the group may contain fluorine, chlorine, bromine, iodine, a hydroxy moiety, cyano moiety, carbonyl moiety, ether bond, ester bond, sulfonic ester bond, carbonate bond, lactone ring, sultone ring, carboxylic anhydride, or haloalkyl moiety.

Examples of the optionally heteroatom-containing $C_1$-$C_{40}$ hydrocarbyl group $R^{q1}$ include $C_1$-$C_{40}$ alkyl groups such as methyl, ethyl, propyl, isopropyl, n-butyl, sec-butyl, tert-butyl, tert-pentyl, n-pentyl, n-hexyl, n-octyl, 2-ethylhexyl, n-nonyl, and n-decyl; $C_3$-$C_{40}$ cyclic saturated hydrocarbyl groups such as cyclopentyl, cyclohexyl, cyclopentylmethyl, cyclopentylethyl, cyclopentylbutyl, cyclohexylmethyl, cyclohexylethyl, cyclohexylbutyl, norbornyl, tricyclo[5.2.1.0$^{2,6}$]decanyl, adamantyl, and adamantylmethyl; $C_2$-$C_{40}$ alkenyl groups such as vinyl, allyl, propenyl, butenyl, and hexenyl; $C_3$-$C_{40}$ cyclic unsaturated hydrocarbyl groups such as cyclohexenyl; $C_6$-$C_{40}$ aryl groups such as phenyl, naphthyl, hydroxyphenyl groups such as 4-hydroxyphenyl, alkoxyphenyl groups such as 4-methoxyphenyl, 3-methoxyphenyl, 2-methoxyphenyl, 4-ethoxyphenyl, 4-tert-butoxyphenyl, and 3-tert-butoxyphenyl, alkylphenyl groups such as 2-methylphenyl, 3-methylphenyl, 4-methylphenyl, 4-ethylphenyl, 4-tert-butylphenyl, 4-n-butylphenyl, 2,4-dimethylphenyl and 2,4,6-triisopropylphenyl, alkylnaphthyl groups such as methylnaphthyl and ethylnaphthyl, alkoxynaphthyl groups such as methoxynaphthyl, ethoxynaphthyl, n-propoxynaphthyl and n-butoxynaphthyl, dialkylnaphthyl groups such as dimethylnaphthyl and diethylnaphthyl, dialkoxynaphthyl groups such as dimethoxynaphthyl and diethoxynaphthyl; $C_7$-$C_{40}$ aralkyl groups such as benzyl, 1-phenylethyl and 2-phenylethyl; $C_3$-$C_{40}$ heteroaryl groups such as thienyl; $C_8$-$C_{40}$ aryloxoalkyl groups, typically 2-aryl-2-oxoethyl groups such as 2-phenyl-2-oxoethyl, 2-(1-naphthyl)-2-oxoethyl, 2-(2-naphthyl)-2-oxoethyl; and combinations thereof.

In formula (5B), $R^{q2}$ is hydrogen, hydroxy or a $C_1$-$C_{40}$ hydrocarbyl group which may contain a heteroatom.

The optionally heteroatom-containing $C_1$-$C_{40}$ hydrocarbyl group $R^{q2}$ may be saturated or unsaturated and straight, branched or cyclic. Examples thereof include those exemplified above for the optionally heteroatom-containing hydrocarbyl group $R^{q1}$ and groups obtained by removing a carboxy group from the carboxylate anions having formulae (Z-1) to (Z-5).

With respect to the sulfonic onium salt having formula (5A) and carboxylic onium salt having formula (5B), reference is made to JP-A 2008-158339 and JP-A 2010-155824. Examples of these compounds are as exemplified in these patent documents.

Examples of the anion in the sulfonic onium salt having formula (5A) are shown below, but not limited thereto.

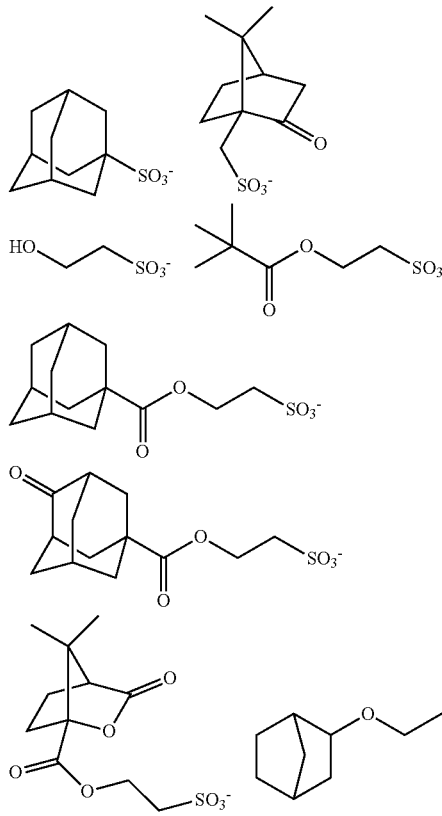

259
-continued
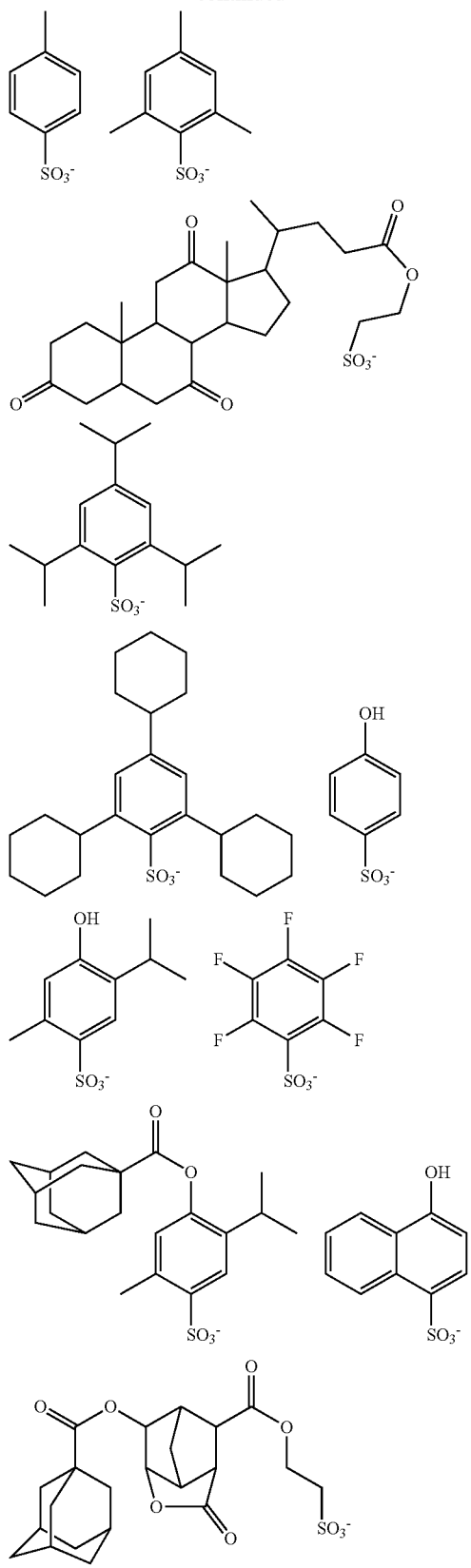
Examples of the anion in the carboxylic onium salt having formula (5B) are shown below, but not limited thereto.
260
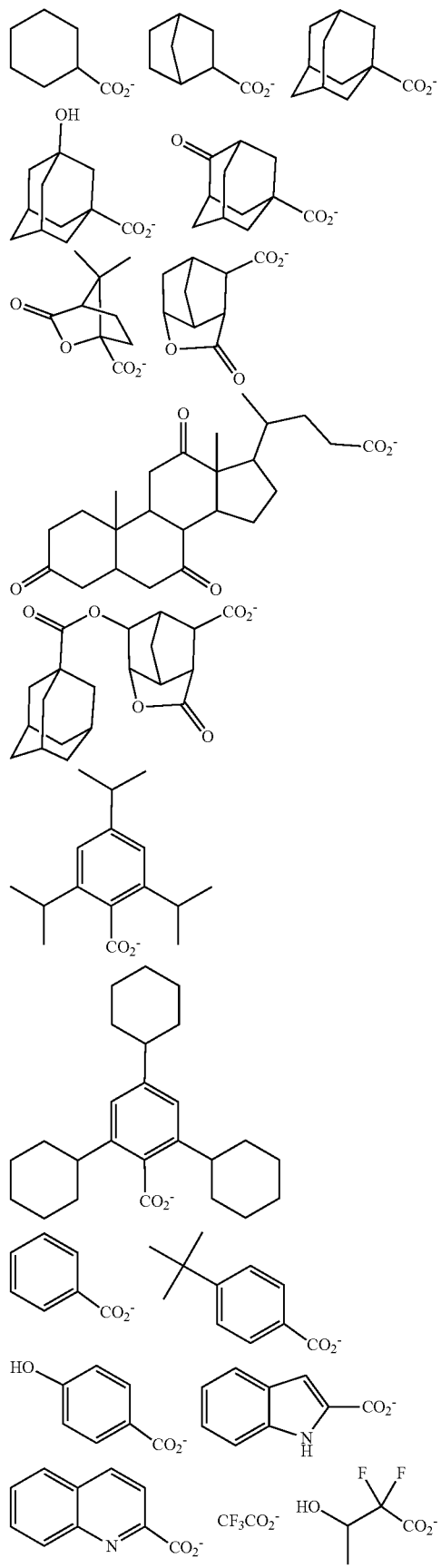

-continued

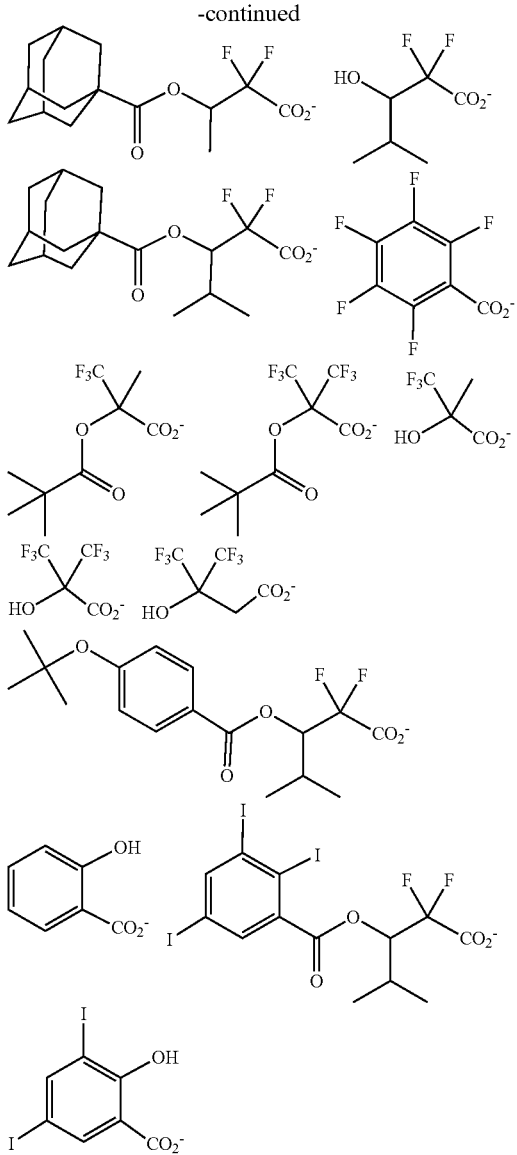

In formulae (5A) and (5B), $Mq^+$ is an onium cation, which is preferably selected from cations having the formulae (5C), (5D) and (5E).

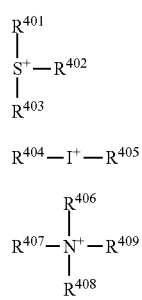

In formulae (5C) to (5E), $R^{401}$ to $R^{409}$ are each independently a $C_1$-$C_{40}$ hydrocarbyl group which may contain a heteroatom. A pair of $R^{401}$ and $R^{402}$, $R^{404}$ and $R^{405}$, or $R^{406}$ and $R^{407}$ may bond together to form a ring with the sulfur, iodine or nitrogen atom to which they are attached.

Examples of the cation having formula (5C) are as exemplified above for the cation in formulae (d1) to (d4). Examples of the cation having formula (5D) are as exemplified above for the cation in the iodonium salt having formula (3B). Examples of the cation having formula (5E) include tetramethylammonium, tetraethylammonium, tetrabutylammonium, trimethylbenzyl, and trimethylphenyl cations.

Preferred examples of the onium cation $Mq^+$ are shown below, but not limited thereto.

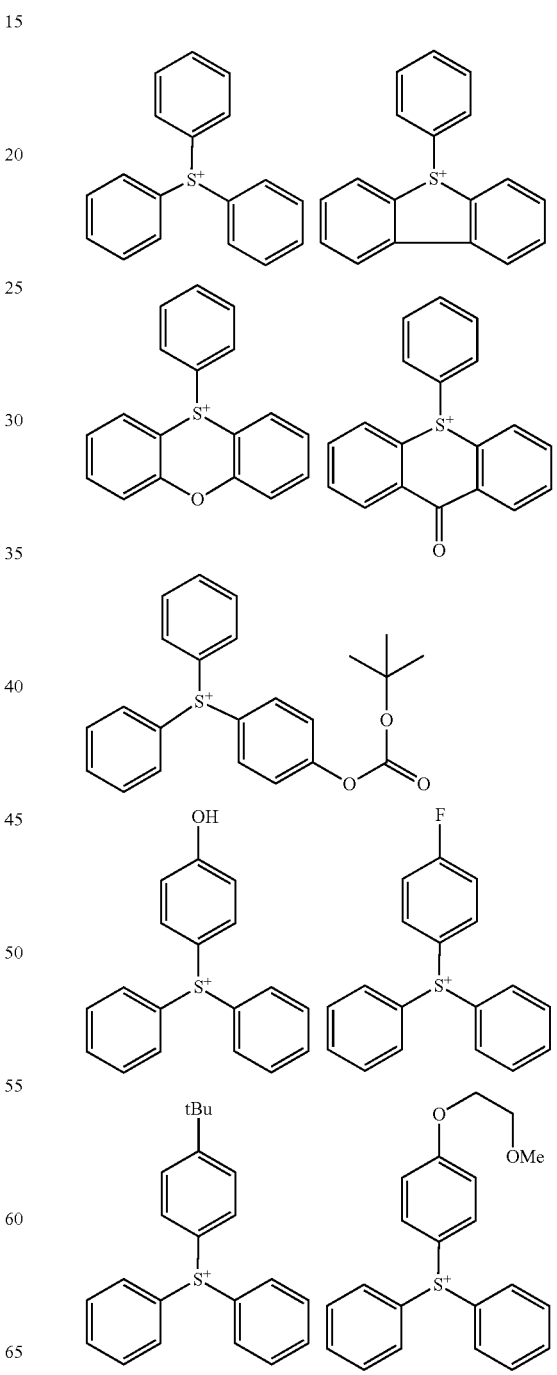

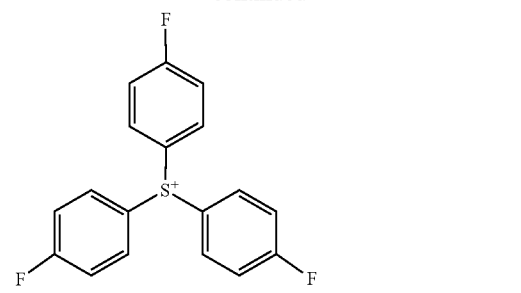
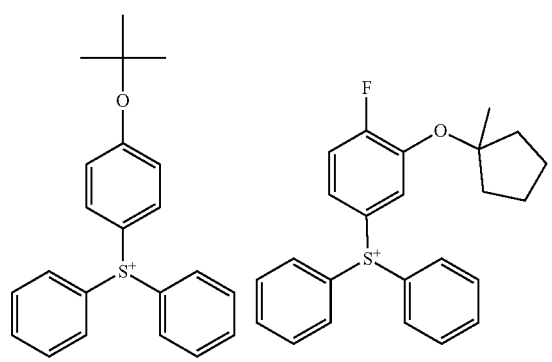
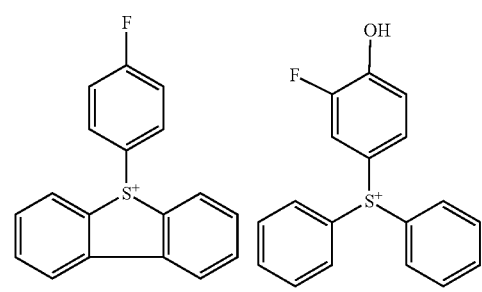
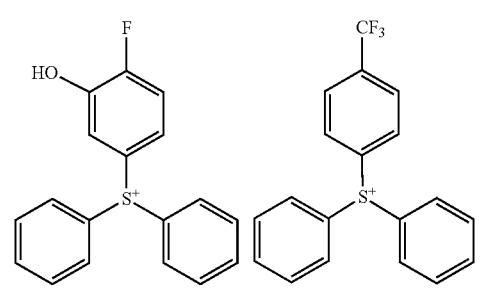
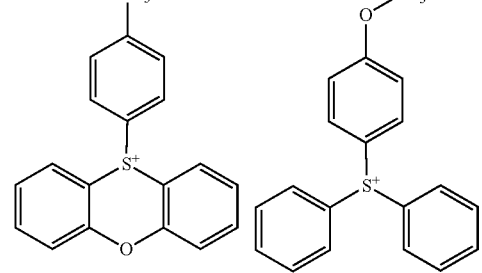
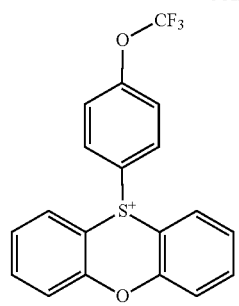
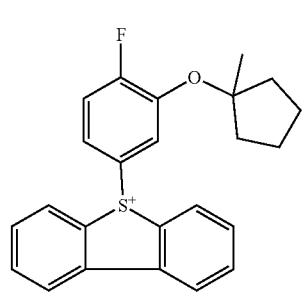
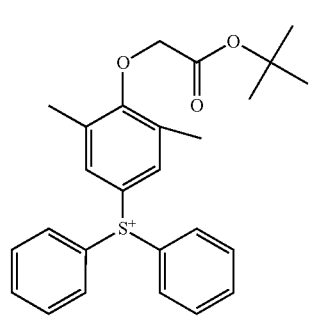
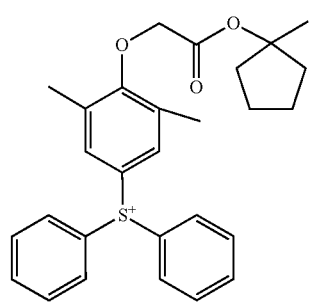
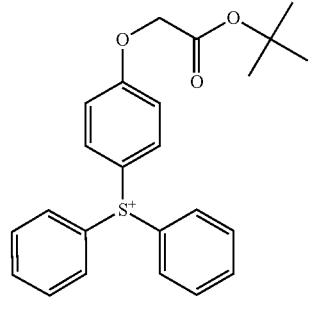

-continued

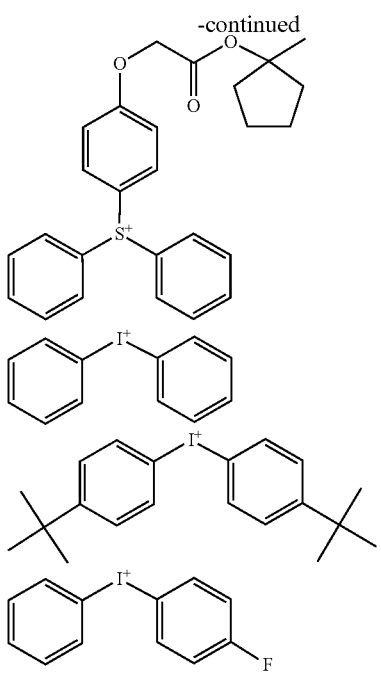

Examples of the sulfonic acid onium salt having formula (5A) and the carboxylic acid onium salt having formula (5B) include arbitrary combinations of anions with cations, both as exemplified above. These onium salts may be readily synthesized by ion exchange reaction according to any well-known organic chemistry technique. For the ion exchange reaction, reference may be made to JP-A 2007-145797, for example.

The onium salt having formula (5A) or (5B) functions as an acid diffusion inhibitor in the resist composition because the counter anion of the onium salt is a conjugated base of a weak acid. As used herein, the weak acid indicates an acidity insufficient to deprotect an acid labile group from an acid labile group-containing unit in the base polymer. The onium salt having formula (5A) or (5B) functions as an acid diffusion inhibitor when used in combination with an onium salt type PAG having a conjugated base of a strong acid (typically α-fluorinated sulfonic acid) as the counter anion. In a system using a mixture of an onium salt capable of generating a strong acid (e.g., α-fluorinated sulfonic acid) and an onium salt capable of generating a weak acid (e.g., non-fluorinated sulfonic acid or carboxylic acid), if the strong acid generated from the PAG upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

Since the onium salt having formula (5A) or (5B) wherein $Mq^+$ is a sulfonium cation (5C) or iodonium cation (5D) is photo-decomposable, the quenching ability is reduced and the concentration of strong acid derived from the PAG is increased in the region with high light intensity. The contrast is thus improved in the exposed region. As a result, a pattern with improved LWR or CDU can be formed.

In case the acid labile group is an acetal group which is quite sensitive to acid, the acid for eliminating the protective group need not necessarily be an α-fluorinated sulfonic acid, imide acid or methide acid. Sometimes, deprotection reaction can take place even with an α-non-fluorinated sulfonic acid. In this case, an amine compound or carboxylic acid onium salt having formula (5B) is preferably used as the acid diffusion inhibitor.

Besides, an onium salt of weak acid such as fluoroalkylsulfonylamide, carbonylsulfonylimide, bis(alkylsulfonyl)imide, or tris(alkylsulfonyl)methide may also be used as the acid diffusion inhibitor. Examples of the anion in these onium salts include those exemplified above for the anion $Z^-$ in formula (1) and the anions shown below.

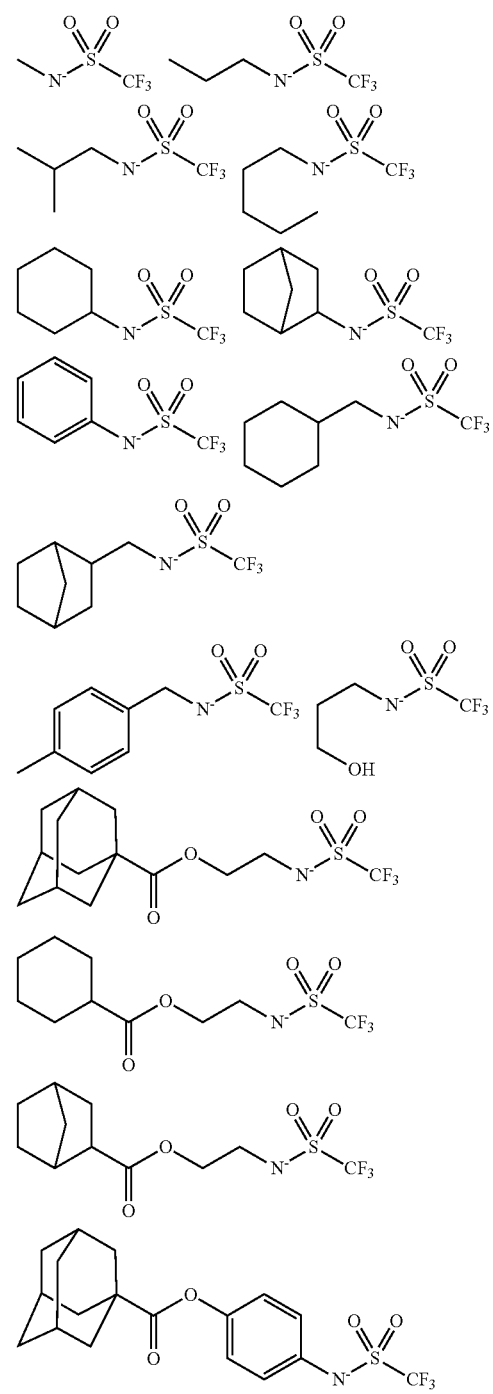

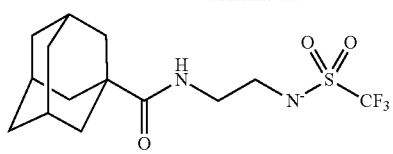
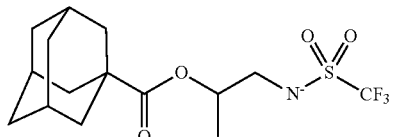
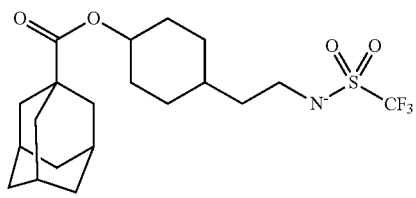
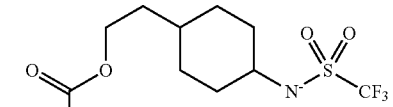
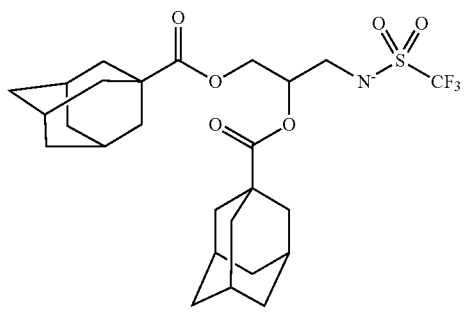
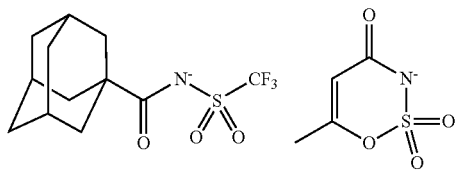
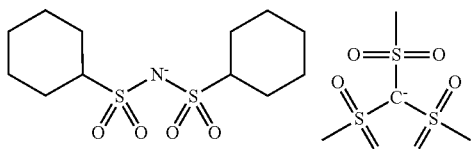
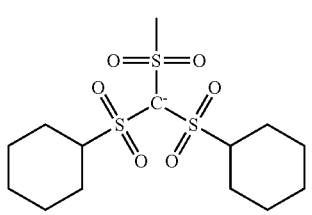

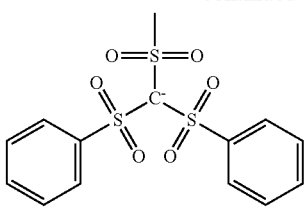

Examples of the cation in the onium salt of weak acid include those exemplified above for the onium cation Mg⁺ in formulae (5A) and (5B).

Examples of the onium salt of weak acid such as fluoroalkylsulfonylamide, carbonylsulfonylimide, bis(alkylsulfonyl)imide, or tris(alkylsulfonyl)methide include combinations of anions with cations, both as exemplified above.

Also, a betaine type compound of weak acid may be used as the acid diffusion inhibitor. The betaine type compound of weak acid is not particularly limited in structure as long as it has the function of acid diffusion inhibitor. Sulfonium and iodonium type compounds are preferred. Also, the compounds whose conjugated acid has an acidity pKa of 1 to 7 are preferred. Suitable examples are shown below, but not limited thereto.

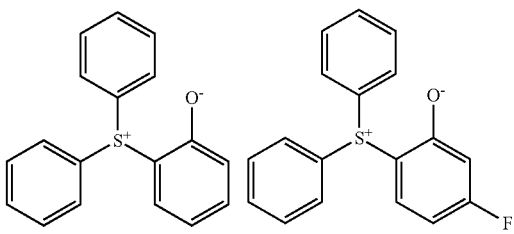
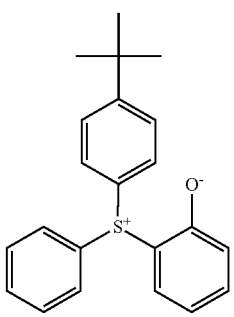
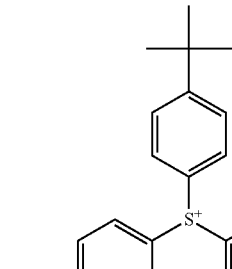
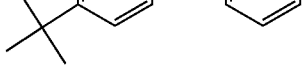

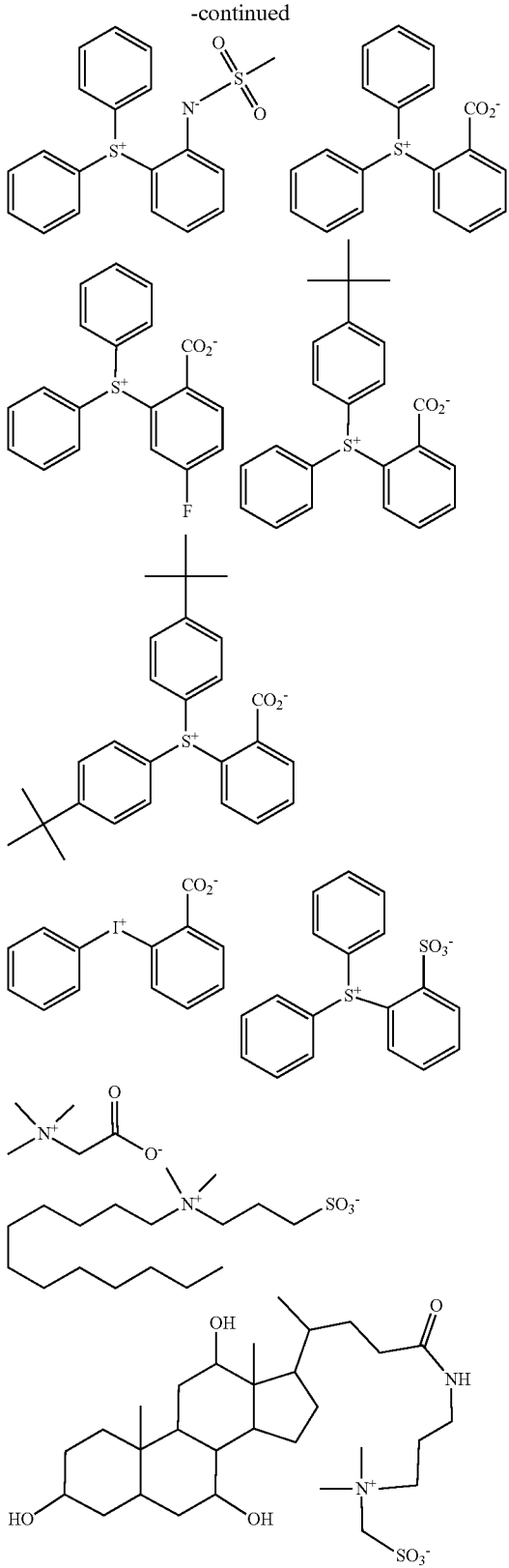

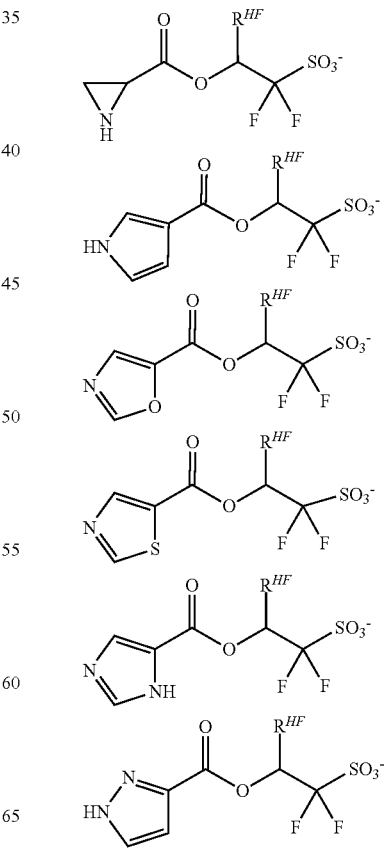

enylsulfonium bromide, triphenylsulfonium nitrate, 4-tert-butylphenyl(diphenyl)sulfonium chloride, bis(4-tert-butylphenyl)phenylsulfonium chloride, tris(4-tert-butylphenyl)sulfonium chloride, 4-tert-butylphenyl(diphenyl)sulfonium nitrate, bis(4-tert-butylphenyl)phenylsulfonium nitrate, tris(4-tert-butylphenyl)sulfonium nitrate, S-phenyldibenzothiophenium chloride, S-phenyldibenzothiophenium nitrate, bis(tert-butylphenyl)iodonium chloride, and bis(tert-butylphenyl)iodonium nitrate. Since the conjugated acid corresponding to the anion has a low boiling point, the acid created after quenching of strong acid is readily removed from the resist film during PEB or the like. Due to easy removal of acid from within the resist film, acid diffusion is fully suppressed, resulting in an improvement in contrast.

Also a photo-decomposable onium salt having a nitrogen-containing substituent may be used as the acid diffusion inhibitor. The photo-decomposable onium salt functions as an acid diffusion inhibitor in the unexposed region, but as a so-called photo-degradable base in the exposed region because it loses the acid diffusion inhibitory ability due to neutralization thereof with the acid generated by itself. Using a photo-degradable base, the contrast between exposed and unexposed regions can be further enhanced. With respect to the photo-degradable base, reference may be made to JP-A 2009-109595, 2012-046501, and 2013-209360, for example.

Examples of the anion in the photo-degradable onium salt are shown below, but not limited thereto. Herein $R^{HF}$ is hydrogen or trifluoromethyl.

Besides the foregoing compounds, sulfonium or iodonium salts having Cl⁻, Br⁻ or $NO_3^-$ as the anion may be used as the acid diffusion inhibitor. Examples include triphenylsulfonium chloride, diphenyliodonium chloride, triph-

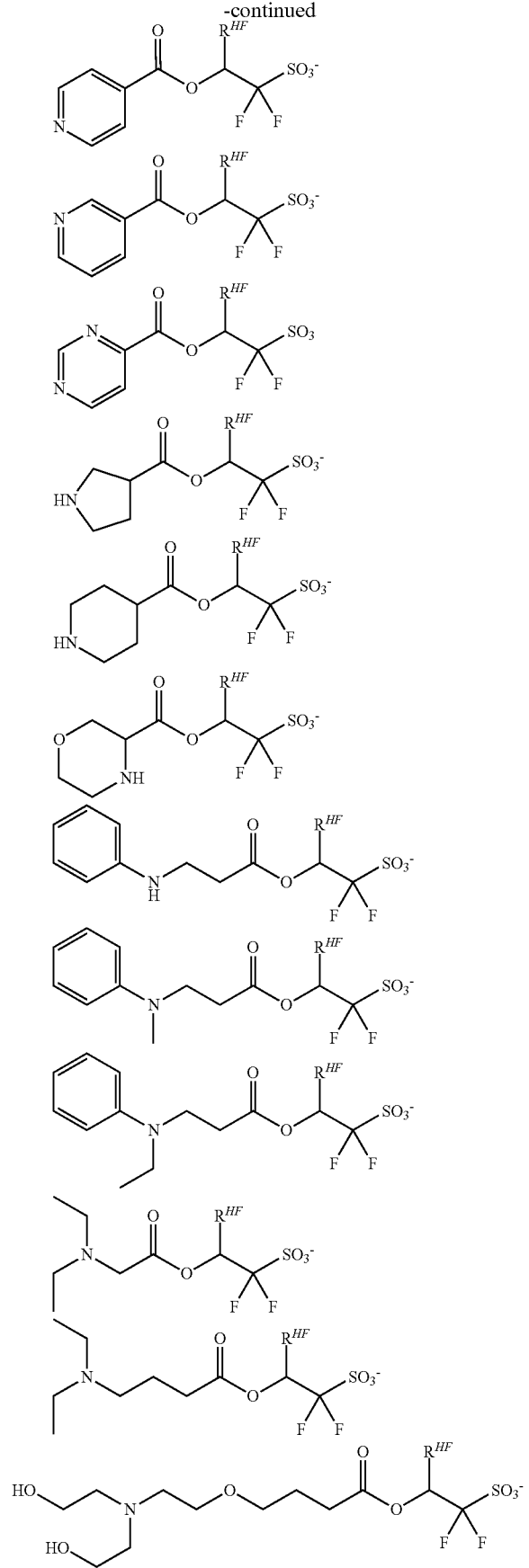
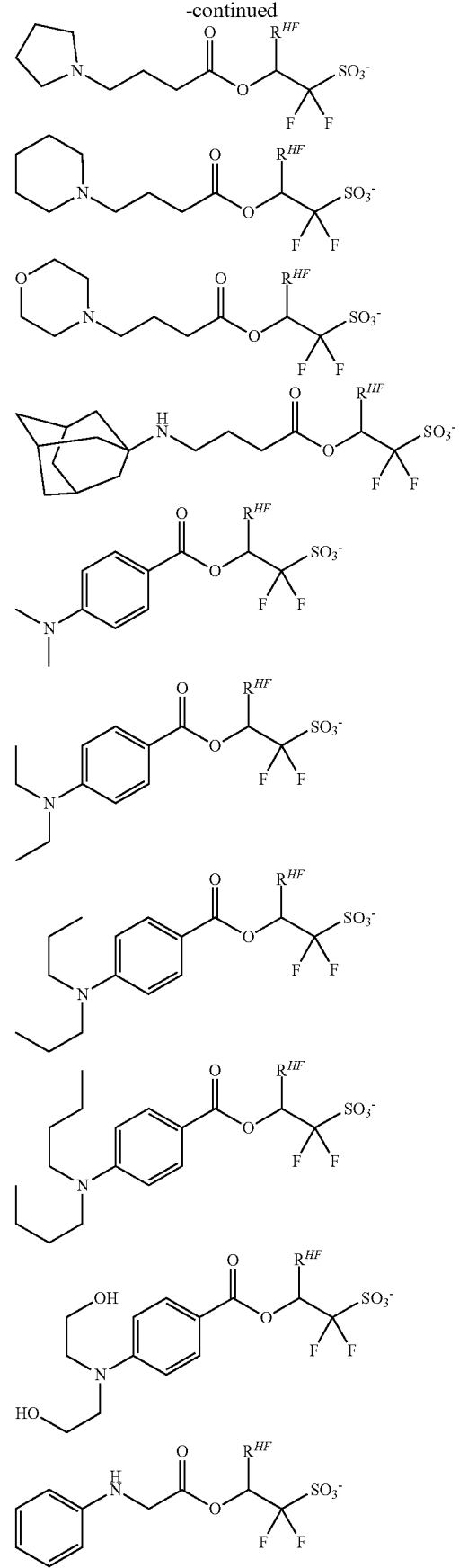

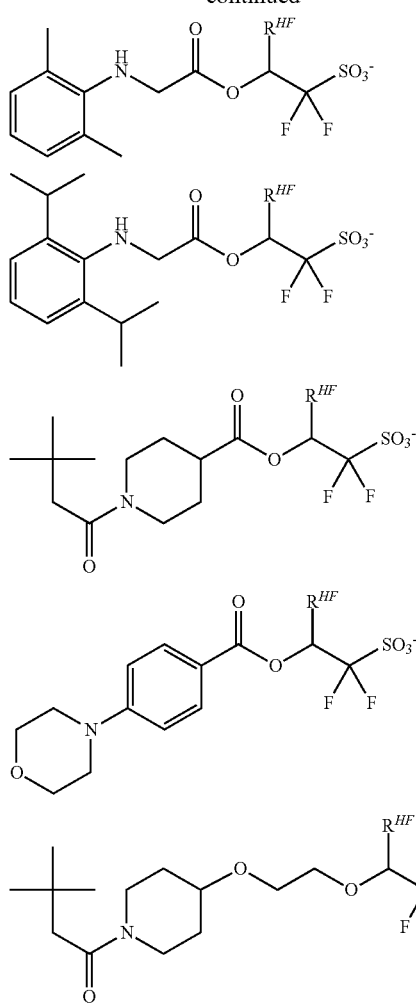
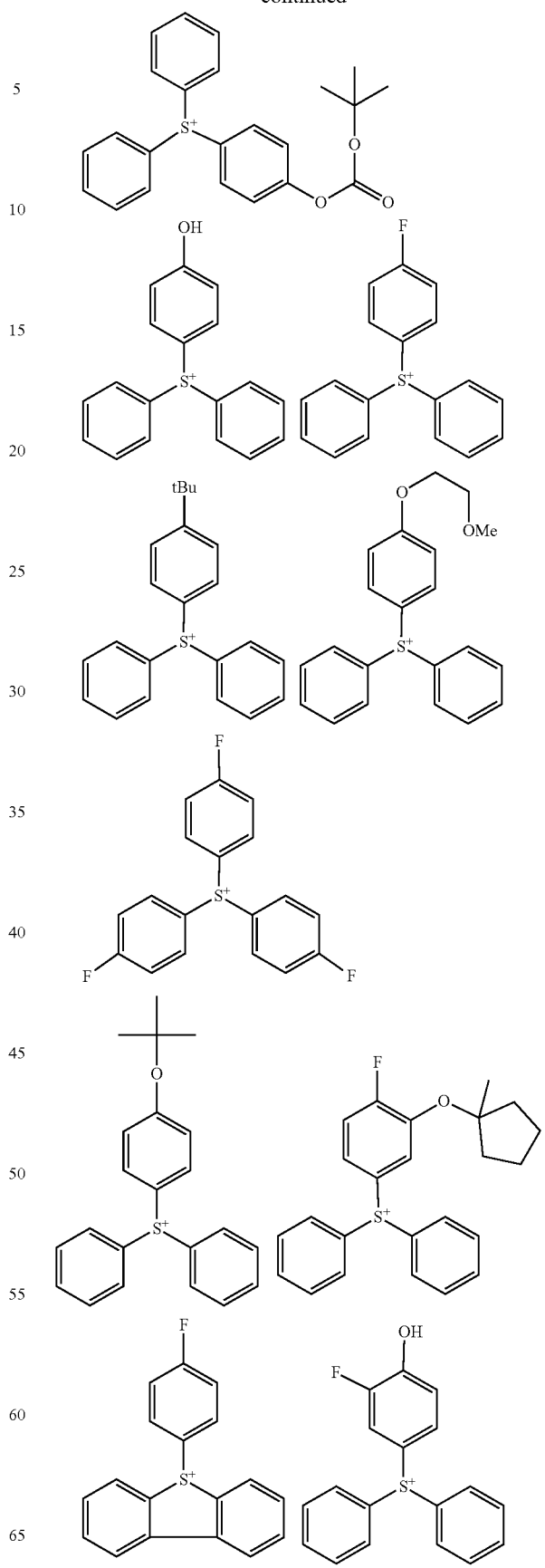
Examples of the cation in the photo-degradable onium salt are as exemplified above for the cation in formulae (d1) to (d3) and the cation in the iodonium salt having formula (3B). Inter alia, the following cations are preferred.
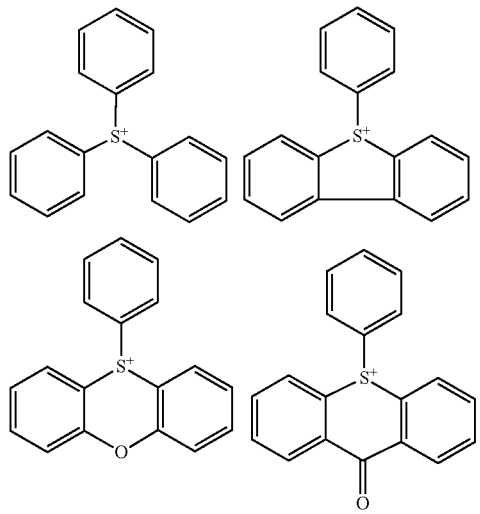

-continued

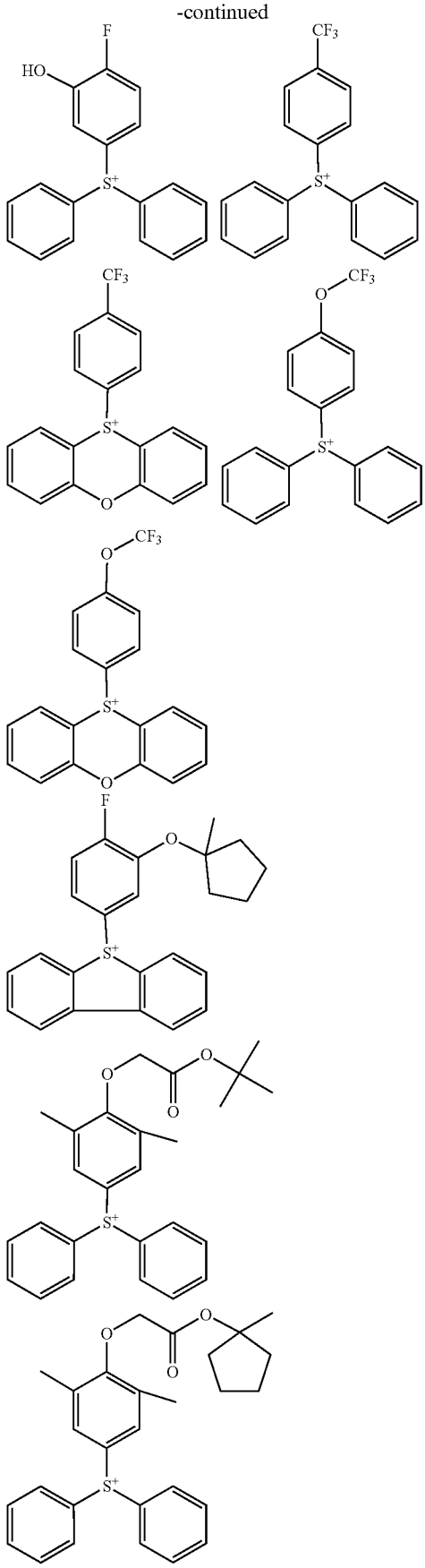

-continued

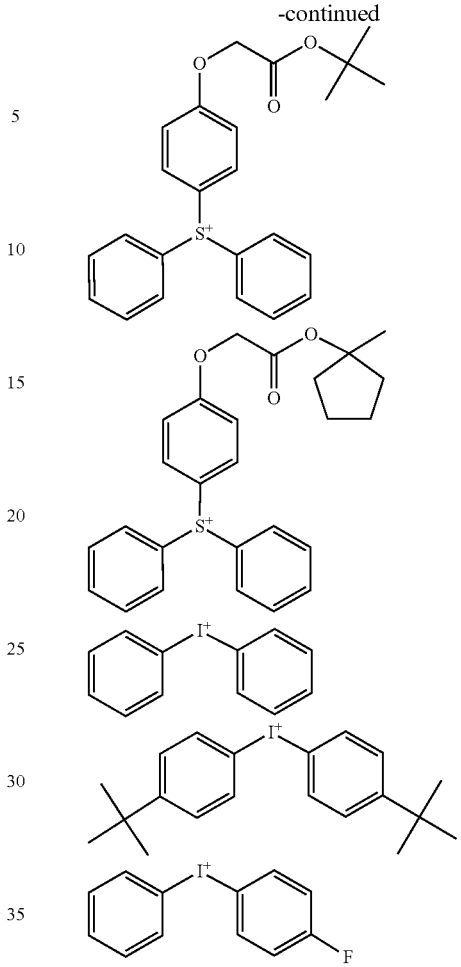

Examples of the photo-decomposable onium salt include arbitrary combinations of cations with anions, both as exemplified above, but are not limited thereto.

Component (C) is preferably used in an amount of 2 to 30 parts by weight, more preferably 5 to 30 parts by weight, even more preferably 8 to 25 parts by weight per 100 parts by weight of the base polymer (A). The acid diffusion inhibitor within the range allows for easy adjustment of resist sensitivity, holds down the diffusion rate of acid within the resist film (with improved resolution), suppresses a sensitivity change after exposure, reduces substrate or environment dependency, and improves exposure latitude and pattern profile. Also the addition of the acid diffusion inhibitor is effective for improving substrate adhesion. It is noted that the amount of component (C) is the total amount of the acid diffusion inhibitor in the form of the onium salt having formula (1) and the acid diffusion inhibitor other than the onium salt having formula (1). In the acid diffusion inhibitor (C), preferably the onium salt having formula (1) accounts for 50 to 100% by weight. The acid diffusion inhibitor as component (C) may be used alone or in admixture.

(D) Organic Solvent

The resist composition further comprises (D) an organic solvent. The organic solvent used herein is not particularly limited as long as the foregoing and other components are dissolvable therein. Examples of the organic solvent used herein are described in JP-A 2008-111103, paragraphs

[0144]-[0145] (U.S. Pat. No. 7,537,880). Exemplary solvents include ketones such as cyclohexanone (CyHO) and methyl-2-n-pentyl ketone; alcohols such as 3-methoxybutanol, 3-methyl-3-methoxybutanol, 1-methoxy-2-propanol, 1-ethoxy-2-propanol, and diacetone alcohol (DAA); ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone (GBL), which may be used alone or in admixture. Where an acid labile group of acetal form is used, a high boiling alcohol solvent such as diethylene glycol, propylene glycol, glycerol, 1,4-butanediol or 1,3-butanediol may be added to accelerate deprotection reaction of acetal.

Of these organic solvents, preference is given to 1-ethoxy-2-propanol, PGMEA, DAA, CyHO, GBL, ethyl lactate and mixtures thereof because the PAG is highly soluble therein. The preferred solvent system is a mixture of PGMEA as solvent X and one or two of 1-ethoxy-2-propanol, DAA, CyHO, GBL, and ethyl lactate as solvent Y in a ratio X:Y of from 90:10 to 30:70.

The organic solvent (D) is preferably added in an amount of 100 to 8,000 parts, and more preferably 400 to 6,000 parts by weight per 100 parts by weight of the base polymer (A).

(E) Surfactant

In addition to the foregoing components, the resist composition may comprise (E) a surfactant which is commonly used for facilitating coating operation.

Component (E) is typically a surfactant which is insoluble or substantially insoluble in water and alkaline developer or a surfactant which is insoluble or substantially insoluble in water and soluble in alkaline developer. For these surfactants, reference should be made to JP-A 2010-215608 and JP-A 2011-016746.

Preferred examples of the surfactant which is insoluble or substantially insoluble in water and alkaline developer include FC-4430 (3M), Surflon® S-381, KH-20 and KH-30 (AGC Seimi Chemical Co., Ltd.), and Olfine® E1004 (Nisshin Chemical Co., Ltd.). Partially fluorinated oxetane ring-opened polymers having the structural formula (surf-1) are also useful.

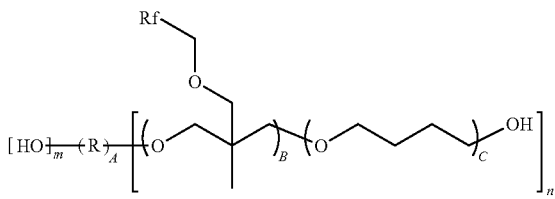

(surf-1)

It is provided herein that R, Rf, A, B, C, m, and n are applied to only formula (surf-1), independent of their descriptions other than for the surfactant. R is a di- to tetra-valent $C_2$-$C_5$ aliphatic group. Exemplary divalent groups include ethylene, 1,4-butylene, 1,2-propylene, 2,2-dimethyl-1,3-propylene and 1,5-pentylene. Exemplary tri- and tetra-valent groups are shown below.

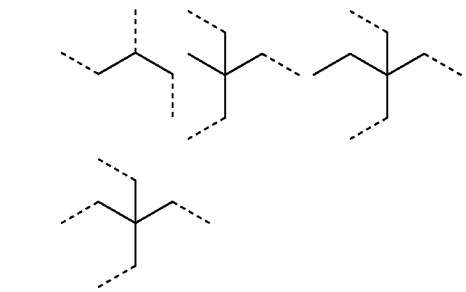

Herein the broken line denotes a valence bond. These formulae are partial structures derived from glycerol, trimethylol ethane, trimethylol propane, and pentaerythritol, respectively. Of these, 1,4-butylene and 2,2-dimethyl-1,3-propylene are preferably used.

Rf is trifluoromethyl or pentafluoroethyl, and preferably trifluoromethyl. The letter m is an integer of 0 to 3, n is an integer of 1 to 4, and the sum of m and n, which represents the valence of R, is an integer of 2 to 4. "A" is equal to 1, B is an integer of 2 to 25, and C is an integer of 0 to 10. Preferably, B is an integer of 4 to 20, and C is 0 or 1. Note that the above structural formula does not prescribe the arrangement of respective constituent units while they may be arranged either blockwise or randomly. For the preparation of surfactants in the form of partially fluorinated oxetane ring-opened polymers, reference should be made to U.S. Pat. No. 5,650,483, for example.

The surfactant which is insoluble or substantially insoluble in water and soluble in alkaline developer is useful when ArF immersion lithography is applied to the resist composition in the absence of a resist protective film. In this embodiment, the surfactant has a propensity to segregate on the resist film surface for achieving a function of minimizing water penetration or leaching. The surfactant is also effective for preventing water-soluble components from being leached out of the resist film for minimizing any damage to the exposure tool. The surfactant becomes solubilized during alkaline development following exposure and PEB, and thus forms few or no foreign particles which become defects. The preferred surfactant is a polymeric surfactant which is insoluble or substantially insoluble in water, but soluble in alkaline developer, also referred to as "hydrophobic resin" in this sense, and especially which is water repellent and enhances water sliding.

Suitable polymeric surfactants include those containing repeat units of at least one type selected from the formulae (6A) to (6E).

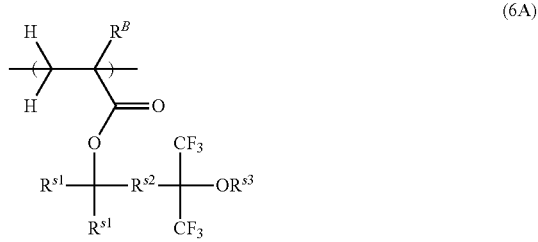

(6A)

(6B)
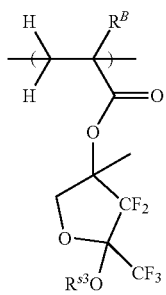

(6C)
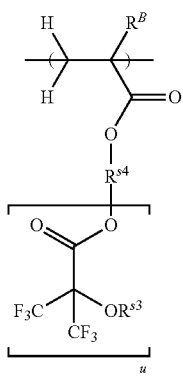

(6D)
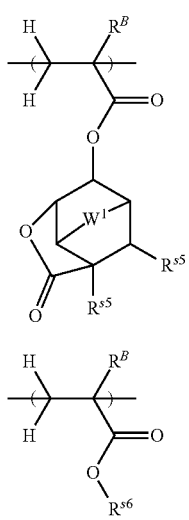

(6E)
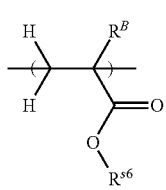

Herein, $R^B$ is hydrogen or methyl. $W^1$ is —CH$_2$—, —CH$_2$CH$_2$— or —O—, or two separate —H. $R^{s1}$ is each independently hydrogen or a C$_1$-C$_{10}$ hydrocarbyl group. $R^{s2}$ is a single bond or a C$_1$-C$_5$ alkanediyl group. IV is each independently hydrogen, a C$_1$-C$_{15}$ hydrocarbyl or fluorinated hydrocarbyl group, or an acid labile group. When IV is a hydrocarbyl or fluorinated hydrocarbyl group, an ether bond (—O—) or carbonyl moiety (—C(=O)—) may intervene in a carbon-carbon bond. $R^{s3}$ is a C$_1$-C$_{20}$ (u+1)-valent hydrocarbon or fluorinated hydrocarbon group, and u is an integer of 1 to 3. IV is each independently hydrogen or a group having the formula: —C(=O)—O—$R^{s5A}$ wherein $R^{s5A}$ is a C$_1$-C$_{20}$ fluorinated hydrocarbyl group. $R^{s6}$ is a C$_1$-C$_{15}$ hydrocarbyl or fluorinated hydrocarbyl group in which —O— or —C(=O)— may intervene in a carbon-carbon bond.

The polymeric surfactant may further contain repeat units other than the repeat units having formulae (6A) to (6E).

Typical other repeat units are those derived from methacrylic acid and α-trifluoromethylacrylic acid derivatives. In the polymeric surfactant, the content of the repeat units having formulae (6A) to (6E) is preferably at least 20 mol %, more preferably at least 60 mol %, most preferably 100 mol % of the overall repeat units.

For the surfactant which is insoluble or substantially insoluble in water and soluble in alkaline developer, reference may be made to JP-A 2008-122932, JP-A 2009-098638, JP-A 2009-191151, JP-A 2009-192784, JP-A 2009-276363, JP-A 2010-107695, JP-A 2010-134012, JP-A 2010-250105, and JP-A 2011-042789.

The amount of component (E) is preferably 0 to 20 parts by weight per 100 parts by weight of the base polymer (A). When added, the amount of component (E) is more preferably 0.001 to 15 parts by weight, even more preferably 0.01 to 10 parts by weight. The surfactant may be used alone or in admixture.

(F) Other Components

The resist composition may further comprise (F) another component, for example, a compound which is decomposed with an acid to generate another acid (i.e., acid amplifier compound), an organic acid derivative, a fluorinated alcohol, a crosslinker, a compound having a Mw of up to 3,000 which changes its solubility in developer under the action of an acid (i.e., dissolution inhibitor), and an acetylene alcohol. Specifically, the acid amplifier compound is described in JP-A 2009-269953 and JP-A 2010-215608 and preferably used in an amount of 0 to 5 parts, more preferably 0 to 3 parts by weight per 100 parts by weight of the base polymer (A). An extra amount of the acid amplifier compound can make the acid diffusion control difficult and cause degradations to resolution and pattern profile. With respect to the remaining additives, reference should be made to JP-A 2008-122932, paragraphs [0155]-[0182], JP-A 2009-269953 and JP-A 2010-215608.

The chemically amplified resist composition comprising the onium salt having formula (1) as an acid diffusion inhibitor, when processed by photolithography using high-energy radiation such as KrF excimer laser, ArF excimer laser, EB or EUV as the energy source, forms a pattern with minimal defects and improved lithography performance factors such as CDU, LWR and DOF.

Process

A further embodiment of the invention is a pattern forming process using the chemically amplified resist composition defined above. The process includes the steps of applying the resist composition to form a resist film on a substrate, exposing a selected region of the resist film to high-energy radiation, and developing the exposed resist film in a developer. Any desired steps may be added to the process if necessary.

The substrate used herein may be a substrate for integrated circuitry fabrication, e.g., Si, SiO$_2$, SiN, SiON, TiN, WSi, BPSG, SOG, organic antireflective film, etc. or a substrate for mask circuitry fabrication, e.g., Cr, CrO, CrON, MoSi$_2$, SiO$_2$, etc.

The resist composition is applied onto a substrate by a suitable coating technique such as spin coating. The coating is prebaked on a hot plate preferably at a temperature of 60 to 180° C. for 10 to 600 seconds, more preferably at 70 to 150° C. for 15 to 300 seconds. The resulting resist film preferably has a thickness of 10 to 2,000 nm.

The resist film is then exposed to high-energy radiation. On use of KrF excimer laser, ArF excimer laser or EUV of wavelength 13.5 nm, the resist film is exposed through a mask having the desired pattern in a dose of preferably 1 to 200 mJ/cm$^2$, more preferably 10 to 100 mJ/cm$^2$. On use of EB, a pattern may be written directly or through a mask having the desired pattern, preferably in a dose of 1 to 300 μC/cm$^2$, more preferably 10 to 200 μC/cm$^2$.

The exposure may be performed by conventional lithography whereas the immersion lithography of holding a liquid between the mask and the resist film may be employed if desired. In the immersion lithography, preferably a liquid having a refractive index of at least 1.0 is held between the resist film and the projection lens. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB), for example, on a hotplate at 60 to 150° C. for 1 to 5 minutes, preferably at 80 to 140° C. for 1 to 3 minutes.

The resist film is then developed with a developer in the form of an aqueous base solution, for example, 0.1 to 5 wt %, preferably 2 to 3 wt % aqueous solution of tetramethylammonium hydroxide (TMAH) for 0.1 to 3 minutes, preferably 0.5 to 2 minutes by conventional techniques such as dip, puddle and spray techniques. In this way, a desired resist pattern is formed on the substrate.

With respect to the formation of a positive pattern using an alkaline aqueous solution as the developer, reference may be made to U.S. Pat. No. 8,647,808 (JP-A 2011-231312, paragraphs [0138]-[0146]). With respect to the formation of a negative pattern using an organic solvent as the developer, reference may be made to U.S. Pat. No. 9,256,127 (JP-A 2015-214634, paragraphs [0173]-[0183]).

Any desired step may be added to the pattern forming process. For example, after the resist film is formed, a step of rinsing with pure water (post-soaking) may be introduced to extract the acid generator or the like from the film surface or wash away particles. After exposure, a step of rinsing (post-soaking) may be introduced to remove any water remaining on the film after exposure.

Also, a double patterning process may be used for pattern formation. The double patterning process includes a trench process of processing an underlay to a 1:3 trench pattern by a first step of exposure and etching, shifting the position, and forming a 1:3 trench pattern by a second step of exposure, for forming a 1:1 pattern; and a line process of processing a first underlay to a 1:3 isolated left pattern by a first step of exposure and etching, shifting the position, processing a second underlay formed below the first underlay by a second step of exposure through the 1:3 isolated left pattern, for forming a half-pitch 1:1 pattern.

Where a hole pattern is formed by negative tone development using organic solvent developer, exposure by double dipole illuminations of X- and Y-direction line patterns provides the highest contrast light. The contrast may be further increased by combining two dipole illuminations of X- and Y-direction line patterns with s-polarized illumination. These pattern forming processes are described in JP-A 2011-221513.

With respect to the developer in the pattern forming process, examples of the aqueous alkaline solution include TMAH aqueous solutions as mentioned above and aqueous alkaline solutions described in JP-A 2015-180748, paragraphs [0148]-[0149], preferably 2 to 3% by weight TMAH aqueous solutions.

The organic solvent used as the developer is preferably selected from 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, isopentyl acetate, butenyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate. These organic solvents may be used alone or in admixture of two or more.

A hole or trench pattern after development may be shrunk by the thermal flow, RELACS® (resolution enhancement lithography assisted by chemical shrink) or DSA (directed self-assembly) process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

When processed by photolithography, the chemically amplified resist composition comprising the onium salt having formula (1) as an acid diffusion inhibitor forms a fine size pattern with improved lithography performance factors such as CDU, LWR and DOF.

EXAMPLES

Examples of the invention are given below by way of illustration and not by way of limitation. The abbreviation "pbw" is parts by weight. For all polymers, Mw and Mn are determined by GPC versus polystyrene standards using tetrahydrofuran (THF) solvent.

[1] Synthesis of Acid Diffusion Inhibitors

Example 1-1

Synthesis of Acid Diffusion Inhibitor Q-1

(1) Synthesis of Compound SM-2

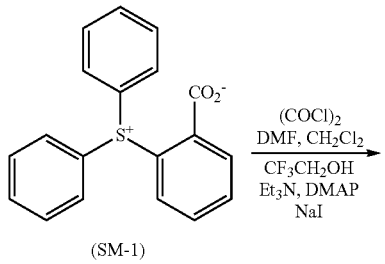

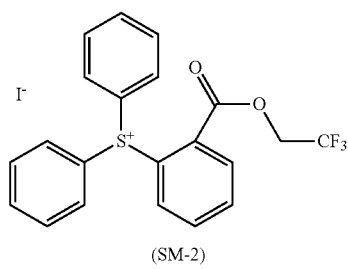

First, 24.5 g of Compound SM-1, 0.06 g of N,N-dimethylformamide, and 147.2 g of methylene chloride were mixed, whereupon 25.4 g of oxalyl chloride was added dropwise at room temperature. Stirring was continued overnight at room temperature. The reaction solution was concentrated at 40° C. under reduced pressure until a solid was obtained. After the solid, 170.1 g of methylene chloride, and 10.4 g of 2,2-trifluoroethanol were mixed, after which, under ice cooling, a mixture of 10.5 g of triethylamine, 1.3 g of N,N-dimethylaminopyridine, and 8 g of methylene chloride was added dropwise. The mixture was continuously stirred for aging. After the progress of reaction was confirmed by $^{19}$F-NMR spectroscopy, under ice cooling, 150 g of 5 wt % hydrochloric acid was added to quench the reaction. Hexane, 180 g, was added to the reaction solution, followed by stirring. The water layer was taken out and washed twice with 75 g of diisopropyl ether. To the water layer, 14.4 g of sodium iodide was added, and further, 60 g of methylene chloride and 120 g of methyl isobutyl ketone were added, followed by 10 minutes of stirring. At the end of stirring, the organic layer was taken out and washed 4 times with 90 g of deionized water. The organic layer was concentrated under reduced pressure. The concentrate was diluted with 40 g of methylene chloride. Diisopropyl ether, 200 g, was added to the dilution, which was stirred. The supernatant was removed. The oily residue was concentrated at 50° C. under reduced pressure, obtaining the desired Compound SM-2 as oily matter (amount 33.5 g, yield 74%).

(2) Synthesis of Compound SM-3

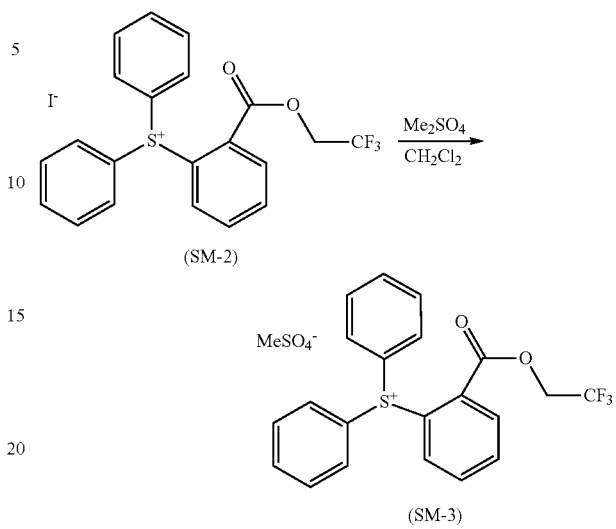

After 33.4 g of Compound SM-2 was dissolved in 100.2 g of methylene chloride, 8.17 g of dimethyl sulfate was added dropwise at room temperature. After overnight stirring, the reaction solution was concentrated at 50° C. under reduced pressure. After methylene chloride was added to the concentrate to form a 50 wt % solution, 120 g of diisopropyl ether was added to the solution. During subsequent stirring, a solid precipitated. The solid precipitate was collected by filtration, washed with diisopropyl ether, and dried at 40° C. in vacuum, obtaining the desired Compound SM-3 in solid form (amount 27.4 g, yield 92%).

(3) Synthesis of Acid Diffusion Inhibitor Q-1

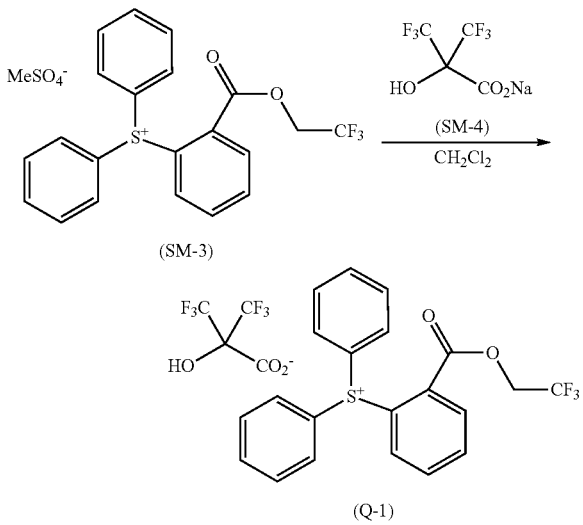

A mixture of 5.7 g of Compound SM-3, 3.47 g of Compound SM-4, 48 g of methylene chloride, and 16 g of deionized water was stirred at room temperature for 1 hour. The organic layer was taken out. Thereafter, the procedure of adding 0.4 g of Compound SM-4 and 18 g of deionized water to the organic layer, stirring, and taking out the organic layer was repeated twice. The resulting organic layer was washed 4 times with 18 g of deionized water and concentrated at 40° C. under reduced pressure. Methylene chloride was added to the concentrate to form a 50 wt % solution. Then, 68 g of diisopropyl ether was added to the solution, which was stirred for 30 minutes. The solid precipitate was collected by filtration, washed with diisopropyl ether, and dried at 30° C. in vacuum, obtaining the target acid diffusion inhibitor Q-1 in solid form (amount 6.4 g, yield 93%).

Figure 2:
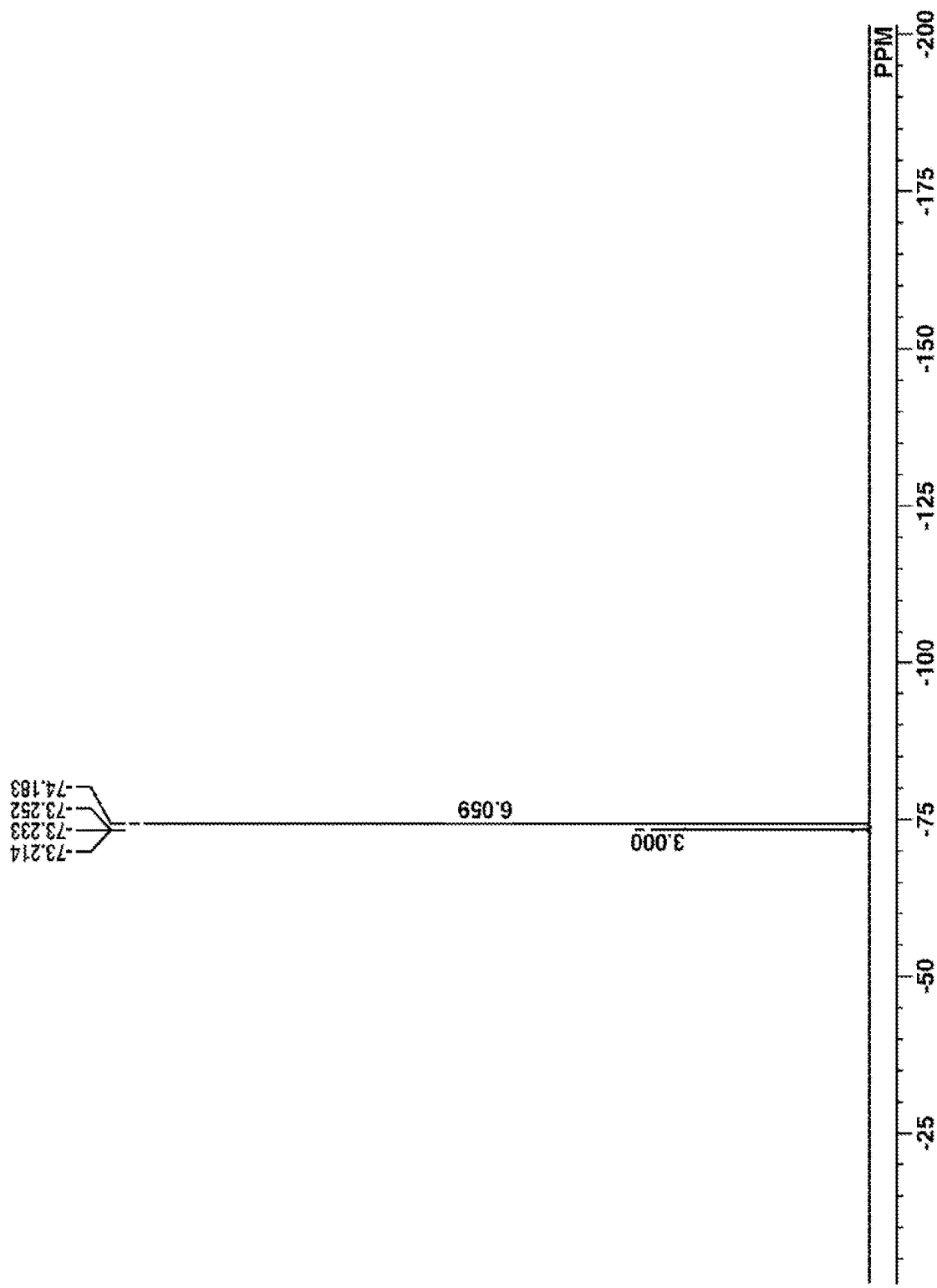
FIG. 2 is a diagram showing $^{19}$F-NMR spectrum of acid diffusion inhibitor Q-1 in Example 1-1.

Q-1 was analyzed by IR, time-of-flight mass spectrometry, and NMR spectroscopy. The IR and TOFMS data are shown below. The $^1$H- and $^{19}$F-NMR/DMSO-d6 spectra are shown in FIGS. 1 and 2, respectively.

IR (D-ATR):
  v=3497, 3238, 3070, 1736, 1695, 1586, 1478, 1448, 1422, 1365, 1315, 1289, 1259, 1207, 1184, 1164, 1145, 1076, 1057, 1013, 1000, 978, 891, 824, 791, 755, 740, 683, 642, 577, 518, 503 cm$^{-1}$

MALDI TOFMS:
  Positive M$^+$ 389.1 (corresponding to $C_{21}H_{16}F_3O_2S^+$)
  Negative M$^-$ 211.0 (corresponding to $C_4HF_6O_3^-$)

Example 1-2

Synthesis of Acid Diffusion Inhibitor Q-2

A mixture of 5.0 g of Compound SM-3, 8.0 g of Compound SM-5, 56 g of methyl isobutyl ketone, 5 g of methanol, and 30 g of deionized water was stirred at room temperature for 1 hour. The organic layer was taken out, whereupon it was washed 3 times with 30 g of deionized water and 3 times with 30 g of 20 wt % methanol aqueous solution. The organic layer was concentrated at 45° C. under reduced pressure. 80 g of diisopropyl ether was added to the concentrate. The dilution was stirred for 1 hour whereupon the supernatant was removed. The procedure of adding 50 g of diisopropyl ether, stirring, and removing the supernatant was repeated twice. The residue was diluted with methylene chloride. 40 g of diisopropyl ether was added to the dilution, which was stirred. The solid precipitate was collected by filtration and dried at 50° C. in vacuum, obtaining the target acid diffusion inhibitor Q-2 in solid form (amount 8.3 g, yield 80%).

Figure 3:
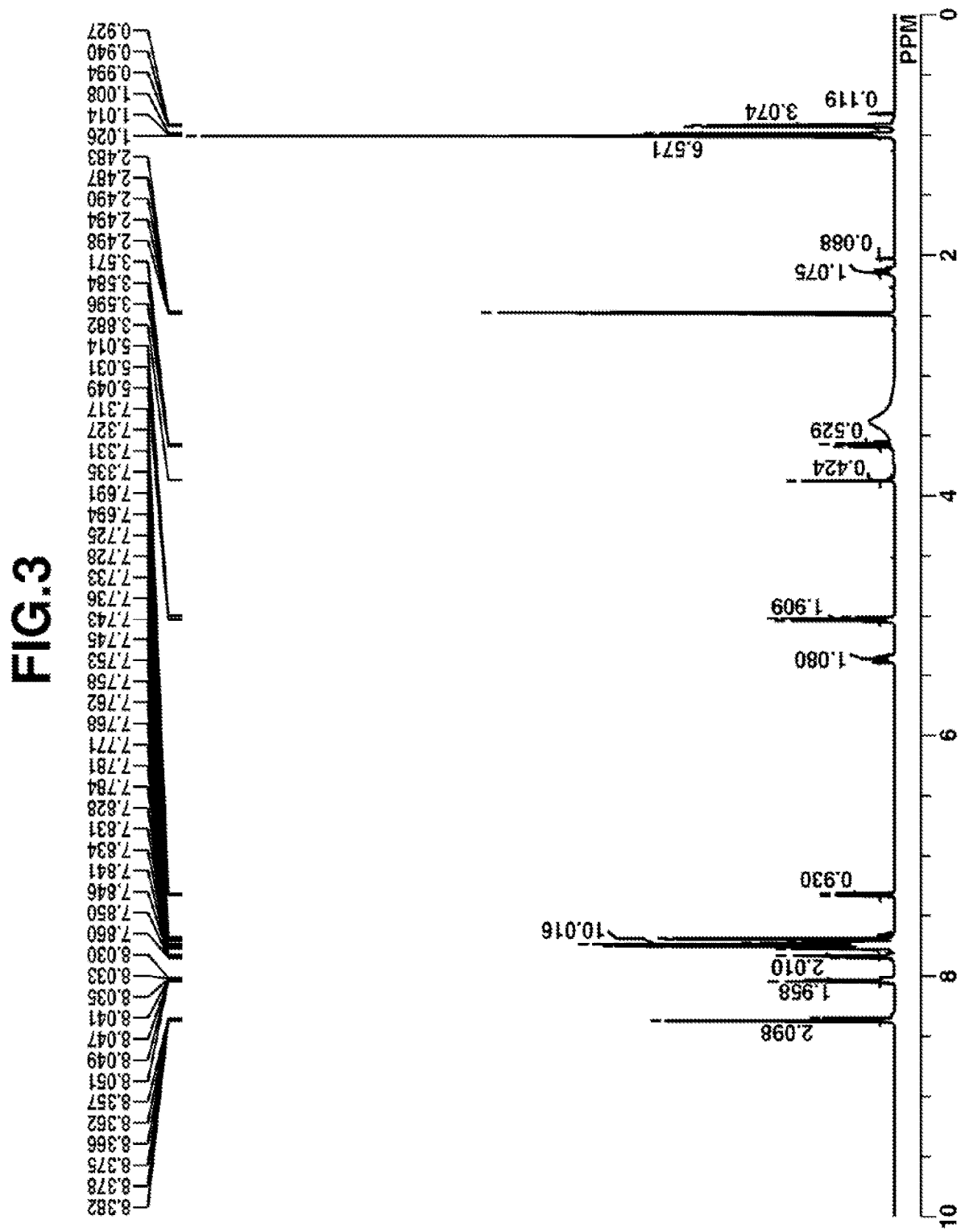
FIG. 3 is a diagram showing $^1$H-NMR spectrum of acid diffusion inhibitor Q-2 in Example 1-2.
Figure 4:
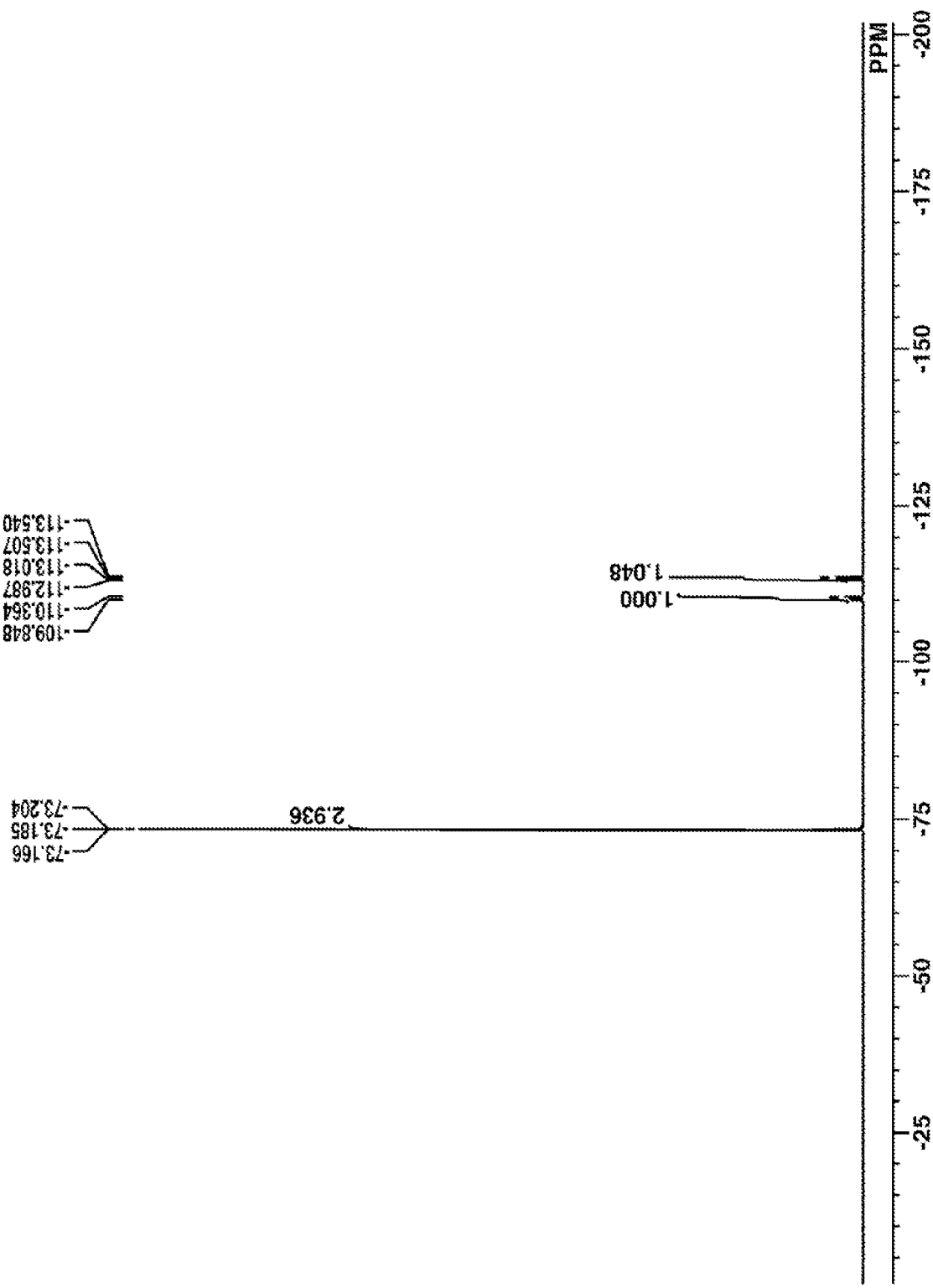
FIG. 4 is a diagram showing $^{19}$F-NMR spectrum of acid diffusion inhibitor Q-2 in Example 1-2.

Q-2 was analyzed by spectroscopy. The TOFMS data are shown below. The $^1$H- and $^{19}$F-NMR/DMSO-d6 spectra are shown in FIGS. 3 and 4, respectively.

MALDI TOFMS:
  Positive M$^+$ 389.1 (corresponding to $C_{21}H_{16}F_3O_2S^+$)
  Negative M$^-$ 648.8 (corresponding to $C_{13}H_{10}F_2I_3O_4^-$)

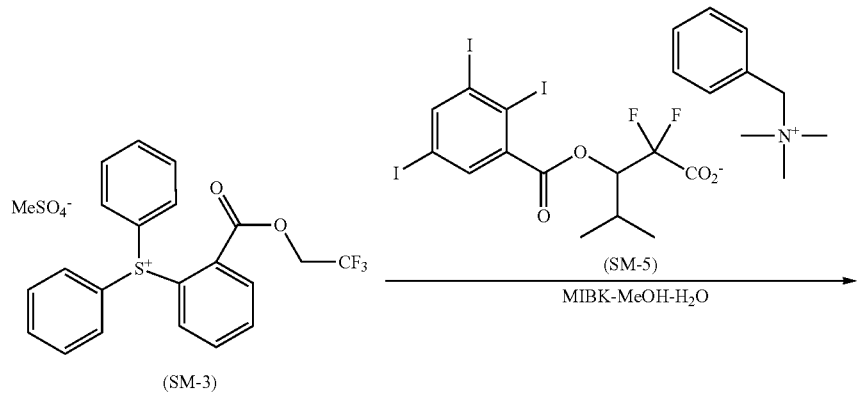

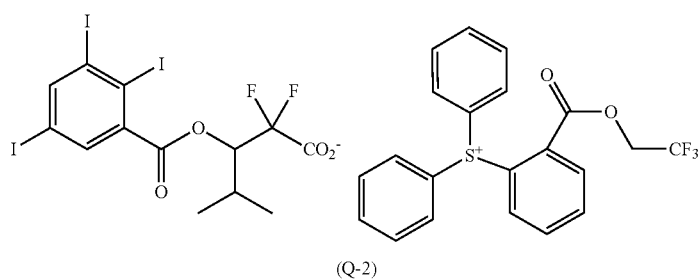

(Q-2)

Example 1-3

Synthesis of Acid Diffusion Inhibitor Q-3

(1) Synthesis of Compound SM-6

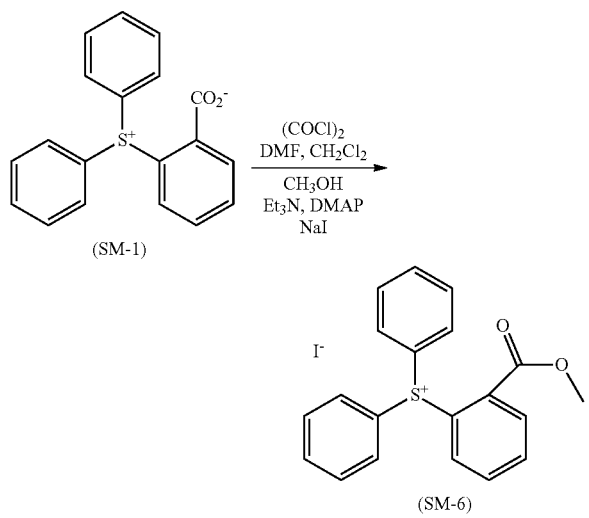

First, 24.5 g of Compound SM-1, 0.06 g of N,N-dimethylformamide, and 147.2 g of methylene chloride were mixed, whereupon 25.4 g of oxalyl chloride was added dropwise at room temperature. Stirring was continued overnight at room temperature. The reaction solution was concentrated at 40° C. under reduced pressure until a solid was obtained. The solid was mixed with 170.1 g of methylene chloride and 10 g of methanol, after which under ice cooling, a mixture of 10.5 g of triethylamine, 1.3 g of N,N-dimethylaminopyridine, and 10 g of methylene chloride was added dropwise. The mixture was stirred at room temperature for 2 hours. Under ice cooling, 150 g of 5 wt % hydrochloric acid was added to quench the reaction. Hexane, 180 g, was added to the reaction solution, followed by stirring. The water layer was taken out and washed twice with 75 g of diisopropyl ether. To the water layer, 14.4 g of sodium iodide was added, and further, 60 g of methylene chloride and 120 g of methyl isobutyl ketone were added, followed by 10 minutes of stirring. At the end of stirring, the organic layer was taken out and washed 5 times with 100 g of deionized water. The organic layer was concentrated under reduced pressure. Diisopropyl ether, 200 g, was added to the concentrate, which was stirred. The supernatant was removed. The oily residue was concentrated at 50° C. under reduced pressure, obtaining the desired Compound SM-6 as oily matter (amount 29.5 g, yield 83%).

(2) Synthesis of Compound SM-7

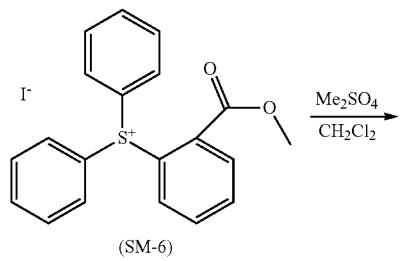

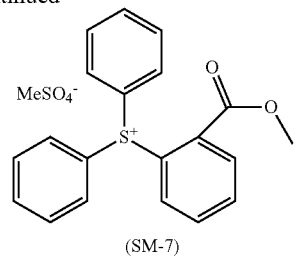

After 29.4 g of Compound SM-6 was dissolved in 88.2 g of methylene chloride, 9.1 g of dimethyl sulfate was added dropwise at room temperature. After 2 hours of stirring, the reaction solution was concentrated at 50° C. under reduced pressure. Methylene chloride was added to the concentrate to form a 50 wt % solution, whereupon 113.7 g of diisopropyl ether was added to the solution. During subsequent stirring, a solid precipitated. The solid precipitate was collected by filtration, washed with diisopropyl ether, and dried at 40° C. in vacuum, obtaining the desired Compound SM-7 in solid form (amount 23.4 g, yield 82%).

(3) Synthesis of Acid Diffusion Inhibitor Q-3

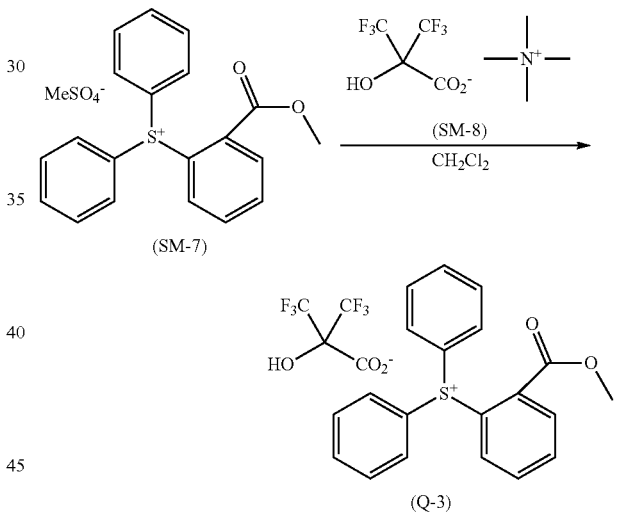

A mixture of 4.3 g of Compound SM-7, 7.9 g of 38.6 wt % aqueous solution of Compound SM-8, 30 g of methylene chloride, and 15 g of deionized water was stirred at room temperature for 15 minutes. The organic layer was taken out. The procedure of adding 0.9 g of 38.6 wt % aqueous solution of Compound SM-8 and 15 g of deionized water to the organic layer, stirring, and taking out the organic layer was repeated twice. The resulting organic layer was washed 3 times with 15 g of deionized water and concentrated at 40° C. under reduced pressure. The concentrate was diluted with methylene chloride, and 5 g of diisopropyl ether was added to the dilution, which was stirred. The supernatant was removed. The residue was diluted with 5 g of methylene chloride. 10 g of diisopropyl ether was added to the dilution, which was stirred. The solid precipitate was collected by filtration, washed with diisopropyl ether, and dried at 40° C. in vacuum, obtaining the target acid diffusion inhibitor Q-3 in solid form (amount 4.9 g, yield 90%).

Figure 5:
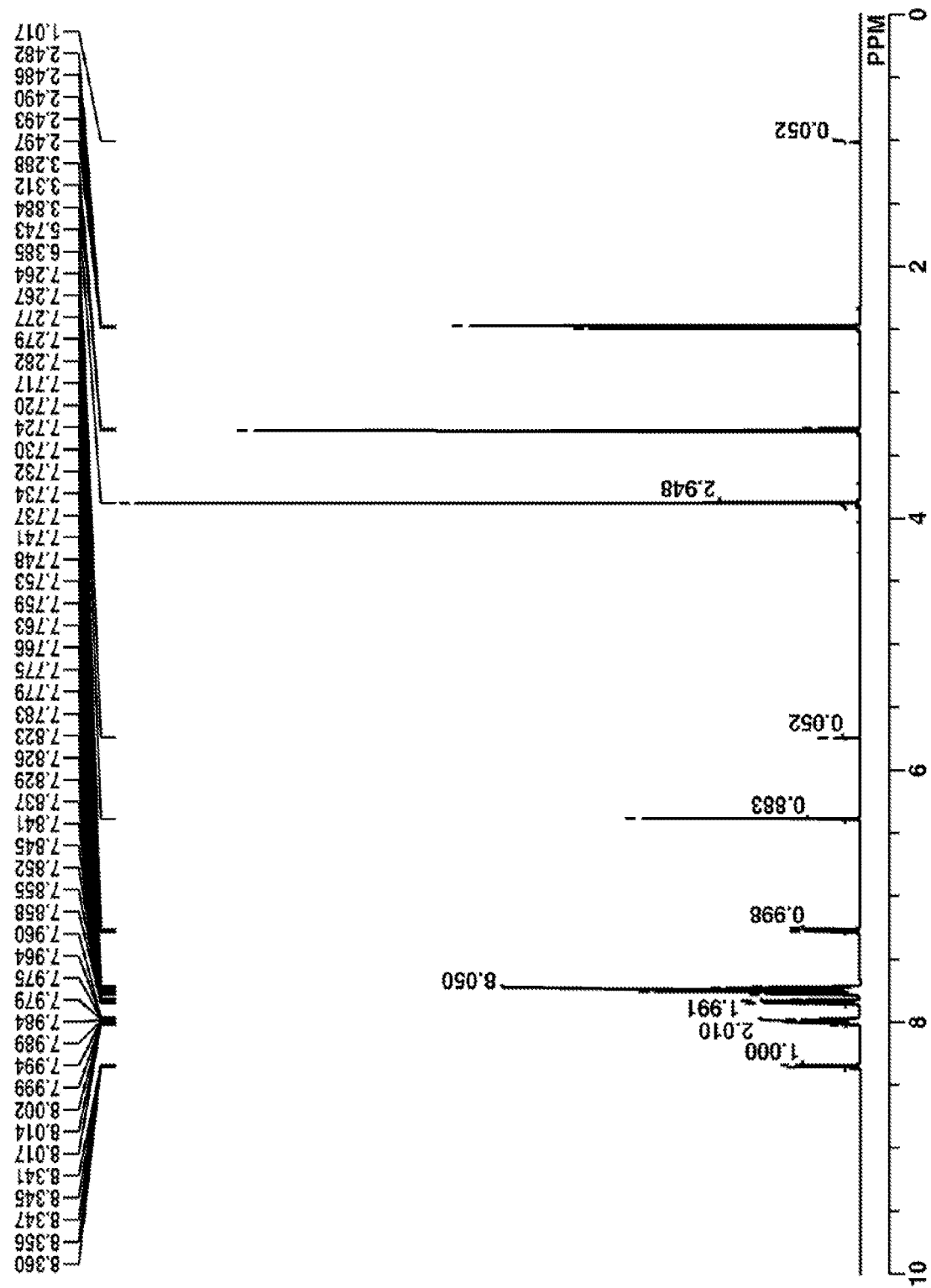
FIG. 5 is a diagram showing $^1$H-NMR spectrum of acid diffusion inhibitor Q-3 in Example 1-3.
Figure 6:
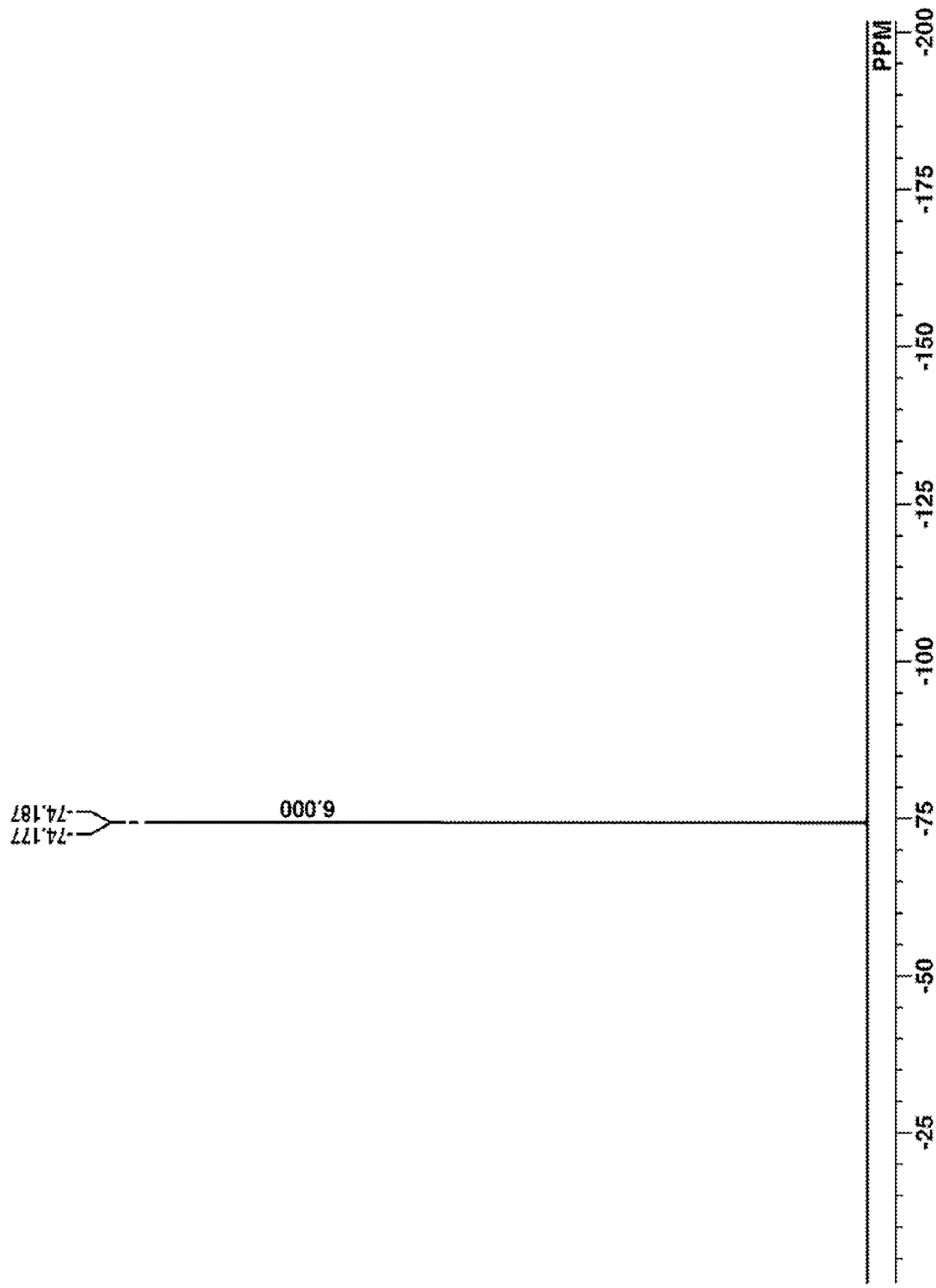
FIG. 6 is a diagram showing $^{19}$F-NMR spectrum of acid diffusion inhibitor Q-3 in Example 1-3.

Q-3 was analyzed by spectroscopy. The IR and TOFMS data are shown below. The $^1$H- and $^{19}$F-NMR/DMSO-d6 spectra are shown in FIGS. 5 and 6, respectively.

IR (D-ATR):
ν=3072, 2961, 1707, 1589, 1476, 1441, 1378, 1293, 1223, 1212, 1187, 1165, 1142, 1118, 1074, 1055, 998, 978, 956, 788, 752, 738, 683, 653, 529, 517, 504 cm$^{-1}$

MALDI TOFMS:
Positive M$^+$ 321.1 (corresponding to $C_{20}H_{17}O_2S^+$)
Negative M$^-$ 211.0 (corresponding to $C_4HF_6O_3^-$)

Example 1-4

Synthesis of Acid Diffusion Inhibitor Q-4

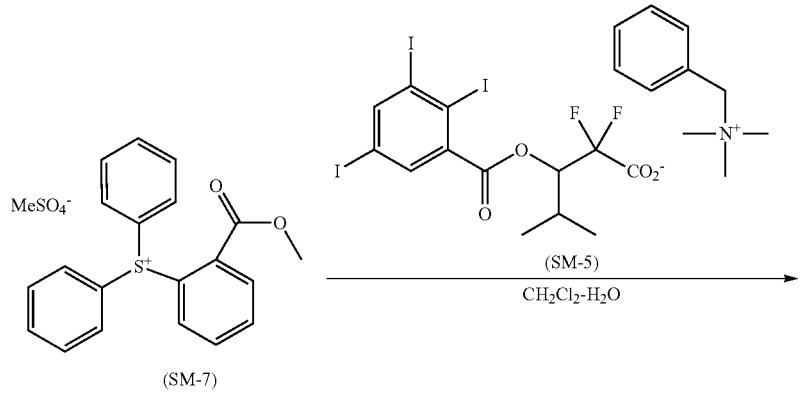

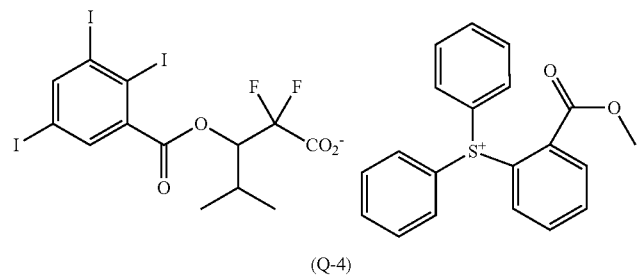

A mixture of 4.3 g of Compound SM-7, 7.2 g of Compound SM-5, 60 g of methylene chloride, 0.06 g of 29 wt % ammonia water, and 30 g of deionized water was stirred at room temperature for 10 minutes. The organic layer was taken out, after which it was washed once with a solution of 0.43 g Compound SM-7 in 30 g deionized water and 3 times with 30 g of deionized water. The organic layer was concentrated at 40° C. under reduced pressure. 7 g of methylene chloride was added to the concentrate, followed by stirring. 30 g of diisopropyl ether was added to the solution, which was stirred for 1 hour. The supernatant was removed. The residue was diluted with acetone. 40 g of diisopropyl ether was added to the dilution, which was stirred. The supernatant was removed. The oily residue was dissolved in methylene chloride, which was concentrated at 40° C. under reduced pressure and evaporated to dryness. The resulting powder was dried at 50° C. in vacuum, obtaining the target acid diffusion inhibitor Q-4 in solid form (amount 7.4 g, yield 79%).

Figure 7:
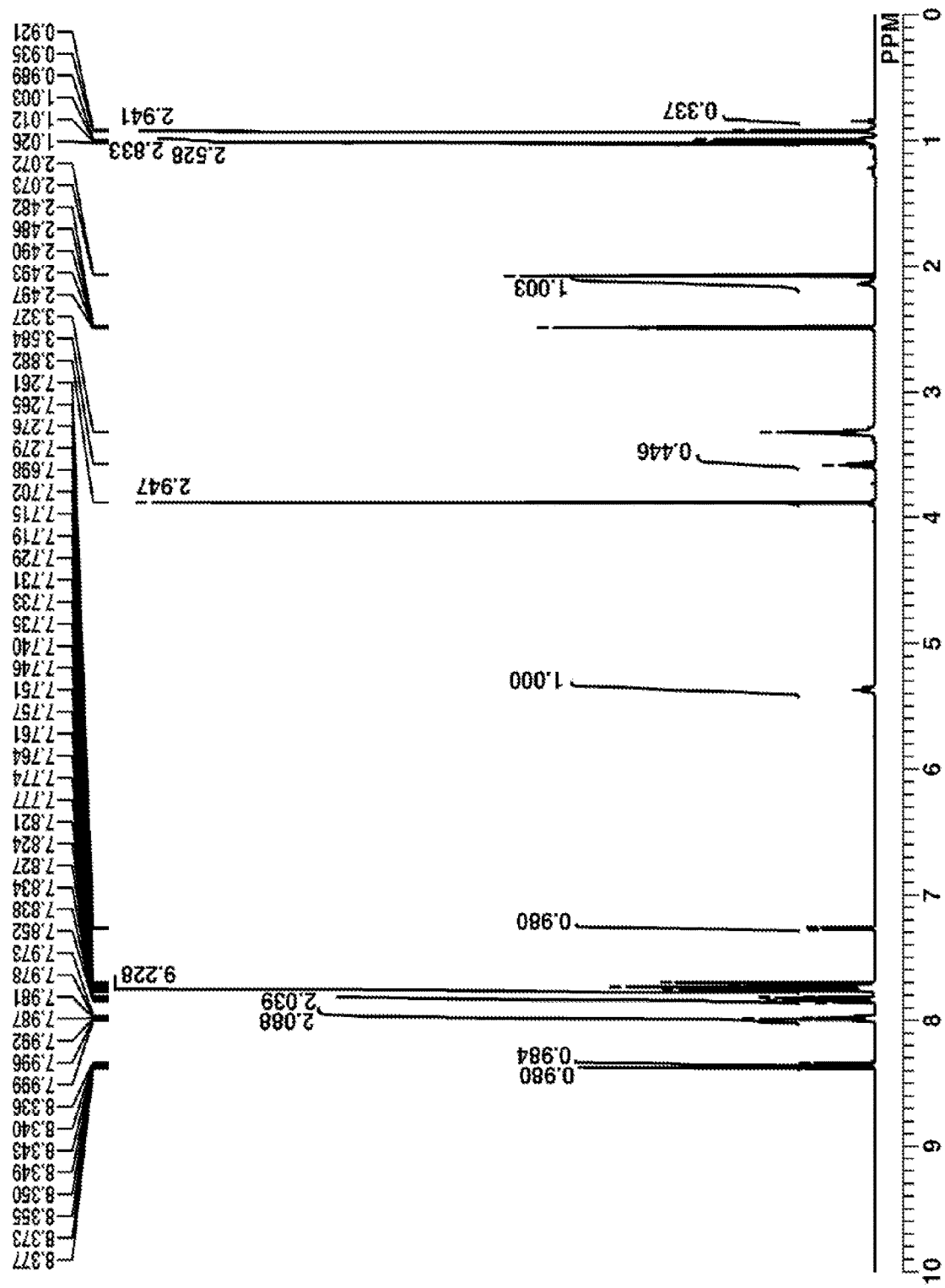
FIG. 7 is a diagram showing $^1$H-NMR spectrum of acid diffusion inhibitor Q-4 in Example 1-4.
Figure 8:
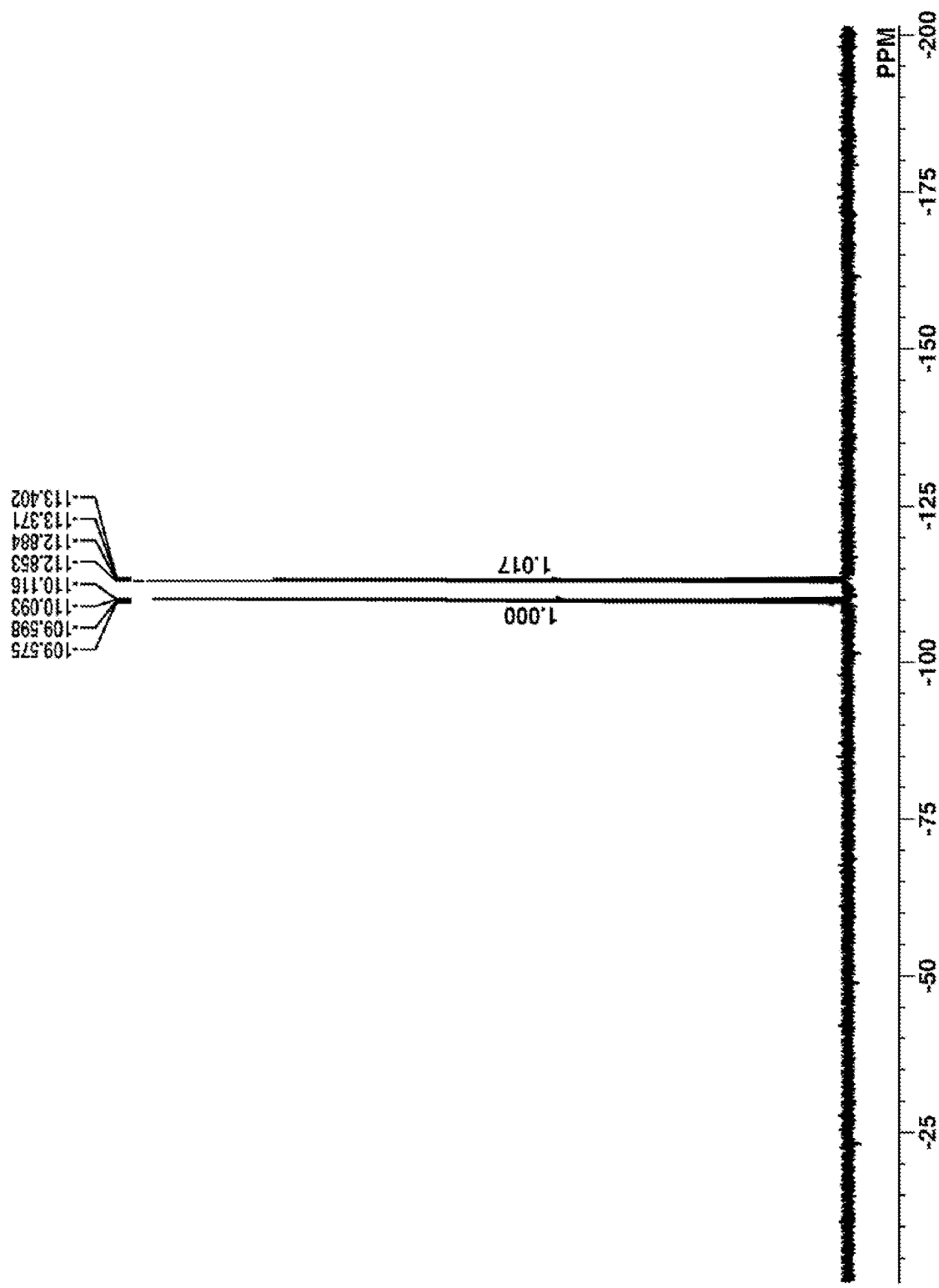
FIG. 8 is a diagram showing $^{19}$F-NMR spectrum of acid diffusion inhibitor Q-4 in Example 1-4.

Q-4 was analyzed by spectroscopy. The TOFMS data are shown below. The $^1$H- and $^{19}$F-NMR/DMSO-d6 spectra are shown in FIGS. 7 and 8, respectively.

MALDI TOFMS:
Positive M$^+$ 321.1 (corresponding to $C_{20}H_{17}O_2S^+$)
Negative M$^-$ 648.8 (corresponding to $C_{13}H_{10}F_2I_3O_4^-$)

Example 1-5

Synthesis of Acid Diffusion Inhibitor Q-5

(1) Synthesis of Compound SM-9

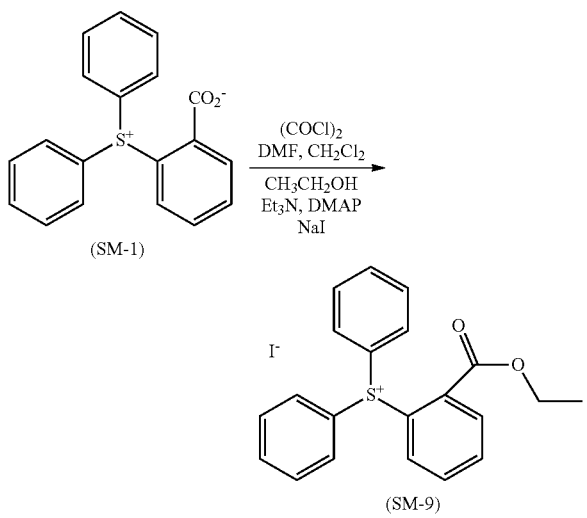

First, 15.0 g of Compound SM-1, 0.04 g of N,N-dimethylformamide, and 90 g of methylene chloride were mixed, whereupon 15.5 g of oxalyl chloride was added dropwise at room temperature. Stirring was continued overnight at room temperature. The reaction solution was concentrated at 40° C. under reduced pressure until a solid was obtained. The solid was mixed with 90 g of methylene chloride and 22 g of ethanol, after which under ice cooling, a mixture of 9.9 g of triethylamine, 0.6 g of N,N-dimethylaminopyridine, and 10 g of methylene chloride was added dropwise. The mixture was stirred at room temperature for 3.5 hours. Under ice cooling, 120 g of 5 wt % hydrochloric acid was added to quench the reaction. Hexane, 150 g, was added to the reaction solution, followed by stirring. The water layer was taken out and washed twice with 75 g of diisopropyl ether. To the water layer, 14.4 g of sodium iodide was added, and further, 60 g of methylene chloride and 10 g of methyl isobutyl ketone were added, followed by 10 minutes of stirring. At the end of stirring, the organic layer was taken out and washed 5 times with 50 g of deionized water. The organic layer was concentrated under reduced pressure. Diisopropyl ether, 20 g, was added to the concentrate, which was stirred. The supernatant was removed. The oily residue was concentrated at 50° C. under reduced pressure, obtaining the desired Compound SM-9 as oily matter (amount 23.7 g, yield 99%).

(2) Synthesis of Compound SM-10

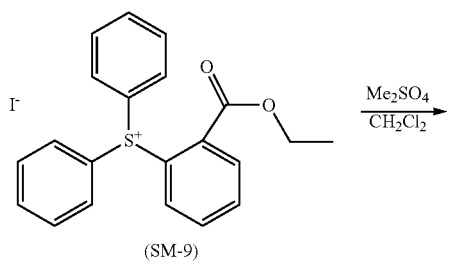

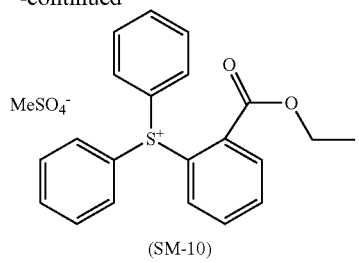

After 22.6 g of Compound SM-9 was dissolved in 67.8 g of methylene chloride, 6.8 g of dimethyl sulfate was added dropwise at room temperature. After overnight stirring, the reaction solution was concentrated at 50° C. under reduced pressure until a solid precipitated. 30 g of diisopropyl ether was added to the solid, followed by stirring. The solid was collected by filtration, washed with diisopropyl ether, and dried at 40° C. in vacuum, obtaining the desired Compound SM-10 in solid form (amount 16.2 g, yield 74%).

(3) Synthesis of Acid Diffusion Inhibitor Q-5

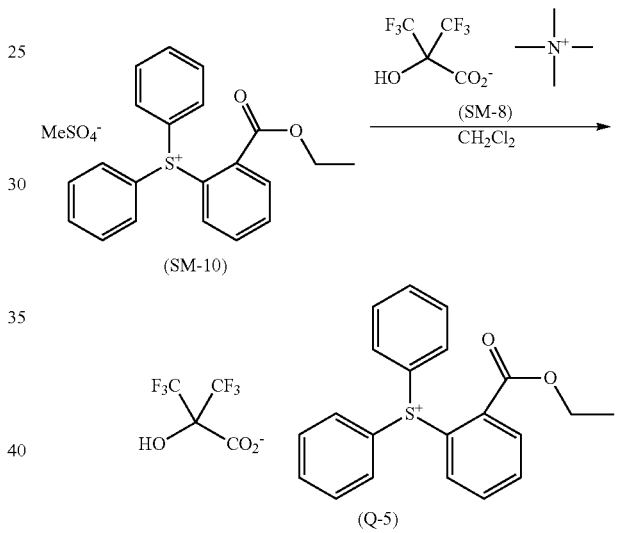

A mixture of 4.5 g of Compound SM-10, 6.0 g of 38.6 wt % aqueous solution of Compound SM-8, 31 g of methylene chloride, and 15 g of deionized water was stirred at room temperature for 20 minutes. The organic layer was taken out, washed 5 times with 20 g of deionized water, and concentrated at 40° C. under reduced pressure. 10 g of diisopropyl ether was added to the concentrate, which was stirred. The supernatant was removed. 10 g of diisopropyl ether and 10 g of hexane were added to the residue, which was stirred. The solid precipitate was collected by filtration, washed with diisopropyl ether, and dried at 40° C. in vacuum, obtaining the target acid diffusion inhibitor Q-5 in solid form (amount 4.9 g, yield 91%).

Figure 9:
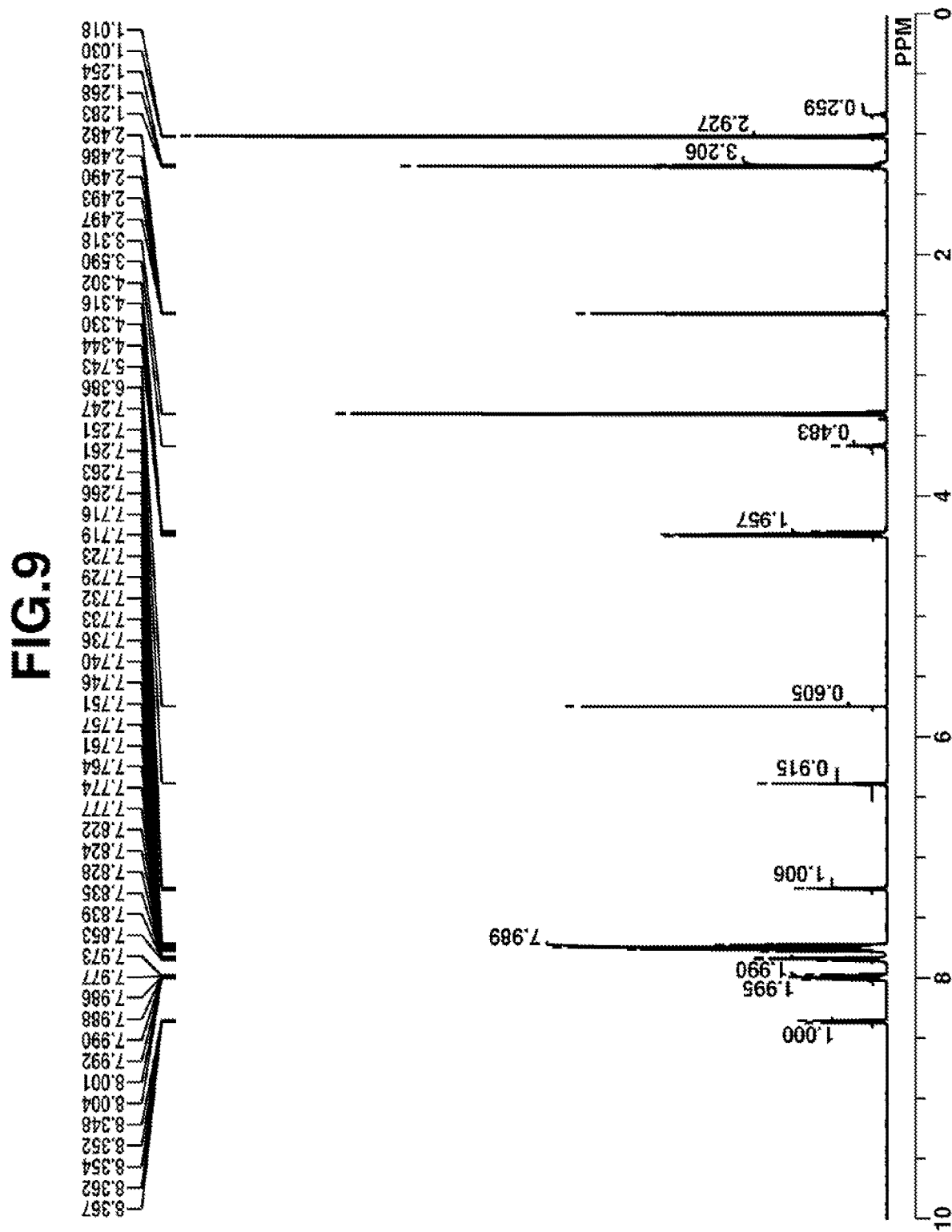
FIG. 9 is a diagram showing $^1$H-NMR spectrum of acid diffusion inhibitor Q-5 in Example 1-5.
Figure 10:
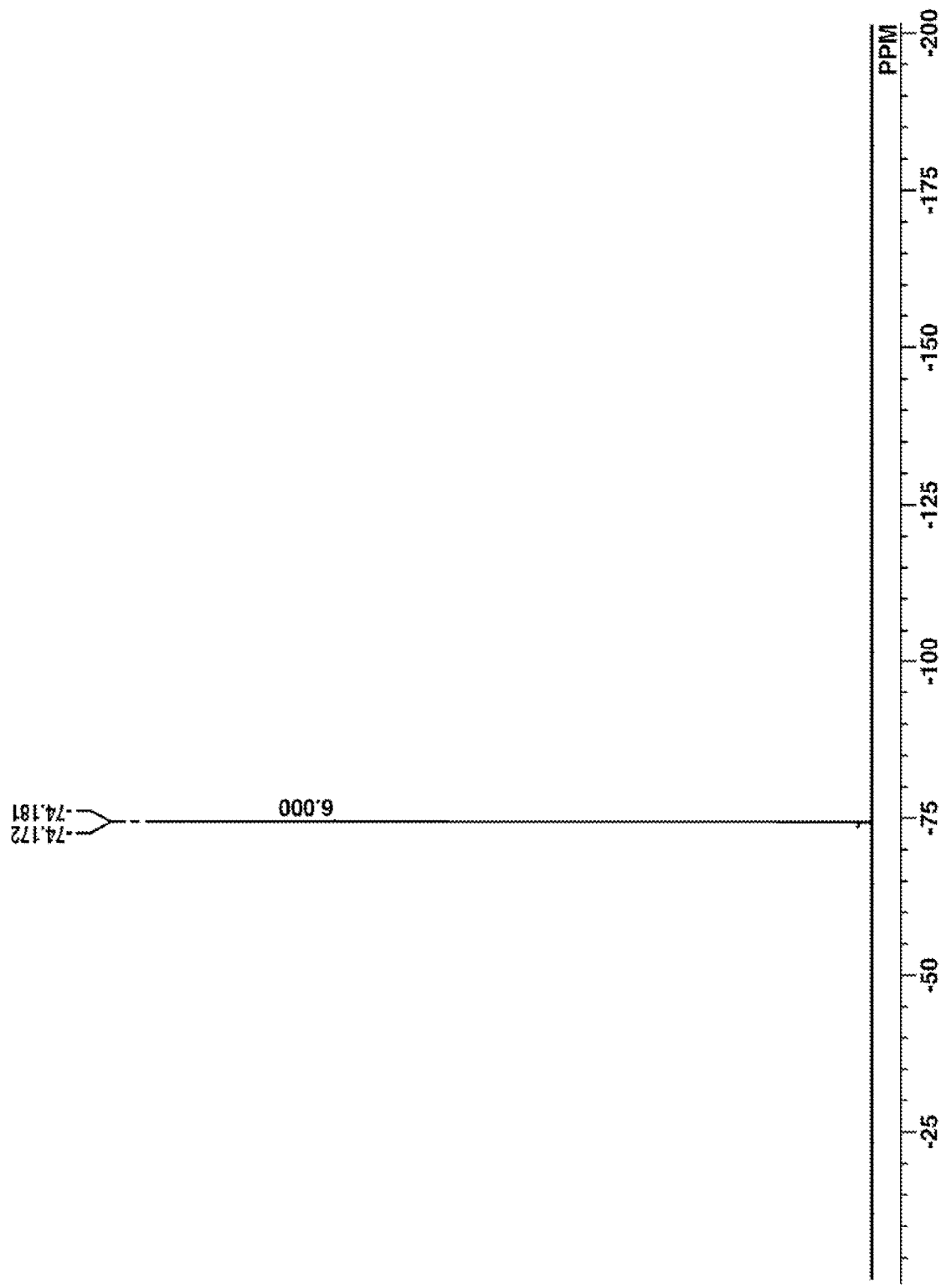
FIG. 10 is a diagram showing $^{19}$F-NMR spectrum of acid diffusion inhibitor Q-5 in Example 1-5.

Q-5 was analyzed by spectroscopy. The IR and TOFMS data are shown below. The $^1$H- and $^{19}$F-NMR/DMSO-d6 spectra are shown in FIGS. 9 and 10, respectively.

IR (D-ATR):
  ν=3494, 3379, 3248, 3096, 3000, 2976, 2934, 1745, 1698, 1585, 1478, 1466, 1447, 1409, 1371, 1289, 1249, 1199, 1149, 1111, 1076, 1053, 1023, 1000, 980, 872, 858, 793, 765, 758, 747, 741, 682, 612, 594, 519, 506, 495 cm$^{-1}$

MALDI TOFMS:
  Positive M$^+$ 335.1 (corresponding to $C_{21}H_{19}O_2S^+$)
  Negative M$^-$ 211.0 (corresponding to $C_4HF_6O_3^-$)

Example 1-6

Synthesis of Acid Diffusion Inhibitor Q-6

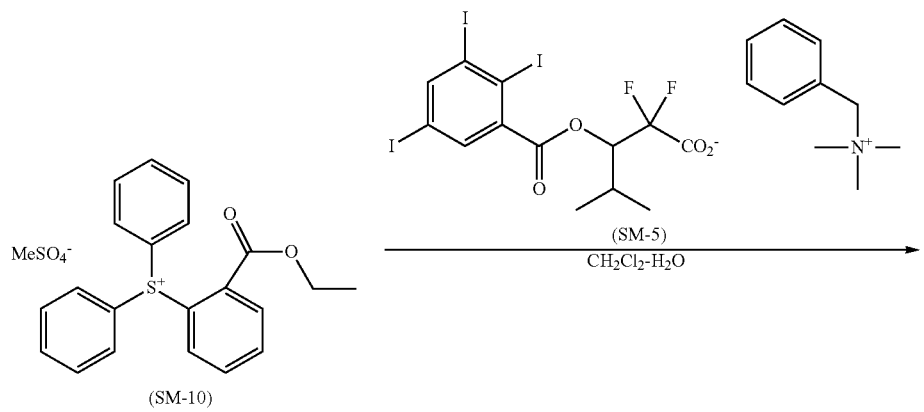

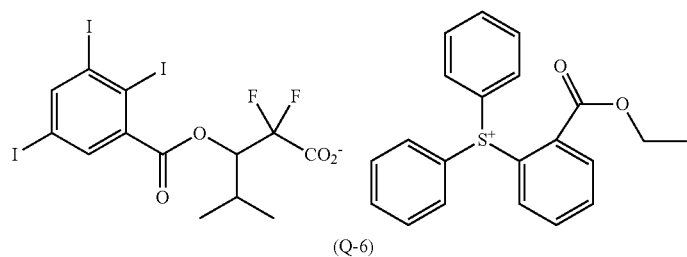

(Q-6)

A mixture of 4.5 g of Compound SM-10, 7.2 g of Compound SM-5, 50 g of methylene chloride, and 25 g of deionized water was stirred at room temperature for 15 minutes. The organic layer was taken out, after which it was washed twice with a solution of 0.41 g Compound SM-9 in 25 g deionized water and 7 times with 30 g of deionized water. The organic layer was concentrated at 40° C. under reduced pressure. 20 g of diisopropyl ether and 10 g of hexane were added to the concentrate, followed by overnight stirring. The solid precipitate was collected by filtration. The resulting powder was dried at 40° C. in vacuum, obtaining the target acid diffusion inhibitor Q-6 in solid form (amount 8.3 g, yield 92%).

Figure 11:
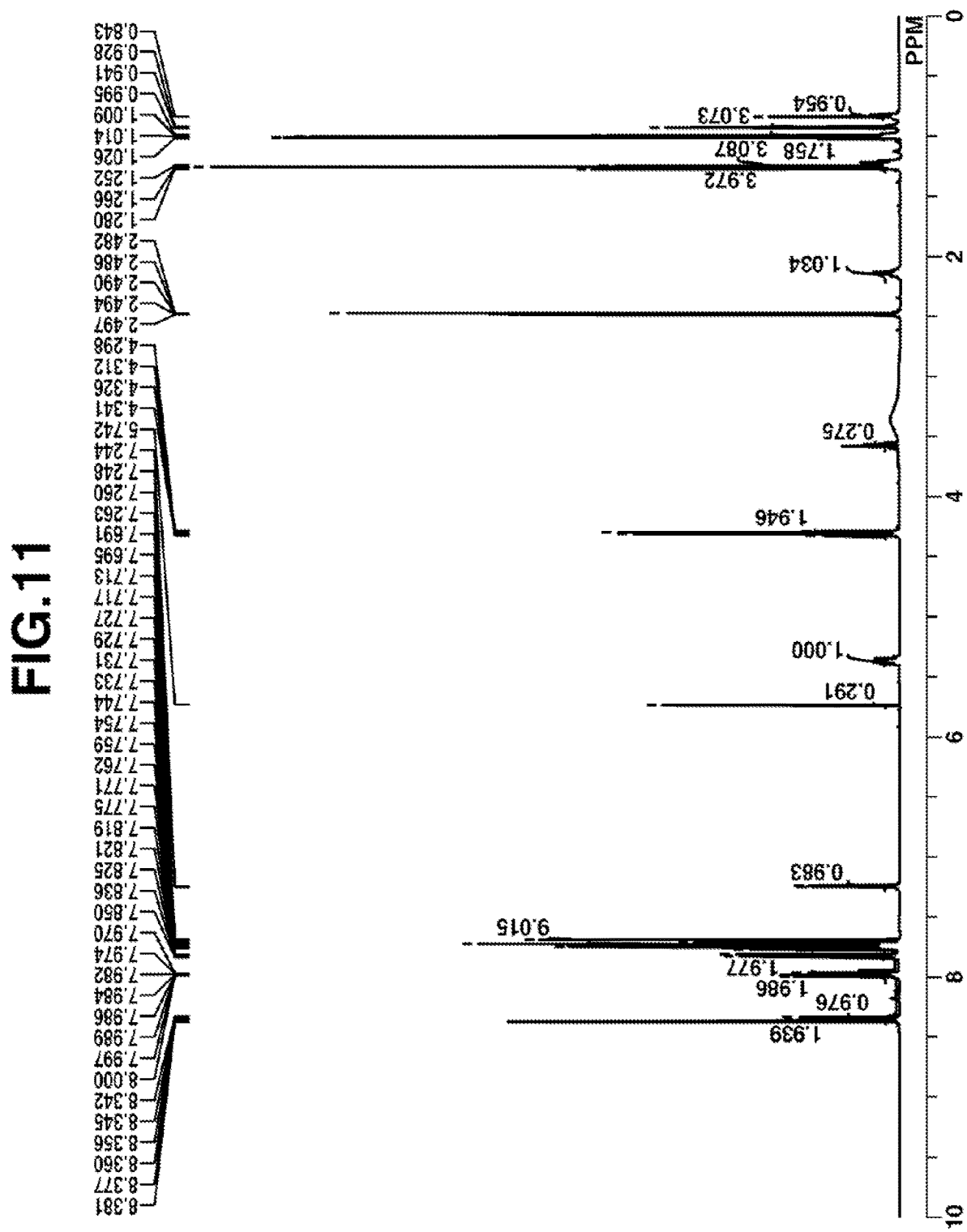
FIG. 11 is a diagram showing $^1$H-NMR spectrum of acid diffusion inhibitor Q-6 in Example 1-6.
Figure 12:
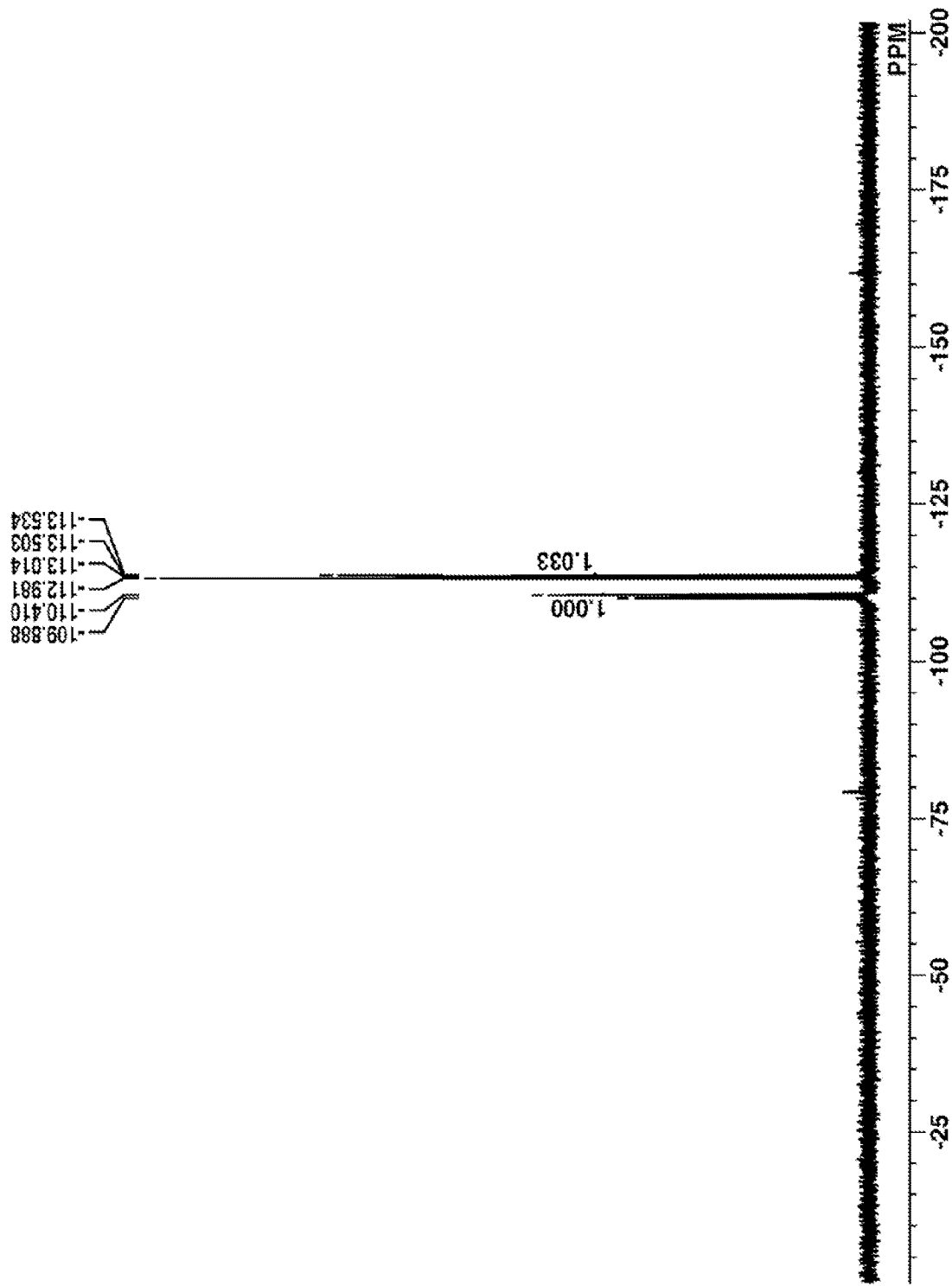
FIG. 12 is a diagram showing $^{19}$F-NMR spectrum of acid diffusion inhibitor Q-6 in Example 1-6.

Q-6 was analyzed by spectroscopy. The TOFMS data are shown below. The $^1$H- and $^{19}$F-NMR/DMSO-d6 spectra are shown in FIGS. 11 and 12, respectively.

MALDI TOFMS:
Positive $M^+$ 335.1 (corresponding to $C_{21}H_{19}O_2S^+$)
Negative $M^-$ 648.8 (corresponding to $C_{13}H_{10}F_2I_3O_4^-$)

Example 1-7

Synthesis of Acid Diffusion Inhibitor Q-7

(1) Synthesis of Compound SM-11

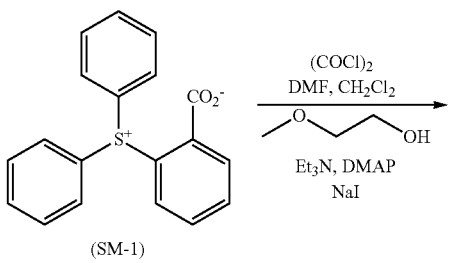

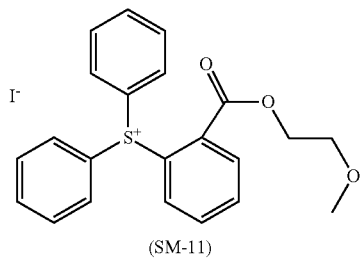

(SM-11)

First, 15.0 g of Compound SM-1, 0.04 g of N,N-dimethylformamide, and 90 g of methylene chloride were mixed, whereupon 15.5 g of oxalyl chloride was added dropwise at room temperature. Stirring was continued overnight at room temperature. The reaction solution was concentrated at 40° C. under reduced pressure until a solid was obtained. The solid was mixed with 90 g of methylene chloride and 37 g of ethylene glycol monomethyl ether, after which, under ice cooling, a mixture of 9.9 g of triethylamine, 0.6 g of N,N-dimethylaminopyridine, and 10 g of methylene chloride was added dropwise. The mixture was stirred at room temperature for 23 hours. Under ice cooling, 120 g of 5 wt % hydrochloric acid was added to quench the reaction. Hexane, 150 g, was added to the reaction solution, followed by stirring. The water layer was taken out and washed twice with 75 g of diisopropyl ether. To the water layer, 10 g of sodium iodide was added, and further, 150 g of methylene chloride and 10 g of methyl isobutyl ketone were added, followed by 10 minutes of stirring. At the end of stirring, the organic layer was taken out and washed 5 times with 100 g of deionized water. The organic layer was concentrated under reduced pressure. Diisopropyl ether, 30 g, was added to the concentrate, which was stirred. The supernatant was removed. The oily residue was concentrated at 50° C. under reduced pressure, obtaining the desired Compound SM-11 as oily matter.

(2) Synthesis of Compound SM-12

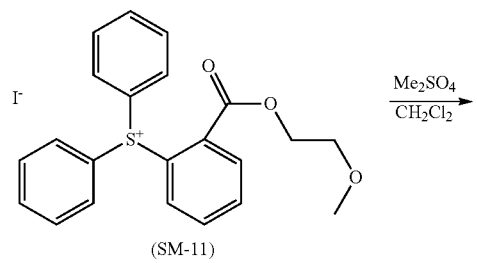

(SM-11)

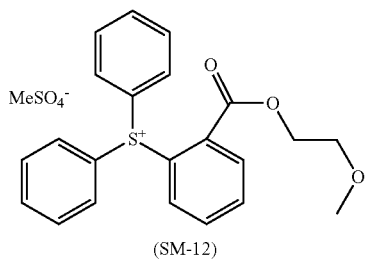

(SM-12)

21.3 g of Compound SM-11 was dissolved in 67.8 g of methylene chloride, after which 6.8 g of dimethyl sulfate was added dropwise at room temperature. After overnight stirring, the reaction solution was concentrated at 50° C. under reduced pressure. 30 g of diisopropyl ether was added to the concentrate, followed by 10 minutes of stirring. The supernatant was removed. 30 g of diisopropyl ether and 10 g of hexane were added to the residue, followed by stirring. The supernatant was removed. The oily residue was concentrated at 50° C. under reduced pressure, obtaining the desired Compound SM-12 as oily matter (amount 20.6 g, two-step yield 84%).

(3) Synthesis of Acid Diffusion Inhibitor Q-7

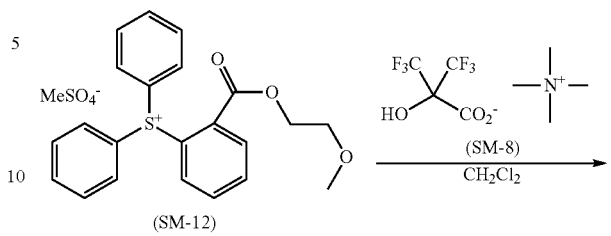

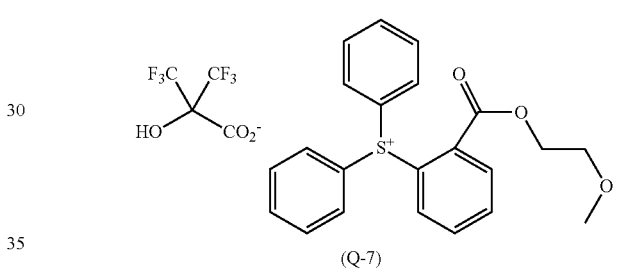

(Q-7)

A mixture of 4.8 g of Compound SM-12, 5.5 g of 38.6 wt % aqueous solution of Compound SM-8, 33 g of methylene chloride, and 16 g of deionized water was stirred at room temperature for 10 minutes. The organic layer was taken out, washed twice with 0.5 g of 38.6 wt % aqueous solution of Compound SM-8 and 20 g of deionized water, and 7 times with 20 g of deionized water. The organic layer was concentrated at 40° C. under reduced pressure. 10 g of diisopropyl ether and 2 mL of hexane were added to the concentrate, which was stirred until a solid precipitated. The solid precipitate was collected by filtration, washed with diisopropyl ether, and dried at 40° C. in vacuum, obtaining the target acid diffusion inhibitor Q-7 in solid form (amount 3.8 g, yield 69%).

Figure 13:
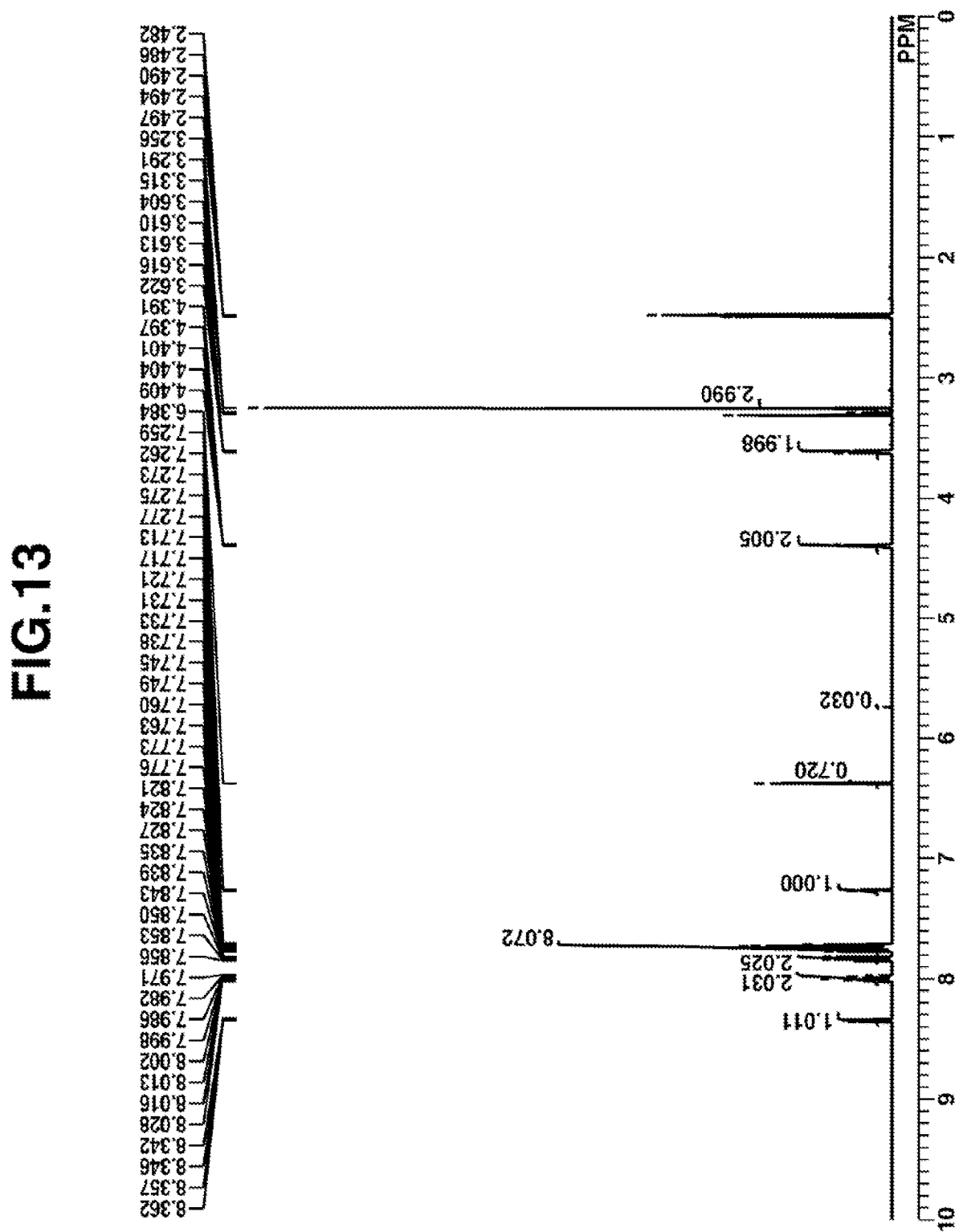
FIG. 13 is a diagram showing $^1$H-NMR spectrum of acid diffusion inhibitor Q-7 in Example 1-7.
Figure 14:
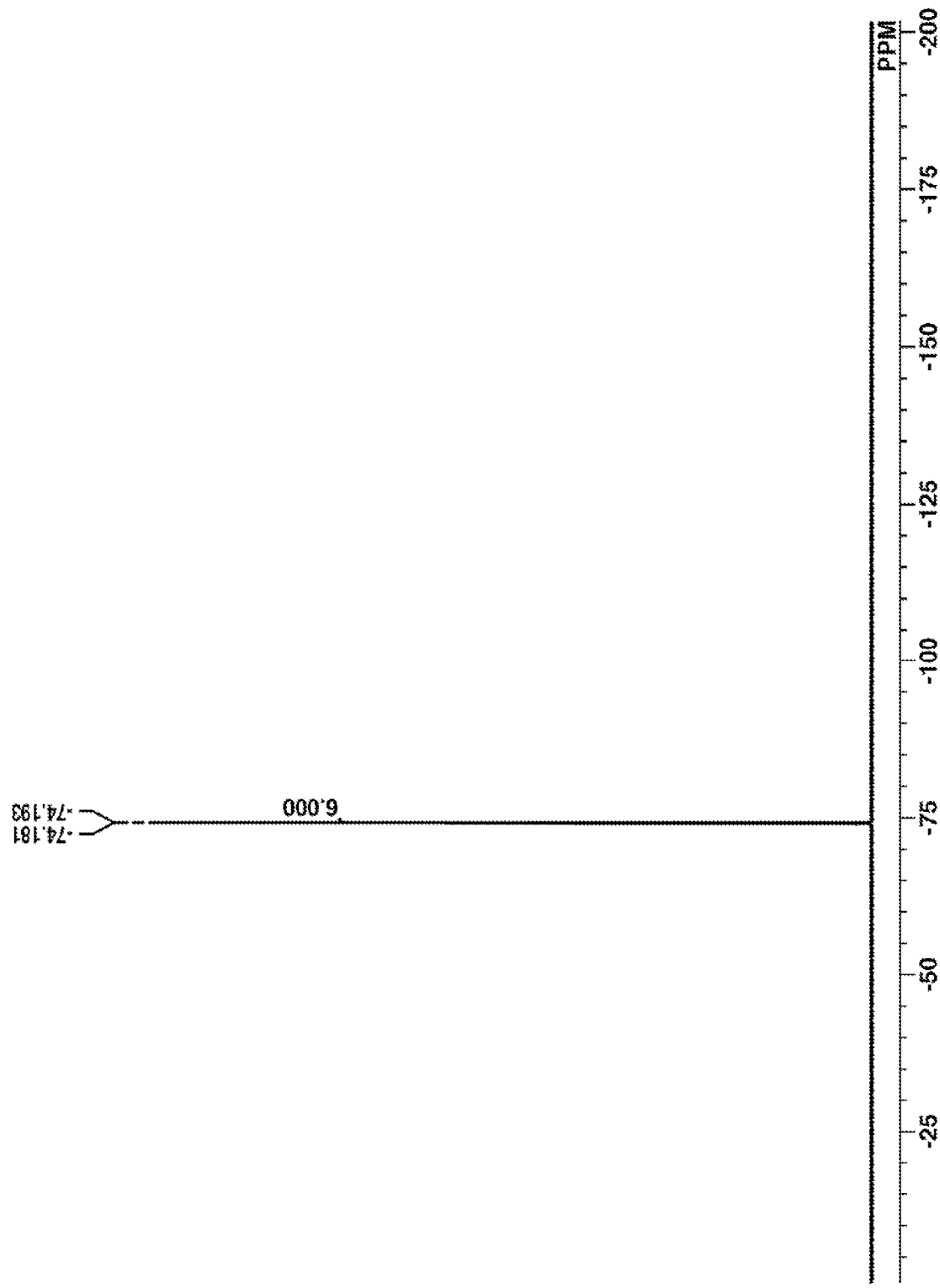
FIG. 14 is a diagram showing $^{19}$F-NMR spectrum of acid diffusion inhibitor Q-7 in Example 1-7.

Q-7 was analyzed by spectroscopy. The IR and TOFMS data are shown below. The $^1$H- and $^{19}$F-NMR/DMSO-d6 spectra are shown in FIGS. 13 and 14, respectively.

IR (D-ATR):

ν=3071, 3024, 2956, 2888, 2847, 1712, 1589, 1480, 1454, 1406, 1369, 1295, 1280, 1245, 1216, 1180, 1157, 1144, 1114, 1095, 1076, 1055, 1041, 1025, 996, 976, 874, 826, 806, 788, 760, 744, 703, 692, 682, 654, 530, 516, 495 cm$^{-1}$

MALDI TOFMS:

Positive M$^+$ 365.1 (corresponding to $C_{22}H_{21}O_3S^+$)

Negative M$^-$ 211.0 (corresponding to $C_4HF_6O_3^-$)

Example 1-8

Synthesis of Acid Diffusion Inhibitor Q-8

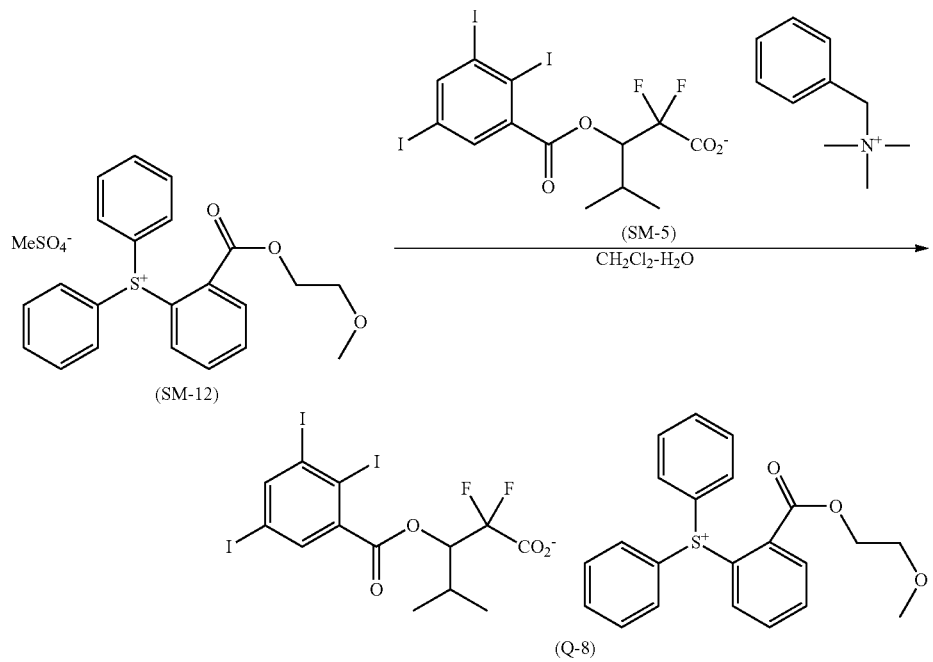

A mixture of 1.5 g of Compound SM-12, 2.2 g of Compound SM-5, 10 g of methylene chloride, and 5 g of deionized water was stirred at room temperature for 15 minutes. The organic layer was taken out, after which it was washed twice with a solution of 0.1 g Compound SM-11 in 10 g deionized water and 5 times with 15 g of deionized water. The organic layer was concentrated at 40° C. under reduced pressure. The concentrate was diluted with 2 g of methylene chloride, and 5 g of diisopropyl ether was added thereto, followed by overnight stirring. The supernatant was removed. The oily residue was concentrated at 40° C. under reduced pressure, obtaining the target acid diffusion inhibitor Q-8 as oily matter (amount 1.1 g, yield 34%).

Figure 15:
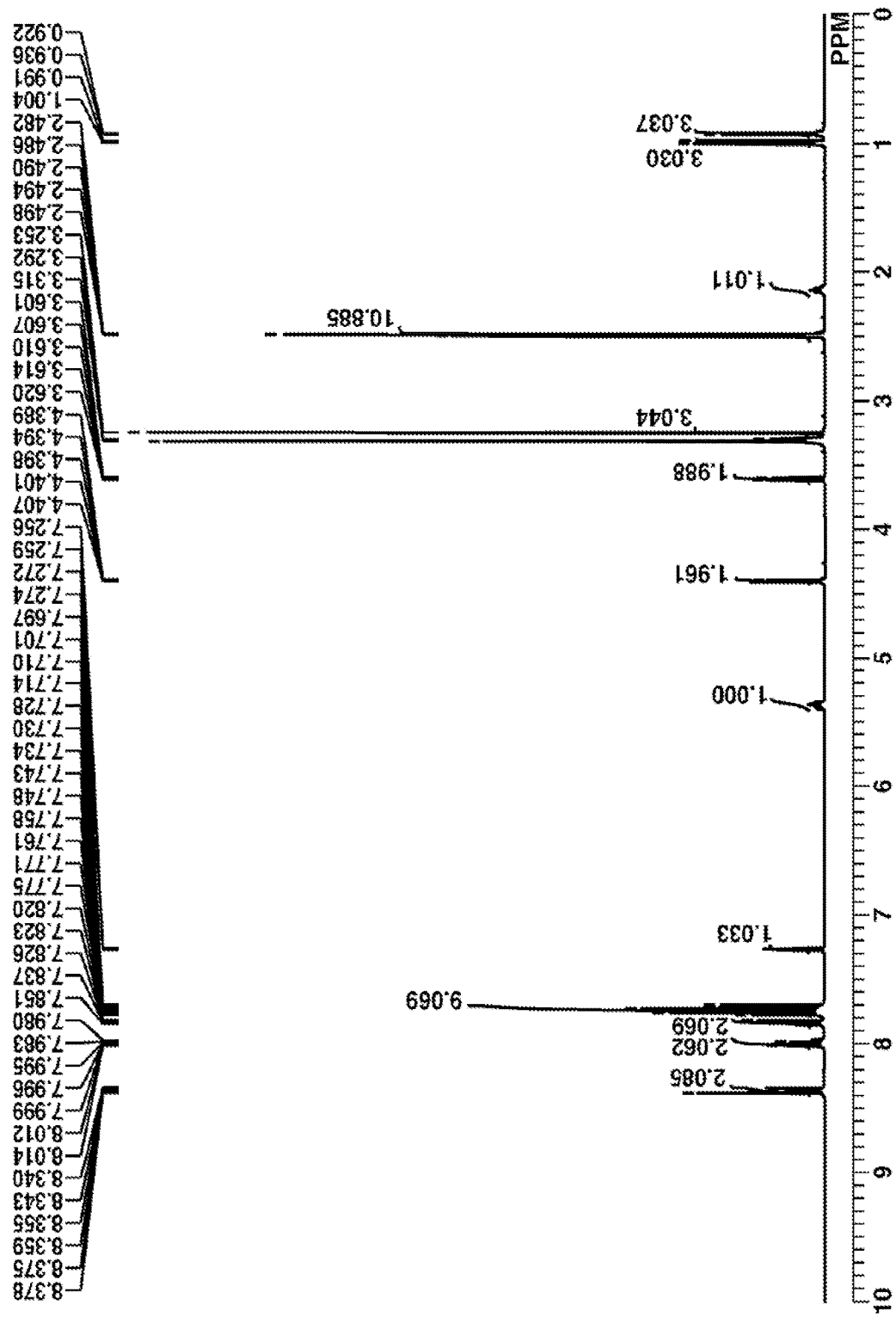
FIG. 15 is a diagram showing $^1$H-NMR spectrum of acid diffusion inhibitor Q-8 in Example 1-8.
Figure 16:
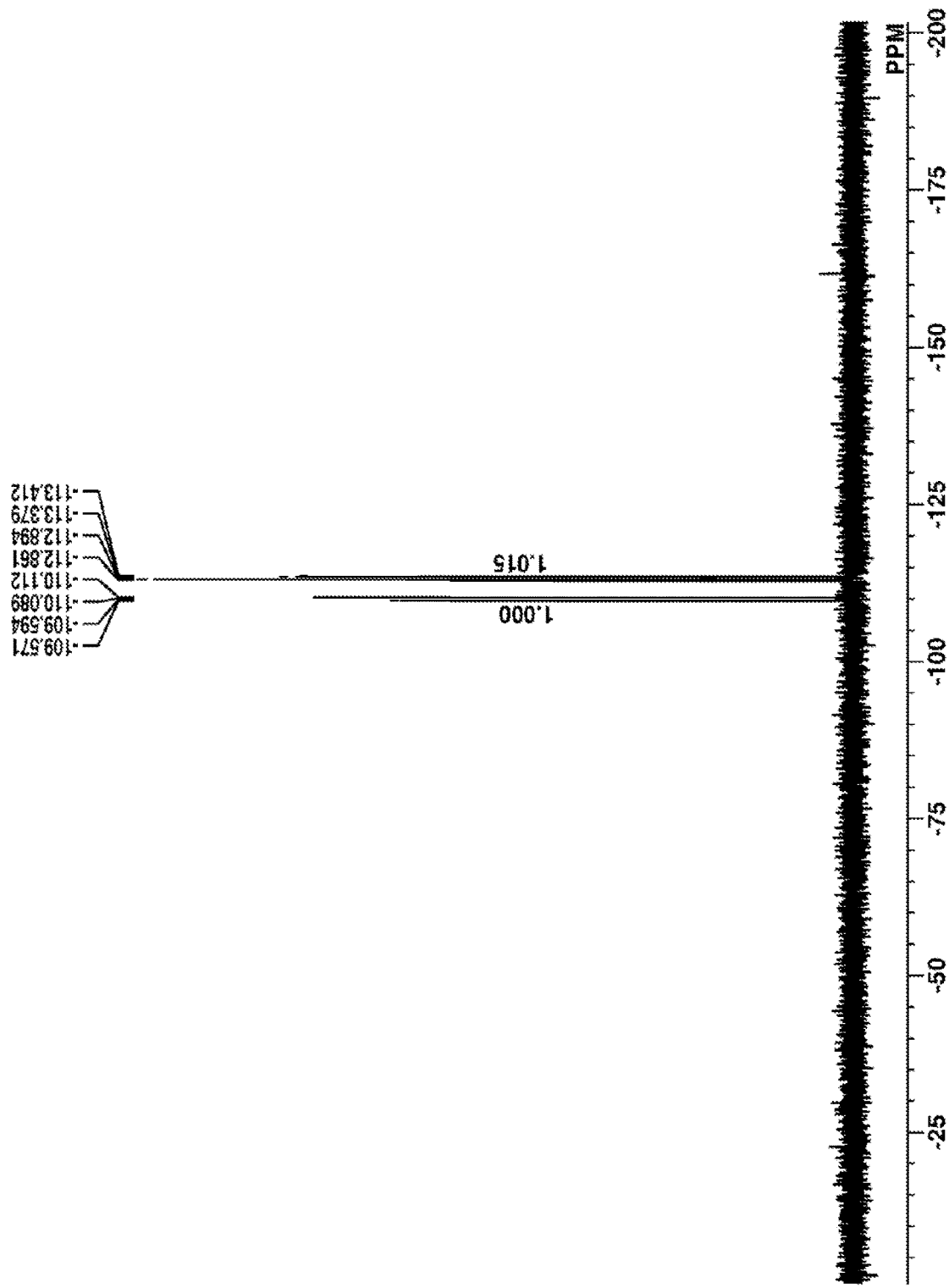
FIG. 16 is a diagram showing $^{19}$F-NMR spectrum of acid diffusion inhibitor Q-8 in Example 1-8.

Q-8 was analyzed by spectroscopy. The TOFMS data are shown below. The $^1$H- and $^{19}$F-NMR/DMSO-d6 spectra are shown in FIGS. 15 and 16, respectively.

MALDI TOFMS:
Positive M$^+$ 365.1 (corresponding to $C_{22}H_{21}O_3S^+$)
Negative M$^-$ 648.8 (corresponding to $C_{13}H_{10}F_2I_3O_4^-$)

Example 1-9

Synthesis of Acid Diffusion Inhibitor Q-9

(1) Synthesis of Compound SM-14

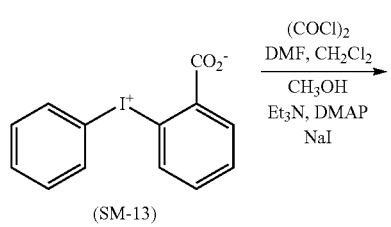

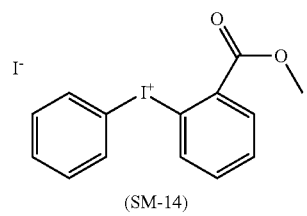

First, 6.0 g of Compound SM-13, 0.01 g of N,N-dimethylformamide, and 42 g of methylene chloride were mixed, whereupon 5.8 g of oxalyl chloride was added dropwise at room temperature. Stirring was continued overnight at room temperature. The reaction solution was concentrated at 40° C. under reduced pressure. 42 g of methylene chloride and 40 g of methanol were added to the concentrate, after which, under ice cooling, a mixture of 3.7 g of triethylamine, 0.2 g of N,N-dimethylaminopyridine, and 10 g of methylene chloride was added dropwise. The mixture was stirred overnight at room temperature. Under ice cooling, 50 g of 5 wt % hydrochloric acid was added to quench the reaction. Hexane, 50 g, was added to the reaction solution, followed by stirring. The water layer was taken out and washed twice with 30 g of diisopropyl ether. To the water layer, 10 g of sodium iodide was added, and further, 60 g of methylene chloride was added, followed by 10 minutes of stirring. At the end of stirring, the organic layer was taken out and washed 5 times with 50 g of deionized water. The organic layer was concentrated at 40° C. under reduced pressure and evaporated to dryness, obtaining the desired Compound SM-14 in solid form (amount 8.6 g, yield 98%).

(2) Synthesis of Compound SM-15

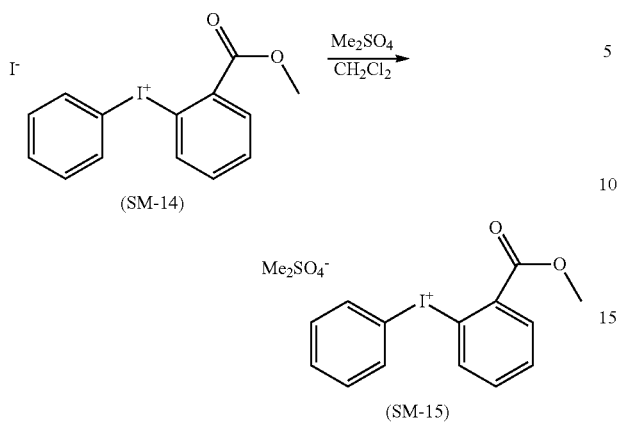

8.6 g of Compound SM-14 was dissolved in 60.2 g of methylene chloride, after which 2.5 g of dimethyl sulfate was added dropwise at room temperature. After overnight stirring, the reaction solution was concentrated at 40° C. under reduced pressure. 20 g of diisopropyl ether was added to the concentrate, followed by 1 hour of stirring. The solid precipitate was collected by filtration, washed with diisopropyl ether, and concentrated at 40° C. under reduced pressure, obtaining the desired Compound SM-15 in solid form (amount 7.3 g, yield 86%).

(3) Synthesis of Acid Diffusion Inhibitor Q-9

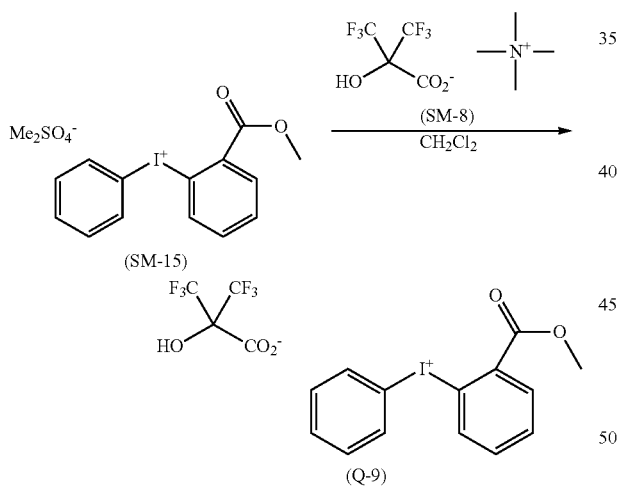

A mixture of 4.5 g of Compound SM-15, 5.5 g of 38.6 wt % aqueous solution of Compound SM-8, 31 g of methylene chloride, and 15 g of deionized water was stirred at room temperature for 15 minutes. The organic layer was taken out, whereupon it was washed twice with 0.5 g of 38.6 wt % aqueous solution of Compound SM-8 and 15 g of deionized water and 5 times with 40 g of deionized water. The organic layer was concentrated at 40° C. under reduced pressure. 10 g of methylene chloride and 20 g of diisopropyl ether were added to the concentrate, which was stirred until a solid precipitated. The solid precipitate was collected by filtration, washed with diisopropyl ether, and dried at 40° C. in vacuum, obtaining the target acid diffusion inhibitor Q-9 in solid form (amount 4.3 g, yield 85%).

Figure 17:
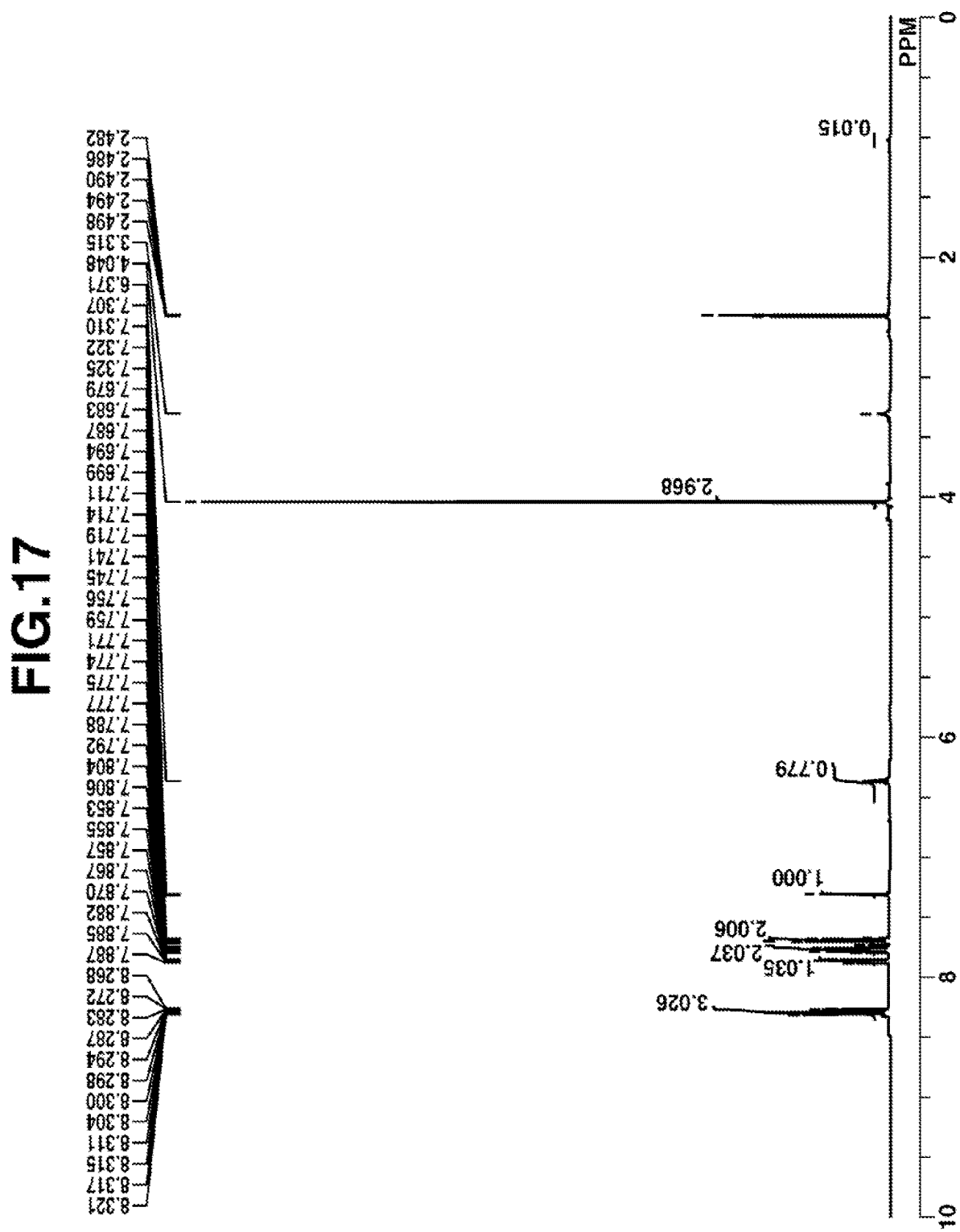
FIG. 17 is a diagram showing $^1$H-NMR spectrum of acid diffusion inhibitor Q-9 in Example 1-9.
Figure 18:
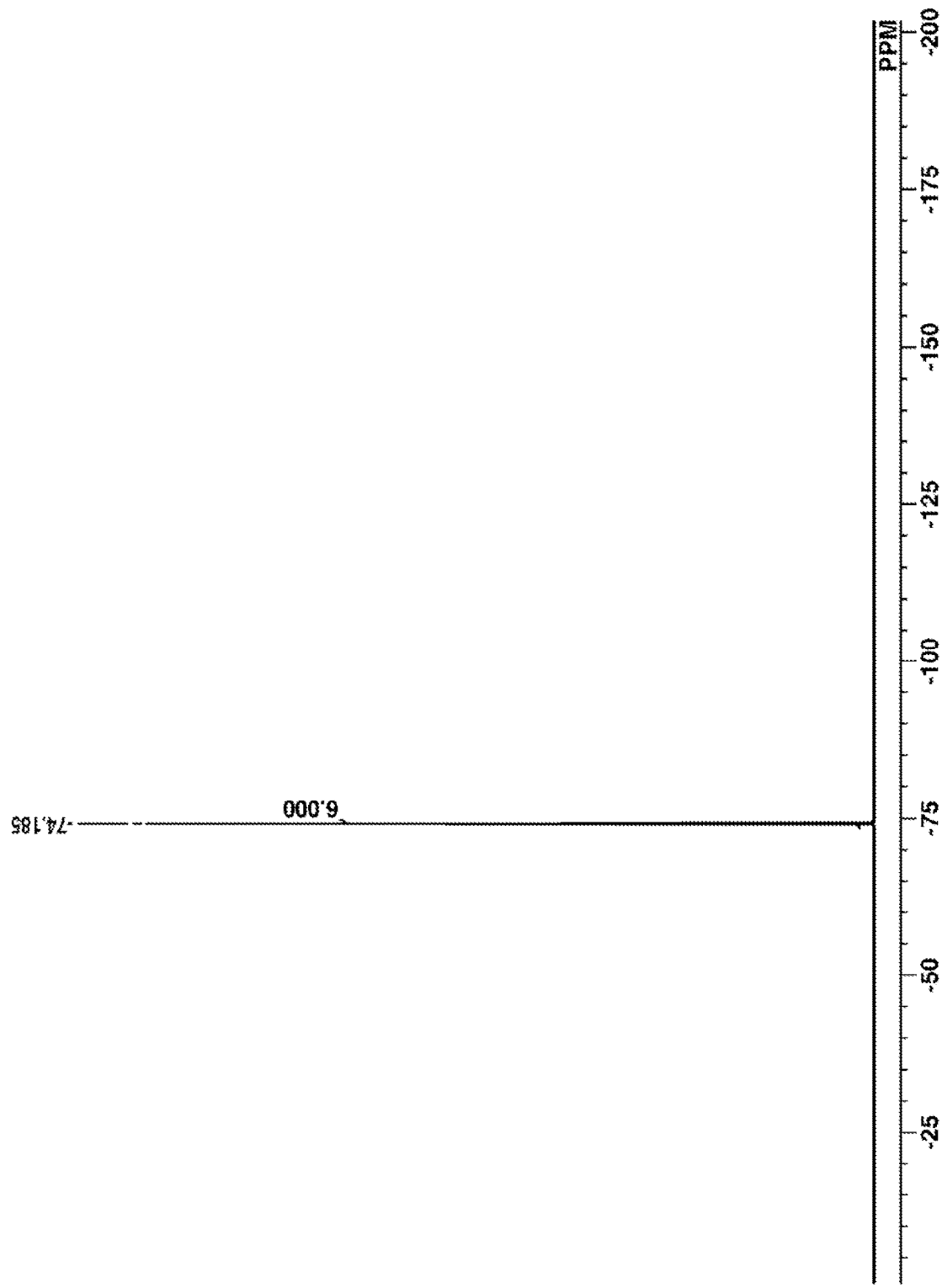
FIG. 18 is a diagram showing $^{19}$F-NMR spectrum of acid diffusion inhibitor Q-9 in Example 1-9.

Q-9 was analyzed by spectroscopy. The IR and TOFMS data are shown below. The $^1$H- and $^{19}$F-NMR/DMSO-d6 spectra are shown in FIGS. 17 and 18, respectively.

IR (D-ATR):
  ν=3281, 3059, 2966, 1693, 1654, 1586, 1464, 1440, 1385, 1311, 1291, 1275, 1245, 1197, 1166, 1144, 1114, 1100, 1010, 993, 978, 968, 833, 795, 746, 680, 518, 506, 462 cm$^{-1}$

MALDI TOFMS:
  Positive M$^+$ 339.0 (corresponding to $C_{14}H_{12}IO_2^+$)
  Negative M$^-$ 211.0 (corresponding to $C_4HF_6O_3^-$)

Example 1-10

Synthesis of Acid Diffusion Inhibitor Q-10

(1) Synthesis of Compound SM-16

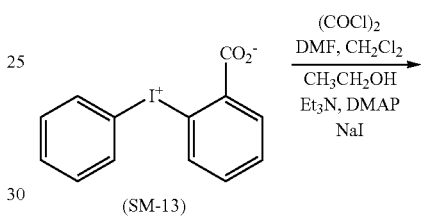

First, 6.0 g of Compound SM-13, 0.01 g of N,N-dimethylformamide, and 42 g of methylene chloride were mixed, whereupon 5.8 g of oxalyl chloride was added dropwise at room temperature. Stirring was continued overnight at room temperature. The reaction solution was concentrated at 40° C. under reduced pressure. 42 g of methylene chloride and 40 g of ethanol were added to the concentrate, after which, under ice cooling, a mixture of 3.7 g of triethylamine, 0.2 g of N,N-dimethylaminopyridine, and 10 g of methylene chloride was added dropwise. The mixture was stirred overnight at room temperature. Under ice cooling, 50 g of 5 wt % hydrochloric acid was added to quench the reaction. Hexane, 50 g, was added to the reaction solution, followed by stirring. The water layer was taken out and washed twice with 30 g of diisopropyl ether. To the water layer, 10 g of sodium iodide was added, and further, 60 g of methylene chloride was added, followed by 10 minutes of stirring. At the end of stirring, the organic layer was taken out and washed 5 times with 50 g of deionized water. The organic layer was concentrated at 40° C. under reduced pressure and evaporated to dryness, obtaining the desired Compound SM-16 in solid form (amount 7.9 g, yield 86%).

(2) Synthesis of Compound SM-17

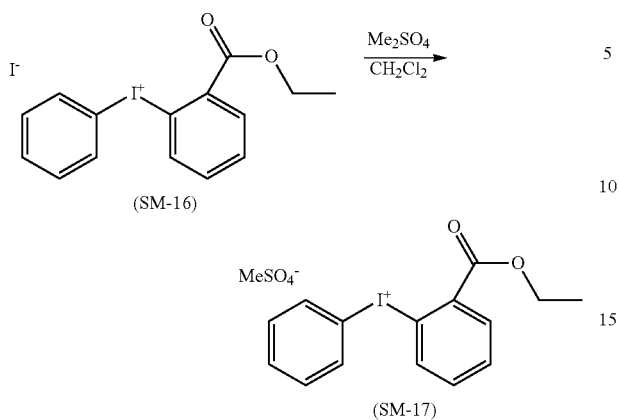

7.9 g of Compound SM-16 was dissolved in 56 g of methylene chloride, after which 2.2 g of dimethyl sulfate was added dropwise at room temperature. After overnight stirring, the reaction solution was concentrated at 40° C. under reduced pressure. 10 g of methylene chloride and 20 g of diisopropyl ether were added to the concentrate, followed by stirring. The solid precipitate was collected by filtration. The precipitate was dissolved again in 10 g of methylene chloride, after which 20 g of diisopropyl ether was added for recrystallization. The precipitate was collected by filtration and concentrated at 40° C. under reduced pressure, obtaining the desired Compound SM-17 in solid form (amount 5.8 g, yield 74%).

(3) Synthesis of Acid Diffusion Inhibitor Q-10

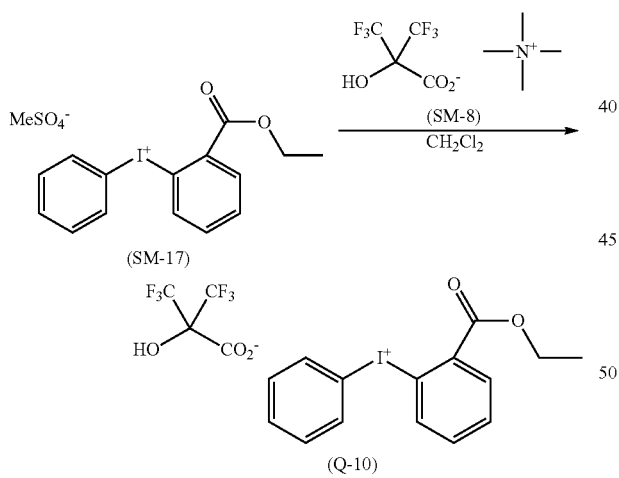

A mixture of 4.7 g of Compound SM-17, 5.5 g of 38.6 wt % aqueous solution of Compound SM-8, 31 g of methylene chloride, and 15 g of deionized water was stirred at room temperature for 15 minutes. The organic layer was taken out, whereupon it was washed twice with 0.2 g of 38.6 wt % aqueous solution of Compound SM-8 and 15 g of deionized water and 5 times with 30 g of deionized water. The organic layer was concentrated at 40° C. under reduced pressure. 10 g of methylene chloride and 20 g of diisopropyl ether were added to the concentrate, which was stirred until a solid precipitated. The solid precipitate was collected by filtration, washed with diisopropyl ether, and dried at 40° C. in vacuum, obtaining the target acid diffusion inhibitor Q-10 in solid form (amount 4.8 g, yield 92%).

Figure 19:
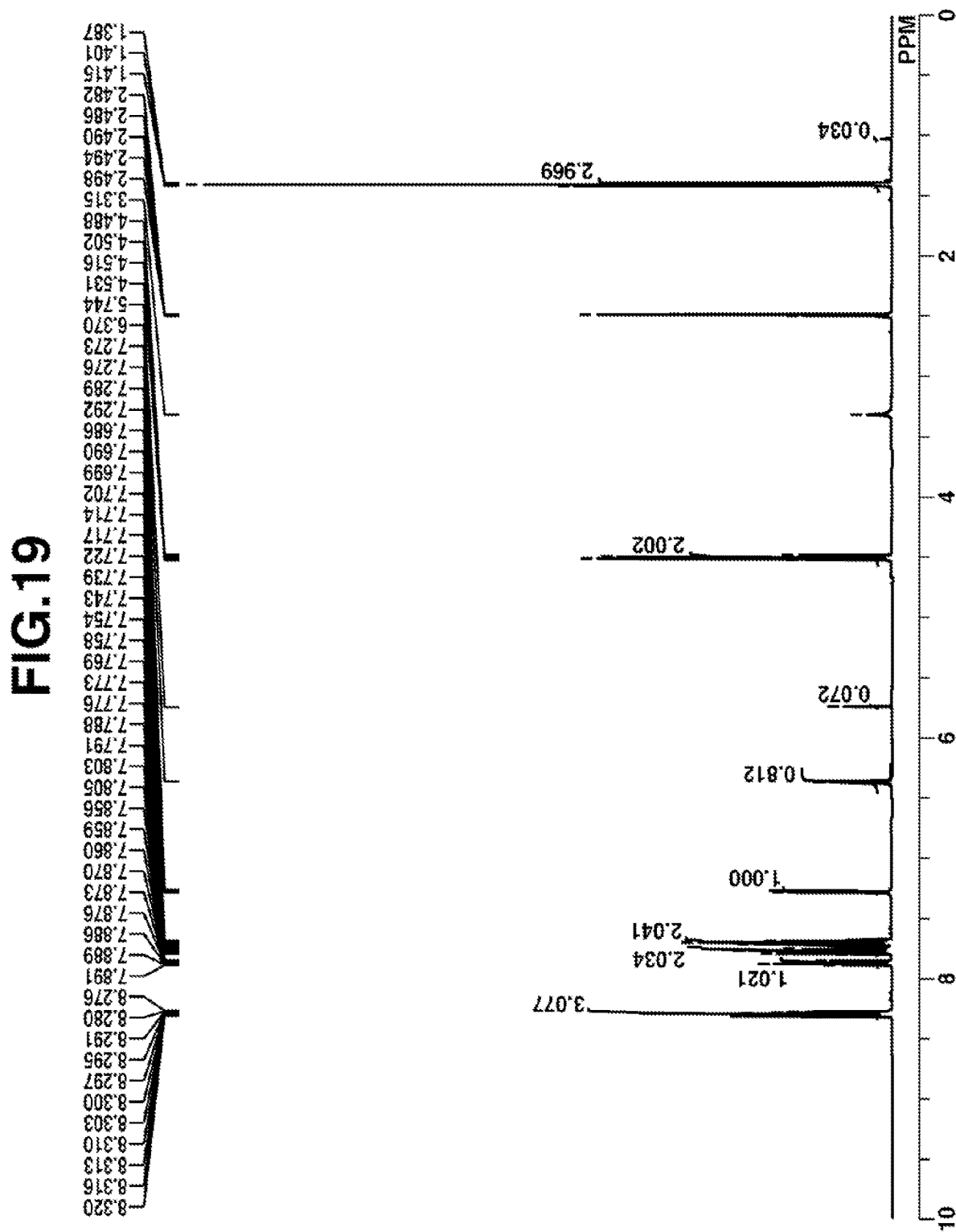
FIG. 19 is a diagram showing $^1$H-NMR spectrum of acid diffusion inhibitor Q-10 in Example 1-10.
Figure 20:
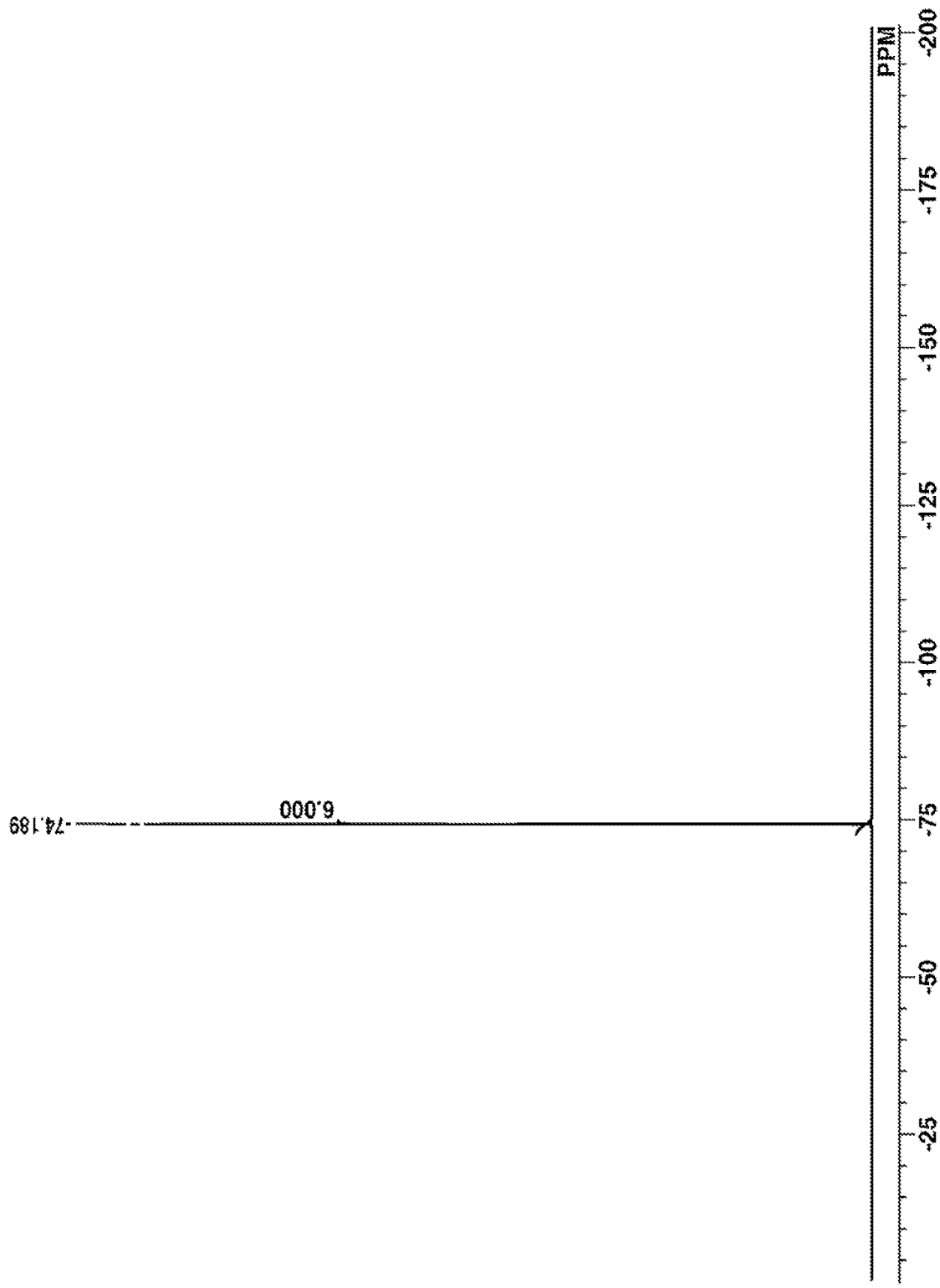
FIG. 20 is a diagram showing $^{19}$F-NMR spectrum of acid diffusion inhibitor Q-10 in Example 1-10.

Q-10 was analyzed by spectroscopy. The IR and TOFMS data are shown below. The $^1$H- and $^{19}$F-NMR/DMSO-d6 spectra are shown in FIGS. 19 and 20, respectively.

IR (D-ATR):
  ν=6260, 3102, 3072, 3001, 1681, 1662, 1585, 1567, 1477, 1460, 1444, 1378, 1310, 1293, 1276, 1245, 1196, 1165, 1111, 1068, 1054, 1043, 1017, 993, 978, 924, 876, 862, 839, 794, 746, 680, 557, 519, 473, 462 cm$^{-1}$

MALDI TOFMS:
  Positive M$^+$ 353.0 (corresponding to $C_{15}H_{14}IO_2^+$)
  Negative M$^-$ 211.0 (corresponding to $C_4HF_6O_3^-$)

Examples 1-11 to 1-25

Acid diffusion inhibitors Q-11 to Q-25 as shown below were synthesized in accordance with the above Examples.

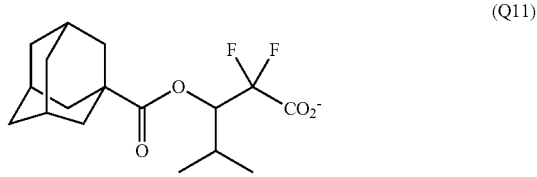

(Q11)

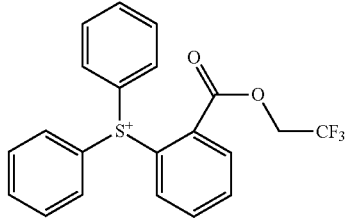

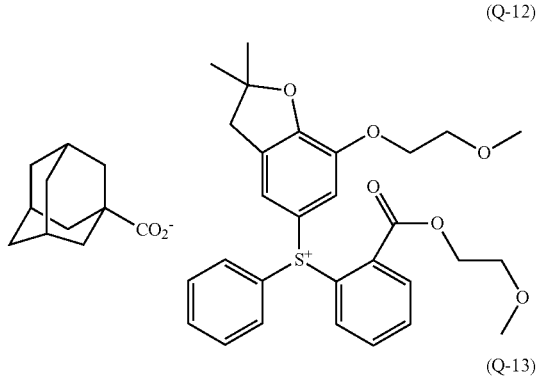

(Q-12)

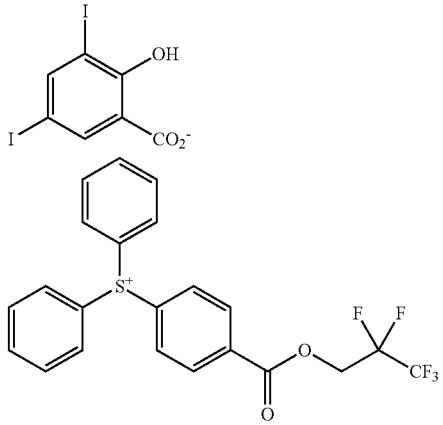

(Q-13)

(Q-14)
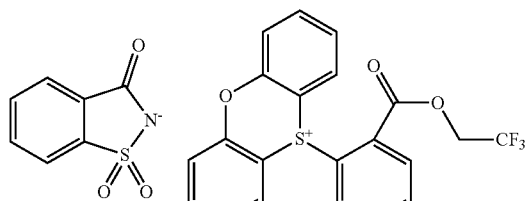
(Q-15)
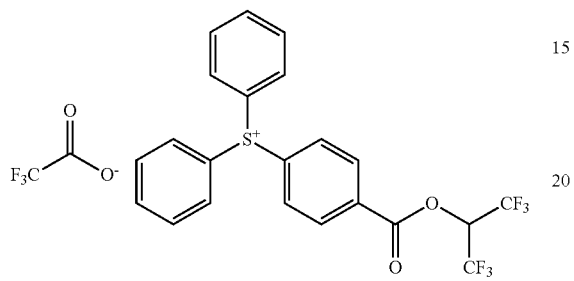
(Q-16)
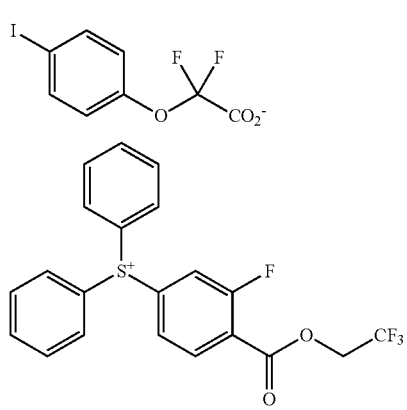
(Q-17)
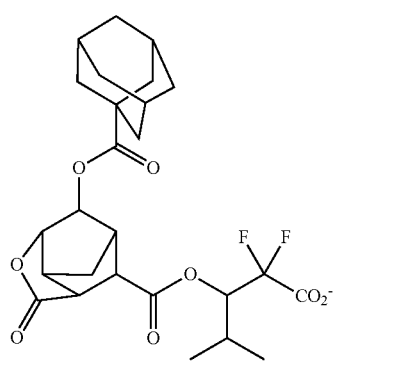
(Q-18)
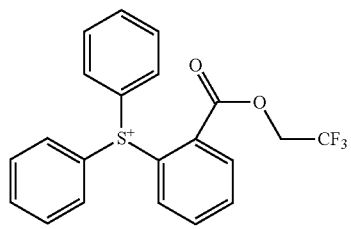
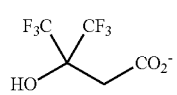
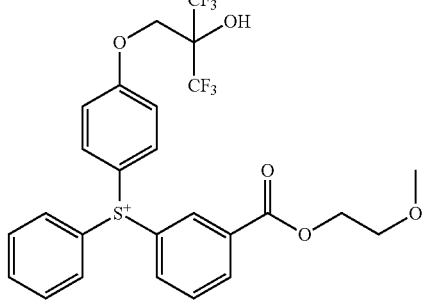
(Q-19)
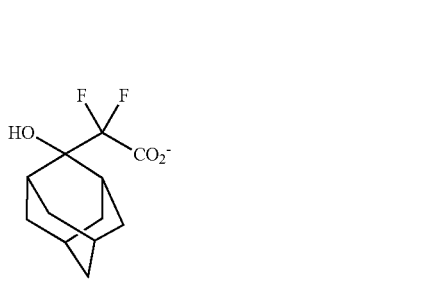
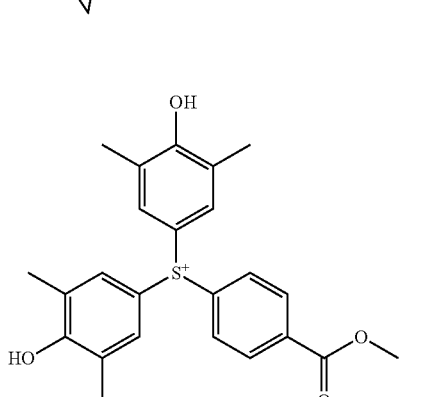
(Q-20)
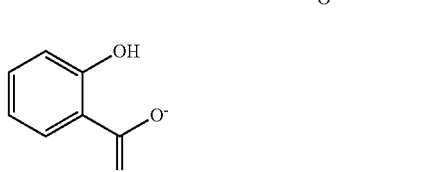
(Q-21)
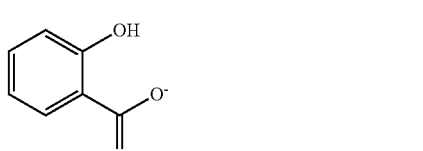

-continued

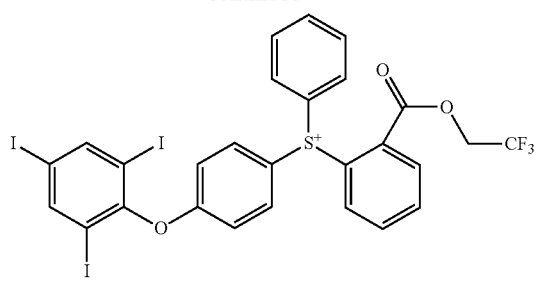

(Q-22)

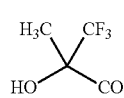

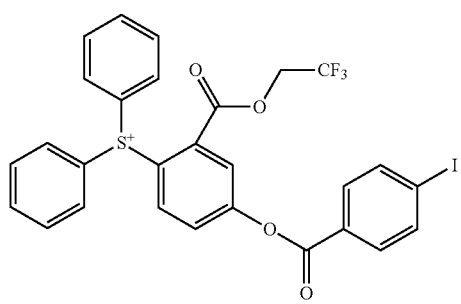

(Q-23)

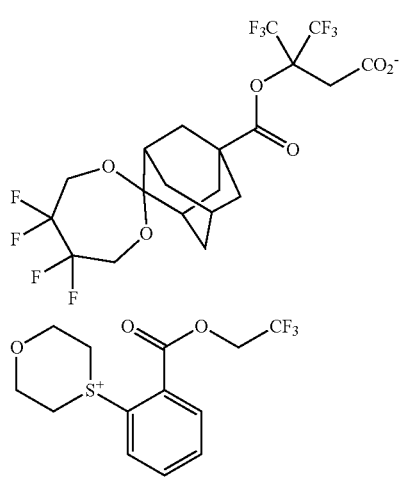

(Q-24)

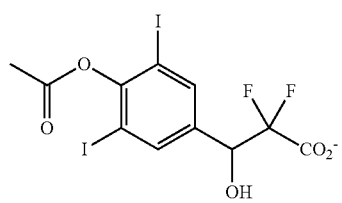

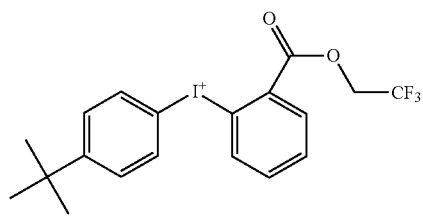

-continued

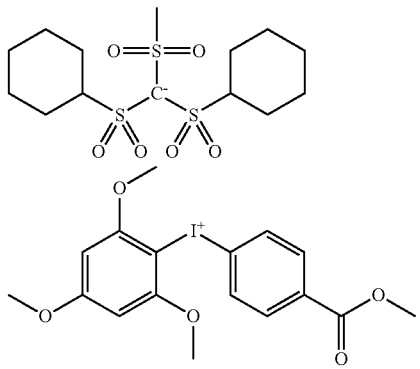

(Q-25)

[2] Synthesis of Base Polymers

Synthesis Example 1

Synthesis of Base Polymer P-1

In nitrogen atmosphere, 22 g of 1-tert-butylcyclopentyl methacrylate, 17 g of 2-oxotetrahydrofuran-3-yl methacrylate, 0.49 g of dimethyl 2,2'-azobis(2-methylpropionate) (V-601 by Fuji Film Wako Pure Chemical Industries, Ltd.), 0.40 g of 2-mercaptoethanol, and 50 g of methyl ethyl ketone were combined to form a monomer/initiator solution. A flask in nitrogen atmosphere was charged with 23 g of methyl ethyl ketone, which was heated at 80° C. with stirring. With stirring, the monomer/initiator solution was added dropwise to the flask over 4 hours. After the completion of dropwise addition, the polymerization solution was continuously stirred for 2 hours while maintaining the temperature of 80° C. The polymerization solution was cooled to room temperature, whereupon it was added dropwise to 640 g of methanol with vigorous stirring. The solid precipitate was collected by filtration, washed twice with 240 g of methanol, and vacuum dried at 50° C. for 20 hours, obtaining Base Polymer P-1 in white powder form (amount 36 g, yield 90%). On GPC analysis, Base Polymer P-1 had a Mw of 7,800 and a dispersity Mw/Mn of 1.80.

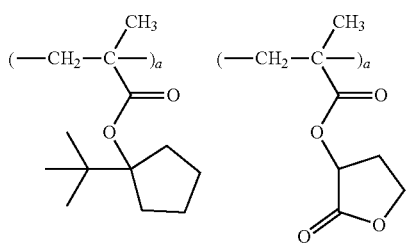

P-1
(a = 50, b = 50)
Mw = 7,800
Mw/Mn = 1.80

Synthesis Examples 2 to 4

Synthesis of Base Polymers P-2 to P-4

Base Polymers P-2 to P-4 were synthesized by the same procedure as in Synthesis Example 1 aside from changing the type and amount of monomers.

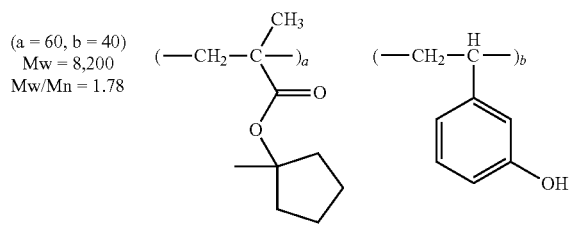

P-2

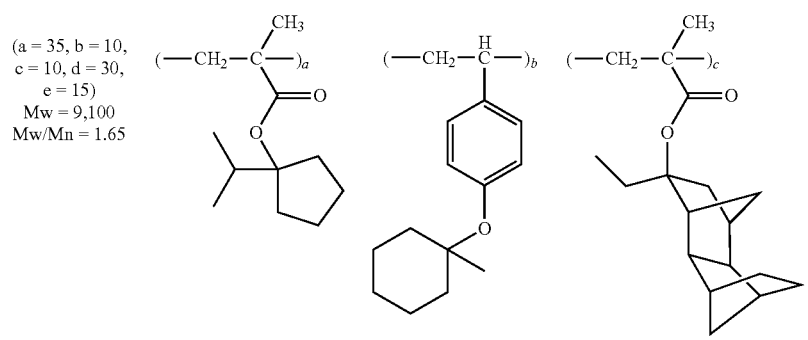

P-3

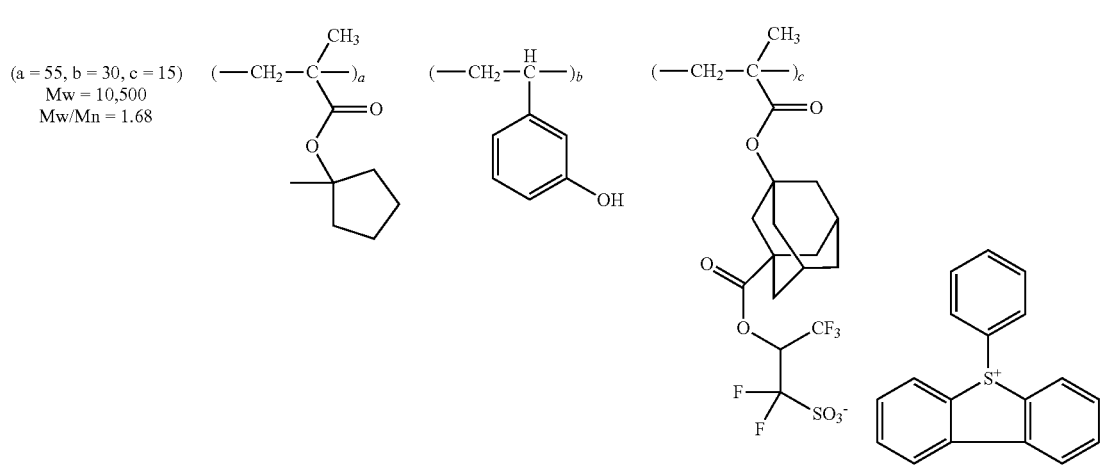

P-4

[3] Preparation of Resist Compositions

Examples 2-1 to 2-58 and Comparative Examples 1-1 to 1-36

Resist compositions were prepared by dissolving an acid diffusion inhibitor (Q-1 to Q-25), base polymer (P-1 to P-4), photoacid generator (PAG-1 to PAG-4), another acid diffusion inhibitor (Q-A to Q-N), and alkali-soluble surfactant (SF-1) in a solvent containing 0.01 wt % of surfactant Polyfox 636 (Omnova Solutions, Inc.) in accordance with the formulation in Tables 1 to 5, and filtering the solution through a Teflon® filter with a pore size of 0.2 μm.

The components in Tables 1 to 5 are identified below.

Photoacid Generators PAG-1 to PAG-4:

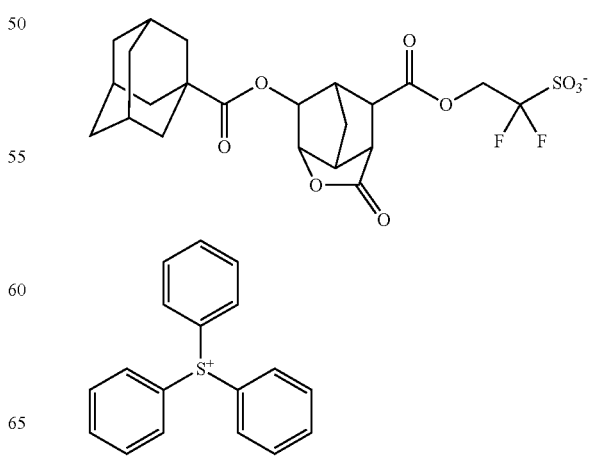

(PAG-1)

309
-continued
310
Acid Diffusion Inhibitors Q-A to Q-N:
(PAG-2)
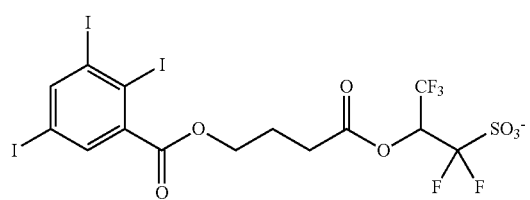
(Q-A)
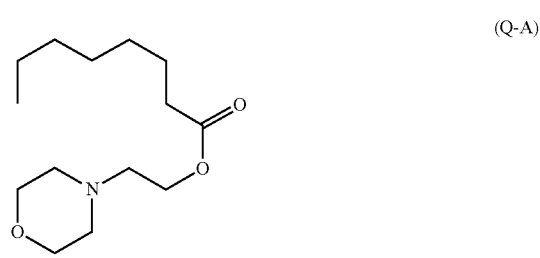
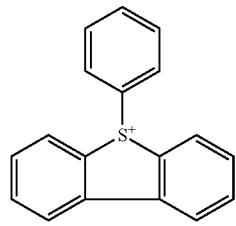
(PAG-3)
(Q-B)
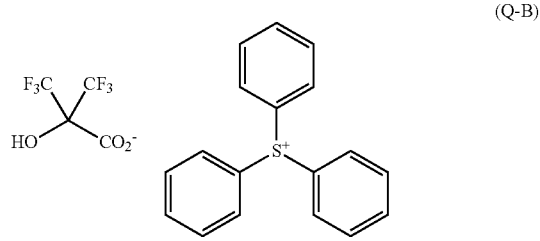
(Q-C)
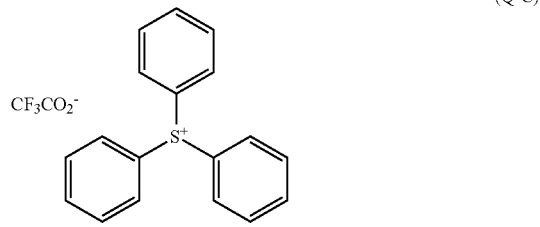
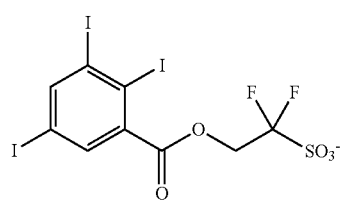
(PAG-4)
(Q-D)
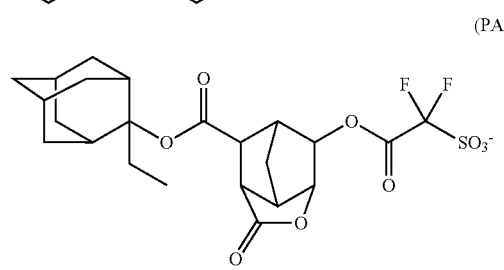
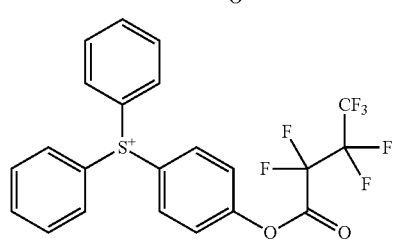
Solvent:
PGMEA=propylene glycol monomethyl ether acetate
GBL=γ-butyrolactone
CyHO=cyclohexanone
DAA=diacetone alcohol
(Q-E)
(Q-F)

(Q-G)
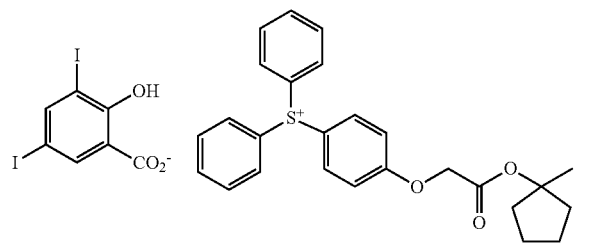
(Q-L)
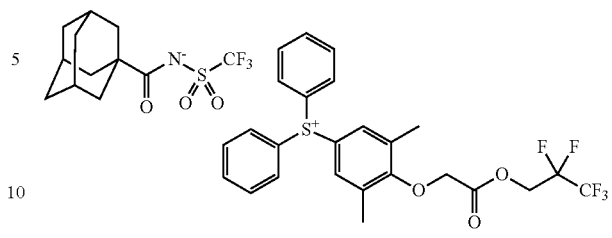
(Q-H)
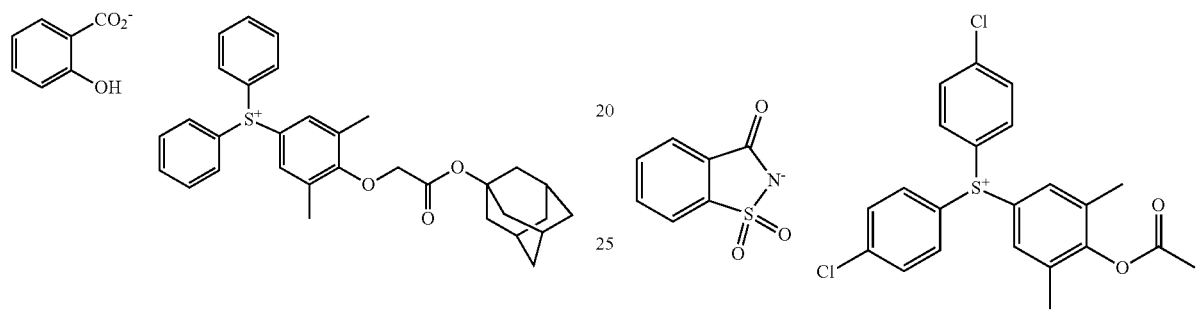
(Q-M)
(Q-I)
(Q-N)
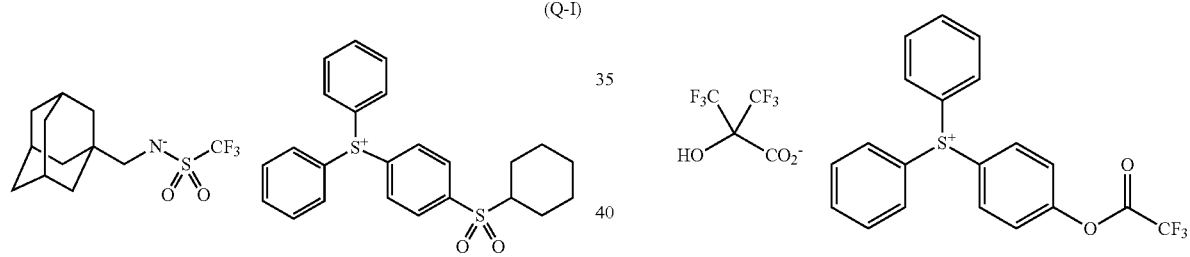
Alkali-Soluble Surfactant SF-1:
poly(2,2,3,3,4,4,4-heptafluoro-1-isobutyl-1-butyl methacrylate/9-(2,2,2-trifluoro-1-trifluoromethylethyloxycarbonyl)-4-oxatricyclo[4.2.1.0$^{3,7}$]nonan-5-on-2-yl methacrylate)
(Q-J)
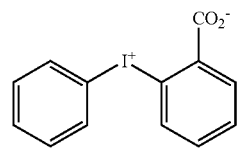
(Q-K)
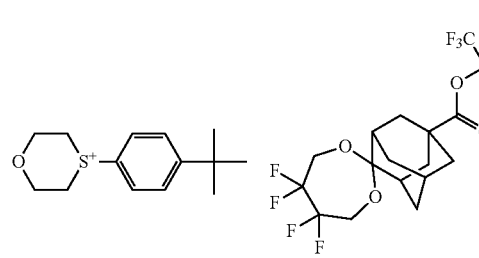
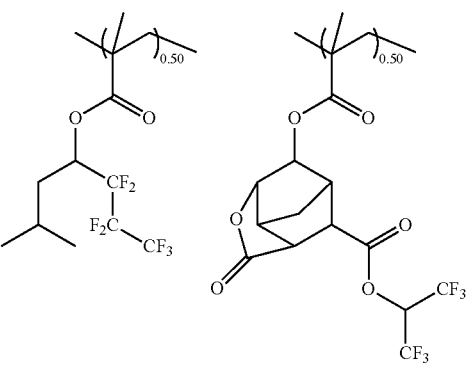
SF-1
Mw = 7,700
Mw/Mn = 1.82

TABLE 1

| | Resist composition | Base Polymer (pbw) | Photoacid generator (pbw) | Acid diffusion inhibitor (pbw) | Surfactant (pbw) | Solvent (pbw) |
|---|---|---|---|---|---|---|
| Example 2-1 | R-1 | P-1 (100) | PAG-1 (8.0) | Q-1 (7.0) | SF-1 (3.0) | PGMEA/GBL (1,920/480) |
| 2-2 | R-2 | P-1 (100) | PAG-1 (8.0) | Q-2 (6.5) | SF-1 (3.0) | PGMEA/GBL (1,920/480) |
| 2-3 | R-3 | P-1 (100) | PAG-1 (8.0) | Q-3 (7.0) | SF-1 (3.0) | PGMEA/GBL (1,920/480) |
| 2-4 | R-4 | P-1 (100) | PAG-1 (8.0) | Q-4 (6.5) | SF-1 (3.0) | PGMEA/GBL (1,920/480) |
| 2-5 | R-5 | P-1 (100) | PAG-1 (8.0) | Q-5 (7.0) | SF-1 (3.0) | PGMEA/GBL (1,920/480) |
| 2-6 | R-6 | P-1 (100) | PAG-1 (8.0) | Q-7 (7.0) | SF-1 (3.0) | PGMEA/GBL (1,920/480) |
| 2-7 | R-7 | P-1 (100) | PAG-1 (8.0) | Q-9 (6.2) | SF-1 (3.0) | PGMEA/GBL (1,920/480) |
| 2-8 | R-8 | P-1 (100) | PAG-1 (8.0) | Q-11 (7.0) | SF-1 (3.0) | PGMEA/GBL (1,920/480) |
| 2-9 | R-9 | P-1 (100) | PAG-1 (8.0) | Q-15 (7.0) | SF-1 (3.0) | PGMEA/GBL (1,920/480) |
| 2-10 | R-10 | P-1 (100) | PAG-1 (8.0) | Q-17 (7.0) | SF-1 (3.0) | PGMEA/GBL (1,920/480) |
| 2-11 | R-11 | P-1 (100) | PAG-1 (8.0) | Q-20 (6.4) | SF-1 (3.0) | PGMEA/GBL (1,920/480) |
| 2-12 | R-12 | P-1 (100) | PAG-1 (8.0) | Q-22 (6.0) | SF-1 (3.0) | PGMEA/GBL (1,920/480) |
| 2-13 | R-13 | P-1 (100) | PAG-1 (8.0) | Q-23 (8.0) | SF-1 (3.0) | PGMEA/GBL (1,920/480) |
| 2-14 | R-14 | P-1 (100) | PAG-1 (8.0) | Q-1 (6.0) Q-A (0.8) | SF-1 (3.0) | PGMEA/GBL (1,920/480) |
| 2-15 | R-15 | P-1 (100) | PAG-1 (8.0) | Q-1 (5.0) Q-B (2.0) | SF-1 (3.0) | PGMEA/GBL (1,920/480) |
| 2-16 | R-16 | P-2 (100) | PAG-2 (20.0) | Q-1 (10.0) | SF-1 (3.0) | PGMEA/DAA (2,100/900) |
| 2-17 | R-17 | P-2 (100) | PAG-2 (20.0) | Q-2 (9.9) | SF-1 (3.0) | PGMEA/DAA (2,100/900) |
| 2-18 | R-18 | P-2 (100) | PAG-2 (20.0) | Q-3 (10.0) | SF-1 (3.0) | PGMEA/DAA (2,100/900) |
| 2-19 | R-19 | P-2 (100) | PAG-2 (20.0) | Q-4 (9.9) | SF-1 (3.0) | PGMEA/DAA (2,100/900) |
| 2-20 | R-20 | P-2 (100) | PAG-2 (20.0) | Q-5 (10.0) | SF-1 (3.0) | PGMEA/DAA (2,100/900) |

TABLE 2

| | Resist composition | Base Polymer (pbw) | Photoacid generator (pbw) | Acid diffusion inhibitor (pbw) | Surfactant (pbw) | Solvent (pbw) |
|---|---|---|---|---|---|---|
| Example 2-21 | R-21 | P-2 (100) | PAG-2 (20.0) | Q-6 (9.9) | SF-1 (3.0) | PGMEA/DAA (2,100/900) |
| 2-22 | R-22 | P-2 (100) | PAG-2 (20.0) | Q-7 (10.0) | SF-1 (3.0) | PGMEA/DAA (2,100/900) |
| 2-23 | R-23 | P-2 (100) | PAG-2 (20.0) | Q-8 (9.9) | SF-1 (3.0) | PGMEA/DAA (2,100/900) |
| 2-24 | R-24 | P-2 (100) | PAG-2 (20.0) | Q-9 (9.8) | SF-1 (3.0) | PGMEA/DAA (2,100/900) |
| 2-25 | R-25 | P-2 (100) | PAG-2 (20.0) | Q-10 (9.8) | SF-1 (3.0) | PGMEA/DAA (2,100/900) |
| 2-26 | R-26 | P-2 (100) | PAG-2 (20.0) | Q-11 (10.0) | SF-1 (3.0) | PGMEA/DAA (2,100/900) |
| 2-27 | R-27 | P-2 (100) | PAG-2 (20.0) | Q-12 (9.1) | SF-1 (3.0) | PGMEA/DAA (2,100/900) |
| 2-28 | R-28 | P-2 (100) | PAG-2 (20.0) | Q-13 (9.5) | SF-1 (3.0) | PGMEA/DAA (2,100/900) |
| 2-29 | R-29 | P-2 (100) | PAG-2 (20.0) | Q-14 (9.3) | SF-1 (3.0) | PGMEA/DAA (2,100/900) |
| 2-30 | R-30 | P-2 (100) | PAG-2 (20.0) | Q-15 (9.7) | SF-1 (3.0) | PGMEA/DAA (2,100/900) |
| 2-31 | R-31 | P-2 (100) | PAG-2 (20.0) | Q-16 (10.0) | SF-1 (3.0) | PGMEA/DAA (2,100/900) |
| 2-32 | R-32 | P-2 (100) | PAG-2 (20.0) | Q-17 (9.9) | SF-1 (3.0) | PGMEA/DAA (2,100/900) |

TABLE 2-continued

| | Resist composition | Base Polymer (pbw) | Photoacid generator (pbw) | Acid diffusion inhibitor (pbw) | Surfactant (pbw) | Solvent (pbw) |
|---|---|---|---|---|---|---|
| 2-33 | R-33 | P-2 (100) | PAG-2 (20.0) | Q-18 (9.6) | SF-1 (3.0) | PGMEA/DAA (2,100/900) |
| 2-34 | R-34 | P-2 (100) | PAG-2 (20.0) | Q-19 (9.1) | SF-1 (3.0) | PGMEA/DAA (2,100/900) |
| 2-35 | R-35 | P-2 (100) | PAG-2 (20.0) | Q-20 (9.5) | SF-1 (3.0) | PGMEA/DAA (2,100/900) |
| 2-36 | R-36 | P-2 (100) | PAG-2 (20.0) | Q-21 (9.9) | SF-1 (3.0) | PGMEA/DAA (2,100/900) |
| 2-37 | R-37 | P-2 (100) | PAG-2 (20.0) | Q-22 (9.7) | SF-1 (3.0) | PGMEA/DAA (2,100/900) |
| 2-38 | R-38 | P-2 (100) | PAG-2 (20.0) | Q-24 (9.8) | SF-1 (3.0) | PGMEA/DAA (2,100/900) |
| 2-39 | R-39 | P-2 (100) | PAG-2 (20.0) | Q-25 (9.7) | SF-1 (3.0) | PGMEA/DAA (2,100/900) |
| 2-40 | R-40 | P-3 (100) | PAG-3 (19.5) | Q-1 (10.0) | SF-1 (3.0) | PGMEA/DAA/CyHO (2,100/600/300) |

TABLE 3

| | | Resist composition | Base Polymer (pbw) | Photoacid generator (pbw) | Acid diffusion inhibitor (pbw) | Surfactant (pbw) | Solvent (pbw) |
|---|---|---|---|---|---|---|---|
| Example | 2-41 | R-41 | P-3 (100) | PAG-3 (19.5) | Q-2 (10.0) | SF-1 (3.0) | PGMEA/DAA/CyHO (2,100/600/300) |
| | 2-42 | R-42 | P-3 (100) | PAG-3 (19.5) | Q-3 (10.0) | SF-1 (3.0) | PGMEA/DAA/CyHO (2,100/600/300) |
| | 2-43 | R-43 | P-3 (100) | PAG-3 (19.5) | Q-4 (10.0) | SF-1 (3.0) | PGMEA/DAA/CyHO (2,100/600/300) |
| | 2-44 | R-44 | P-3 (100) | PAG-3 (19.5) | Q-9 (7.0) Q-B (3.0) | SF-1 (3.0) | PGMEA/DAA/CyHO (2,100/600/300) |
| | 2-45 | R-45 | P-3 (100) | PAG-3 (19.5) | Q-11 (10.0) | SF-1 (3.0) | PGMEA/DAA/CyHO (2,100/600/300) |
| | 2-46 | R-46 | P-4 (100) | — | Q-1 (10.0) | SF-1 (3.0) | PGMEA/DAA (2,100/900) |
| | 2-47 | R-47 | P-4 (100) | — | Q-2 (10.0) | SF-1 (3.0) | PGMEA/DAA (2,100/900) |
| | 2-48 | R-48 | P-4 (100) | — | Q-3 (10.0) | SF-1 (3.0) | PGMEA/DAA (2,100/900) |
| | 2-49 | R-49 | P-4 (100) | — | Q-4 (10.0) | SF-1 (3.0) | PGMEA/DAA (2,100/900) |
| | 2-50 | R-50 | P-4 (100) | — | Q-5 (10.0) | SF-1 (3.0) | PGMEA/DAA (2,100/900) |
| | 2-51 | R-51 | P-4 (100) | — | Q-6 (10.0) | SF-1 (3.0) | PGMEA/DAA (2,100/900) |
| | 2-52 | R-52 | P-4 (100) | — | Q-7 (10.0) | SF-1 (3.0) | PGMEA/DAA (2,100/900) |
| | 2-53 | R-53 | P-4 (100) | — | Q-8 (10.0) | SF-1 (3.0) | PGMEA/DAA (2,100/900) |
| | 2-54 | R-54 | P-4 (100) | — | Q-9 (10.0) | SF-1 (3.0) | PGMEA/DAA (2,100/900) |
| | 2-55 | R-55 | P-4 (100) | — | Q-10 (10.0) | SF-1 (3.0) | PGMEA/DAA (2,100/900) |
| | 2-56 | R-56 | P-4 (100) | — | Q-11 (10.0) | SF-1 (3.0) | PGMEA/DAA (2,100/900) |
| | 2-57 | R-57 | P-4 (100) | — | Q-16 (10.0) | SF-1 (3.0) | PGMEA/DAA (2,100/900) |
| | 2-58 | R-58 | P-4 (100) | — | Q-24 (10.0) | SF-1 (3.0) | PGMEA/DAA (2,100/900) |

TABLE 4

|  |  | Resist composition | Base Polymer (pbw) | Photoacid generator (pbw) | Acid diffusion inhibitor (pbw) | Surfactant (pbw) | Solvent (pbw) |
|---|---|---|---|---|---|---|---|
| Comparative Example | 1-1 | CR-1 | P-1 (100) | PAG-1 (8.0) | Q-A (5.0) | SF-1 (3.0) | PGMEA/GBL (1,920/480) |
|  | 1-2 | CR-2 | P-1 (100) | PAG-1 (8.0) | Q-B (8.0) | SF-1 (3.0) | PGMEA/GBL (1,920/480) |
|  | 1-3 | CR-3 | P-1 (100) | PAG-1 (8.0) | Q-C (8.0) | SF-1 (3.0) | PGMEA/GBL (1,920/480) |
|  | 1-4 | CR-4 | P-1 (100) | PAG-1 (8.0) | Q-D (8.0) | SF-1 (3.0) | PGMEA/GBL (1,920/480) |
|  | 1-5 | CR-5 | P-1 (100) | PAG-1 (8.0) | Q-E (7.5) | SF-1 (3.0) | PGMEA/GBL (1,920/480) |
|  | 1-6 | CR-6 | P-1 (100) | PAG-1 (8.0) | Q-F (8.0) | SF-1 (3.0) | PGMEA/GBL (1,920/480) |
|  | 1-7 | CR-7 | P-1 (100) | PAG-1 (8.0) | Q-G (8.0) | SF-1 (3.0) | PGMEA/GBL (1,920/480) |
|  | 1-8 | CR-8 | P-1 (100) | PAG-1 (8.0) | Q-H (7.5) | SF-1 (3.0) | PGMEA/GBL (1,920/480) |
|  | 1-9 | CR-9 | P-1 (100) | PAG-1 (8.0) | Q-I (8.0) | SF-1 (3.0) | PGMEA/GBL (1,920/480) |
|  | 1-10 | CR-10 | P-1 (100) | PAG-1 (8.0) | Q-J (7.5) | SF-1 (3.0) | PGMEA/GBL (1,920/480) |
|  | 1-11 | CR-11 | P-1 (100) | PAG-1 (8.0) | Q-K (8.0) | SF-1 (3.0) | PGMEA/GBL (1,920/480) |
|  | 1-12 | CR-12 | P-1 (100) | PAG-1 (8.0) | Q-L (6.8) | SF-1 (3.0) | PGMEA/GBL (1,920/480) |
|  | 1-13 | CR-13 | P-1 (100) | PAG-1 (8.0) | Q-M (8.0) | SF-1 (3.0) | PGMEA/GBL (1,920/480) |
|  | 1-14 | CR-14 | P-1 (100) | PAG-1 (8.0) | Q-N (8.0) | SF-1 (3.0) | PGMEA/GBL (1,920/480) |
|  | 1-15 | CR-15 | P-1 (100) | PAG-4 (8.0) | Q-B (8.0) | SF-1 (3.0) | PGMEA/GBL (1,920/480) |
|  | 1-16 | CR-16 | P-2 (100) | PAG-2 (20.0) | Q-A (8.0) | SF-1 (3.0) | PGMEA/GBL (1,920/480) |
|  | 1-17 | CR-17 | P-2 (100) | PAG-2 (20.0) | Q-C (10.0) | SF-1 (3.0) | PGMEA/GBL (1,920/480) |
|  | 1-18 | CR-I8 | P-2 (100) | PAG-2 (20.0) | Q-E (10.0) | SF-1 (3.0) | PGMEA/GBL (1,920/480) |
|  | 1-19 | CR-19 | P-2 (100) | PAG-2 (20.0) | Q-F (10.0) | SF-1 (3.0) | PGMEA/GBL (1,920/480) |
|  | 1-20 | CR-20 | P-2 (100) | PAG-2 (20.0) | Q-G (10.0) | SF-1 (3.0) | PGMEA/GBL (1,920/480) |

TABLE 5

|  |  | Resist composition | Base Polymer (pbw) | Photoacid generator (pbw) | Acid diffusion inhibitor (pbw) | Surfactant (pbw) | Solvent (pbw) |
|---|---|---|---|---|---|---|---|
| Comparative Example | 1-21 | CR-21 | P-2 (100) | PAG-2 (20.0) | Q-H (10.0) | SF-1 (3.0) | PGMEA/DAA (2,100/900) |
|  | 1-22 | CR-22 | P-2 (100) | PAG-2 (20.0) | Q-I (10.0) | SF-1 (3.0) | PGMEA/DAA (2,100/900) |
|  | 1-23 | CR-23 | P-2 (100) | PAG-2 (20.0) | Q-J (10.0) | SF-1 (3.0) | PGMEA/DAA (2,100/900) |
|  | 1-24 | CR-24 | P-2 (100) | PAG-2 (20.0) | Q-L (10.0) | SF-1 (3.0) | PGMEA/DAA (2,100/900) |
|  | 1-25 | CR-25 | P-2 (100) | PAG-2 (20.0) | Q-N (10.0) | SF-1 (3.0) | PGMEA/DAA (2,100/900) |
|  | 1-26 | CR-26 | P-2 (100) | PAG-4 (20.0) | Q-B (10.0) | SF-1 (3.0) | PGMEA/DAA (2,100/900) |
|  | 1-27 | CR-27 | P-4 (100) | — | Q-A (8.0) | SF-1 (3.0) | PGMEA/DAA (2,100/900) |
|  | 1-28 | CR-28 | P-4 (100) | — | Q-C (10.0) | SF-1 (3.0) | PGMEA/DAA (2,100/900) |
|  | 1-29 | CR-29 | P-4 (100) | — | Q-D (10.0) | SF-1 (3.0) | PGMEA/DAA (2,100/900) |
|  | 1-30 | CR-30 | P-4 (100) | — | Q-E (10.0) | SF-1 (3.0) | PGMEA/DAA (2,100/900) |
|  | 1-31 | CR-31 | P-4 (100) | — | Q-F (10.0) | SF-1 (3.0) | PGMEA/DAA (2,100/900) |

TABLE 5-continued

| | Resist composition | Base Polymer (pbw) | Photoacid generator (pbw) | Acid diffusion inhibitor (pbw) | Surfactant (pbw) | Solvent (pbw) |
|---|---|---|---|---|---|---|
| 1-32 | CR-32 | P-4 (100) | — | Q-H (10.0) | SF-1 (3.0) | PGMEA/DAA (2,100/900) |
| 1-33 | CR-33 | P-4 (100) | — | Q-J (10.0) | SF-1 (3.0) | PGMEA/DAA (2,100/900) |
| 1-34 | CR-34 | P-4 (100) | — | Q-L (10.0) | SF-1 (3.0) | PGMEA/DAA (2,100/900) |
| 1-35 | CR-35 | P-4 (100) | — | Q-M (10.0) | SF-1 (3.0) | PGMEA/DAA (2,100/900) |
| 1-36 | CR-36 | P-4 (100) | — | Q-N (10.0) | SF-1 (3.0) | PGMEA/DAA (2,100/900) |

[4] ArF Lithography Patterning Test

Examples 3-1 to 3-15 and Comparative Examples 2-1 to 2-15

On a silicon substrate, an antireflective coating solution (ARC-29A by Nissan Chemical Corp.) was coated and baked at 180° C. for 60 seconds to form an ARC of 100 nm thick. On the ARC, each of the resist compositions (R-1 to R-15, CR-1 to CR-15) was spin coated and baked on a hotplate at 100° C. for 60 seconds to form a resist film of 90 nm thick.

Using an ArF excimer laser scanner (NSR-S610C by Nikon Corp., NA 1.30, σ 0.94/0.74, dipole 35 deg. illumination, 6% halftone phase shift mask), the resist film was exposed by the immersion lithography. Water was used as the immersion liquid. After exposure, the resist film was baked (PEB) at 90° C. for 60 seconds and developed in 2.38 wt % TMAH aqueous solution for 60 seconds to form a line-and-space (LS) pattern.

The LS pattern as developed was observed under CD-SEM (CG-5000 by Hitachi High-Technologies Corp.) and evaluated for sensitivity, LWR and defect density by the following methods. The results are shown in Tables 6 and 7.

Evaluation of Sensitivity

The optimum dose (Eop) is a dose (mJ/cm$^2$) which provides a LS pattern having a line width of 40 nm at a pitch of 80 nm and reported as sensitivity. A smaller value indicates a higher sensitivity.

Evaluation of LWR

On the L/S pattern formed by exposure in the optimum dose Eop, the line width was measured at longitudinally spaced apart 10 points, from which a 3-fold value (3σ) of standard deviation (σ) was determined and reported as LWR. A smaller value of 3σ indicates a pattern having a lower roughness and more uniform line width. A pattern with a LWR value of 2.5 nm or less is rated Good while a pattern with a LWR value in excess of 2.5 nm is rated NG.

Evaluation of Defect Density

Defects in the pattern as developed were inspected by a flaw detector KLA2905 (KLA-Tencor). A defect density (count/cm$^2$) was computed by dividing the total number of detected defects by a detection area. The defect inspection conditions included light source UV, inspected pixel size 0.22 μm, and array mode. In this test, the sample was rated Good for a defect density of less than 0.03 defect/cm$^2$, Mediocre for a defect density of from 0.03 defect/cm$^2$ to less than 0.05 defect/cm$^2$, and NG for a density of 0.05 defect/cm$^2$ or more.

TABLE 6

| | | Resist composition | Eop (mJ/cm$^2$) | LWR (nm) | Defect density |
|---|---|---|---|---|---|
| Example | 3-1 | R-1 | 35 | Good (2.3) | Good |
| | 3-2 | R-2 | 39 | Good (2.2) | Good |
| | 3-3 | R-3 | 36 | Good (2.3) | Good |
| | 3-4 | R-4 | 40 | Good (2.2) | Good |
| | 3-5 | R-5 | 36 | Good (2.3) | Good |
| | 3-6 | R-6 | 36 | Good (2.4) | Good |
| | 3-7 | R-7 | 41 | Good (2.4) | Good |
| | 3-8 | R-8 | 35 | Good (2.2) | Good |
| | 3-9 | R-9 | 36 | Good (2.5) | Good |
| | 3-10 | R-10 | 37 | Good (2.0) | Good |
| | 3-11 | R-11 | 46 | Good (2.1) | Good |
| | 3-12 | R-12 | 45 | Good (2.1) | Good |
| | 3-13 | R-13 | 40 | Good (2.3) | Good |
| | 3-14 | R-14 | 37 | Good (2.4) | Good |
| | 3-15 | R-15 | 38 | Good (2.3) | Good |

TABLE 7

| | | Resist composition | Eop (mJ/cm$^2$) | LWR (nm) | Defect density |
|---|---|---|---|---|---|
| Comparative Example | 2-1 | CR-1 | 44 | NG (3.4) | NG |
| | 2-2 | CR-2 | 35 | NG (2.6) | Mediocre |
| | 2-3 | CR-3 | 37 | NG (3.1) | NG |
| | 2-4 | CR-4 | 39 | NG (2.7) | Mediocre |
| | 2-5 | CR-5 | 42 | NG (2.7) | NG |
| | 2-6 | CR-6 | 40 | NG (2.8) | NG |
| | 2-7 | CR-7 | 38 | NG (2.9) | NG |
| | 2-8 | CR-8 | 38 | NG (2.8) | NG |
| | 2-9 | CR-9 | 38 | NG (2.9) | NG |
| | 2-10 | CR-10 | 40 | NG (2.7) | NG |
| | 2-11 | CR-11 | 39 | NG (3.0) | NG |
| | 2-12 | CR-12 | 40 | NG (2.7) | Mediocre |
| | 2-13 | CR-13 | 49 | NG (2.9) | NG |
| | 2-14 | CR-14 | 39 | NG (2.7) | Mediocre |
| | 2-15 | CR-15 | 38 | NG (2.7) | Mediocre |

As is evident from Tables 6 and 7, the chemically amplified resist compositions containing onium salts within the scope of the invention exhibit minimal defects and satisfactory LWR. The resist compositions are useful as the ArF immersion lithography material.

[5] EUV Lithography Test

Examples 4-1 to 4-43 and Comparative Examples 3-1 to 3-21

Each of the resist compositions (R-16 to R-58, CR-16 to CR-36) was spin coated on a silicon substrate having a 20-nm coating of silicon-containing spin-on hard mask SHB-A940 (silicon content 43 wt %, Shin-Etsu Chemical Co., Ltd.) and prebaked on a hotplate at 105° C. for 60 seconds to form a resist film of 50 nm thick. Using an EUV scanner NXE3300 (ASML, NA 0.33, σ 0.9/0.6, quadrupole illumination), the resist film was exposed to EUV through a mask bearing a hole pattern having a pitch 46 nm+20% bias (on-wafer size). The resist film was baked (PEB) on a hotplate at 85° C. for 60 seconds and developed in a 2.38 wt % TMAH aqueous solution for 30 seconds to form a hole pattern having a size of 23 nm.

The hole pattern as developed was observed under CD-SEM (CG-5000 by Hitachi High-Technologies Corp.) and evaluated for sensitivity, CDU and DOF by the following methods. The results are shown in Tables 8 to 10.

Evaluation of Sensitivity

The optimum dose (Eop) is a dose (mJ/cm$^2$) which provides a hole pattern having a hole size of 23 nm and reported as sensitivity. A smaller value indicates a higher sensitivity.

Evaluation of CDU

For the hole pattern at the optimum dose (Eop), the size of 50 holes within the same dose shot was measured, from which a 3-fold value (3σ) of standard deviation (σ) was computed and reported as CDU. A smaller value of CDU indicates better dimensional uniformity of hole pattern. The sample was rated Good for a CDU value of up to 3.0 nm and NG for a CDU value in excess of 3.0 nm.

Evaluation of DOF

Hole patterns were formed by exposure in Eop while changing the focus stepwise. The span of focus within which the hole size was in the range of 23 nm±5% (from 21.85 to 24.15 nm) was determined as DOF. A larger value indicates a smaller change of pattern size per DOF change and hence, better DOF. The sample was rated Good for a value of more than 90 nm, Fair for 85 to 90 nm, and NG for less than 85 nm.

TABLE 8

| | | Resist composition | Eop (mJ/cm$^2$) | CDU (nm) | DOF (nm) |
|---|---|---|---|---|---|
| Example | 4-1 | R-16 | 40 | Good (2.7) | Good (100) |
| | 4-2 | R-17 | 38 | Good (2.6) | Good (90) |
| | 4-3 | R-18 | 41 | Good (2.8) | Good (100) |
| | 4-4 | R-19 | 38 | Good (2.6) | Good (90) |
| | 4-5 | R-20 | 41 | Good (2.8) | Good (100) |
| | 4-6 | R-21 | 38 | Good (2.7) | Good (90) |
| | 4-7 | R-22 | 40 | Good (2.8) | Good (95) |
| | 4-8 | R-23 | 38 | Good (2.6) | Good (90) |
| | 4-9 | R-24 | 38 | Good (2.7) | Good (100) |
| | 4-10 | R-25 | 39 | Good (2.7) | Good (100) |
| | 4-11 | R-26 | 42 | Good (2.6) | Good (95) |
| | 4-12 | R-27 | 39 | Good (2.5) | Good (95) |
| | 4-13 | R-28 | 42 | Good (2.9) | Good (105) |
| | 4-14 | R-29 | 40 | Good (2.9) | Good (100) |
| | 4-15 | R-30 | 37 | Good (2.6) | Good (90) |
| | 4-16 | R-31 | 38 | Good (2.6) | Good (100) |
| | 4-17 | R-32 | 42 | Good (2.8) | Good (105) |
| | 4-18 | R-33 | 45 | Good (2.8) | Good (105) |
| | 4-19 | R-34 | 43 | Good (2.7) | Good (95) |
| | 4-20 | R-35 | 40 | Good (2.6) | Good (100) |
| | 4-21 | R-36 | 41 | Good (2.7) | Good (90) |
| | 4-22 | R-37 | 38 | Good (2.9) | Good (90) |
| | 4-23 | R-38 | 39 | Good (2.9) | Good (95) |
| | 4-24 | R-39 | 35 | Good (2.6) | Good (100) |
| | 4-25 | R-40 | 34 | Good (2.5) | Good (95) |
| | 4-26 | R-41 | 36 | Good (2.7) | Good (90) |
| | 4-27 | R-42 | 35 | Good (2.7) | Good (100) |
| | 4-28 | R-43 | 34 | Good (2.7) | Good (90) |
| | 4-29 | R-44 | 35 | Good (2.7) | Good (90) |
| | 4-30 | R-45 | 29 | Good (2.4) | Good (95) |

TABLE 9

| | | Resist composition | Eop (mJ/cm$^2$) | CDU (nm) | DOF (nm) |
|---|---|---|---|---|---|
| Example | 4-31 | R-46 | 28 | Good (2.3) | Good (100) |
| | 4-32 | R-47 | 30 | Good (2.4) | Good (90) |
| | 4-33 | R-48 | 29 | Good (2.3) | Good (100) |
| | 4-34 | R-49 | 31 | Good (2.4) | Good (90) |
| | 4-35 | R-50 | 29 | Good (2.5) | Good (95) |
| | 4-36 | R-51 | 30 | Good (2.5) | Good (90) |
| | 4-37 | R-52 | 28 | Good (2.4) | Good (95) |
| | 4-38 | R-53 | 28 | Good (2.5) | Good (90) |
| | 4-39 | R-54 | 28 | Good (2.5) | Good (95) |
| | 4-40 | R-55 | 29 | Good (2.5) | Good (100) |
| | 4-41 | R-56 | 28 | Good (2.5) | Good (95) |
| | 4-42 | R-57 | 28 | Good (2.3) | Good (100) |
| | 4-43 | R-58 | 30 | Good (2.5) | Good (100) |

TABLE 10

| | | Resist composition | Eop (mJ/cm$^2$) | CDU (nm) | DOF (nm) |
|---|---|---|---|---|---|
| Comparative Example | 3-1 | CR-16 | 49 | NG (3.6) | NG (80) |
| | 3-2 | CR-17 | 39 | NG (3.4) | NG (80) |
| | 3-3 | CR-18 | 42 | NG (3.4) | NG (75) |
| | 3-4 | CR-19 | 40 | NG (3.3) | NG (80) |
| | 3-5 | CR-20 | 38 | NG (3.1) | NG (85) |
| | 3-6 | CR-21 | 43 | NG (3.1) | NG (75) |
| | 3-7 | CR-22 | 43 | NG (3.4) | NG (70) |
| | 3-8 | CR-23 | 40 | NG (3.2) | NG (85) |
| | 3-9 | CR-24 | 41 | NG (3.1) | Fair (85-90) |
| | 3-10 | CR-25 | 39 | NG (3.3) | NG (80) |
| | 3-11 | CR-26 | 38 | NG (3.3) | Fair (85-90) |
| | 3-12 | CR-27 | 34 | NG (3.4) | NG (70) |
| | 3-13 | CR-28 | 29 | NG (3.3) | NG (75) |
| | 3-14 | CR-29 | 29 | NG (3.1) | NG (85) |
| | 3-15 | CR-30 | 29 | NG (3.4) | NG (75) |
| | 3-16 | CR-31 | 29 | NG (3.3) | NG (80) |
| | 3-17 | CR-32 | 32 | NG (3.2) | NG (80) |
| | 3-18 | CR-33 | 30 | NG (3.2) | NG (85) |
| | 3-19 | CR-34 | 31 | NG (3.3) | Fair (85-90) |
| | 3-20 | CR-35 | 33 | NG (3.4) | NG (80) |
| | 3-21 | CR-36 | 29 | NG (3.2) | Fair (85-90) |

As is evident from Tables 8 to 10, the chemically amplified resist compositions containing onium salts within the scope of the invention exhibit satisfactory values of CDU and DOF. The resist compositions are useful as the EUV lithography material.

Japanese Patent Application No. 2020-177024 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A chemically amplified resist composition comprising:
   (A) a base polymer comprising repeat units having the formula (a) or repeat units having the formula (b),
   (B) a photoacid generator,
   (C-1) an acid diffusion inhibitor comprising an onium salt having the formula (1), and
   (D) an organic solvent,

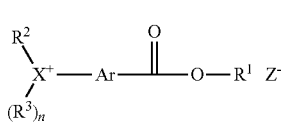

(1)

wherein X is sulfur,
  n is 1 when X is sulfur,
  $R^1$ is a $C_1$-$C_5$ straight or branched hydrocarbyl group in which at least one of hydrogen atoms of the $C_1$-$C_5$ straight or branched hydrocarbyl group may be replaced with fluorine or in which at least one of carbons which is not terminal may be replaced with oxygen to form an ether, and $R^1$ is exclusive of a tertiary hydrocarbyl group,
  $R^2$ and $R^3$ are each independently a $C_1$-$C_{30}$ hydrocarbyl group which may contain fluorine, chlorine, bromine, iodine, cyano moiety, carbonyl moiety, ether bond, ester bond, sulfonate bond, carbonate bond, lactone ring, sultone ring, carboxylic anhydride or haloalkyl moiety, $R^2$ and $R^3$ may bond together to form a ring with X to which they are attached,
  Ar is a $C_6$-$C_{14}$ arylene group which may be substituted with a substituent selected from a halogen atom, hydroxy group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, and $C_2$-$C_{10}$ hydrocarbylcarbonyloxy group which may contain a heteroatom, $R^2$ and Ar may bond together to form a ring with X to which they are attached, wherein Ar does not include a hydroxyl group, and
  $Z^-$ is a carboxylate, sulfonamide, sulfonimide or methide anion,

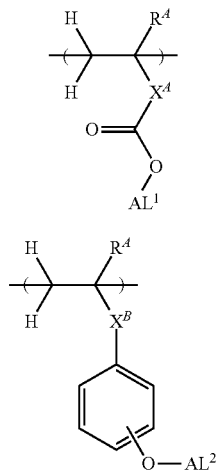

wherein $R^A$ is each independently hydrogen or methyl,
  $X^A$ is a single bond, phenylene group, naphthylene group or (backbone)-C(=O)-O-$X^{A1}$-, $X^{A1}$ is a $C_1$-$C_{15}$ hydrocarbylene group which may contain a hydroxy moiety, ether bond, ester bond, or lactone ring,
  $X^B$ is a single bond or ester bond,
  $AL^1$ and $AL^2$ are each independently an acid labile group.

2. The chemically amplified resist composition of claim 1, having the formula (2):

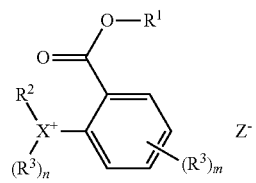

(2)

wherein $R^1$, $R^2$, $R^3$, n, X, and Z are as defined above,
  $R^4$ is a halogen atom, hydroxy group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, or $C_2$-$C_{10}$ hydrocarbylcarbonyloxy group which may contain a heteroatom, and
  m is an integer of 0 to 4.

3. The chemically amplified resist composition of claim 1 wherein $R^1$ is methyl, ethyl, propyl, isopropyl, n-butyl, 2,2,2-trifluoroethyl, 3,3,3-trifluoropropyl, 2,2,3,3,3-pentafluoropropyl, 1-trifluoromethyl-2,2,2-trifluoroethyl or 2-methoxyethyl.

4. The chemically amplified resist composition of claim 1 wherein $Z^-$ is a carboxylate anion having at least one fluorine atom or trifluoromethyl group at α- or β-position relative to the carboxy group.

5. The chemically amplified resist composition of claim 1 wherein $Z^-$ is an anion having any one of the formulae (Z-1) to (Z-5):

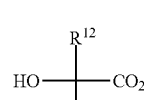

(Z-1)

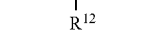

(Z-2)

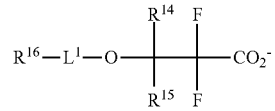

(Z-3)

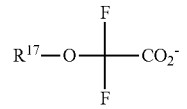

(Z-4)

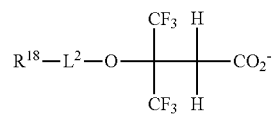

(Z-5)

wherein $R^{11}$ is a $C_1$-$C_4$ perfluoroalkyl group,
  $R^{12}$ and $R^{13}$ are each independently hydrogen, fluorine, methyl or trifluoromethyl, at least one of $R^{12}$ and $R^{13}$ is fluorine or trifluoromethyl,
  $R^{14}$ and $R^{15}$ are each independently hydrogen or a $C_1$-$C_{15}$ hydrocarbyl group which may contain a heteroatom,
  $R^{16}$, $R^{17}$ and $R^{18}$ are each independently hydrogen or a $C_1$-$C_{30}$ hydrocarbyl group which may contain a heteroatom,
  $L^1$ and $L^2$ are each independently a single bond, carbonyl group or sulfonyl group.

6. A chemically amplified resist composition comprising:
(A') a base polymer comprising repeat units having the formula (a) or repeat units having the formula (b) and repeat units adapted to generate an acid upon light exposure,
(C-1) the acid diffusion inhibitor, comprising an onium salt having the formula (1), and
(D) an organic solvent,

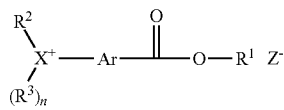
(1)

wherein X is sulfur,
n is 1 when X is sulfur,
$R^1$ is a $C_1$-$C_5$ hydrocarbyl group which may contain fluorine or oxygen,
$R^2$ and $R^3$ are each independently a $C_1$-$C_{30}$ hydrocarbyl group which may contain a heteroatom, $R^2$ and $R^3$ may bond together to form a ring with X to which they are attached,
Ar is a $C_6$-$C_{14}$ arylene group which may be substituted with a substituent selected from a halogen atom, hydroxy group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, and $C_2$-$C_{10}$ hydrocarbylcarbonyloxy group which may contain a heteroatom, $R^2$ and Ar may bond together to form a ring with X to which they are attached, and
$Z^-$ is a carboxylate, sulfonamide, sulfonimide or methide anion,

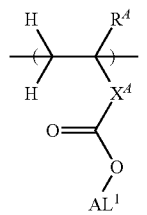
(a)

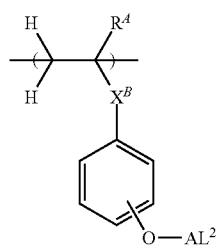
(b)

wherein $R^A$ is each independently hydrogen or methyl,
$X^A$ is a single bond, phenylene group, naphthylene group or (backbone)-C(=O)-O-$X^{A1}$-, $X^{A1}$ is a $C_1$-$C_{15}$ hydrocarbylene group which may contain a hydroxy moiety, ether bond, ester bond, or lactone ring,
$X^B$ is a single bond or ester bond,
$AL^1$ and $AL^2$ are each independently an acid labile group.
7. The chemically amplified resist composition of claim 1 wherein the acid labile group has the formula (L1):

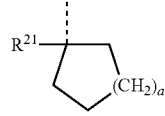
(L1)

wherein $R^{21}$ is a $C_1$-$C_7$ hydrocarbyl group in which any constituent —$CH_2$— may be replaced by —O—, a is 1 or 2, and the broken line designates a valence bond.

8. The chemically amplified resist composition of claim 1, wherein the base polymer comprises repeat units having the formula (c):

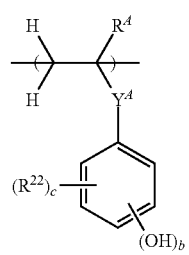
(c)

wherein $R^A$ is hydrogen or methyl,
$Y^A$ is a single bond or ester bond,
$R^{22}$ is fluorine, iodine, a carboxy group, formyl group, formyloxy group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, $C_2$-$C_{10}$ hydrocarbylcarbonyloxy group which may contain a heteroatom, or $C_2$-$C_{10}$ hydrocarbyloxycarbonyloxy group which may contain a heteroatom,
b is an integer of 1 to 5, c is an integer of 0 to 4, and b+c is 1 to 5.

9. The chemically amplified resist composition of claim 6 wherein the base polymer comprises repeat units adapted to generate an acid upon light exposure, having any one of the formulae (d1) to (d4):

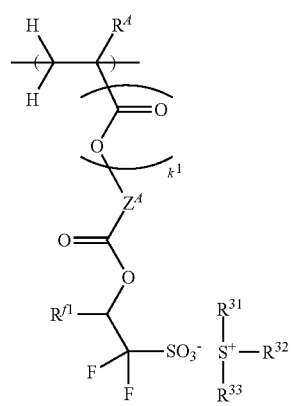
(d1)

-continued (d2)

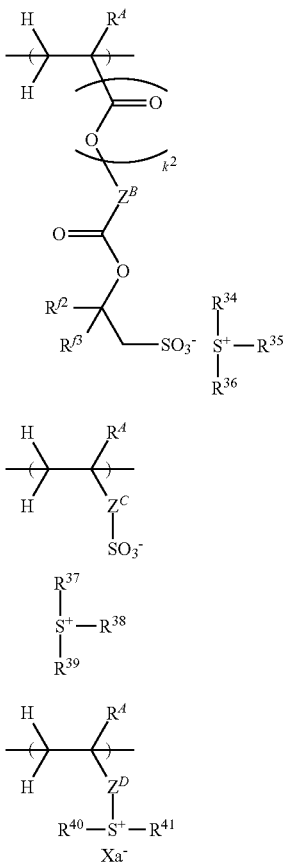

(d3)

(d4)

wherein $R^A$ is each independently hydrogen or methyl,
$R^{f1}$, $R^{f2}$ and $R^{f3}$ are each independently hydrogen or trifluoromethyl,
$Z^A$ and $Z^B$ are each independently a single bond or a $C_1$-$C_{20}$ hydrocarbylene group which may contain a heteroatom,
$Z^C$ is a single bond, —$Z^{C1}$—, —O—$Z^{C1}$—, or —C(=O)—O—$Z^{C1}$—, $Z^{C1}$ is a phenylene group which may be substituted with a substituent selected from a hydroxy group, fluorine, iodine, trifluoromethyl group, $C_1$-$C_{10}$ hydrocarbyl group which may contain a heteroatom, $C_1$-$C_{10}$ hydrocarbyloxy group which may contain a heteroatom, $C_2$-$C_{10}$ hydrocarbylcarbonyl group which may contain a heteroatom, and $C_2$-$C_{10}$ hydrocarbylcarbonyloxy group which may contain a heteroatom, $Z^D$ is a single bond, phenylene group, —O—$Z^{D1}$—, —C(=O)—O—$Z^{D1}$— or —C(=O)—NH—$Z^{D1}$—, $Z^{D1}$ is a hydrocarbylene group which may contain a heteroatom, $R^{31}$ to $R^{41}$ are each independently a $C_1$-$C_{30}$ hydrocarbyl group which may contain a heteroatom, a pair of $R^{31}$ and $R^{32}$, $R^{34}$ and $R^{35}$, $R^{37}$ and $R^{38}$, or $R^{40}$ and $R^{41}$ may bond together to form a ring with the sulfur atom to which they are attached, $k^1$ is 0 or 1, $k^1$ is 0 when $Z^A$ is a single bond, $k^2$ is 0 or 1, $k^2$ is 0 when $Z^B$ is a single bond, and $Xa^-$ is a non-nucleophilic counter ion.

10. A pattern forming process comprising the steps of applying the chemically amplified resist composition of claim 1 to form a resist film on a substrate, exposing the resist film to KrF or ArF excimer laser radiation, and developing the exposed resist film in a developer.

11. A pattern forming process comprising the steps of applying the chemically amplified resist composition of claim 1 to form a resist film on a substrate, exposing the resist film to EB or EUV, and developing the exposed resist film in a developer.

12. The process of claim 10 wherein the developing step uses an alkaline aqueous solution as the developer to form a positive pattern in which an exposed region of the resist film is dissolved away and an unexposed region of the resist film is not dissolved.

13. The process of claim 10 wherein the developing step uses an organic solvent as the developer to form a negative pattern in which an unexposed region of the resist film is dissolved away and an exposed region of the resist film is not dissolved.

14. The onium salt of claim 1 wherein $R^1$ is a $C_1$-$C_5$ straight or branched hydrocarbyl group which may contain fluorine, and $R^1$ is exclusive of a tertiary hydrocarbyl group.

15. The onium salt of claim 1 wherein $R^1$ is a $C_1$-$C_3$ straight or branched hydrocarbyl group which may contain fluorine or oxygen.

* * * * *